(12) United States Patent
Heyes et al.

(10) Patent No.: US 8,466,122 B2
(45) Date of Patent: Jun. 18, 2013

(54) TRIALKYL CATIONIC LIPIDS AND METHODS OF USE THEREOF

(75) Inventors: James Heyes, Vancouver (CA); Mark Wood, Port Moody (CA); Alan Martin, Burnaby (CA)

(73) Assignee: Protiva Biotherapeutics, Inc., Burnaby, BC (CA)

( * ) Notice: Subject to any disclaimer, the term of this patent is extended or adjusted under 35 U.S.C. 154(b) by 0 days.

(21) Appl. No.: 13/235,253

(22) Filed: Sep. 16, 2011

(65) Prior Publication Data

US 2012/0172411 A1    Jul. 5, 2012

Related U.S. Application Data

(60) Provisional application No. 61/384,191, filed on Sep. 17, 2010.

(51) Int. Cl.
  *C12N 15/11*  (2006.01)
  *C07H 21/02*  (2006.01)
  *A61K 9/127*  (2006.01)

(52) U.S. Cl.
  USPC ......... 514/44 A; 424/450; 536/24.5; 977/797; 977/800; 977/907; 977/911; 977/916

(58) Field of Classification Search
  None
  See application file for complete search history.

(56) References Cited

U.S. PATENT DOCUMENTS

| | | | |
|---|---|---|---|
| 5,334,761 A | 8/1994 | Gebeyehu et al. |
| 5,578,475 A | 11/1996 | Jessee |
| 5,627,159 A | 5/1997 | Shih et al. |
| 5,674,908 A | 10/1997 | Haces et al. |
| 5,736,392 A | 4/1998 | Hawley-Nelson et al. |
| 5,877,220 A | 3/1999 | Schwartz et al. |
| 5,958,901 A | 9/1999 | Dwyer et al. |
| 6,020,202 A | 2/2000 | Jessee |
| 6,020,526 A | 2/2000 | Schwartz et al. |
| 6,034,135 A | 3/2000 | Schwartz et al. |
| 6,051,429 A | 4/2000 | Hawley-Nelson et al. |
| 6,075,012 A | 6/2000 | Gebeyehu et al. |
| 6,172,049 B1 | 1/2001 | Dwyer et al. |
| 6,251,939 B1 | 6/2001 | Schwartz et al. |
| 6,339,173 B1 | 1/2002 | Schwartz et al. |
| 6,376,248 B1 | 4/2002 | Hawley-Nelson et al. |
| 6,638,529 B2 | 10/2003 | Schwartz et al. |
| 6,671,393 B2 | 12/2003 | Hays et al. |
| 7,166,745 B1 | 1/2007 | Chu et al. |
| 7,479,573 B2 | 1/2009 | Chu et al. |
| 7,601,872 B2 | 10/2009 | Chu et al. |
| 7,687,070 B2 | 3/2010 | Gebeyehu et al. |
| 7,745,651 B2 | 6/2010 | Heyes et al. |
| 7,799,565 B2 | 9/2010 | MacLachlan et al. |
| 7,915,450 B2 | 3/2011 | Chu et al. |
| 8,058,068 B2 | 11/2011 | Hawley-Nelson et al. |
| 8,158,827 B2 | 4/2012 | Chu et al. |
| 2003/0069173 A1 | 4/2003 | Hawley-Nelson et al. |
| 2005/0260757 A1 | 11/2005 | Gebeyehu et al. |
| 2006/0147514 A1 | 7/2006 | Gebeyehu et al. |
| 2006/0228406 A1 | 10/2006 | Chiou et al. |
| 2007/0202598 A1 | 8/2007 | Chu et al. |
| 2007/0202600 A1 | 8/2007 | Chu et al. |
| 2009/0143583 A1 | 6/2009 | Chu et al. |
| 2010/0159593 A1 | 6/2010 | Chu et al. |
| 2012/0136073 A1 | 5/2012 | Yang et al. |
| 2012/0238747 A1 | 9/2012 | Chu et al. |

FOREIGN PATENT DOCUMENTS

| | | |
|---|---|---|
| WO | WO 2009/086558 | 7/2009 |
| WO | WO 2010/144740 | 1/2010 |
| WO | WO 2010/042877 | 4/2010 |
| WO | WO 2010/054401 | 5/2010 |
| WO | WO 2010/054405 | 5/2010 |
| WO | WO 2010/054406 | 5/2010 |
| WO | WO 2011/000106 | 1/2011 |

OTHER PUBLICATIONS

Eustache et al (Tetrahedron 50 (21): 6721-6728, 1994).*
Sparks et al (Polymeric Materials: Science & Engineering (97): 695 (2007).*

* cited by examiner

*Primary Examiner* — Richard Schnizer
(74) *Attorney, Agent, or Firm* — Kilpatrick Townsend & Stockton LLP

(57) ABSTRACT

The present invention provides compositions and methods for the delivery of therapeutic agents to cells. In particular, these include novel cationic lipids and nucleic acid-lipid particles that provide efficient encapsulation of nucleic acids and efficient delivery of the encapsulated nucleic acid to cells in vivo. The compositions of the present invention are highly potent, thereby allowing effective knock-down of a specific target protein at relatively low doses. In addition, the compositions and methods of the present invention are less toxic and provide a greater therapeutic index compared to compositions and methods previously known in the art.

18 Claims, 1 Drawing Sheet

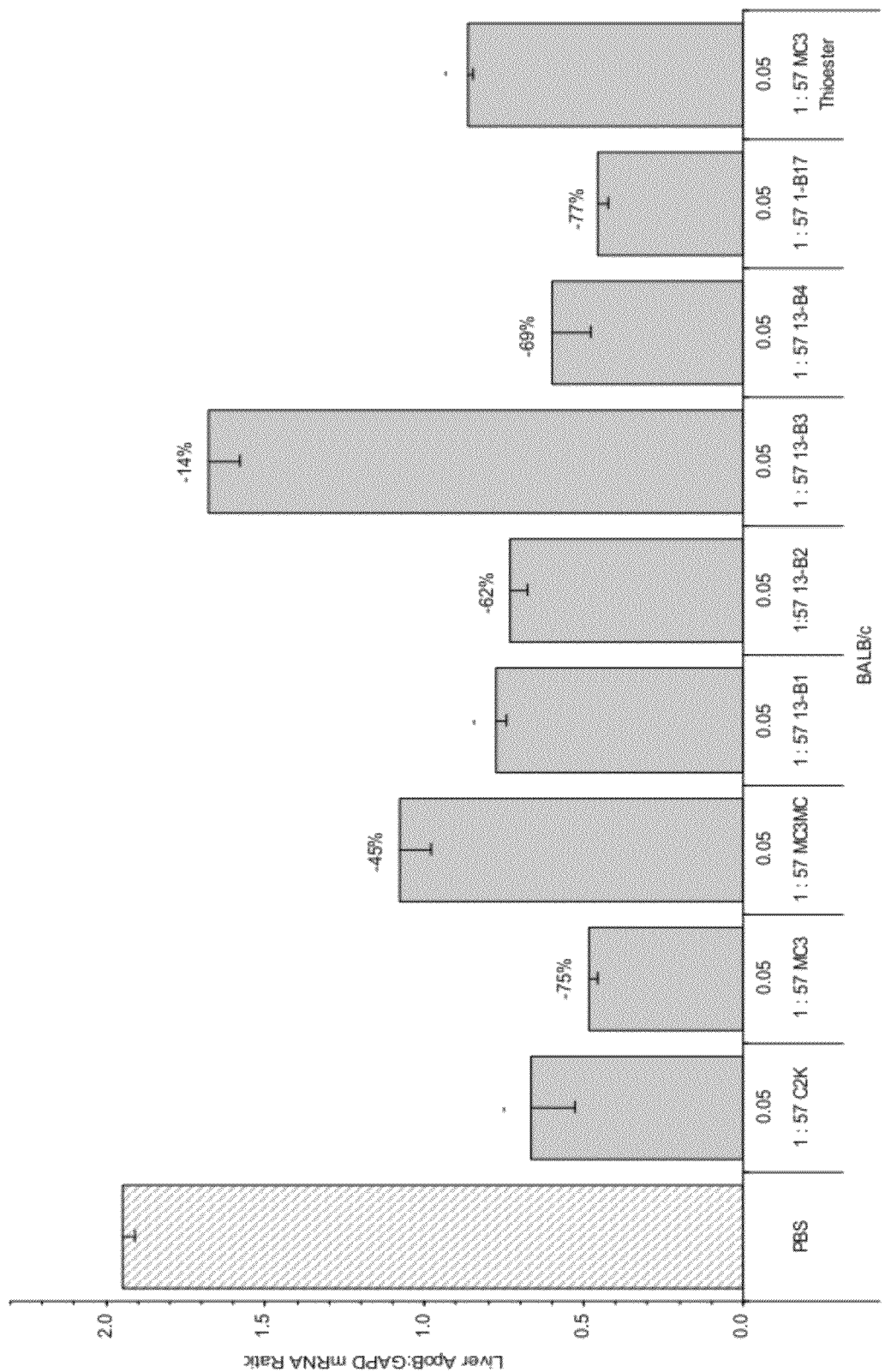

TRIALKYL CATIONIC LIPIDS AND METHODS OF USE THEREOF

CROSS REFERENCE TO RELATED APPLICATIONS

The present application claims the benefit of priority of U.S. Provisional Patent Application No. 61/384,191, filed on Sep. 17, 2010, the contents of which is hereby incorporated in its entirety by reference.

REFERENCE TO A "SEQUENCE LISTING," A TABLE, OR A COMPUTER PROGRAM LISTING APPENDIX SUBMITTED AS AN ASCII TEXT FILE

The Sequence Listing written in file -111-1.TXT, created on Nov. 16, 2011, 4,096 bytes, machine format IBM-PC, MS-Windows operating system, is hereby incorporated by reference in its entirety for all purposes.

BACKGROUND OF THE INVENTION

Therapeutic nucleic acids include, e.g., small interfering RNA (siRNA), microRNA (miRNA), antisense oligonucleotides, ribozymes, plasmids, and immune-stimulating nucleic acids. These nucleic acids act via a variety of mechanisms. In the case of interfering RNA molecules such as siRNA and miRNA, these nucleic acids can down-regulate intracellular levels of specific proteins through a process termed RNA interference (RNAi). Following introduction of interfering RNA into the cell cytoplasm, these double-stranded RNA constructs can bind to a protein termed RISC. The sense strand of the interfering RNA is displaced from the RISC complex, providing a template within RISC that can recognize and bind mRNA with a complementary sequence to that of the bound interfering RNA. Having bound the complementary mRNA, the RISC complex cleaves the mRNA and releases the cleaved strands. RNAi can provide down-regulation of specific proteins by targeting specific destruction of the corresponding mRNA that encodes for protein synthesis.

The therapeutic applications of RNAi are extremely broad, since interfering RNA constructs can be synthesized with any nucleotide sequence directed against a target protein. To date, siRNA constructs have shown the ability to specifically down-regulate target proteins in both in vitro and in vivo models. In addition, siRNA constructs are currently being evaluated in clinical studies.

However, two problems currently faced by interfering RNA constructs are, first, their susceptibility to nuclease digestion in plasma and, second, their limited ability to gain access to the intracellular compartment where they can bind RISC when administered systemically as free interfering RNA molecules. These double-stranded constructs can be stabilized by the incorporation of chemically modified nucleotide linkers within the molecule, e.g., phosphothioate groups. However, such chemically modified linkers provide only limited protection from nuclease digestion and may decrease the activity of the construct. Intracellular delivery of interfering RNA can be facilitated by the use of carrier systems such as polymers, cationic liposomes, or by the covalent attachment of a cholesterol moiety to the molecule. However, improved delivery systems are required to increase the potency of interfering RNA molecules such as siRNA and miRNA and to reduce or eliminate the requirement for chemically modified nucleotide linkers.

In addition, problems remain with the limited ability of therapeutic nucleic acids such as interfering RNA to cross cellular membranes (see, Vlassov et al., *Biochim. Biophys. Acta,* 1197:95-1082 (1994)) and in the problems associated with systemic toxicity, such as complement-mediated anaphylaxis, altered coagulatory properties, and cytopenia (Galbraith et al., *Antisense Nucl. Acid Drug Des.,* 4:201-206 (1994)).

To attempt to improve efficacy, investigators have also employed lipid-based carrier systems to deliver chemically modified or unmodified therapeutic nucleic acids. Zelphati et al. (*J. Contr. Rel.,* 41:99-119 (1996)) describes the use of anionic (conventional) liposomes, pH sensitive liposomes, immunoliposomes, fusogenic liposomes, and cationic lipid/antisense aggregates. Similarly, siRNA has been administered systemically in cationic liposomes, and these nucleic acid-lipid particles have been reported to provide improved down-regulation of target proteins in mammals including non-human primates (Zimmermann et al., *Nature,* 441: 111-114 (2006)).

In spite of this progress, there remains a need in the art for improved lipid-therapeutic nucleic acid compositions that are suitable for general therapeutic use. Preferably, these compositions would encapsulate nucleic acids with high efficiency, have high drug:lipid ratios, protect the encapsulated nucleic acid from degradation and clearance in serum, be suitable for systemic delivery, and provide intracellular delivery of the encapsulated nucleic acid. In addition, these nucleic acid-lipid particles should be well-tolerated and provide an adequate therapeutic index, such that patient treatment at an effective dose of the nucleic acid is not associated with significant toxicity and/or risk to the patient. The present invention provides such compositions, methods of making the compositions, and methods of using the compositions to introduce nucleic acids into cells, including for the treatment of diseases.

BRIEF SUMMARY OF THE INVENTION

The present invention provides novel cationic ammonium lipids and lipid particles comprising these lipids, which are advantageous for the in vivo delivery of nucleic acids, as well as nucleic acid-lipid particle compositions suitable for in vivo therapeutic use. The present invention also provides methods of making these compositions, as well as methods of introducing nucleic acids into cells using these compositions, e.g. for the treatment of various disease conditions.

In one embodiment, the present invention provides a cationic lipid of Formula I having the following structure:

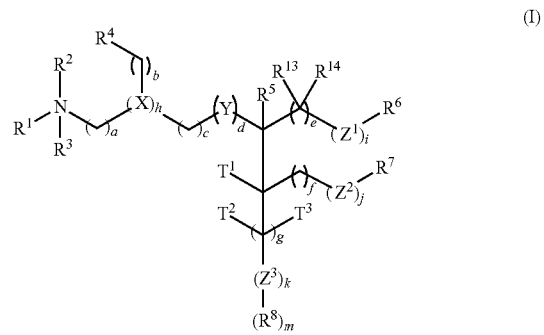

or salts and isomers thereof, wherein:

$R^1$ and $R^2$ are independently selected from hydrogen (H), optionally substituted $C_1$-$C_6$ alkyl, $C_2$-$C_6$ alkenyl, and $C_2$-$C_6$ alkynyl. Alternatively, $R^1$ and $R^2$ may join to form an optionally substituted heterocycloalkyl of 4 to 6 carbon atoms and 1 to 2 heteroatoms selected from nitrogen (N), oxygen (O), and mixtures thereof. $R^3$ is absent or is hydrogen (H) or a $C_1$-$C_6$ alkyl to provide a quaternary amine. $R^4$ is absent or is selected from —$CH_2$—, optionally substituted $C_{10}$-$C_{30}$ alkyl, $C_{10}$-$C_{30}$ alkenyl, $C_{10}$-$C_{30}$ alkynyl, $C_{10}$-$C_{30}$ acyl, and $NR^{4a}R^{4b}$, wherein $R^{4a}$ and $R^{4b}$ are independently selected from hydrogen (H), an optionally substituted $C_1$-$C_6$ alkyl, $C_2$-$C_6$ alkenyl, and $C_2$-$C_6$ alkynyl. $R^5$ is selected from hydrogen (H), oxygen (O), optionally substituted $C_{10}$-$C_{30}$ alkyl, $C_{10}$-$C_{30}$ alkenyl, $C_{10}$-$C_{30}$ alkynyl, and $OR^{5a}$, wherein $R^{5a}$ is selected from hydrogen (H), an optionally substituted $C_1$-$C_6$ alkyl, $C_2$-$C_6$ alkenyl, and $C_2$-$C_6$ alkynyl.

Alternatively, $R^4$ and $R^5$ may join to form a $C_{3-10}$ heterocycloalkyl having from 1 to 3 heteroatoms each independently selected from nitrogen (N), oxygen (O), and sulfur (S), and optionally substituted with from 1 to 3 groups each independently selected from hydrogen (H) and $C_1$-$C_6$ alkyl. $R^6$ and $R^7$ are independently selected from optionally substituted $C_{10}$-$C_{30}$ alkyl, $C_{10}$-$C_{30}$ alkenyl, $C_{10}$-$C_{30}$ alkynyl, and $C_{10}$-$C_{30}$ acyl. $R^8$ is selected from optionally substituted $C_{10}$-$C_{30}$ alkyl, $C_{10}$-$C_{30}$ alkenyl, $C_{10}$-$C_{30}$ alkynyl, and $C_{10}$-$C_{30}$ acyl. $R^{13}$ and $R^{14}$ are independently selected from hydrogen (H), optionally substituted $C_1$-$C_6$ alkyl, $C_2$-$C_6$ alkenyl, and $C_2$-$C_6$ alkynyl. X is selected from —CH—, nitrogen (N), oxygen (O), sulfur (S), $N(R^9)$, C(O), C(O)O, OC(O), $C(O)N(R^9)$, $N(R^9)C(O)$, $OC(O)N(R^9)$, $N(R^9)C(O)O$, C(O)S, SC(O), C(S)O, OC(S), S(O), S(O)(O), and C(S), wherein $R^9$ is selected from hydrogen (H), optionally substituted $C_1$-$C_6$ alkyl, $C_2$-$C_6$ alkenyl, $C_2$-$C_6$ alkynyl, and

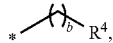

wherein * represents the point of attachment to N. Y is selected from —$CR^{11}R^{12}$— and oxygen (O), wherein $R^{11}$ and $R^{12}$ are independently selected from hydrogen (H), optionally substituted $C_1$-$C_6$ alkyl, $C_2$-$C_6$ alkenyl, and $C_2$-$C_6$ alkynyl. $Z^1$, $Z^2$, and $Z^3$ are independently selected from oxygen (O), C(O)O, or OC(O). $T^1$, $T^2$, and $T^3$ are independently selected from hydrogen (H) or $OR^{10}$, wherein $R^{10}$ is hydrogen (H) or optionally substituted $C_1$-$C_6$ alkyl, $C_2$-$C_6$ alkenyl, or $C_2$-$C_6$ alkynyl. Subscripts a, b, c, d, e, f, and g are independently selected from 0, 1, 2, 3, 4, 5, 6, 7 and 8. Subscripts h, i, j, k, and m are independently selected from 0 and 1. When $R^5$ is an optionally substituted $C_{10}$-$C_{30}$ alkyl, $C_{10}$-$C_{30}$ alkenyl, $C_{10}$-$C_{30}$ alkynyl, and $C_{10}$-$C_{30}$ acyl, then either h is 0 or at least one of $Z^1$ and $Z^2$ is oxygen (O). At least three of $R^4$, $R^5$, $R^6$, $R^7$, and $R^8$ are selected from optionally substituted $C_{10}$-$C_{30}$ alkyl, $C_{10}$-$C_{30}$ alkenyl, and $C_{10}$-$C_{30}$ alkynyl.

In particular embodiments, the cationic lipid of Formula I has one of the following structures:

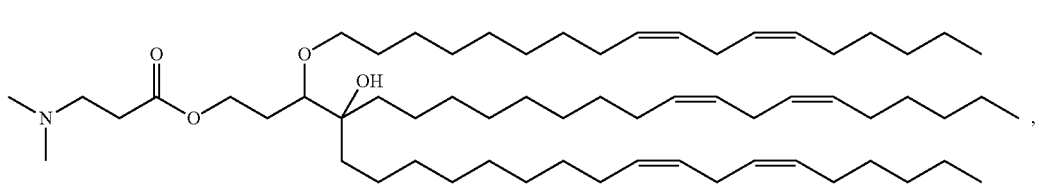

13-B1

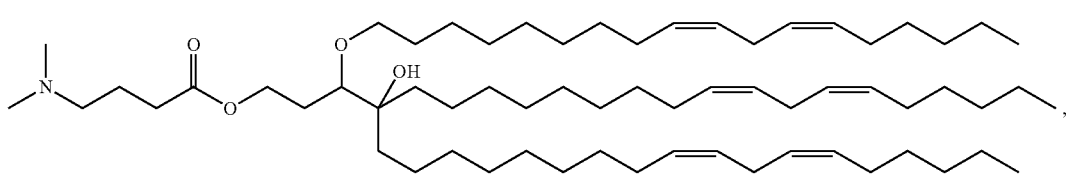

13-B3

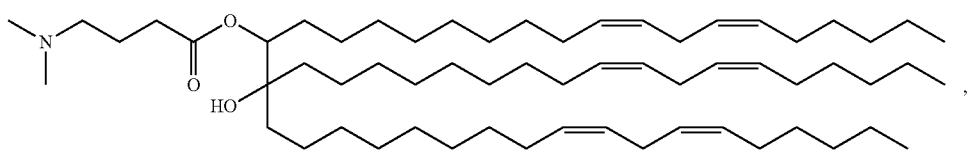

13-B2

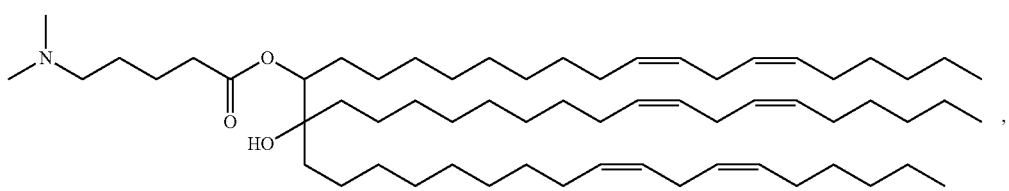

13-B4

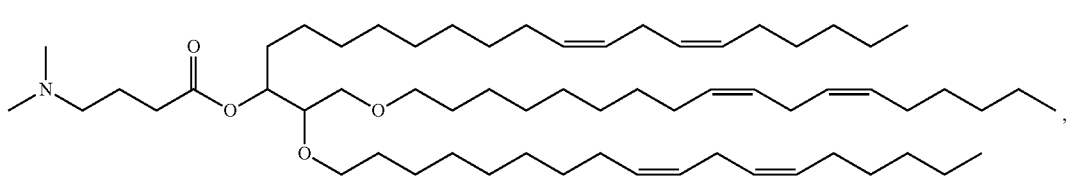

13-B5

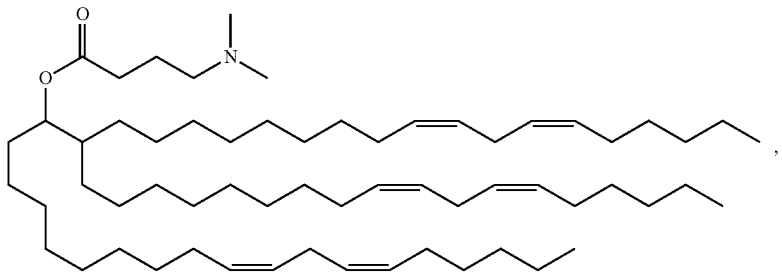

13-B6

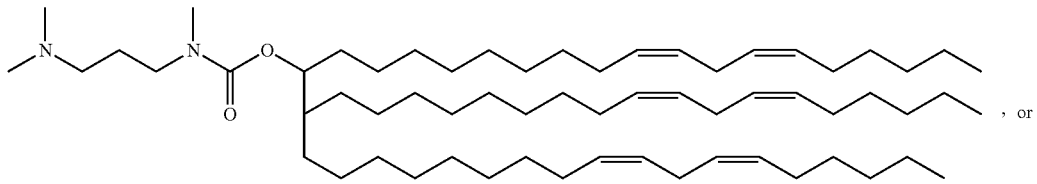

13-B7, or

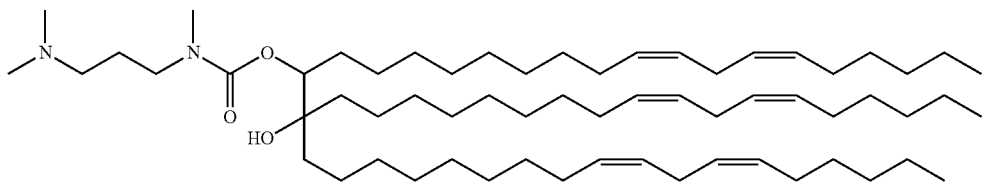

13-B8.

In a further aspect, the present invention provides a lipid particle comprising one or more of the above cationic lipids of Formula I or salts thereof. In certain embodiments, the lipid particle further comprises one or more non-cationic lipids such as neutral lipids. In certain other embodiments, the lipid particle further comprises one or more conjugated lipids capable of reducing or inhibiting particle aggregation. In additional embodiments, the lipid particle further comprises one or more active agents or therapeutic agents.

In certain embodiments, the non-cationic lipid component of the lipid particle may comprise a phospholipid, cholesterol (or cholesterol derivative), or a mixture thereof. In one particular embodiment, the phospholipid comprises dipalmitoylphosphatidylcholine (DPPC), distearoylphosphatidylcholine (DSPC), or a mixture thereof. In some embodiments, the conjugated lipid component of the lipid particle comprises a polyethyleneglycol (PEG)-lipid conjugate. In certain instances, the PEG-lipid conjugate comprises a PEG-diacylglycerol (PEG-DAG) conjugate, a PEG-dialkyloxypropyl (PEG-DAA) conjugate, or a mixture thereof. In other embodiments, the lipid conjugate comprises a polyoxazoline (POZ)-lipid conjugate such as a POZ-DAA conjugate.

In some embodiments, the active agent or therapeutic agent comprises a nucleic acid. In certain instances, the nucleic acid comprises an interfering RNA molecule such as, e.g., an siRNA, aiRNA, miRNA, Dicer-substrate dsRNA, shRNA, or mixtures thereof. In certain other instances, the nucleic acid comprises single-stranded or double-stranded DNA, RNA, or a DNA/RNA hybrid such as, e.g., an antisense oligonucleotide, a ribozyme, a plasmid, an immunostimulatory oligonucleotide, or mixtures thereof.

In other embodiments, the active agent or therapeutic agent is fully encapsulated within the lipid portion of the lipid particle such that the active agent or therapeutic agent in the lipid particle is resistant in aqueous solution to enzymatic degradation, e.g., by a nuclease or protease. In further embodiments, the lipid particle is substantially non-toxic to mammals such as humans.

In preferred embodiments, the present invention provides serum-stable nucleic acid-lipid particles (SNALP) comprising: (a) one or more nucleic acids such as interfering RNA molecules; (b) one or more cationic lipids of Formula I-VI or salts thereof; (c) one or more non-cationic lipids; and (d) one or more conjugated lipids that inhibit aggregation of particles.

In some embodiments, the present invention provides nucleic acid-lipid particles (e.g., SNALP) comprising: (a) one or more nucleic acids; (b) one or more cationic lipids of Formula I or salts thereof comprising from about 50 mol % to about 85 mol % of the total lipid present in the particle; (c) one or more non-cationic lipids comprising from about 13 mol % to about 49.5 mol % of the total lipid present in the particle; and (d) one or more conjugated lipids that inhibit aggregation of particles comprising from about 0.5 mol % to about 2 mol % of the total lipid present in the particle.

In one aspect of this embodiment, the nucleic acid-lipid particle comprises: (a) a nucleic acid; (b) a cationic lipid of Formula I or a salt thereof comprising from about 52 mol % to about 62 mol % of the total lipid present in the particle; (c) a mixture of a phospholipid and cholesterol or a derivative thereof comprising from about 36 mol % to about 47 mol % of the total lipid present in the particle; and (d) a PEG-lipid conjugate comprising from about 1 mol % to about 2 mol % of the total lipid present in the particle. This embodiment of nucleic acid-lipid particle is generally referred to herein as the "1:57" formulation. In one particular embodiment, the 1:57 formulation is a four-component system comprising about 1.4 mol % PEG-lipid conjugate (e.g., PEG2000-C-DMA), about 57.1 mol % cationic lipid of Formula I or a salt thereof, about 7.1 mol % DPPC (or DSPC), and about 34.3 mol % cholesterol (or derivative thereof).

In another aspect of this embodiment, the nucleic acid-lipid particle comprises: (a) a nucleic acid; (b) a cationic lipid of Formula I or a salt thereof comprising from about 56.5 mol % to about 66.5 mol % of the total lipid present in the particle; (c) cholesterol or a derivative thereof comprising from about 31.5 mol % to about 42.5 mol % of the total lipid present in the particle; and (d) a PEG-lipid conjugate comprising from about 1 mol % to about 2 mol % of the total lipid present in the particle. This embodiment of nucleic acid-lipid particle is generally referred to herein as the "1:62" formulation. In one particular embodiment, the 1:62 formulation is a three-component system which is phospholipid-free and comprises about 1.5 mol % PEG-lipid conjugate (e.g., PEG2000-C-DMA), about 61.5 mol % cationic lipid of Formula I or a salt thereof, and about 36.9 mol % cholesterol (or derivative thereof).

Additional embodiments related to the 1:57 and 1:62 formulations are described in PCT Publication No. WO 09/127,060 and U.S. application Ser. No. 12/794,701, filed Jun. 4, 2010, the disclosures of which are herein incorporated by reference in their entirety for all purposes.

In other embodiments, the present invention provides nucleic acid-lipid particles (e.g., SNALP) comprising: (a) one or more nucleic acids; (b) one or more cationic lipids of Formula I or salts thereof comprising from about 2 mol % to about 50 mol % of the total lipid present in the particle; (c) one or more non-cationic lipids comprising from about 5 mol % to about 90 mol % of the total lipid present in the particle; and (d) one or more conjugated lipids that inhibit aggregation of particles comprising from about 0.5 mol % to about 20 mol % of the total lipid present in the particle.

In one aspect of this embodiment, the nucleic acid-lipid particle comprises: (a) a nucleic acid; (b) a cationic lipid of Formula I or a salt thereof comprising from about 30 mol % to about 50 mol % of the total lipid present in the particle; (c) a mixture of a phospholipid and cholesterol or a derivative thereof comprising from about 47 mol % to about 69 mol % of the total lipid present in the particle; and (d) a PEG-lipid conjugate comprising from about 1 mol % to about 3 mol % of the total lipid present in the particle. This embodiment of nucleic acid-lipid particle is generally referred to herein as the "2:40" formulation. In one particular embodiment, the 2:40 formulation is a four-component system which comprises about 2 mol % PEG-lipid conjugate (e.g., PEG2000-C-DMA), about 40 mol % cationic lipid of Formula I or a salt thereof, about 10 mol % DPPC (or DSPC), and about 48 mol % cholesterol (or derivative thereof).

In further embodiments, the present invention provides nucleic acid-lipid particles (e.g., SNALP) comprising: (a) one or more nucleic acids; (b) one or more cationic lipids of Formula I or salts thereof comprising from about 50 mol % to about 65 mol % of the total lipid present in the particle; (c) one or more non-cationic lipids comprising from about 25 mol % to about 45 mol % of the total lipid present in the particle; and (d) one or more conjugated lipids that inhibit aggregation of particles comprising from about 5 mol % to about 10 mol % of the total lipid present in the particle.

In one aspect of this embodiment, the nucleic acid-lipid particle comprises: (a) a nucleic acid; (b) a cationic lipid of Formula I or a salt thereof comprising from about 50 mol % to about 60 mol % of the total lipid present in the particle; (c) a mixture of a phospholipid and cholesterol or a derivative thereof comprising from about 35 mol % to about 45 mol % of the total lipid present in the particle; and (d) a PEG-lipid conjugate comprising from about 5 mol % to about 10 mol % of the total lipid present in the particle. This embodiment of nucleic acid-lipid particle is generally referred to herein as the "7:54" formulation. In certain instances, the non-cationic lipid mixture in the 7:54 formulation comprises: (i) a phospholipid of from about 5 mol % to about 10 mol % of the total lipid present in the particle; and (ii) cholesterol or a derivative thereof of from about 25 mol % to about 35 mol % of the total lipid present in the particle. In one particular embodiment, the 7:54 formulation is a four-component system which comprises about 7 mol % PEG-lipid conjugate (e.g., PEG750-C-DMA), about 54 mol % cationic lipid of Formula I or a salt thereof, about 7 mol % DPPC (or DSPC), and about 32 mol % cholesterol (or derivative thereof).

In another aspect of this embodiment, the nucleic acid-lipid particle comprises: (a) a nucleic acid; (b) a cationic lipid of Formula I or a salt thereof comprising from about 55 mol % to about 65 mol % of the total lipid present in the particle; (c) cholesterol or a derivative thereof comprising from about 30 mol % to about 40 mol % of the total lipid present in the particle; and (d) a PEG-lipid conjugate comprising from about 5 mol % to about 10 mol % of the total lipid present in the particle. This embodiment of nucleic acid-lipid particle is generally referred to herein as the "7:58" formulation. In one particular embodiment, the 7:58 formulation is a three-component system which is phospholipid-free and comprises about 7 mol % PEG-lipid conjugate (e.g., PEG750-C-DMA), about 58 mol % cationic lipid of Formula I or a salt thereof, and about 35 mol % cholesterol (or derivative thereof).

Additional embodiments related to the 7:54 and 7:58 formulations are described in U.S. application Ser. No. 12/828,189, filed Jun. 30, 2010, the disclosure of which is herein incorporated by reference in its entirety for all purposes.

The present invention also provides pharmaceutical compositions comprising a lipid particle such as a nucleic acid-lipid particle (e.g., SNALP) and a pharmaceutically acceptable carrier.

In another aspect, the present invention provides methods for introducing one or more therapeutic agents such as nucleic acids into a cell, the method comprising contacting the cell with a lipid particle described herein (e.g., SNALP). In one embodiment, the cell is in a mammal and the mammal is a human.

In yet another aspect, the present invention provides methods for the in vivo delivery of one or more therapeutic agents such as nucleic acids, the method comprising administering to a mammal a lipid particle described herein (e.g., SNALP). In certain embodiments, the lipid particles (e.g., SNALP) are administered by one of the following routes of administration: oral, intranasal, intravenous, intraperitoneal, intramuscular, intra-articular, intralesional, intratracheal, subcutaneous, and intradermal. In particular embodiments, the lipid particles (e.g., SNALP) are administered systemically, e.g., via enteral or parenteral routes of administration. In preferred embodiments, the mammal is a human.

In a further aspect, the present invention provides methods for treating a disease or disorder in a mammal in need thereof, the method comprising administering to the mammal a therapeutically effective amount of a lipid particle (e.g., SNALP) comprising one or more therapeutic agents such as nucleic acids. Non-limiting examples of diseases or disorders include a viral infection, a liver disease or disorder, and cancer. Preferably, the mammal is a human.

In certain embodiments, the present invention provides methods for treating a liver disease or disorder by administering a nucleic acid such as an interfering RNA (e.g., siRNA) in nucleic acid-lipid particles (e.g., SNALP), alone or in combination with a lipid-lowering agent. Examples of lipid diseases and disorders include, but are not limited to, dyslipidemia (e.g., hyperlipidemias such as elevated triglyceride levels (hypertriglyceridemia) and/or elevated cholesterol levels (hypercholesterolemia)), atherosclerosis, coronary heart disease, coronary artery disease, atherosclerotic cardiovascular disease (CVD), fatty liver disease (hepatic steatosis), abnormal lipid metabolism, abnormal cholesterol metabolism, diabetes (including Type 2 diabetes), obesity, cardiovascular disease, and other disorders relating to abnormal metabolism. Non-limiting examples of lipid-lowering agents include statins, fibrates, ezetimibe, thiazolidinediones, niacin, beta-blockers, nitroglycerin, calcium antagonists, and fish oil.

In one particular embodiment, the present invention provides a method for lowering or reducing cholesterol levels in a mammal (e.g., human) in need thereof (e.g., a mammal with elevated blood cholesterol levels), the method comprising administering to the mammal a therapeutically effective amount of a nucleic acid-lipid particle (e.g., a SNALP formulation) described herein comprising one or more interfering RNAs (e.g., siRNAs) that target one or more genes associated with metabolic diseases and disorders. In another particular embodiment, the present invention provides a method for lowering or reducing triglyceride levels in a mammal (e.g., human) in need thereof (e.g., a mammal with elevated blood triglyceride levels), the method comprising administering to the mammal a therapeutically effective amount of a nucleic acid-lipid particle (e.g., a SNALP formulation) described herein comprising one or more interfering RNAs (e.g., siRNAs) that target one or more genes associated with metabolic diseases and disorders. These methods can be carried out in vitro using standard tissue culture techniques or in vivo by administering the interfering RNA (e.g., siRNA) using any means known in the art. In preferred embodiments, the interfering RNA (e.g., siRNA) is delivered to a liver cell (e.g., hepatocyte) in a mammal such as a human.

Additional embodiments related to treating a liver disease or disorder using a lipid particle are described in, e.g., PCT Application No. PCT/CA2010/000120, filed Jan. 26, 2010, and U.S. Patent Publication No. 20060134189, the disclosures of which are herein incorporated by reference in their entirety for all purposes.

In other embodiments, the present invention provides methods for treating a cell proliferative disorder such as cancer by administering a nucleic acid such as an interfering RNA (e.g., siRNA) in nucleic acid-lipid particles (e.g., SNALP), alone or in combination with a chemotherapy drug. The methods can be carried out in vitro using standard tissue culture techniques or in vivo by administering the interfering RNA (e.g., siRNA) using any means known in the art. In preferred embodiments, the interfering RNA (e.g., siRNA) is delivered to a cancer cell in a mammal such as a human, alone or in combination with a chemotherapy drug. The nucleic acid-lipid particles and/or chemotherapy drugs may also be co-administered with conventional hormonal, immunotherapeutic, and/or radiotherapeutic agents.

Additional embodiments related to treating a cell proliferative disorder using a lipid particle are described in, e.g., PCT Publication No. WO 09/082,817, U.S. Patent Publication No. 20090149403, PCT Publication No. WO 09/129, 319, and U.S. Provisional Application No. 61/245,143, filed Sep. 23, 2009, the disclosures of which are herein incorporated by reference in their entirety for all purposes.

In further embodiments, the present invention provides methods for preventing or treating a viral infection such as an arenavirus (e.g., Lassa virus) or filovirus (e.g., Ebola virus, Marburg virus, etc.) infection which causes hemorrhagic fever or a hepatitis (e.g., Hepatitis C virus) infection which causes acute or chronic hepatitis by administering a nucleic acid such as an interfering RNA (e.g., siRNA) in nucleic acid-lipid particles (e.g., SNALP), alone or in combination with the administration of conventional agents used to treat or ameliorate the viral condition or any of the symptoms associated therewith. The methods can be carried out in vitro using standard tissue culture techniques or in vivo by administering the interfering RNA using any means known in the art. In certain preferred embodiments, the interfering RNA (e.g., siRNA) is delivered to cells, tissues, or organs of a mammal such as a human that are infected and/or susceptible of being infected with the hemorrhagic fever virus, such as, e.g., cells of the reticuloendothelial system (e.g., monocytes, macrophages, etc.). In certain other preferred embodiments, the interfering RNA (e.g., siRNA) is delivered to cells, tissues, or organs of a mammal such as a human that are infected and/or susceptible of being infected with the hepatitis virus, such as, e.g., cells of the liver (e.g., hepatocytes).

Additional embodiments related to preventing or treating a viral infection using a lipid particle are described in, e.g., U.S. Patent Publication No. 20070218122, U.S. Patent Publication No. 20070135370, U.S. application Ser. No. 12/840,225, filed Jul. 20, 2010, PCT Application No. PCT/CA2010/000444, entitled "Compositions and Methods for Silencing Hepatitis C Virus Expression," filed Mar. 19, 2010, and U.S. Provisional Application No. 61/319,855, filed Mar. 31, 2010, the disclosures of which are herein incorporated by reference in their entirety for all purposes.

The lipid particles of the invention (e.g., SNALP) comprising one or more cationic lipids of Formula I or salts thereof are particularly advantageous and suitable for use in the administration of nucleic acids such as interfering RNA to a subject (e.g., a mammal such as a human) because they are stable in circulation, of a size required for pharmacodynamic behavior resulting in access to extravascular sites, and are capable of reaching target cell populations.

Other objects, features, and advantages of the present invention will be apparent to one of skill in the art from the following detailed description and figures.

BRIEF DESCRIPTION OF THE DRAWING

The FIGURE shows a comparison of the liver ApoB mRNA knockdown activity of exemplary SNALP formulations containing cationic lipids of Formula I.

DETAILED DESCRIPTION OF THE INVENTION

I. Introduction

The present invention is based, in part, upon the discovery of novel cationic ammonium lipids that provide advantages when used in lipid particles for the in vivo delivery of an active or therapeutic agent such as a nucleic acid into a cell of a mammal. In particular, the present invention provides nucleic acid-lipid particle compositions comprising one or more of the novel cationic lipids described herein that provide increased activity of the nucleic acid (e.g., interfering RNA) and improved tolerability of the compositions in vivo, resulting in a significant increase in the therapeutic index as compared to nucleic acid-lipid particle compositions previously described.

In particular embodiments, the present invention provides novel cationic lipids that enable the formulation of improved compositions for the in vitro and in vivo delivery of interfering RNA such as siRNA. It is shown herein that these improved lipid particle compositions are effective in down-regulating (e.g., silencing) the protein levels and/or mRNA levels of target genes. Furthermore, it is shown herein that the activity of these improved lipid particle compositions is dependent on the presence of the novel cationic lipids of the invention.

The lipid particles and compositions of the present invention may be used for a variety of purposes, including the delivery of encapsulated or associated (e.g., complexed) therapeutic agents such as nucleic acids to cells, both in vitro and in vivo. Accordingly, the present invention further provides methods of treating diseases or disorders in a subject in need thereof by contacting the subject with a lipid particle that encapsulates or is associated with a suitable therapeutic agent, wherein the lipid particle comprises one or more of the novel cationic lipids described herein.

As described herein, the lipid particles of the present invention are particularly useful for the delivery of nucleic acids, including, e.g., interfering RNA molecules such as siRNA. Therefore, the lipid particles and compositions of the present invention may be used to decrease the expression of target genes and proteins both in vitro and in vivo by contacting cells with a lipid particle comprising one or more novel cationic lipids described herein, wherein the lipid particle encapsulates or is associated with a nucleic acid that reduces target gene expression (e.g., an siRNA). Alternatively, the lipid particles and compositions of the present invention may be used to increase the expression of a desired protein both in vitro and in vivo by contacting cells with a lipid particle comprising one or more novel cationic lipids described herein, wherein the lipid particle encapsulates or is associated with a nucleic acid that enhances expression of the desired protein (e.g., a plasmid encoding the desired protein).

Various exemplary embodiments of the cationic lipids of the present invention, lipid particles and compositions comprising the same, and their use to deliver active or therapeutic agents such as nucleic acids to modulate gene and protein expression, are described in further detail below.

II. Definitions

As used herein, the following terms have the meanings ascribed to them unless specified otherwise.

As used herein, the terms "interfering RNA" or "RNAi" or "interfering RNA sequence" as used herein includes single-stranded RNA (e.g., mature miRNA, ssRNAi oligonucleotides, ssDNAi oligonucleotides) or double-stranded RNA (i.e., duplex RNA such as siRNA, Dicer-substrate dsRNA, shRNA, aiRNA, or pre-miRNA) that is capable of reducing or inhibiting the expression of a target gene or sequence (e.g., by mediating the degradation or inhibiting the translation of mRNAs which are complementary to the interfering RNA sequence) when the interfering RNA is in the same cell as the target gene or sequence. Interfering RNA thus refers to the single-stranded RNA that is complementary to a target mRNA sequence or to the double-stranded RNA formed by two complementary strands or by a single, self-complementary strand. Interfering RNA may have substantial or complete identity to the target gene or sequence, or may comprise a region of mismatch (i.e., a mismatch motif). The sequence of the interfering RNA can correspond to the full-length target gene, or a subsequence thereof. Preferably, the interfering RNA molecules are chemically synthesized.

Interfering RNA includes "small-interfering RNA" or "siRNA," e.g., interfering RNA of about 15-60, 15-50, or 15-40 (duplex) nucleotides in length, more typically about 15-30, 15-25, or 19-25 (duplex) nucleotides in length, and is preferably about 20-24, 21-22, or 21-23 (duplex) nucleotides in length (e.g., each complementary sequence of the double-stranded siRNA is 15-60, 15-50, 15-40, 15-30, 15-25, or 19-25 nucleotides in length, preferably about 20-24, 21-22, or 21-23 nucleotides in length, and the double-stranded siRNA is about 15-60, 15-50, 15-40, 15-30, 15-25, or 19-25 base pairs in length, preferably about 18-22, 19-20, or 19-21 base pairs in length). siRNA duplexes may comprise 3' overhangs of about 1 to about 4 nucleotides or about 2 to about 3 nucleotides and 5' phosphate termini. Examples of siRNA include, without limitation, a double-stranded polynucleotide molecule assembled from two separate stranded molecules, wherein one strand is the sense strand and the other is the complementary antisense strand; a double-stranded polynucleotide molecule assembled from a single stranded molecule, where the sense and antisense regions are linked by a nucleic acid-based or non-nucleic acid-based linker; a double-stranded polynucleotide molecule with a hairpin secondary structure having self-complementary sense and antisense regions; and a circular single-stranded polynucleotide molecule with two or more loop structures and a stem having self-complementary sense and antisense regions, where the circular polynucleotide can be processed in vivo or in vitro to generate an active double-stranded siRNA molecule.

Preferably, siRNA are chemically synthesized. siRNA can also be generated by cleavage of longer dsRNA (e.g., dsRNA greater than about 25 nucleotides in length) with the *E. coli* RNase III or Dicer. These enzymes process the dsRNA into biologically active siRNA (see, e.g., Yang et al., *Proc. Natl. Acad. Sci. USA*, 99:9942-9947 (2002); Calegari et al., *Proc. Natl. Acad. Sci. USA*, 99:14236 (2002); Byrom et al., *Ambion TechNotes*, 10(1):4-6 (2003); Kawasaki et al., *Nucleic Acids Res.*, 31:981-987 (2003); Knight et al., *Science*, 293:2269-2271 (2001); and Robertson et al., *J. Biol. Chem.*, 243:82 (1968)). Preferably, dsRNA are at least 50 nucleotides to about 100, 200, 300, 400, or 500 nucleotides in length. A dsRNA may be as long as 1000, 1500, 2000, 5000 nucleotides in length, or longer. The dsRNA can encode for an entire gene transcript or a partial gene transcript. In certain instances, siRNA may be encoded by a plasmid (e.g., transcribed as sequences that automatically fold into duplexes with hairpin loops).

As used herein, the terms "mismatch motif" or "mismatch region" refers to a portion of an interfering RNA (e.g., siRNA) sequence that does not have 100% complementarity to its target sequence. An interfering RNA may have at least one, two, three, four, five, six, or more mismatch regions. The mismatch regions may be contiguous or may be separated by 1, 2, 3, 4, 5, 6, 7, 8, 9, 10, 11, 12, or more nucleotides. The mismatch motifs or regions may comprise a single nucleotide or may comprise two, three, four, five, or more nucleotides.

As used herein, the terms "inhibiting expression of a target gene" refers to the ability of an interfering RNA (e.g., siRNA) to silence, reduce, or inhibit the expression of a target gene. To examine the extent of gene silencing, a test sample (e.g., a sample of cells in culture expressing the target gene) or a test mammal (e.g., a mammal such as a human or an animal model such as a rodent (e.g., mouse) or a non-human primate (e.g., monkey) model) is contacted with an interfering RNA (e.g., siRNA) that silences, reduces, or inhibits expression of the target gene. Expression of the target gene in the test sample or test animal is compared to expression of the target gene in a control sample (e.g., a sample of cells in culture expressing the target gene) or a control mammal (e.g., a mammal such as a human or an animal model such as a rodent (e.g., mouse) or non-human primate (e.g., monkey) model) that is not contacted with or administered the interfering RNA (e.g., siRNA). The expression of the target gene in a control sample or a control mammal may be assigned a value of 100%. In particular embodiments, silencing, inhibition, or reduction of expression of a target gene is achieved when the level of target gene expression in the test sample or the test mammal relative to the level of target gene expression in the control sample or the control mammal is about 95%, 90%, 85%, 80%, 75%, 70%, 65%, 60%, 55%, 50%, 45%, 40%, 35%, 30%, 25%, 20%, 15%, 10%, 5%, or 0%. In other words, the interfering RNA (e.g., siRNA) silences, reduces, or inhibits the expression of a target gene by at least about 5%, 10%, 15%, 20%, 25%, 30%, 35%, 40%, 45%, 50%, 55%, 60%, 65%, 70%, 75%, 80%, 85%, 90%, 95%, or 100% in a test sample or a test mammal relative to the level of target gene expression in a control sample or a control mammal not contacted with or administered the interfering RNA (e.g., siRNA). Suitable assays for determining the level of target gene expression include, without limitation, examination of protein or mRNA levels using techniques known to those of skill in the art, such as, e.g., dot blots, Northern blots, in situ hybridization, ELISA, immunoprecipitation, enzyme function, as well as phenotypic assays known to those of skill in the art.

As used herein, the terms "effective amount" or "therapeutically effective amount" of an active agent or therapeutic agent such as an interfering RNA is an amount sufficient to produce the desired effect, e.g., an inhibition of expression of a target sequence in comparison to the normal expression level detected in the absence of an interfering RNA. Inhibition of expression of a target gene or target sequence is achieved when the value obtained with an interfering RNA relative to the control is about 95%, 90%, 85%, 80%, 75%, 70%, 65%, 60%, 55%, 50%, 45%, 40%, 35%, 30%, 25%, 20%, 15%, 10%, 5%, or 0%. Suitable assays for measuring expression of a target gene or target sequence include, e.g., examination of protein or RNA levels using techniques known to those of skill in the art such as dot blots, northern blots, in situ hybridization, ELISA, immunoprecipitation, enzyme function, as well as phenotypic assays known to those of skill in the art.

As used herein, the terms "decrease," "decreasing," "reduce," or "reducing" of an immune response by an interfering RNA is intended to mean a detectable decrease of an immune response to a given interfering RNA (e.g., a modified interfering RNA). The amount of decrease of an immune response by a modified interfering RNA may be determined relative to the level of an immune response in the presence of an unmodified interfering RNA. A detectable decrease can be about 5%, 10%, 15%, 20%, 25%, 30%, 35%, 40%, 45%, 50%, 55%, 60%, 65%, 70%, 75%, 80%, 85%, 90%, 95%, 100%, or more lower than the immune response detected in the presence of the unmodified interfering RNA. A decrease in the immune response to interfering RNA is typically measured by a decrease in cytokine production (e.g., IFNγ, IFNα, TNFα, IL-6, or IL-12) by a responder cell in vitro or a decrease in cytokine production in the sera of a mammalian subject after administration of the interfering RNA.

As used herein, the term "responder cell" refers to a cell, preferably a mammalian cell, that produces a detectable immune response when contacted with an immunostimulatory interfering RNA such as an unmodified siRNA. Exemplary responder cells include, e.g., dendritic cells, macrophages, peripheral blood mononuclear cells (PBMCs), splenocytes, and the like. Detectable immune responses include, e.g., production of cytokines or growth factors such as TNF-α, IFN-α, IFN-β, IFN-γ, IL-1, IL-2, IL-3, IL-4, IL-5, IL-6, IL-10, IL-12, IL-13, TGF, and combinations thereof. Detectable immune responses also include, e.g., induction of interferon-induced protein with tetratricopeptide repeats 1 (IFIT1) mRNA.

As used herein, the terms "substantial identity" refers to a sequence that hybridizes to a reference sequence under stringent conditions, or to a sequence that has a specified percent identity over a specified region of a reference sequence.

As used herein, the phrase "stringent hybridization conditions" refers to conditions under which a nucleic acid will hybridize to its target sequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

Exemplary stringent hybridization conditions can be as follows: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec.-2 min., an annealing phase lasting 30 sec.-2 min., and an extension phase of about 72° C. for 1-2 min. Protocols and guidelines for low and high stringency amplification reactions are provided, e.g., in Innis et al., *PCR Protocols, A Guide to Methods and Applications*, Academic Press, Inc. N.Y. (1990).

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, Ausubel et al., eds.

As used herein, the terms "substantially identical" or "substantial identity," in the context of two or more nucleic acids, refer to two or more sequences or subsequences that are the same or have a specified percentage of nucleotides that are the same (i.e., at least about 60%, preferably at least about 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. This definition, when the context indicates, also refers analogously to the complement of a sequence. Preferably, the substantial identity exists over a region that is at least about 5, 10, 15, 20, 25, 30, 35, 40, 45, 50, 55, or 60 nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

As used herein, the terms "comparison window," includes reference to a segment of any one of a number of contiguous positions selected from the group consisting of from about 5 to about 60, usually about 10 to about 45, more usually about 15 to about 30, in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, *Adv. Appl. Math.*, 2:482 (1981), by the homology alignment algorithm of Needleman and Wunsch, *J. Mol. Biol.*, 48:443 (1970), by the search for similarity method of Pearson and Lipman, *Proc. Natl. Acad. Sci. USA*, 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology*, Ausubel et al., eds. (1995 supplement)).

Non-limiting examples of algorithms that are suitable for determining percent sequence identity and sequence similarity are the BLAST and BLAST 2.0 algorithms, which are described in Altschul et al., *Nuc. Acids Res.*, 25:3389-3402 (1977) and Altschul et al., *J. Mol. Biol.*, 215:403-410 (1990), respectively. BLAST and BLAST 2.0 are used, with the parameters described herein, to determine percent sequence identity for the nucleic acids of the invention. Software for performing BLAST analyses is publicly available through the National Center for Biotechnology Information. Another example is a global alignment algorithm for determining percent sequence identity such as the Needleman-Wunsch algorithm for aligning protein or nucleotide (e.g., RNA) sequences.

The BLAST algorithm also performs a statistical analysis of the similarity between two sequences (see, e.g., Karlin and Altschul, *Proc. Natl. Acad. Sci. USA*, 90:5873-5787 (1993)). One measure of similarity provided by the BLAST algorithm is the smallest sum probability (P(N)), which provides an indication of the probability by which a match between two nucleotide sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

As used herein, the term "nucleic acid" as used herein refers to a polymer containing at least two deoxyribonucleotides or ribonucleotides in either single- or double-stranded form and includes DNA and RNA. DNA may be in the form of, e.g., antisense molecules, plasmid DNA, pre-condensed DNA, a PCR product, vectors (P1, PAC, BAC, YAC, artificial chromosomes), expression cassettes, chimeric sequences, chromosomal DNA, or derivatives and combinations of these groups. RNA may be in the form of small interfering RNA (siRNA), Dicer-substrate dsRNA, small hairpin RNA (shRNA), asymmetrical interfering RNA (aiRNA), microRNA (miRNA), mRNA, tRNA, rRNA, tRNA, viral RNA (vRNA), and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260:2605-2608 (1985); Rossolini et al., *Mol. Cell. Probes*, 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

As used herein, the term "gene" refers to a nucleic acid (e.g., DNA or RNA) sequence that comprises partial length or entire length coding sequences necessary for the production of a polypeptide or precursor polypeptide.

As used herein, the terms "gene product," refer to a product of a gene such as an RNA transcript or a polypeptide.

As used herein, the term "lipid" refers to a group of organic compounds that include, but are not limited to, esters of fatty acids and are characterized by being insoluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

As used herein, the terms "lipid particle" includes a lipid formulation that can be used to deliver an active agent or therapeutic agent, such as a nucleic acid (e.g., an interfering RNA), to a target site of interest (e.g., cell, tissue, organ, and the like). In preferred embodiments, the lipid particle of the invention is a nucleic acid-lipid particle, which is typically formed from a cationic lipid, a non-cationic lipid, and optionally a conjugated lipid that prevents aggregation of the particle. In other preferred embodiments, the active agent or therapeutic agent, such as a nucleic acid, may be encapsulated in the lipid portion of the particle, thereby protecting it from enzymatic degradation.

As used herein, the term "SNALP" refers to a stable nucleic acid-lipid particle. A SNALP represents a particle made from lipids (e.g., a cationic lipid, a non-cationic lipid, and optionally a conjugated lipid that prevents aggregation of the particle), wherein the nucleic acid (e.g., an interfering RNA) is fully encapsulated within the lipid. In certain instances, SNALP are extremely useful for systemic applications, as they can exhibit extended circulation lifetimes following intravenous (i.v.) injection, they can accumulate at distal sites (e.g., sites physically separated from the administration site), and they can mediate silencing of target gene expression at these distal sites. The nucleic acid may be complexed with a condensing agent and encapsulated within a SNALP as set forth in PCT Publication No. WO 00/03683, the disclosure of which is herein incorporated by reference in its entirety for all purposes.

The lipid particles of the invention (e.g., SNALP) typically have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In addition, nucleic acids, when present in the lipid particles of the present invention, are resistant in aqueous solution to degradation with a nuclease. Nucleic acid-lipid particles and their method of preparation are disclosed in, e.g., U.S. Patent Publication Nos. 20040142025 and 20070042031, the disclosures of which are herein incorporated by reference in their entirety for all purposes.

As used herein, "lipid encapsulated" can refer to a lipid particle that provides an active agent or therapeutic agent, such as a nucleic acid (e.g., an interfering RNA), with full encapsulation, partial encapsulation, or both. In a preferred embodiment, the nucleic acid is fully encapsulated in the lipid particle (e.g., to form a SNALP or other nucleic acid-lipid particle).

As used herein, the term "lipid conjugate" refers to a conjugated lipid that inhibits aggregation of lipid particles. Such lipid conjugates include, but are not limited to, PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides (see, e.g., U.S. Pat. No. 5,885,613), cationic PEG lipids, polyoxazoline (POZ)-lipid conjugates (e.g., POZ-DAA conjugates; see, e.g., U.S. Provisional Application No. 61/294,828, filed Jan. 13, 2010, and U.S. Provisional Application No. 61/295,140, filed Jan. 14, 2010), polyamide oligomers (e.g., ATTA-lipid conjugates), and mixtures thereof. Additional examples of POZ-lipid conjugates are described in PCT Publication No. WO 2010/006282. PEG or POZ can be conjugated directly to the lipid or may be linked to the lipid via a linker moiety. Any linker moiety suitable for coupling the PEG or the POZ to a lipid can be used including, e.g., non-ester containing linker moieties and ester-containing linker moieties. In certain preferred embodiments, non-ester containing linker moieties, such as amides or carbamates, are used. The disclosures of each of the above patent documents are herein incorporated by reference in their entirety for all purposes.

As used herein, the terms "amphipathic lipid" refers, in part, to any suitable material wherein the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipids described above can be mixed with other lipids including triglycerides and sterols.

As used herein, the terms "neutral lipid" refer to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

As used herein, the terms "non-cationic lipid" refer to any amphipathic lipid as well as any other neutral lipid or anionic lipid.

As used herein, the terms "anionic lipid" refer to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

As used herein, the term "hydrophobic lipid" refer to compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacyloxy-3-aminopropane, and 1,2-dialkyl-3-aminopropane.

As used herein, the term "fusogenic" refers to the ability of a lipid particle, such as a SNALP, to fuse with the membranes of a cell. The membranes can be either the plasma membrane or membranes surrounding organelles, e.g., endosome, nucleus, etc.

As used herein, the term "aqueous solution" refers to a composition comprising in whole, or in part, water.

As used herein, the term "organic lipid solution" refers to a composition comprising in whole, or in part, an organic solvent having a lipid.

As used herein, the terms "distal site," refer to a physically separated site, which is not limited to an adjacent capillary bed, but includes sites broadly distributed throughout an organism.

As used herein, the terms "serum-stable" in relation to nucleic acid-lipid particles such as SNALP mean that the particle is not significantly degraded after exposure to a serum or nuclease assay that would significantly degrade free DNA or RNA. Suitable assays include, for example, a standard serum assay, a DNAse assay, or an RNAse assay.

As used herein, the terms "systemic delivery," refer to delivery of lipid particles that leads to a broad biodistribution of an active agent such as an interfering RNA (e.g., siRNA) within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of lipid particles can be by any means known in the art including, for example, intravenous, subcutaneous, and intraperitoneal. In a preferred embodiment, systemic delivery of lipid particles is by intravenous delivery.

As used herein, the terms "local delivery," refer to delivery of an active agent such as an interfering RNA (e.g., siRNA) directly to a target site within an organism. For example, an agent can be locally delivered by direct injection into a disease site such as a tumor or other target site such as a site of inflammation or a target organ such as the liver, heart, pancreas, kidney, and the like.

As used herein, the term "mammal" refers to any mammalian species such as a human, mouse, rat, dog, cat, hamster, guinea pig, rabbit, livestock, and the like.

As used herein, the term "cancer" refers to any member of a class of diseases characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Examples of different types of cancer include, but are not limited to, liver cancer, lung cancer, colon cancer, rectal cancer, anal cancer, bile duct cancer, small intestine cancer, stomach (gastric) cancer, esophageal cancer; gallbladder cancer, pancreatic cancer, appendix cancer, breast cancer, ovarian cancer; cervical cancer, prostate cancer, renal cancer (e.g., renal cell carcinoma), cancer of the central nervous system, glioblastoma, skin cancer, lymphomas, choriocarcinomas, head and neck cancers, osteogenic sarcomas, and blood cancers. Non-limiting examples of specific types of liver cancer include hepatocellular carcinoma (HCC), secondary liver cancer (e.g., caused by metastasis of some other non-liver cancer cell type), and hepatoblastoma. As used herein, a "tumor" comprises one or more cancerous cells.

The compounds of the invention may be prepared by known organic synthesis techniques, including the methods described in the Examples. In some embodiments, the synthesis of the cationic lipids of the invention may require the use of protecting groups. Protecting group methodology is well known to those skilled in the art (see, e.g., PROTECTIVE GROUPS IN ORGANIC SYNTHESIS, Green, T. W. et. al., Wiley-Interscience, New York City, 1999). Briefly, protecting groups within the context of this invention are any group that reduces or eliminates the unwanted reactivity of a functional group. A protecting group can be added to a functional group to mask its reactivity during certain reactions and then removed to reveal the original functional group. In certain instances, an "alcohol protecting group" is used. An "alcohol protecting group" is any group which decreases or eliminates the unwanted reactivity of an alcohol functional group. Protecting groups can be added and removed using techniques well known in the art.

In certain embodiments, the cationic lipids of the present invention have at least one protonatable or deprotonatable group, such that the lipid is positively charged at a pH at or below physiological pH (e.g., pH 7.4), and neutral at a second pH, preferably at or above physiological pH. It will be understood by one of ordinary skill in the art that the addition or removal of protons as a function of pH is an equilibrium process, and that the reference to a charged or a neutral lipid refers to the nature of the predominant species and does not require that all of the lipid be present in the charged or neutral form. Lipids that have more than one protonatable or deprotonatable group, or which are zwitterionic, are not excluded from use in the invention.

In certain other embodiments, protonatable lipids according to the invention have a $pK_a$ of the protonatable group in the range of about 4 to about 11. Most preferred is a $pK_a$ of about 4 to about 7, because these lipids will be cationic at a lower pH formulation stage, while particles will be largely (though not completely) surface neutralized at physiological pH of around pH 7.4. One of the benefits of this $pK_a$ is that at least some nucleic acid associated with the outside surface of the particle will lose its electrostatic interaction at physiological pH and be removed by simple dialysis, thus greatly reducing the particle's susceptibility to clearance.

As used herein, the term "isomers" refers to refers to compounds with the same chemical formula but which are structurally distinguishable.

The terms "optionally substituted alkyl," "optionally substituted cyclic alkyl," "optionally substituted alkenyl," "optionally substituted alkynyl," "optionally substituted acyl," and "optionally substituted heterocycle" mean that, when substituted, at least one hydrogen atom is replaced with a substituent. In the case of an "oxo" substituent (=O), two hydrogen atoms are replaced. Non-limiting examples of substituents include oxo, —OH, halogen, heterocycle, —CN, —OR$^x$, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$, and —SO$_n$NR$^x$R$^y$, wherein n is 0, 1, or 2, R$^x$ and R$^y$ are the same or different and are independently hydrogen, alkyl, or heterocycle, and each of the alkyl and heterocycle substituents may be further substituted with one or more of oxo, halogen, —OH, —CN, alkyl, —OR$^x$, heterocycle, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$, and —SO$_n$NR$^x$R$^y$. The term "optionally substituted," when used before a list of substituents, means that each of the substituents in the list may be optionally substituted as described herein.

As used herein, the terms "quaternary amine" refers to an amine group with four substituents bonded to the N atom.

III. Novel Cationic Lipids

The present invention provides, inter alia, novel cationic (amino) lipids that can advantageously be used in the lipid particles described herein for the in vitro and/or in vivo delivery of therapeutic agents such as nucleic acids to cells. The novel cationic lipids of the present invention have the structures set forth in Formulas I-VI herein, and include the (R) and/or (S) enantiomers thereof.

In some embodiments, a lipid of the present invention comprises a racemic mixture. In other embodiments, a lipid of the present invention comprises a mixture of one or more diastereomers. In certain embodiments, a lipid of the present invention is enriched in one enantiomer, such that the lipid comprises at least about 55%, 60%, 65%, 70%, 75%, 80%, 85%, 90%, or 95% enantiomeric excess. In certain other embodiments, a lipid of the present invention is enriched in one diastereomer, such that the lipid comprises at least about 55%, 60%, 65%, 70%, 75%, 80%, 85%, 90%, or 95% diastereomeric excess. In certain additional embodiments, a lipid of the present invention is chirally pure (e.g., comprises a single optical isomer). In further embodiments, a lipid of the present invention is enriched in one optical isomer (e.g., an optically active isomer), such that the lipid comprises at least about 55%, 60%, 65%, 70%, 75%, 80%, 85%, 90%, or 95% isomeric excess. The present invention provides the synthesis of the cationic lipids of Formulas I-VI as a racemic mixture or in optically pure form.

As used herein, the terms "cationic lipid" and "amino lipid" are used interchangeably to include those lipids and salts thereof having one, two, three, or more fatty acid or fatty alkyl chains and a pH-titratable amino head group (e.g., an alkylamino or dialkylamino head group). The cationic lipid is typically protonated (i.e., positively charged) at a pH below the $pK_a$ of the cationic lipid and is substantially neutral at a pH above the $pK_a$. The cationic lipids of the invention may also be termed titratable cationic lipids.

As used herein, the term "salts" includes any anionic and cationic complex, such as the complex formed between a cationic lipid disclosed herein and one or more anions. Non-limiting examples of anions include inorganic and organic anions, e.g., hydride, fluoride, chloride, bromide, iodide, oxalate (e.g., hemioxalate), phosphate, phosphonate, hydrogen phosphate, dihydrogen phosphate, oxide, carbonate, bicarbonate, nitrate, nitrite, nitride, bisulfite, sulfide, sulfite, bisulfate, sulfate, thiosulfate, hydrogen sulfate, borate, formate, acetate, benzoate, citrate, tartrate, lactate, acrylate, polyacrylate, fumarate, maleate, itaconate, glycolate, gluconate, malate, mandelate, tiglate, ascorbate, salicylate, polymethacrylate, perchlorate, chlorate, chlorite, hypochlorite, bromate, hypobromite, iodate, an alkylsulfonate, an arylsulfonate, arsenate, arsenite, chromate, dichromate, cyanide, cyanate, thiocyanate, hydroxide, peroxide, permanganate, and mixtures thereof. In particular embodiments, the salts of the cationic lipids disclosed herein are crystalline salts.

The term "alkyl" includes a straight chain or branched, noncyclic or cyclic, saturated aliphatic hydrocarbon containing from 1 to 30 carbon atoms. Representative saturated straight chain alkyls include, but are not limited to, methyl, ethyl, n-propyl, n-butyl, n-pentyl, n-hexyl, and the like, while saturated branched alkyls include, without limitation, isopropyl, sec-butyl, isobutyl, tert-butyl, isopentyl, and the like. Representative saturated cyclic alkyls include, but are not limited to, the $C_{3-8}$ cycloalkyls described herein, while unsaturated cyclic alkyls include, without limitation, the $C_{3-8}$ cycloalkenyls described herein.

The term "heteroalkyl," includes a straight chain or branched, noncyclic or cyclic, saturated aliphatic hydrocarbon as defined above having from about 1 to about 5 heteroatoms (i.e., 1, 2, 3, 4, or 5 heteroatoms) such as, for example, O, N, Si, and/or S, wherein the nitrogen and sulfur atoms may optionally be oxidized and the nitrogen heteroatom may optionally be quaternized. The heteroalkyl group can be attached to the remainder of the molecule through a carbon atom or a heteroatom.

The term "cyclic alkyl" includes any of the substituted or unsubstituted cycloalkyl, heterocycloalkyl, cycloalkenyl, and heterocycloalkenyl groups described below.

The term "cycloalkyl" includes a substituted or unsubstituted cyclic alkyl group having from about 3 to about 8 carbon atoms (i.e., 3, 4, 5, 6, 7, or 8 carbon atoms) as ring vertices. Preferred cycloalkyl groups include those having from about 3 to about 6 carbon atoms as ring vertices. Examples of $C_{3-8}$ cycloalkyl groups include, but are not limited to, cyclopropyl, methyl-cyclopropyl, dimethyl-cyclopropyl, cyclobutyl, methyl-cyclobutyl, cyclopentyl, methyl-cyclopentyl, cyclohexyl, methyl-cyclohexyl, dimethyl-cyclohexyl, cycloheptyl, and cyclooctyl, as well as other substituted $C_{3-8}$ cycloalkyl groups.

The term "heterocycloalkyl" includes a substituted or unsubstituted cyclic alkyl group as defined above having from about 1 to about 3 heteroatoms as ring members selected from the group consisting of O, N, Si and S, wherein the nitrogen and sulfur atoms may optionally be oxidized and the nitrogen heteroatom may optionally be quaternized. The heterocycloalkyl group can be attached to the remainder of the molecule through a carbon atom or a heteroatom.

The term "cycloalkenyl" includes a substituted or unsubstituted cyclic alkenyl group having from about 3 to about 8 carbon atoms (i.e., 3, 4, 5, 6, 7, or 8 carbon atoms) as ring vertices. Preferred cycloalkenyl groups are those having from about 3 to about 6 carbon atoms as ring vertices. Examples of $C_{3-8}$ cycloalkenyl groups include, but are not limited to, cyclopropenyl, methyl-cyclopropenyl, dimethyl-cyclopropenyl, cyclobutenyl, cyclopentenyl, cyclohexenyl, cycloheptenyl, and cyclooctenyl, as well as other substituted $C_{3-8}$ cycloalkenyl groups.

The term "heterocycloalkenyl" includes a substituted or unsubstituted cyclic alkenyl group as defined above having from about 1 to about 3 heteroatoms as ring members selected from the group consisting of O, N, Si and S, wherein the nitrogen and sulfur atoms may optionally be oxidized and the nitrogen heteroatom may optionally be quaternized. The heterocycloalkenyl group can be attached to the remainder of the molecule through a carbon atom or a heteroatom.

The term "alkoxy" includes a group of the formula alkyl-O—, wherein "alkyl" has the previously given definition. Non-limiting examples of alkoxy groups include methoxy, ethoxy, n-propoxy, iso-propoxy, n-butoxy, iso-butoxy, sec-butoxy and tert-butoxy.

The term "alkenyl" includes an alkyl, as defined above, containing at least one double bond between adjacent carbon atoms. Alkenyls include both cis and trans isomers. Representative straight chain and branched alkenyls include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like. Representative cyclic alkenyls are described above.

The term "alkynyl" includes any alkyl or alkenyl, as defined above, which additionally contains at least one triple bond between adjacent carbons. Representative straight chain and branched alkynyls include, without limitation, acetylenyl, propynyl, 1-butynyl, 2-butynyl, 1-pentynyl, 2-pentynyl, 3-methyl-1 butynyl, and the like.

The term "aryl" includes a polyunsaturated, typically aromatic, hydrocarbon group which can be a single ring or multiple rings (up to three rings) which are fused together or linked covalently, and which optionally carries one or more substituents, such as, for example, halogen, trifluoromethyl, amino, alkyl, alkoxy, alkylcarbonyl, cyano, carbamoyl, alkoxycarbamoyl, methylendioxy, carboxy, alkoxycarbonyl, aminocarbonyl, alkylaminocarbonyl, dialkylaminocarbonyl, hydroxy, nitro, and the like. Non-limiting examples of unsubstituted aryl groups include phenyl, naphthyl, and biphenyl. Examples of substituted aryl groups include, but are not limited to, phenyl, chlorophenyl, trifluoromethylphenyl, chlorofluorophenyl, and aminophenyl.

The term "acyl" includes any alkyl, alkenyl, or alkynyl wherein the carbon at the point of attachment is substituted with an oxo group, as defined below. The following are non-limiting examples of acyl groups: —C(=O)alkyl, —C(=O) alkenyl, and —C(=O)alkynyl.

The term "heterocycle" includes a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include, but are not limited to, heteroaryls as defined below, as well as morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, tetrahydropyrimidinyl, tetrahydrothiophenyl, tetrahydrothiopyranyl, and the like.

The term "heteroaryl" includes an aromatic 5- to 10-membered heterocycle which contains one, two, or more heteroatoms selected from nitrogen (N), oxygen (O), and sulfur (S). The heteroaryl can be substituted on one or more carbon atoms with substituents such as, for example, halogen, alkyl, alkoxy, cyano, haloalkyl (e.g., trifluoromethyl), heterocyclyl (e.g., morpholinyl or pyrrolidinyl), and the like. Non-limiting examples of heteroaryls include pyridinyl and furanyl.

The term "halogen" includes fluoro, chloro, bromo, and iodo.

A. Exemplary Embodiments of Trialkyl Cationic Lipids

In one aspect, the present invention provides a cationic lipid of Formula I having the following structure:

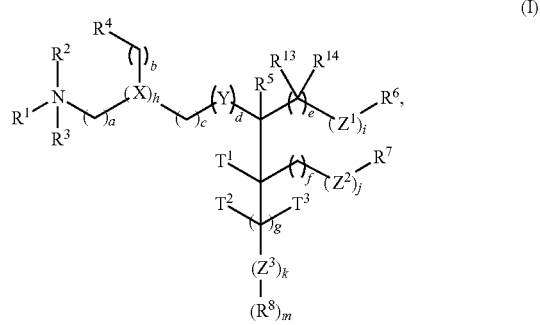

or salts and isomers thereof, wherein:

$R^1$ and $R^2$ are independently selected from hydrogen (H), optionally substituted $C_1$-$C_6$ alkyl, $C_2$-$C_6$ alkenyl, and $C_2$-$C_6$ alkynyl. Alternatively, $R^1$ and $R^2$ may join to form an optionally substituted heterocycloalkyl of 4 to 6 carbon atoms and 1 to 2 heteroatoms selected from nitrogen (N), oxygen (O), and mixtures thereof. $R^3$ is absent or is hydrogen (H) or a $C_1$-$C_6$ alkyl to provide a quaternary amine. $R^4$ is absent or is selected from —CH$_2$—, optionally substituted $C_{10}$-$C_{30}$ alkyl, $C_{10}$-$C_{30}$ alkenyl, $C_{10}$-$C_{30}$ alkynyl, $C_{10}$-$C_{30}$ acyl, and $NR^{4a}R^{4b}$, wherein $R^{4a}$ and $R^{4b}$ are independently selected from hydrogen (H), an optionally substituted $C_1$-$C_6$ alkyl, $C_2$-$C_6$ alkenyl, and $C_2$-$C_6$ alkynyl. $R^5$ is selected from hydrogen (H), oxygen (O), optionally substituted $C_{10}$-$C_{30}$ alkyl, $C_{10}$-$C_{30}$ alkenyl, $C_{10}$-$C_{30}$ alkynyl, and $OR^{5a}$, wherein $R^{5a}$ is selected from hydrogen (H), an optionally substituted $C_1$-$C_6$ alkyl, $C_2$-$C_6$ alkenyl, and $C_2$-$C_6$ alkynyl. Alternatively, $R^4$ and $R^5$ may join to form a $C_{3-10}$ heterocycloalkyl having from 1 to 3 heteroatoms each independently selected from nitrogen (N), oxygen (O), and sulfur (S), and optionally substituted with from 1 to 3 groups each independently selected from hydrogen (H) and $C_1$-$C_6$ alkyl. $R^6$ and $R^7$ are independently selected from optionally substituted $C_{10}$-$C_{30}$ alkyl, $C_{10}$-$C_{30}$ alkenyl, $C_{10}$-$C_{30}$ alkynyl, and $C_{10}$-$C_{30}$ acyl. $R^8$ is selected from optionally substituted $C_{10}$-$C_{30}$ alkyl, $C_{10}$-$C_{30}$ alkenyl, $C_{10}$-$C_{30}$ alkynyl, and $C_{10}$-$C_{30}$ acyl. $R^{13}$ and $R^{14}$ are independently selected from hydrogen (H), optionally substituted $C_1$-$C_6$ alkyl, $C_2$-$C_6$ alkenyl, and $C_2$-$C_6$ alkynyl. X is selected from —CH—, nitrogen (N), oxygen (O), sulfur (S), $N(R^9)$, C(O), C(O)O, OC(O), C(O)N($R^9$), N($R^9$)C(O), OC(O)N($R^9$), N($R^9$)C(O)O, C(O)S, SC(O), C(S)O, OC(S), S(O), S(O)(O), and C(S), wherein $R^9$ is selected from hydrogen (H), optionally substituted $C_1$-$C_6$ alkyl, $C_2$-$C_6$ alkenyl, $C_2$-$C_6$ alkynyl, and

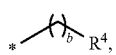

wherein * represents the point of attachment to nitrogen (N). Y is selected from —CR$^{11}$R$^{12}$— and oxygen (O), wherein $R^{11}$ and $R^{12}$ are independently selected from hydrogen (H), optionally substituted $C_1$-$C_6$ alkyl, $C_2$-$C_6$ alkenyl, and $C_2$-$C_6$ alkynyl. $Z^1$, $Z^2$, and $Z^3$ are independently selected from oxygen (O), C(O)O, or OC(O). $T^1$, $T^2$, and $T^3$ are independently selected from hydrogen (H) or OR$^{10}$, wherein $R^{10}$ is hydrogen (H) or optionally substituted $C_1$-$C_6$ alkyl, $C_2$-$C_6$ alkenyl, or $C_2$-$C_6$ alkynyl. Subscripts a, b, c, d, e, f, and g are independently selected from 0, 1, 2, 3, 4, 5, 6, 7 and 8. Subscripts h, i, j, k, and m are independently selected from of 0 and 1. When $R^5$ is an optionally substituted $C_{10}$-$C_{30}$ alkyl, $C_{10}$-$C_{30}$ alkenyl, $C_{10}$-$C_{30}$ alkynyl, and $C_{10}$-$C_{30}$ acyl, then either subscript h is 0 or at least one of $Z^1$ and $Z^2$ is oxygen (O). At least three of $R^4$, $R^5$, $R^6$, $R^7$, and $R^8$ are selected from optionally substituted $C_{10}$-$C_{30}$ alkyl, $C_{10}$-$C_{30}$ alkenyl, and $C_{10}$-$C_{30}$ alkynyl.

A person of ordinary skill in the art will recognize that, in some embodiments, the X linker in Formula I can be oriented in either possible orientation. For instance, when X is an ester, i.e., C(O)O or OC(O), X can connect to the rest of Formula I with the single-bonded oxygen (O) atom bonded to either the carbon with subscript a or the carbon with subscript c. Similarly, when X is a carbamate, i.e., OC(O)N($R^9$) or N($R^9$)C(O) O, X can connect to the rest of Formula I with the single-bonded oxygen (O) atom bonded to either the carbon with subscript a or with subscript c.

In some embodiments, $R^1$ and $R^2$ are each independently hydrogen (H) or an optionally substituted $C_1$-$C_6$ alkyl (e.g., $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, $C_5$-$C_6$ alkyl, or $C_1$, $C_2$, $C_3$, $C_4$, $C_5$, or $C_6$ alkyl), $C_2$-$C_6$ alkenyl (e.g., $C_2$-$C_3$ alkenyl, $C_2$-$C_4$ alkenyl, $C_2$-$C_5$ alkenyl, $C_2$-$C_6$ alkenyl, $C_3$-$C_4$ alkenyl, $C_3$-$C_5$ alkenyl, $C_3$-$C_6$ alkenyl, $C_4$-$C_5$ alkenyl, $C_4$-$C_6$ alkenyl, $C_5$-$C_6$ alkenyl, or $C_2$, $C_3$, $C_4$, $C_5$, or $C_6$ alkenyl), or $C_2$-$C_6$ alkynyl (e.g., $C_2$-$C_3$ alkynyl, $C_2$-$C_4$ alkynyl, $C_2$-$C_5$ alkynyl, $C_2$-$C_6$ alkynyl, $C_3$-$C_4$ alkynyl, $C_3$-$C_5$ alkynyl, $C_3$-$C_6$ alkynyl, $C_4$-$C_5$ alkynyl, $C_4$-$C_6$ alkynyl, or $C_5$-$C_6$ alkynyl, or $C_2$, $C_3$, $C_4$, $C_5$, or $C_6$ alkynyl). In other embodiments, $R^1$ and $R^2$ are joined to form a heterocyclic ring of 5 carbon atoms and 1 nitrogen atom, wherein the heterocyclic ring can be substituted with a substituent such as a hydroxyl (—OH) group at the ortho, meta, and/or para positions. In particular embodiments, $R^1$ and $R^2$ are both methyl groups (i.e., $C_1$ alkyls). In certain instances, R3 is absent when the pH is above the pK$_a$ of the cationic lipid and R$^3$ is hydrogen (H) when the pH is below the pK$_a$ of the cationic lipid such that the amino head group is protonated. In certain other instances, R$^3$ is an optionally substituted $C_1$-$C_6$ alkyl, $C_2$-$C_6$ alkenyl, or $C_2$-$C_6$ alkynyl group to provide a quaternary amine.

In certain embodiments, at least three, four, or all five of R$^4$, R$^5$, R$^6$, R$^7$, and R$^8$ are independently selected from an optionally substituted $C_{10}$-$C_{24}$, $C_{12}$-$C_{24}$, $C_{12}$-$C_{22}$, $C_{12}$-$C_{20}$, $C_{14}$-$C_{24}$, $C_{14}$-$C_{22}$, $C_{14}$-$C_{20}$, $C_{16}$-$C_{24}$, $C_{16}$-$C_{22}$, or $C_{16}$-$C_{20}$ alkyl or acyl group (i.e., $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, or $C_{24}$ alkyl or acyl group). In other embodiments, at least one, two, three, four, or all five of R$^4$, R$^5$, R$^6$, R$^7$, and R$^8$ independently comprise at least 1, 2, 3, 4, 5, or 6 sites of unsaturation (e.g., 1-2, 1-3, 1-4, 1-5, 1-6, 2-3, 2-4, 2-5, or 2-6) or a branched alkyl or acyl group. In certain instances, the unsaturated side-chain may comprise a myristoleyl moiety, a palmitoleyl moiety, an oleyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, or an acyl derivative thereof (e.g., linoleoyl, linolenoyl, γ-linolenoyl, etc.). In some instances, the octadecadienyl moiety is a linoleyl moiety. In particular embodiments, at least three, four, or all five of R$^4$, R$^5$, R$^6$, R$^7$, and R$^8$ are linoleyl moieties. In other instances, the octadecatrienyl moiety is a linolenyl moiety or a γ-linolenyl moiety. In particular embodiments, at least three, four, or all five of R$^4$, R$^5$, R$^6$, R$^7$, and R$^8$ are linolenyl moieties or γ-linolenyl moieties. In embodiments where at least one, two, three, four, or all five of R$^4$, R$^5$, R$^6$, R$^7$, and R$^8$ independently comprise a branched alkyl or acyl group (e.g., a substituted alkyl or acyl group), the branched alkyl or acyl group may comprise a $C_{12}$-$C_{24}$ alkyl or acyl having at least 1-6 (e.g., 1, 2, 3, 4, 5, 6, or more) $C_1$-$C_6$ alkyl substituents. In particular embodiments, the branched alkyl or acyl group comprises a $C_{12}$-$C_{20}$ or $C_{14}$-$C_{22}$ alkyl or acyl with 1-6 (e.g., 1, 2, 3, 4, 5, 6) $C_1$-$C_4$ alkyl (e.g., methyl, ethyl, propyl, or butyl) substituents. In some embodiments, the branched alkyl group comprises a phytanyl (3,7,11,15-tetramethyl-hexadecanyl) moiety and the branched acyl group comprises a phytanoyl (3,7,11,15-tetramethyl-hexadecanoyl) moiety. In particular embodiments, at least one, two, three, or all five of R$^4$, R$^5$, R$^6$, R$^7$, and R$^8$ are phytanyl moieties.

In other embodiments, at least one, two, three, four, or all five of R$^4$, R$^5$, R$^6$, R$^7$, and R$^8$ independently comprise at least 1, 2, 3, 4, 5, 6, or more optionally substituted $C_{1-6}$ cyclic alkyl groups (e.g., 1-2, 1-3, 1-4, 1-5, 1-6, 2-3, 2-4, 2-5, or 2-6). In certain instances, at least one, two, three, four, or all five of R$^4$, R$^5$, R$^6$, R$^7$, and R$^8$ independently comprise an optionally substituted $C_{10}$-$C_{24}$, $C_{12}$-$C_{24}$, $C_{14}$-$C_{24}$, or $C_{16}$-$C_{20}$ alkyl, alkenyl, alkynyl, or acyl group, wherein at least one, two, three, four, or all five of R$^4$, R$^5$, R$^6$, R$^7$, and R$^8$ independently comprise at least 1, 2, 3, 4, 5, or 6 optionally substituted cyclic alkyl groups (e.g., 1-2, 1-3, 1-4, 1-5, 1-6, 2-3, 2-4, 2-5, or 2-6).

In particular embodiments, one or more of the optionally substituted cyclic alkyl groups present in R$^4$, R$^5$, R$^6$, R$^7$, and/or R$^8$ are independently selected from the group consisting of an optionally substituted saturated cyclic alkyl group, an optionally substituted unsaturated cyclic alkyl group, and combinations thereof. In certain instances, the optionally substituted saturated cyclic alkyl group comprises an optionally substituted $C_{3-8}$ cycloalkyl group (e.g., cyclopropyl, cyclobutyl, cyclopentyl, cyclohexyl, cycloheptyl, cyclooctyl, etc.). In preferred embodiments, the optionally substituted saturated cyclic alkyl group comprises a cyclopropyl group, optionally containing one or more substituents and/or heteroatoms. In other instances, the optionally substituted unsaturated cyclic alkyl group comprises an optionally substituted $C_{3-8}$ cycloalkenyl group (e.g., cyclopropenyl, cyclobutenyl, cyclopentenyl, cyclohexenyl, cycloheptenyl, cyclooctenyl, etc.).

In particular embodiments, at least one, two, three, four, or all five of R$^4$, R$^5$, R$^6$, R$^7$, and R$^8$ are independently selected from $C_{10}$-$C_{24}$, $C_{12}$-$C_{24}$, $C_{14}$-$C_{24}$, or $C_{16}$-$C_{20}$ alkyl groups having at least 1, 2, 3, 4, 5, or 6 optionally substituted cyclic alkyl groups. In preferred embodiments, at least one, two, three, four, or all five of R$^4$, R$^5$, R$^6$, R$^7$, and R$^8$ are $C_{18}$ alkyl groups having at least one, two, three, or more optionally substituted cyclic alkyl groups such as, for example, an optionally substituted $C_{3-8}$ cycloalkyl group (e.g., a cyclopropyl group, optionally containing one or more substituents and/or heteroatoms). In certain embodiments, each of the optionally substituted cyclic alkyl groups is independently selected and can be the same cyclic alkyl group (e.g., all cyclopropyl groups) or different cyclic alkyl groups (e.g., cyclopropyl and other cycloalkyl, heterocycloalkyl, cycloalkenyl, and/or heterocycloalkenyl groups).

In preferred embodiments, the optionally substituted cyclic alkyl groups present in R$^4$, R$^5$, R$^6$, R$^7$, and/or R$^8$ are located at the site(s) of unsaturation in the corresponding unsaturated side-chain. As a non-limiting example, at least one, two, three, four, or all five of R$^4$, R$^5$, R$^6$, R$^7$, and R$^8$ are $C_{18}$ alkyl groups having 1, 2, or 3 optionally substituted cyclic alkyl groups, wherein the optionally substituted cyclic alkyl groups (e.g., independently selected cyclopropyl groups) are located at one or more (e.g., all) of the sites of unsaturation present in a corresponding oleyl moiety, linoleyl moiety, linolenyl moiety, or γ-linolenyl moiety.

In some embodiments, R$^5$ is hydrogen (H) when subscript m is 1. In other embodiments, R$^5$ is oxygen (O) when subscript m is 1 and R$^4$ and R$^5$ join to form a $C_{3-10}$ heterocycloalkyl. In certain other embodiments, R$^5$ is selected from an optionally substituted $C_{10}$-$C_{30}$ alkyl, $C_{10}$-$C_{30}$ alkenyl, and $C_{10}$-$C_{30}$ alkynyl wherein subscript m is 0. In further embodiments, R$^4$ is —CH$_2$—; R$^5$ and Y are both 0; X is —CH—; subscripts b and c are 0; subscript h is 1; when R$^4$ and R$^5$ are joined to form a $C_5$ heterocycloalkyl.

In certain embodiments X is O, subscript b is 0 and R$^4$ is absent. In some other embodiments, X is either C(O)O or OC(O), and subscript b is 0 and R$^4$ is absent. In some other embodiments, X is either OC(O)N(R$^9$) or N(R$^9$)C(O)O, subscript b is 0 and R$^4$ is absent, wherein R$^9$ is selected from the group consisting of hydrogen (H), optionally substituted $C_1$-$C_6$ alkyl (e.g., $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, $C_5$-$C_6$ alkyl, or $C_1$, $C_2$, $C_3$, $C_4$, $C_5$, or $C_6$ alkyl), $C_2$-$C_6$ alkenyl (e.g., $C_2$-$C_3$ alkenyl, $C_2$-$C_4$ alkenyl, $C_2$-$C_5$ alkenyl, $C_2$-$C_6$ alkenyl, $C_3$-$C_4$ alkenyl, $C_3$-$C_5$ alkenyl, $C_3$-$C_6$ alkenyl, $C_4$-$C_5$ alkenyl, $C_4$-$C_6$ alkenyl, $C_5$-$C_6$ alkenyl, or $C_2$, $C_3$, $C_4$, $C_5$, or $C_6$ alkenyl), $C_2$-$C_6$ alkynyl (e.g., $C_2$-$C_3$ alkynyl, $C_2$-$C_4$ alkynyl, $C_2$-$C_5$ alkynyl, $C_2$-$C_6$ alkynyl, $C_3$-$C_4$ alkynyl, $C_3$-$C_5$ alkynyl, $C_3$-$C_6$ alkynyl, $C_4$-$C_5$ alkynyl, $C_4$-$C_6$ alkynyl, or $C_5$-$C_6$ alkynyl, or $C_2$, $C_3$, $C_4$, $C_5$, or $C_6$ alkynyl). In some other embodiments, X is either OC(O)N(R$^9$) or N(R$^9$)C(O)O, wherein R$^9$ is selected from the group consisting of hydrogen (H), optionally substituted $C_1$-$C_6$ alkyl, $C_2$-$C_6$ alkenyl, $C_2$-$C_6$ alkynyl, and

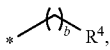

wherein * represents the point of attachment to N. In some instances, $R^9$ is methyl. $R^4$ is as described above.

In some other embodiments Y is —$CR^{11}R^{12}$— and $R^{11}$ and $R^{12}$ are independently selected from hydrogen (H) and $C_1$-$C_6$ alkyl (e.g., $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, $C_5$-$C_6$ alkyl, or $C_1$, $C_2$, $C_3$, $C_4$, $C_5$, or $C_6$ alkyl), $C_2$-$C_6$ alkenyl (e.g., $C_2$-$C_3$ alkenyl, $C_2$-$C_4$ alkenyl, $C_2$-$C_5$ alkenyl, $C_2$-$C_6$ alkenyl, $C_3$-$C_4$ alkenyl, $C_3$-$C_5$ alkenyl, $C_3$-$C_6$ alkenyl, $C_4$-$C_5$ alkenyl, $C_4$-$C_6$ alkenyl, $C_5$-$C_6$ alkenyl, or $C_2$, $C_3$, $C_4$, $C_5$, or $C_6$ alkenyl), or $C_2$-$C_6$ alkynyl (e.g., $C_2$-$C_3$ alkynyl, $C_2$-$C_4$ alkynyl, $C_2$-$C_5$ alkynyl, $C_2$-$C_6$ alkynyl, $C_3$-$C_4$ alkynyl, $C_3$-$C_5$ alkynyl, $C_3$-$C_6$ alkynyl, $C_4$-$C_5$ alkynyl, $C_4$-$C_6$ alkynyl, or $C_5$-$C_6$ alkynyl, or $C_2$, $C_3$, $C_4$, $C_5$, or $C_6$ alkynyl). In some embodiments, Y is —$CR^{11}R^{11}$ and $R^{12}$ are both either hydrogen (H) or methyl, and subscript c is 1.

In some embodiments, at least one, two, or three of $Z^1$, $Z^2$, and $Z^3$ are independently selected from oxygen (O), C(O)O, or OC(O). In certain embodiments both $Z^2$ and $Z^3$ are either (O), C(O)O, or OC(O) and subscript i is 0. In certain other embodiments, $Z^1$ is either (O), C(O)O, or OC(O) and subscripts j and k are both 0. In certain other embodiments, $Z^2$ is either (O), C(O)O, or OC(O) and subscripts i and k are both 0. In certain other embodiments, $Z^3$ is either (O), C(O)O, or OC(O) and subscripts i and j are both 0.

In some embodiments at least one, two, or three of $T^1$, $T^2$, and $T^3$ are independently selected from hydrogen (H) or $OR^{10}$, wherein $R^{10}$ is hydrogen (H) or optionally substituted $C_1$-$C_6$ alkyl (e.g., $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, $C_5$-$C_6$ alkyl, or $C_1$, $C_2$, $C_3$, $C_4$, $C_5$, or $C_6$ alkyl), $C_2$-$C_6$ alkenyl (e.g., $C_2$-$C_3$ alkenyl, $C_2$-$C_4$ alkenyl, $C_2$-$C_5$ alkenyl, $C_2$-$C_6$ alkenyl, $C_3$-$C_4$ alkenyl, $C_3$-$C_5$ alkenyl, $C_3$-$C_6$ alkenyl, $C_4$-$C_5$ alkenyl, $C_4$-$C_6$ alkenyl, $C_5$-$C_6$ alkenyl, or $C_2$, $C_3$, $C_4$, $C_5$, or $C_6$ alkenyl), or $C_2$-$C_6$ alkynyl (e.g., $C_2$-$C_3$ alkynyl, $C_2$-$C_4$ alkynyl, $C_2$-$C_5$ alkynyl, $C_2$-$C_6$ alkynyl, $C_3$-$C_4$ alkynyl, $C_3$-$C_5$ alkynyl, $C_3$-$C_6$ alkynyl, $C_4$-$C_5$ alkynyl, $C_4$-$C_6$ alkynyl, or $C_5$-$C_6$ alkynyl, or $C_2$, $C_3$, $C_4$, $C_5$, or $C_6$ alkynyl). In some preferred embodiments, $T^1$ is $OR^{10}$, $R^{10}$ is hydrogen (H), and subscript g is 0. In some other preferred embodiments, $T^2$ is $OR^{10}$, $R^{10}$ is hydrogen (H), and both $T^1$ and $T^3$ are hydrogen (H). In some other preferred embodiments, both $T^2$ and $T^3$ are $OR^{10}$, $R^{10}$ is hydrogen (H), and $T^1$ is hydrogen (H). In some other preferred embodiments, $T^1$ and $T^2$ are $OR^{10}$, $R^{10}$ is hydrogen (H), and $T^3$ is hydrogen (H). In some other preferred embodiments, $T^1$, $T^2$ and $T^3$ are $OR^{10}$, $R^{10}$ is hydrogen (H).

In some embodiments, subscripts a, b, c, d, e, f, and g are independently selected from 0, 1, 2, 3, 4, 5, 6, 7 and 8. More preferably, subscript a is selected from 1, 2, 3, 4, and 5. Even more preferably, subscript a is selected from 2, 3, or 4. Subscript b is preferably selected from 0 or 1. More preferably, subscript b is 0, Subscript c is preferably selected from 0, 1, or 2. Subscript d is preferably 0 or 1. In certain instances, subscripts c and d and both 1. Subscript e is preferably 0 or 1. Subscript f is preferably 0 or 1. More preferably, subscript f is 0. Subscript g is preferably 0 or 1.

In some embodiments, subscripts h, i, j, k, and m are independently selected from 0 and 1. In some instances, subscript h is 1. In other instances, subscript h is 0. In some embodiments, subscript i is 0 and subscripts j and k are 1. In some embodiments, subscript i is 1 and subscripts j and k are 0. In some embodiments, subscript m is 1. In some other embodiments, subscripts h, i, j, and k are all 0. In some other embodiments, subscripts i, j, and k are all 0. In some other embodiments, subscripts h, i, j, and k are all 1.

In some embodiments, the cationic lipid of Formula I forms a salt (preferably a crystalline salt) with one or more anions. In one particular embodiment, the cationic lipid of Formula I is the oxalate (e.g., hemioxalate) salt thereof, which is preferably a crystalline salt.

In a related aspect, the present invention provides a cationic lipid of Formula II having the following structure:

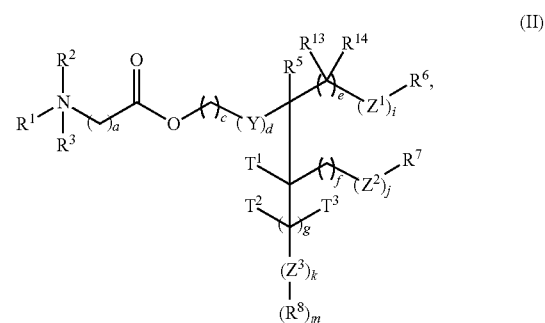

(II)

or salts and isomers thereof,
wherein $R^1$, $R^2$, $R^3$, $R^4$, $R^5$, $R^6$, $R^7$, $R^8$, $R^9$, $R^{10}$, $R^{11}$, $R^{12}$, Y, $Z^1$, $Z^2$, $Z^3$, $T^1$, $T^2$, $T^3$, and subscripts a, b, c, d, e, f, g, h, i, j, k, and m are the same as described above for Formula I.

In one embodiment, $R^1$ and $R^2$ are each independently hydrogen (H) or an optionally substituted $C_1$-$C_6$ alkyl, preferably $C_1$-$C_4$ alkyl (e.g., methyl, ethyl, propyl, butyl). In particular embodiments, $R^1$ and $R^2$ are both methyl groups (i.e., $C_1$ alkyls). In certain instances, $R^3$ is absent when the pH is above the $pK_a$ of the cationic lipid and $R^3$ is hydrogen (H) when the pH is below the $pK_a$ of the cationic lipid such that the amino head group is protonated. In another embodiment, subscript a is 2, 3, 4, 5, or 6. In a preferred embodiment, subscript a is 2, 3, or 4. In yet another embodiment, subscript c is 0, 1, or 2 and subscript d is 0. In one particular embodiment, subscripts c and d are both 0. In still yet another embodiment, $R^5$ is hydrogen (H). In a further embodiment, subscripts e, f, and g are all 0. In another embodiment, subscripts i, j, and k are all 0. In yet another embodiment, $T^1$ is hydrogen (H) or $OR^{10}$, wherein $R^{10}$ is H or optionally substituted $C_1$-$C_4$ alkyl. In one particular embodiment, $T^1$ is H or OH. In still yet another embodiment, subscript m is 1 and $R^6$, $R^7$, and $R^8$ are independently selected from an optionally substituted $C_{10}$-$C_{24}$ alkyl, $C_{10}$-$C_{24}$ alkenyl, and $C_{10}$-$C_{24}$ alkynyl. In some instances, $R^6$, $R^7$, and $R^8$ independently comprise an optionally substituted $C_{12}$-$C_{24}$, $C_{14}$-$C_{24}$, or $C_{16}$-$C_{20}$ alkyl group. In other instances, at least one, two, or all three of $R^6$, $R^7$, and $R^8$ independently comprises at least 1, 2, 3, 4, 5, or 6 sites of unsaturation or a substituted alkyl group such as a phytanyl moiety. The unsaturated side-chains may independently comprise a myristoleyl moiety, a palmitoleyl moiety, an oleyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, or an icosatrienyl moiety. In some instances, the octadecadienyl moiety is a linoleyl moiety. In particular embodiments, $R^6$, $R^7$, and $R^8$ are all linoleyl moieties. In other embodiments, $R^7$ and $R^8$ are the same and $R^6$ is different. In certain instances, $R^6$ is an oleyl moiety and $R^7$ and $R^8$ are linoleyl moieties. In certain other instances, $R^6$ is a linoleyl moiety and $R^7$ and $R^8$ are oleyl moieties. One of skill in the art will appreciate that the compounds of Formula II may comprise a combination of two or more of the features described in this paragraph. As a non-limiting example, in certain preferred embodiments, subscripts e, f, g, i, j, and k are all 0, m is 1, and $R^6$, $R^7$, and $R^8$ are independently selected $C_{18}$ alkyl groups (e.g., $R^6$, $R^7$, and $R^8$ are all linoleyl moieties). Exemplary methods of making the ester-containing lipids of Formula II described in this paragraph are illustrated for Compound 4 of Scheme 1 and Compound 8 of Scheme 2 below.

In preferred embodiments, $R^1$ and $R^2$ are each independently methyl or ethyl groups; subscript a is 2, 3, or 4; subscripts c and d are both 0; $R^5$ is hydrogen (H); subscripts e, f, g, i, j, and k are all 0; $T^1$ is H or OH; subscript m is 1; and $R^6$, $R^7$, and $R^8$ are independently selected from $C_{16}$-$C_{20}$ (e.g., $C_{18}$) alkenyl groups (e.g., $R^6$, $R^7$, and $R^8$ are all linoleyl moieties or oleyl moieties; at least two of $R^6$, $R^7$, and $R^8$ are oleyl moieties and the other is a linoleyl moiety; or at least two of $R^6$, $R^7$, and $R^8$ are linoleyl moieties and the other is an oleyl moiety).

In particularly preferred embodiments, the cationic lipid of Formula II has one of the following structures:

In one embodiment, $R^1$ and $R^2$ are each independently hydrogen (H) or an optionally substituted $C_1$-$C_6$ alkyl, preferably $C_1$-$C_4$ alkyl (e.g., methyl, ethyl, propyl, butyl). In particular embodiments, $R^1$ and $R^2$ are both methyl groups (i.e., $C_1$ alkyls). In certain instances, $R^3$ is absent when the pH is above the $pK_a$ of the cationic lipid and $R^3$ is hydrogen (H) when the pH is below the $pK_a$ of the cationic lipid such that the amino head group is protonated. In another embodiment, subscript a is 2, 3, 4, or 5. In a preferred embodiment, subscript a is 2, 3, or 4. In yet another embodiment, subscript c is 0, 1, or 2 and subscript d is 0 or 1. In one particular embodiment, subscript c is 2 and subscript d is 0. In another particular embodiment, subscripts c and d are both 1. In yet another embodiment, $R^5$ is hydrogen (H). In a further embodiment, subscripts e, f, and g are all 0. In another embodiment, subscript i is either 0 or 1 and subscripts j and k are both 0. In a further embodiment, $Z^1$ is oxygen (O). In yet another embodiment, $T^1$ is hydrogen (H) or $OR^{10}$, wherein $R^{10}$ is H or optionally substituted $C_1$-$C_4$ alkyl. In one particular embodiment, $T^1$ is H or OH. In still yet another embodiment, subscript m is 1 and $R^6$, $R^7$, and $R^8$ are independently selected from an optionally substituted $C_{10}$-$C_{24}$ alkyl, $C_{10}$-$C_{24}$ alkenyl, and $C_{10}$-$C_{24}$ alkynyl. In some instances, $R^6$, $R^7$, and $R^8$ independently comprise an optionally substituted $C_{12}$-$C_{24}$, $C_{14}$-$C_{24}$, or $C_{16}$-$C_{20}$ alkyl group. In other instances, at least one, two, or

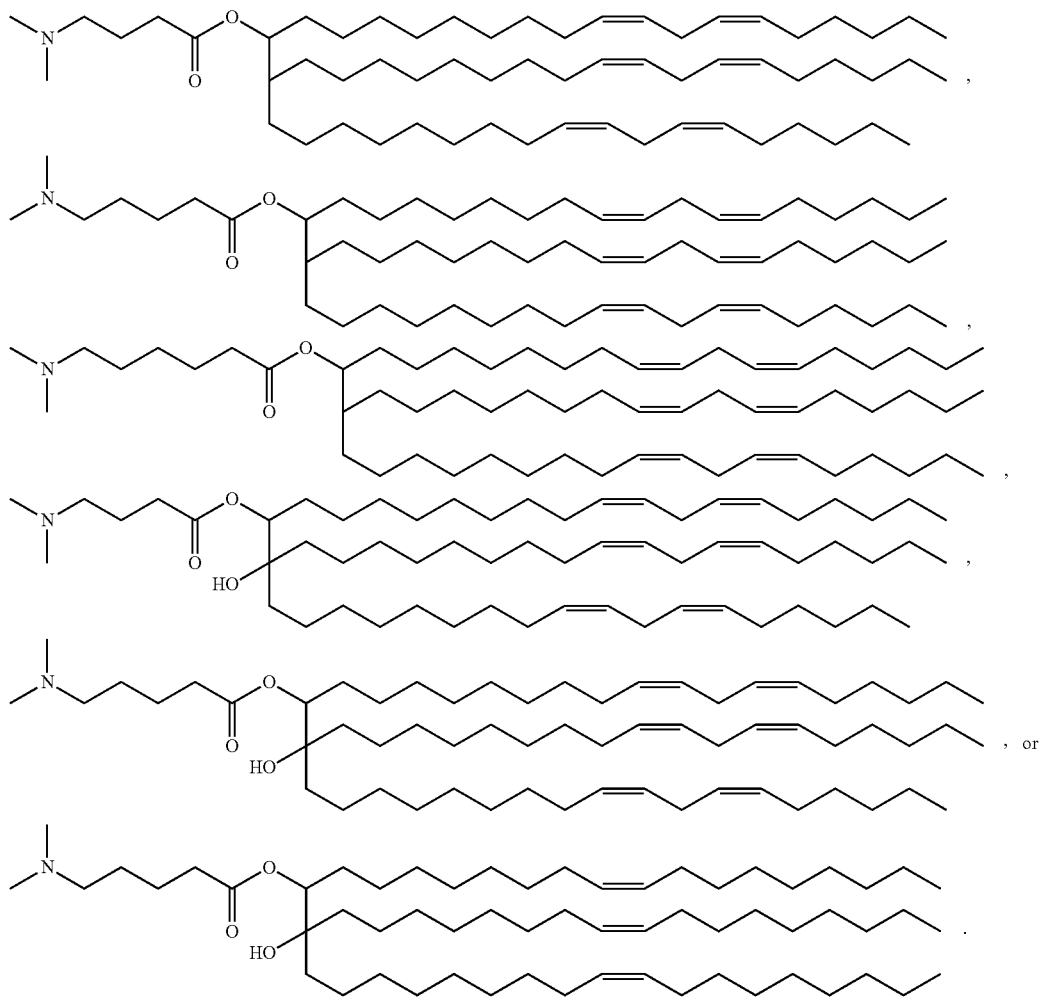

all three of $R^6$, $R^7$, and $R^8$ independently comprises at least 1, 2, 3, 4, 5, or 6 sites of unsaturation or a substituted alkyl group such as a phytanyl moiety. The unsaturated side-chains may independently comprise a myristoleyl moiety, a palmitoleyl moiety, an oleyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, or an icosatrienyl moiety. In some instances, the octadecadienyl moiety is a linoleyl moiety. In particular embodiments, $R^6$, $R^7$, and $R^8$ are all linoleyl moieties. In other embodiments, $R^7$ and $R^8$ are the same and $R^6$ is different. In certain instances, $R^6$ is an oleyl moiety and $R^7$ and $R^8$ are linoleyl moieties. In certain other instances, $R^6$ is a linoleyl moiety and $R^7$ and $R^8$ are oleyl moieties. One of skill in the art will appreciate that the compounds of Formula II may comprise a combination of two or more of the features described in this paragraph. As a non-limiting example, in certain preferred embodiments, subscripts i and m are both 1; subscripts e, f, g, j, and k are all 0; and $R^6$, $R^7$, and $R^8$ are independently selected $C_{18}$ alkyl groups (e.g., $R^6$, $R^7$, and $R^8$ are all linoleyl moieties). An exemplary method of making the ester-containing lipids of Formula II described in this paragraph is illustrated for Compound 12 in Scheme 3 below.

In preferred embodiments, $R^1$ and $R^2$ are each independently methyl or ethyl groups; subscript a is 2, 3, or 4; subscripts c and d are both 1; Y is —$CR^{11}R^{12}$—, wherein $R^{11}$ and $R^{12}$ are independently selected from H, $CH_3$, and ethyl; $R^5$ is hydrogen (H); subscripts e, f, g, j, and k are all 0; subscript i is 1 and $Z^1$ is O; $T^1$ is OH; subscript m is 1; and $R^6$, $R^7$, and $R^8$ are independently selected from $C_{16}$-$C_{20}$ (e.g., $C_{18}$) alkyl groups (e.g., $R^6$, $R^7$, and $R^8$ are all linoleyl moieties or oleyl moieties; at least two of $R^6$, $R^7$, and $R^8$ are oleyl moieties and the other is a linoleyl moiety; or at least two of $R^6$, $R^7$, and $R^8$ are linoleyl moieties and the other is an oleyl moiety).

In particularly preferred embodiments, the cationic lipid of Formula II has one of the following structures:

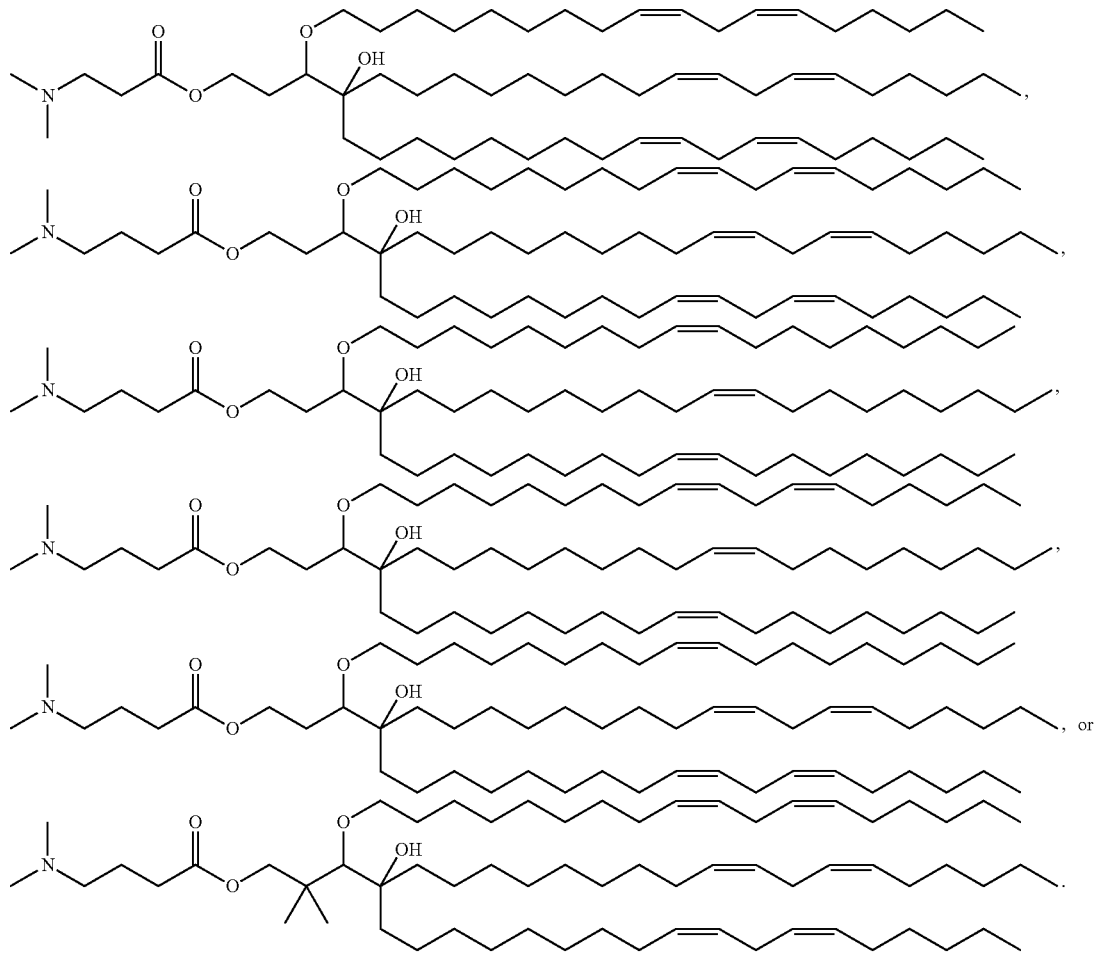

In another embodiment, $R^1$ and $R^2$ are each independently hydrogen (H) or an optionally substituted $C_1$-$C_6$ alkyl, preferably $C_1$-$C_4$ alkyl (e.g., methyl, ethyl, propyl, butyl). In particular embodiments, $R^1$ and $R^2$ are both methyl groups (i.e., $C_1$ alkyls). In certain instances, $R^3$ is absent when the pH is above the $pK_a$ of the cationic lipid and $R^3$ is hydrogen (H) when the pH is below the $pK_a$ of the cationic lipid such that the amino head group is protonated. In another embodiment, subscript a is 2, 3, 4, 5, or 6. In a preferred embodiment, subscript a is 2, 3, or 4. In yet another embodiment, subscript c is 0, 1, or 2 and subscript d is 0 or 1. In a preferred embodiment subscript c is 0. In yet another embodiment, $R^5$ is hydrogen (H). In a further embodiment, subscript f is 1 and subscripts e and g are both 0. In another embodiment, subscript i is 0, subscripts j and k are both 1, and $Z^2$ and $Z^3$ are independently selected from oxygen (O), C(O)O, and OC(O). In a preferred embodiment, $Z^2$ and $Z^3$ are both oxygen (O). In yet another embodiment, $T^1$ is hydrogen (H) or $OR^{10}$, wherein $R^{10}$ is H or optionally substituted $C_1$-$C_4$ alkyl. In one particular embodiment, $T^1$ is H or OH. In still yet another embodiment, subscript m is 1 and $R^6$, $R^7$, and $R^8$ are independently selected from an optionally substituted $C_{10}$-$C_{24}$ alkyl, $C_{10}$-$C_{24}$ alkenyl, and $C_{10}$-$C_{24}$ alkynyl. In some instances, $R^6$, $R^7$, and $R^8$ independently comprise an optionally substituted $C_{12}$-$C_{24}$, $C_{14}$-$C_{24}$, or $C_{16}$-$C_{20}$ alkyl group. In other instances, at least one, two, or all three of $R^6$, $R^7$, and $R^8$ independently comprises at least 1, 2, 3, 4, 5, or 6 sites of unsaturation or a substituted alkyl group such as a phytanyl moiety. The unsaturated side-chains may independently comprise a myristoleyl moiety, a palmitoleyl moiety, an oleyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, or an icosatrienyl moiety. In some instances, the octadecadienyl moiety is a linoleyl moiety. In particular embodiments, $R^6$, $R^7$, and $R^8$ are all linoleyl moieties. In other embodiments, $R^7$ and $R^8$ are the same and $R^6$ is different. In certain instances, $R^6$ is an oleyl moiety and $R^7$ and $R^8$ are linoleyl moieties. In certain other instances, $R^6$ is a linoleyl moiety and $R^7$ and $R^8$ are oleyl moieties. One of skill in the art will appreciate that the compounds of Formula II may comprise a combination of two or more of the features described in this paragraph. As a non-limiting example, in certain preferred embodiments, subscripts f, j, k and m are all 1; subscripts e, g, and i are all 0; and $R^6$, $R^7$, and $R^8$ are independently selected $C_{18}$ alkyl groups (e.g., $R^6$, $R^7$, and $R^8$ are all linoleyl moieties). An exemplary method of making the ester-containing lipids of Formula II described in this paragraph is illustrated for Compound 16 of Scheme 4 below.

In preferred embodiments, $R^1$ and $R^2$ are each independently methyl or ethyl groups; subscript a is 2, 3, or 4; subscripts c and d are both 0; $R^5$ is hydrogen (H); subscripts f, j, and k are all 1; subscripts e, g, and i are all 0; $Z^2$ and $Z^3$ are both oxygen (O); $T^1$ is hydrogen (H); subscript m is 1; and $R^6$, $R^7$, and $R^8$ are independently selected from $C_{16}$-$C_{20}$ (e.g., $C_{18}$) alkyl groups (e.g., $R^6$, $R^7$, and $R^8$ are all linoleyl moieties or oleyl moieties; at least two of $R^6$, $R^7$, and $R^8$ are oleyl moieties and the other is a linoleyl moiety; or at least two of $R^6$, $R^7$, and $R^8$ are linoleyl moieties and the other is an oleyl moiety).

In particularly preferred embodiments, the cationic lipid of Formula II has one of the following structures:

In a related aspect, the present invention provides a cationic lipid of Formula III having the following structure:

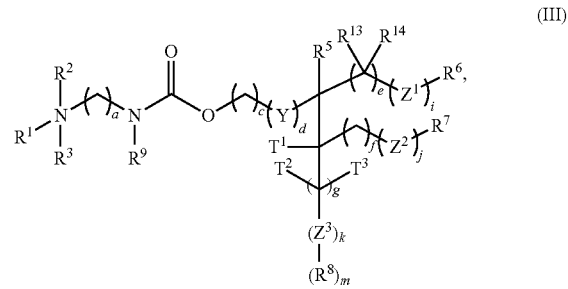

(III)

or salts and isomers thereof, wherein $R^1$, $R^2$, $R^3$, $R^4$, $R^5$, $R^6$, $R^7$, $R^8$, $R^9$, $R^{10}$, $R^{11}$, $R^{12}$, Y, $Z^1$, $Z^2$, $Z^3$, $T^1$, $T^2$, $T^3$, and subscripts a, b, c, d, e, f, g, h, i, j, k, and m are the same as described above for Formula I.

In another embodiment, $R^1$ and $R^2$ are each independently hydrogen (H) or an optionally substituted $C_1$-$C_6$ alkyl, preferably $C_1$-$C_4$ alkyl (e.g., methyl, ethyl, propyl, butyl). In particular embodiments, $R^1$ and $R^2$ are both methyl groups (i.e., $C_1$ alkyls). In certain instances, $R^3$ is absent when the pH is above the $pK_a$ of the cationic lipid and $R^3$ is hydrogen (H) when the pH is below the $pK_a$ of the cationic lipid such that the amino head group is protonated. In another embodiment, subscript a is 2, 3, 4, 5, or 6. In a preferred embodiment, a is 2, 3, or 4. In yet another embodiment, subscript c is 0, 1, or 2 and d is 0 or 1. In a preferred embodiment subscripts c and d are both 0. In yet another embodiment, $R^5$ is hydrogen (H). In a further embodiment, subscripts e, f, and g are 0. In another embodiment, subscripts i, j and k are 0. In one particular embodiment, $R^9$ is selected from hydrogen (H), optionally substituted $C_1$-$C_6$ alkyl (e.g., $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, $C_5$-$C_6$ alkyl, or $C_1$, $C_2$, $C_3$, $C_4$, $C_5$, or $C_6$ alkyl), $C_2$-$C_6$ alkenyl (e.g., $C_2$-$C_3$ alkenyl, $C_2$-$C_4$ alkenyl, $C_2$-$C_5$ alkenyl, $C_2$-$C_6$ alkenyl, $C_3$-$C_4$ alkenyl, $C_3$-$C_5$ alkenyl, $C_3$-$C_6$ alkenyl, $C_4$-$C_5$ alkenyl, $C_4$-$C_6$ alkenyl, $C_5$-$C_6$ alkenyl, or $C_2$, $C_3$, $C_4$, $C_5$, or $C_6$ alkenyl), $C_2$-$C_6$ alkynyl (e.g., $C_2$-$C_3$ alkynyl, $C_2$-$C_4$ alkynyl, $C_2$-$C_5$ alkynyl, $C_2$-$C_6$ alkynyl, $C_3$-$C_4$ alkynyl, alkynyl, $C_3$-$C_6$ alkynyl, $C_4$-$C_5$ alkynyl, $C_4$-$C_6$ alkynyl, or $C_5$-$C_6$ alkynyl, or $C_2$, $C_3$, $C_4$, $C_5$, or $C_6$ alkynyl), and

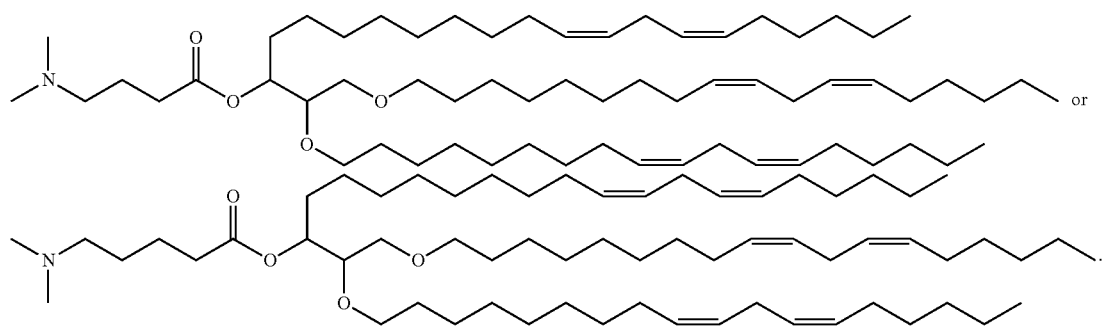

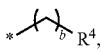

wherein * represents the point of attachment to N. $R^4$ is as described above. In some instances, $R^9$ is methyl. In some other instances, $R^9$ is

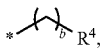

subscript b is 0, and $R^4$ is a linoleyl moiety. In further instances, $R^9$ is

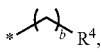

subscript b is 1, 2, or 3, and $R^4$ is $NR^{4a}R^{4b}$, wherein $R^{4a}$ and $R^{4b}$ are independently selected from hydrogen (H), an optionally substituted $C_1$-$C_6$ alkyl, $C_2$-$C_6$ alkenyl, and $C_2$-$C_6$ alkynyl. In preferred embodiments, subscript b is 2 and $R^{4a}$ and $R^{4b}$ are both methyl. In yet another embodiment, $T^1$ is hydrogen (H) or $OR^{10}$, wherein $R^{10}$ is H or optionally substituted $C_1$-$C_4$ alkyl. In one particular embodiment, $T^1$ is H or OH. In still yet another embodiment, subscript m is 1 and $R^6$, $R^7$, and $R^8$ are independently selected from an optionally substituted $C_{10}$-$C_{24}$ alkyl, $C_{10}$-$C_{24}$ alkenyl, and $C_{10}$-$C_{24}$ alkynyl. In some instances, $R^6$, $R^7$, and $R^8$ independently comprise an optionally substituted $C_{12}$-$C_{24}$, $C_{12}$-$C_{24}$, or $C_{16}$-$C_{20}$ alkyl group. In other instances, at least one, two, or all three of $R^6$, $R^7$, and $R^8$ independently comprises at least 1, 2, 3, 4, 5, or 6 sites of unsaturation or a substituted alkyl group such as a phytanyl moiety. The unsaturated side-chains may independently comprise a myristoleyl moiety, a palmitoleyl moiety, an oleyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, or an icosatrienyl moiety. In some instances, the octadecadienyl moiety is a linoleyl moiety. In particular embodiments, $R^6$, $R^7$, and $R^8$ are all linoleyl moieties. In other embodiments, $R^7$ and $R^8$ are the same and $R^6$ is different. In certain instances, $R^6$ is an oleyl moiety and $R^7$ and $R^8$ are linoleyl moieties. In certain other instances, $R^6$ is a linoleyl moiety and $R^7$ and $R^8$ are oleyl moieties. One of skill in the art will appreciate that the compounds of Formula III may comprise a combination of two or more of the features described in this paragraph. As a non-limiting example, in certain preferred embodiments, subscript m is 1; subscripts e, f, g, i, j, and k are all 0; and $R^6$, $R^7$, and $R^8$ are independently selected $C_{18}$ alkyl groups (e.g., $R^6$, $R^7$, and $R^8$ are all linoleyl moieties). Exemplary methods of making the carbamate-containing lipids of Formula III described in this paragraph are illustrated for Compound 2 of Scheme 1, Compound 7 of Scheme 2, and Example 7 below.

In preferred embodiments, $R^1$ and $R^2$ are each independently methyl or ethyl groups; subscript a is 2, 3, or 4; subscripts c and d are both 0; $R^5$ is hydrogen (H); subscripts e, f, g, i, j, k are all 0; $T^1$ is hydrogen (H) or OH; subscript m is 1; $R^6$, $R^7$, and $R^8$ are independently selected from $C_{16}$-$C_{20}$ (e.g., $C_{18}$) alkyl groups (e.g., $R^6$, $R^7$, and $R^8$ are all linoleyl moieties or oleyl moieties; at least two of $R^6$, $R^7$, and $R^8$ are oleyl moieties and the other is a linoleyl moiety; or at least two of $R^6$, $R^7$, and $R^8$ are linoleyl moieties and the other is an oleyl moiety); and $R^9$ is selected from methyl,

wherein subscript b is 0 and $R^4$ is a linoleyl moiety, and

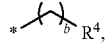

wherein $R^4$ is $NR^{4a}R^{4b}$, subscript b is 2, and $R^{4a}$ and $R^{4b}$ are both methyl.

In particularly preferred embodiments, the cationic lipid of Formula III has one of the following structures:

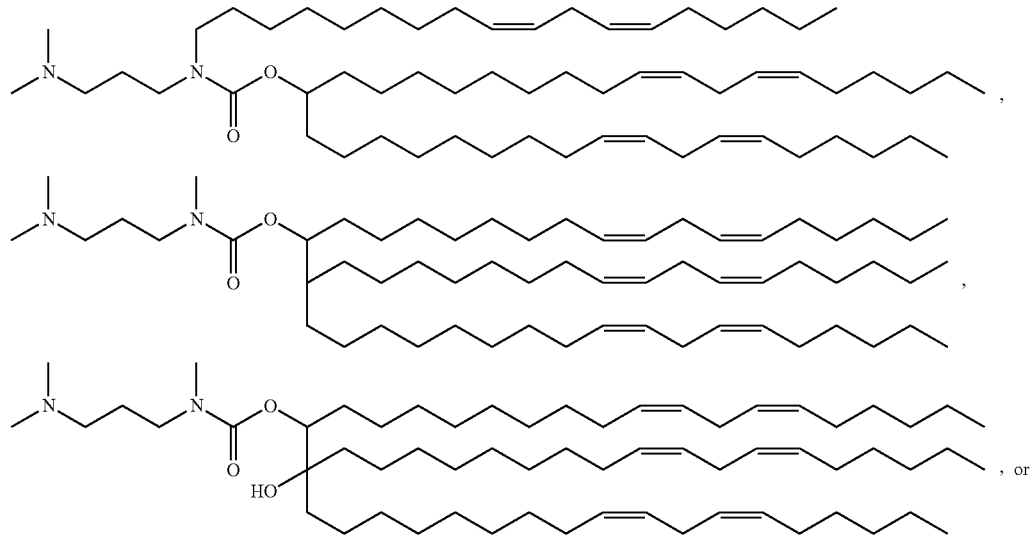

, or

-continued

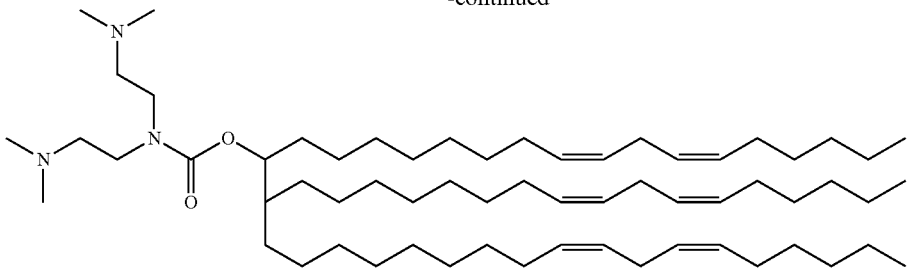

In another embodiment, $R^1$ and $R^2$ are each independently hydrogen (H) or an optionally substituted $C_1$-$C_6$ alkyl, preferably $C_1$-$C_4$ alkyl (e.g., methyl, ethyl, propyl, butyl). In particular embodiments, $R^1$ and $R^2$ are both methyl groups (i.e., $C_1$ alkyls). In certain instances, $R^3$ is absent when the pH is above the $pK_a$ of the cationic lipid and $R^3$ is hydrogen (H) when the pH is below the $pK_a$ of the cationic lipid such that the amino head group is protonated. In another embodiment, subscript a is 2, 3, 4, 5, or 6. In a preferred embodiment, subscript a is 2, 3, or 4. In yet another embodiment, subscript c is 0, 1, or 2 and subscript d is 0 or 1. In a preferred embodiment subscripts c and d are both 1. In yet another embodiment, $R^5$ is hydrogen (H). In a further embodiment, subscripts e, f, and g are all 0. In another embodiment, subscripts i is 1 and j and k are both 0. In a further embodiment, $Z^1$ is O. In one particular embodiment, $R^9$ is selected from hydrogen (H), optionally substituted $C_1$-$C_6$ alkyl, $C_2$-$C_6$ alkenyl, $C_2$-$C_6$ alkynyl, and

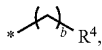

wherein * represents the point of attachment to N. $R^4$ is as described above. In some instances, $R^9$ is methyl. In some other instances, $R^9$ is

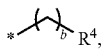

subscript b is 0, and $R^4$ is a linoleyl moiety. In further instances, $R^9$ is

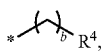

subscript b is 1, 2, or 3, and $R^4$ is $NR^{4a}R^{4b}$, wherein $R^{4a}$ and $R^{4b}$ are independently selected from hydrogen (H), an optionally substituted $C_1$-$C_6$ alkyl, $C_2$-$C_6$ alkenyl, and $C_2$-$C_6$ alkynyl. In preferred embodiments, subscript b is 2 and $R^{4a}$ and $R^{4b}$ are both methyl. In yet another embodiment, $T^1$ is hydrogen (H) or $OR^{10}$, wherein $R^{10}$ is H or optionally substituted $C_1$-$C_4$ alkyl. In one particular embodiment, $T^1$ is H or OH. In still yet another embodiment, subscript m is 1 and $R^6$, $R^7$, and $R^8$ are independently selected from an optionally substituted $C_{10}$-$C_{24}$ alkyl, $C_{10}$-$C_{24}$ alkenyl, and $C_{10}$-$C_{24}$ alkynyl. In some instances, $R^6$, $R^7$, and $R^8$ independently comprise an optionally substituted $C_{12}$-$C_{24}$, $C_{14}$-$C_{24}$, or $C_{16}$-$C_{20}$ alkyl group. In other instances, at least one, two, or all three of $R^6$, $R^7$, and $R^8$ independently comprises at least 1, 2, 3, 4, 5, or 6 sites of unsaturation or a substituted alkyl group such as a phytanyl moiety. The unsaturated side-chains may independently comprise a myristoleyl moiety, a palmitoleyl moiety, an oleyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, or an icosatrienyl moiety. In some instances, the octadecadienyl moiety is a linoleyl moiety. In particular embodiments, $R^6$, $R^7$, and $R^8$ are all linoleyl moieties. In other embodiments, $R^7$ and $R^8$ are the same and $R^6$ is different. In certain instances, $R^6$ is an oleyl moiety and $R^7$ and $R^8$ are linoleyl moieties. In certain other instances, $R^6$ is a linoleyl moiety and $R^7$ and $R^8$ are oleyl moieties. One of skill in the art will appreciate that the compounds of Formula III may comprise a combination of two or more of the features described in this paragraph. As a non-limiting example, in certain preferred embodiments, subscripts i and m are both 1; subscripts e, f, g, j, and k are all 0, and $R^6$, $R^7$, and $R^8$ are independently selected $C_{18}$ alkyl groups (e.g., $R^6$, $R^7$, and $R^8$ are all linoleyl moieties). An exemplary method of making the carbamate-containing lipids of Formula III is illustrated for Compound 11 of Scheme 3 below.

In preferred embodiments, $R^1$ and $R^2$ are each independently methyl or ethyl groups; subscript a is 2, 3, or 4; subscripts c and d are both 1; Y is —$CR^{11}R^{12}$—. $R^{11}$ and $R^{12}$ are independently selected from hydrogen, methyl, and ethyl; $R^5$ is hydrogen (H); subscript i is 1; subscripts e, f, g, j, and k are all 0; $Z^1$ is O; $T^1$ is OH; subscript m is 1; $R^6$, $R^7$, and $R^8$ are independently selected from $C_{16}$-$C_{20}$ (e.g., $C_{18}$) alkyl groups (e.g., $R^6$, $R^7$, and $R^8$ are all linoleyl moieties or oleyl moieties; at least two of $R^6$, $R^7$, and $R^8$ are oleyl moieties and the other is a linoleyl moiety; or at least two of $R^6$, $R^7$, and $R^8$ are linoleyl moieties and the other is an oleyl moiety); and $R^9$ is selected from methyl,

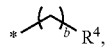

wherein subscript b is 0 and $R^4$ is a linoleyl moiety, and

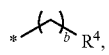

wherein $R^4$ is $NR^{4a}R^{4b}$, subscript b is 2, and $R^{4a}$ and $R^{4b}$ are both methyl.

In particularly preferred embodiments, the cationic lipid of Formula III has the following structure:

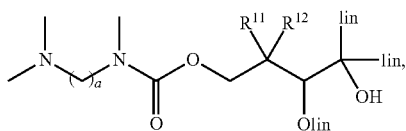

wherein subscript a is 2, 3, or 4; $R^{11}$ and $R^{12}$ are independently selected from hydrogen (H) and methyl; and "lin" refers to a linoleyl moiety.

In another embodiment, $R^1$ and $R^2$ are each independently hydrogen (H) or an optionally substituted $C_1$-$C_6$ alkyl, preferably $C_1$-$C_4$ alkyl (e.g., methyl, ethyl, propyl, butyl). In particular embodiments, $R^1$ and $R^2$ are both methyl groups (i.e., $C_1$ alkyls). In certain instances, $R^3$ is absent when the pH is above the $pK_a$ of the cationic lipid and $R^3$ is hydrogen (H) when the pH is below the $pK_a$ of the cationic lipid such that the amino head group is protonated. In another embodiment, subscript a is 2, 3, 4, 5, or 6. In a preferred embodiment, subscript a is 2, 3, or 4. In yet another embodiment, subscript c is 0, 1, or 2 and subscript d is 0 or 1. In a preferred embodiment subscripts c and d are both 0. In yet another embodiment, $R^5$ is hydrogen (H). In a further embodiment, subscript f is 1 and subscripts e and g are both 0. In another embodiment, subscript i is 0, subscripts j and k are both 1, and $Z^2$ and $Z^3$ are independently selected from oxygen (O), C(O)O, and OC(O). In a preferred embodiment, $Z^2$ and $Z^3$ are both O. In further embodiments, $R^9$ is selected from hydrogen (H), optionally substituted $C_1$-$C_6$ alkyl, $C_2$-$C_6$ alkenyl, $C_2$-$C_6$ alkynyl, and

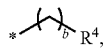

wherein * represents the point of attachment to N. $R^4$ is as described above. In some instances, $R^9$ is methyl. In some other instances, $R^9$ is

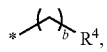

subscript b is 0, and $R^4$ is a linoleyl moiety. In further instances, $R^9$ is

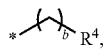

subscript b is 1, 2, or 3, and $R^4$ is $NR^{4a}R^{4b}$, wherein $R^{4a}$ and $R^{4b}$ are independently selected from hydrogen (H), an optionally substituted $C_1$-$C_6$ alkyl, $C_2$-$C_6$ alkenyl, and $C_2$-$C_6$ alkynyl. In preferred embodiments, subscript b is 2 and $R^{4a}$ and $R^{4b}$ are both methyl. In yet another embodiment, $T^1$ is hydrogen (H) or $OR^{10}$, wherein $R^{10}$ is H or optionally substituted $C_1$-$C_4$ alkyl. In one particular embodiment, $T^1$ is H or OH. In still yet another embodiment, subscript m is 1 and $R^6$, $R^7$, and $R^8$ are independently selected from an optionally substituted $C_{10}$-$C_{24}$ alkyl, $C_{10}$-$C_{24}$ alkenyl, and $C_{10}$-$C_{24}$ alkynyl. In some instances, $R^6$, $R^7$, and $R^8$ independently comprise an optionally substituted $C_{12}$-$C_{24}$, $C_{10}$-$C_{24}$, or $C_{16}$-$C_{20}$ alkyl group. In other instances, at least one, two, or all three of $R^6$, $R^7$, and $R^8$ independently comprises at least 1, 2, 3, 4, 5, or 6 sites of unsaturation or a substituted alkyl group such as a phytanyl moiety. The unsaturated side-chains may independently comprise a myristoleyl moiety, a palmitoleyl moiety, an oleyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, or an icosatrienyl moiety. In some instances, the octadecadienyl moiety is a linoleyl moiety. In particular embodiments, $R^6$, $R^7$, and $R^8$ are all linoleyl moieties. In other embodiments, $R^7$ and $R^8$ are the same and $R^6$ is different. In certain instances, $R^6$ is an oleyl moiety and $R^7$ and $R^8$ are linoleyl moieties. In certain other instances, $R^6$ is a linoleyl moiety and $R^7$ and $R^8$ are oleyl moieties. One of skill in the art will appreciate that the compounds of Formula III may comprise a combination of two or more of the features described in this paragraph. As a non-limiting example, in certain preferred embodiments, subscripts f, j, k are all 1; subscripts e, g, and i, are all 0; and $R^6$, $R^7$, and $R^8$ are independently selected $C_{18}$ alkyl groups (e.g., $R^6$, $R^7$, and $R^8$ are all linoleyl moieties). An exemplary method of making the carbamate-containing lipids of Formula III described in this paragraph is illustrated for Compound 15 of Scheme 4 below.

In preferred embodiments, $R^1$ and $R^2$ are each independently methyl or ethyl groups; subscript a is 2, 3, or 4; subscripts c and d are both 0; $R^5$ is hydrogen (H); subscripts f, j, and k are all 1; subscripts e, g, and i are all 0; $Z^2$ and $Z^3$ are both oxygen (O). $T^1$ is hydrogen (H); subscript m is 1; $R^6$, $R^7$, and $R^8$ are independently selected from $C_{16}$-$C_{20}$ (e.g., $C_{18}$) alkyl groups (e.g., $R^6$, $R^7$, and $R^8$ are all linoleyl moieties or oleyl moieties; at least two of $R^6$, $R^7$, and $R^8$ are oleyl moieties and the other is a linoleyl moiety; or at least two of $R^6$, $R^7$, and $R^8$ are linoleyl moieties and the other is an oleyl moiety); and $R^9$ is selected from methyl,

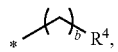

wherein subscript b is 0 and $R^4$ is a linoleyl moiety, and

wherein $R^4$ is $NR^{4a}R^{4b}$, subscript b is 2, and $R^{4a}$ and $R^{4b}$ are both methyl.

In particularly preferred embodiments, the cationic lipid of Formula II has the following structure:

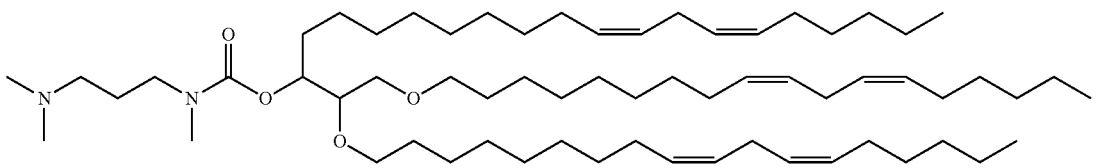 [SMILES: CCCCC/C=C\C/C=C\CCCCCCCCOCC(OCCCCCCCC/C=C\C/C=C\CCCCC)C(CCCCCCCC/C=C\C/C=C\CCCCC)OC(=O)N(C)CCCN(C)C]

In a related aspect, the present invention provides a cationic lipid of Formula IV having the following structure:

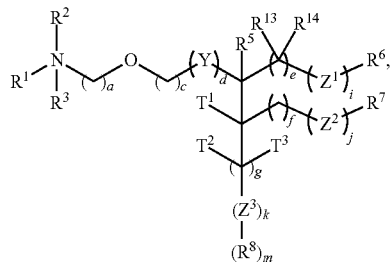

(IV)

wherein $R^1$, $R^2$, $R^3$, $R^4$, $R^5$, $R^6$, $R^7$, $R^8$, $R^9$, $R^{10}$, $R^{11}$, $R^{12}$, Y, $Z^1$, $Z^2$, $Z^3$, $T^1$, $T^2$, $T^3$, and subscripts a, b, c, d, e, f, g, h, i, j, k, and m are the same as described above for Formula I.

In one embodiment, $R^1$ and $R^2$ are each independently hydrogen (H) or an optionally substituted $C_1$-$C_6$ alkyl, preferably $C_1$-$C_4$ alkyl (e.g., methyl, ethyl, propyl, butyl). In particular embodiments, $R^1$ and $R^2$ are both methyl groups (i.e., $C_1$ alkyls). In certain instances, $R^3$ is absent when the pH is above the $pK_a$ of the cationic lipid and $R^3$ is hydrogen (H) when the pH is below the $pK_a$ of the cationic lipid such that the amino head group is protonated. In another embodiment, subscript a is 2, 3, 4, 5, or 6. In a preferred embodiment, subscript a is 2, 3, or 4. In yet another embodiment, subscript c is 0, 1, or 2 and subscript d is 0. In one particular embodiment, c and d are both 0. In still yet another embodiment, $R^5$ is hydrogen (H). In a further embodiment, subscripts e, f, and g are all 0. In another embodiment, subscripts i, j, and k are all 0. In yet another embodiment, $T^1$ is hydrogen (H) or $OR^{10}$, wherein $R^{10}$ is H or optionally substituted $C_1$-$C_4$ alkyl. In one particular embodiment, $T^1$ is H or OH. In still yet another embodiment, subscript m is 1 and $R^6$, $R^7$, and $R^8$ are independently selected from an optionally substituted $C_{10}$-$C_{24}$ alkyl, $C_{10}$-$C_{24}$ alkenyl, and $C_{10}$-$C_{24}$ alkynyl. In some instances, $R^6$, $R^7$, and $R^8$ independently comprise an optionally substituted $C_{12}$-$C_{24}$, $C_{14}$-$C_{24}$, or $C_{16}$-$C_{20}$ alkyl group. In other instances, at least one, two, or all three of $R^6$, $R^7$, and $R^8$ independently comprises at least 1, 2, 3, 4, 5, or 6 sites of unsaturation or a substituted alkyl group such as a phytanyl moiety. The unsaturated side-chains may independently comprise a myristoleyl moiety, a palmitoleyl moiety, an oleyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, or an icosatrienyl moiety. In some instances, the octadecadienyl moiety is a linoleyl moiety. In particular embodiments, $R^6$, $R^7$, and $R^8$ are all linoleyl moieties. In other embodiments, $R^7$ and $R^8$ are the same and $R^6$ is different. In certain instances, $R^6$ is an oleyl moiety and $R^7$ and $R^8$ are linoleyl moieties. In certain other instances, $R^6$ is a linoleyl moiety and $R^7$ and $R^8$ are oleyl moieties. One of skill in the art will appreciate that the compounds of Formula IV may comprise a combination of two or more of the features described in this paragraph. As a non-limiting example, in certain preferred embodiments, subscripts e, f, g, i, j, and k are all 0, subscript m is 1, and $R^6$, $R^7$, and $R^8$ are independently selected $C_{18}$ alkyl groups (e.g., $R^6$, $R^7$, and $R^8$ are all linoleyl moieties). Exemplary methods of making the ether-containing lipids of Formula IV are illustrated for compound 3 of Scheme 1 and for compound 6 of Scheme 2 below.

In preferred embodiments, $R^1$ and $R^2$ are each independently methyl or ethyl groups; subscript a is 2, 3, or 4; subscripts c and d are both 0; $R^5$ is hydrogen (H); subscripts e, f, g, i, j, and k are all 0; $T^1$ is H or OH; subscript m is 1; and $R^6$, $R^7$, and $R^8$ are independently selected from $C_{16}$-$C_{20}$ (e.g., $C_{18}$) alkyl groups (e.g., $R^6$, $R^7$, and $R^8$ are all linoleyl moieties or oleyl moieties; at least two of $R^6$, $R^7$, and $R^8$ are oleyl moieties and the other is a linoleyl moiety; or at least two of $R^6$, $R^7$, and $R^8$ are linoleyl moieties and the other is an oleyl moiety).

In particularly preferred embodiments, the cationic lipid of Formula IV has the structure of compound 3 of Scheme 1 and compound 6 of Scheme 2.

In one embodiment, $R^1$ and $R^2$ are each independently hydrogen (H) or an optionally substituted $C_1$-$C_6$ alkyl, preferably $C_1$-$C_4$ alkyl (e.g., methyl, ethyl, propyl, butyl). In particular embodiments, $R^1$ and $R^2$ are both methyl groups (i.e., $C_1$ alkyls). In certain instances, $R^3$ is absent when the pH is above the $pK_a$ of the cationic lipid and $R^3$ is hydrogen (H) when the pH is below the $pK_a$ of the cationic lipid such that the amino head group is protonated. In another embodiment, subscript a is 2, 3, 4, 5, or 6. In a preferred embodiment, subscript a is 2, 3, or 4. In yet another embodiment, subscript c is 0, 1, or 2 and subscript d is 0. In one particular embodiment, subscripts c and d are both 1. In still yet another embodiment, $R^5$ is hydrogen (H). In a further embodiment, subscripts e, f, and g are all 0. In another embodiment, subscript i is 1 and subscripts j and k are both 0. In another embodiment, $Z^1$ is oxygen (O). In yet another embodiment, $T^1$ is hydrogen (H) or $OR^{10}$, wherein $R^{10}$ is H or optionally substituted $C_1$-$C_4$ alkyl. In one particular embodiment, $T^1$ is H or OH. In still yet another embodiment, subscript m is 1 and $R^6$, $R^7$, and $R^8$ are independently selected from an optionally substituted $C_{10}$-$C_{24}$ alkyl, $C_{10}$-$C_{24}$ alkenyl, and $C_{10}$-$C_{24}$ alkynyl. In some instances, $R^6$, $R^7$, and $R^8$ independently comprise an optionally substituted $C_{12}$-$C_{24}$, $C_{14}$-$C_{24}$, or $C_{16}$-$C_{20}$ alkyl group. In other instances, at least one, two, or all three of $R^6$, $R^7$, and $R^8$ independently comprises at least 1, 2, 3, 4, 5, or 6 sites of unsaturation or a substituted alkyl group such as a phytanyl moiety. The unsaturated side-chains may independently comprise a myristoleyl moiety, a palmitoleyl moiety, an oleyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, or an icosatrienyl moiety. In some instances, the octadecadienyl moiety is a linoleyl moiety. In particular embodiments, $R^6$, $R^7$, and $R^8$ are all linoleyl moieties. In other embodiments, $R^7$ and $R^8$ are the same and $R^6$ is different. In certain instances, $R^6$ is an oleyl moiety and $R^7$ and $R^8$ are linoleyl moieties. In certain other instances, $R^6$ is a linoleyl moiety and $R^7$ and $R^8$ are oleyl moieties. One of skill in the art will appreciate that the compounds of Formula IV may comprise a combination of two or more of the features described in this paragraph. As a non-limiting example, in certain preferred embodiments, subscripts e, f, g, i, j, and k are all 0, subscript m is 1, and $R^6$, $R^7$, and $R^8$ are independently selected $C_{18}$ alkyl groups (e.g., $R^6$, $R^7$, and $R^8$ are all linoleyl moieties). Exemplary methods of making the ether-containing lipids of Formula IV are illustrated for compound 10 in Scheme 3 below.

In preferred embodiments, $R^1$ and $R^2$ are each independently methyl or ethyl groups; subscript a is 2, 3, or 4; subscripts c and d are both 1; Y is —$CR^{11}R^{12}$; $R^{11}$ and $R^{12}$ are independently selected from hydrogen (H), methyl, or ethyl. $R^5$ is hydrogen (H); subscript i is 1 and subscripts e, f, g, j, and k are all 0; $T^1$ is H or OH; subscript m is 1; and $R^6$, $R^7$, and $R^8$ are independently selected from $C_{16}$-$C_{20}$ (e.g., $C_{18}$) alkyl groups (e.g., $R^6$, $R^7$, and $R^8$ are all linoleyl moieties or oleyl moieties; at least two of $R^6$, $R^7$, and $R^8$ are oleyl moieties and the other is a linoleyl moiety; or at least two of $R^6$, $R^7$, and $R^8$ are linoleyl moieties and the other is an oleyl moiety).

In particularly preferred embodiments, the cationic lipid of Formula IV has the structure of compound 10 in Scheme 3.

In one embodiment, $R^1$ and $R^2$ are each independently hydrogen (H) or an optionally substituted $C_1$-$C_6$ alkyl, preferably $C_1$-$C_4$ alkyl (e.g., methyl, ethyl, propyl, butyl). In particular embodiments, $R^1$ and $R^2$ are both methyl groups (i.e., $C_1$ alkyls). In certain instances, $R^3$ is absent when the pH is above the $pK_a$ of the cationic lipid and $R^3$ is hydrogen (H) when the pH is below the $pK_a$ of the cationic lipid such that the amino head group is protonated. In another embodiment, subscript a is 2, 3, 4, 5, or 6. In a preferred embodiment, subscript a is 2, 3, or 4. In yet another embodiment, subscript c is 0, 1, or 2 and subscript d is 0. In one particular embodiment, subscripts c and d are both 1. In still yet another embodiment, $R^5$ is hydrogen (H). In a further embodiment, subscripts e, f, and g are all 0. In another embodiment, subscript i is 0 and subscripts j and k are both 1. $Z^2$ and $Z^3$ are 0. In yet another embodiment, $T^1$ is hydrogen (H) or $OR^{10}$, wherein $R^{10}$ is H or optionally substituted $C_1$-$C_4$ alkyl. In one particular embodiment, $T^1$ is H or OH. In still yet another embodiment, subscript m is 1 and $R^6$, $R^7$, and $R^8$ are independently selected from an optionally substituted $C_{10}$-$C_{24}$ alkyl, $C_{10}$-$C_{24}$ alkenyl, and $C_{10}$-$C_{24}$ alkynyl. In some instances, $R^6$, $R^7$, and $R^8$ independently comprise an optionally substituted $C_{12}$-$C_{24}$, $C_{14}$-$C_{24}$, or $C_{16}$-$C_{20}$ alkyl group. In other instances, at least one, two, or all three of $R^6$, $R^7$, and $R^8$ independently comprises at least 1, 2, 3, 4, 5, or 6 sites of unsaturation or a substituted alkyl group such as a phytanyl moiety. The unsaturated side-chains may independently comprise a myristoleyl moiety, a palmitoleyl moiety, an oleyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, or an icosatrienyl moiety. In some instances, the octadecadienyl moiety is a linoleyl moiety. In particular embodiments, $R^6$, $R^7$, and $R^8$ are all linoleyl moieties. In other embodiments, $R^7$ and $R^8$ are the same and $R^6$ is different. In certain instances, $R^6$ is an oleyl moiety and $R^7$ and $R^8$ are linoleyl moieties. In certain other instances, $R^6$ is a linoleyl moiety and $R^7$ and $R^8$ are oleyl moieties. One of skill in the art will appreciate that the compounds of Formula IV may comprise a combination of two or more of the features described in this paragraph. As a non-limiting example, in certain preferred embodiments, e, f, g, i, j, and k are all 0, m is 1, and $R^6$, $R^7$, and $R^8$ are independently selected $C_{18}$ alkyl groups (e.g., $R^6$, $R^7$, and $R^8$ are all linoleyl moieties). Exemplary methods of making the ether-containing lipids of Formula IV are illustrated for compound 14 in Scheme 4 below.

In preferred embodiments, $R^1$ and $R^2$ are each independently methyl or ethyl groups; subscript a is 2, 3, or 4; subscripts c and d are both 0; $R^5$ is hydrogen (H); subscripts e, f, and g are all 0; subscript i is 0 and subscripts j and k are both 1; $Z^2$ and $Z^3$ are 0; $T^1$ is H or OH; subscript m is 1; and $R^6$, $R^7$, and $R^8$ are independently selected from $C_{16}$-$C_{20}$ (e.g., $C_{18}$) alkyl groups (e.g., $R^6$, $R^7$, and $R^8$ are all linoleyl moieties or oleyl moieties; at least two of $R^6$, $R^7$, and $R^8$ are oleyl moieties and the other is a linoleyl moiety; or at least two of $R^6$, $R^7$, and $R^8$ are linoleyl moieties and the other is an oleyl moiety).

In particularly preferred embodiments, the cationic lipid of Formula IV has the structure of compound 14 in Scheme 4.

In a related aspect, the present invention provides a cationic lipid of Formula V having the following structure:

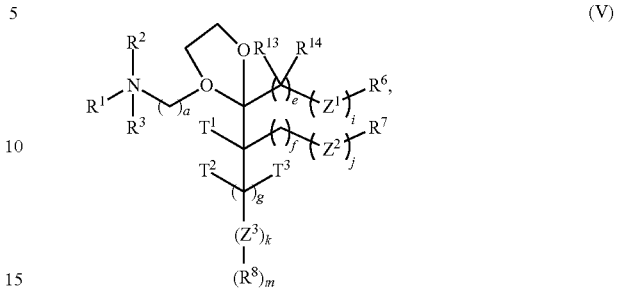

(V)

or salts and isomers thereof, wherein $R^1$, $R^2$, $R^3$, $R^4$, $R^5$, $R^6$, $R^7$, $R^8$, $R^9$, $R^{10}$, $R^{11}$, $R^{12}$, Y, $Z^1$, $Z^2$, $Z^3$, $T^1$, $T^2$, $T^3$, and subscripts a, b, c, d, e, f, g, h, i, j, k, and m are the same as described above for Formula I.

In one embodiment, $R^1$ and $R^2$ are each independently hydrogen (H) or an optionally substituted $C_1$-$C_6$ alkyl, preferably $C_1$-$C_4$ alkyl (e.g., methyl, ethyl, propyl, butyl). In particular embodiments, $R^1$ and $R^2$ are both methyl groups (i.e., $C_1$ alkyls). In certain instances, $R^3$ is absent when the pH is above the $pK_a$ of the cationic lipid and $R^3$ is hydrogen (H) when the pH is below the $pK_a$ of the cationic lipid such that the amino head group is protonated. In another embodiment, subscript a is 2, 3, 4, 5, or 6. In a preferred embodiment, subscript a is 2, 3, or 4. In a further embodiment, subscripts e, f, and g are all 0. In another embodiment, subscripts i, j, and k are all 0. In yet another embodiment, $T^1$ is hydrogen (H) or $OR^{10}$, wherein $R^{10}$ is H or optionally substituted $C_1$-$C_4$ alkyl. In one particular embodiment, $T^1$ is H or OH. In still yet another embodiment, subscript m is 1 and $R^6$, $R^7$, and $R^8$ are independently selected from an optionally substituted $C_{10}$-$C_{24}$ alkyl, $C_{10}$-$C_{24}$ alkenyl, and $C_{10}$-$C_{24}$ alkynyl. In some instances, $R^6$, $R^7$, and $R^8$ independently comprise an optionally substituted $C_{12}$-$C_{24}$, $C_{14}$-$C_{24}$, or $C_{16}$-$C_{20}$ alkyl group. In other instances, at least one, two, or all three of $R^6$, $R^7$, and $R^8$ independently comprises at least 1, 2, 3, 4, 5, or 6 sites of unsaturation or a substituted alkyl group such as a phytanyl moiety. The unsaturated side-chains may independently comprise a myristoleyl moiety, a palmitoleyl moiety, an oleyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, or an icosatrienyl moiety. In some instances, the octadecadienyl moiety is a linoleyl moiety. In particular embodiments, $R^6$, $R^7$, and $R^8$ are all linoleyl moieties. In other embodiments, $R^7$ and $R^8$ are the same and $R^6$ is different. In certain instances, $R^6$ is an oleyl moiety and $R^7$ and $R^8$ are linoleyl moieties. In certain other instances, $R^6$ is a linoleyl moiety and $R^7$ and $R^8$ are oleyl moieties. One of skill in the art will appreciate that the compounds of Formula V may comprise a combination of two or more of the features described in this paragraph. As a non-limiting example, in certain preferred embodiments, subscripts e, f, g, i, j, and k are all 0, subscript m is 1, and $R^6$, $R^7$, and $R^8$ are independently selected $C_{18}$ alkyl groups (e.g., $R^6$, $R^7$, and $R^8$ are all linoleyl moieties). Exemplary methods of making the dioxylanyl-containing lipids of Formula V are illustrated for compound 1 of Scheme 1 and for compound 5 of Scheme 2 below.

In preferred embodiments, $R^1$ and $R^2$ are each independently methyl or ethyl groups; subscript a is 2, 3, or 4; e, f, and g are all 0; subscripts i, j, and k are all 0; $T^1$ is H or OH; subscript m is 1; and $R^6$, $R^7$, and $R^8$ are independently selected from $C_{16}$-$C_{20}$ (e.g., $C_{18}$) alkyl groups (e.g., $R^6$, $R^7$, and $R^8$ are all linoleyl moieties or oleyl moieties; at least two of $R^6$, $R^7$, and $R^8$ are oleyl moieties and the other is a linoleyl moiety; or at least two of $R^6$, $R^7$, and $R^8$ are linoleyl moieties and the other is an oleyl moiety).

In particularly preferred embodiments, the cationic lipid of Formula V has the structure of compound 1 of Scheme 1 and compound 5 of Scheme 2.

In one embodiment, $R^1$ and $R^2$ are each independently hydrogen (H) or an optionally substituted $C_1$-$C_6$ alkyl, preferably $C_1$-$C_4$ alkyl (e.g., methyl, ethyl, propyl, butyl). In particular embodiments, $R^1$ and $R^2$ are both methyl groups (i.e., $C_1$ alkyls). In certain instances, $R^3$ is absent when the pH is above the $pK_a$ of the cationic lipid and $R^3$ is hydrogen (H) when the pH is below the $pK_a$ of the cationic lipid such that the amino head group is protonated. In another embodiment, subscript a is 2, 3, 4, 5, or 6. In a preferred embodiment, subscript a is 2, 3, or 4. In a further embodiment, subscript f is 1 and subscripts e and g are both 0. In another embodiment, subscript j is 1 and subscripts i and k are both 0. In another embodiment $Z^2$ is O. In yet another embodiment, $T^1$ is hydrogen (H) or $OR^{10}$, wherein $R^{10}$ is H or optionally substituted $C_1$-$C_4$ alkyl. In one particular embodiment, $T^1$ is H or OH. In still yet another embodiment, subscript m is 1 and $R^6$, $R^7$, and $R^8$ are independently selected from an optionally substituted $C_{10}$-$C_{24}$ alkyl, $C_{10}$-$C_{24}$ alkenyl, and $C_{10}$-$C_{24}$ alkynyl. In some instances, $R^6$, $R^7$, and $R^8$ independently comprise an optionally substituted $C_{12}$-$C_{24}$, $C_{14}$-$C_{24}$, or $C_{16}$-$C_{20}$ alkyl group. In other instances, at least one, two, or all three of $R^6$, $R^7$, and $R^8$ independently comprises at least 1, 2, 3, 4, 5, or 6 sites of unsaturation or a substituted alkyl group such as a phytanyl moiety. The unsaturated side-chains may independently comprise a myristoleyl moiety, a palmitoleyl moiety, an oleyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, or an icosatrienyl moiety. In some instances, the octadecadienyl moiety is a linoleyl moiety. In particular embodiments, $R^6$, $R^7$, and $R^8$ are all linoleyl moieties. In other embodiments, $R^7$ and $R^8$ are the same and $R^6$ is different. In certain instances, $R^6$ is an oleyl moiety and $R^7$ and $R^8$ are linoleyl moieties. In certain other instances, $R^6$ is a linoleyl moiety and $R^7$ and $R^8$ are oleyl moieties. One of skill in the art will appreciate that the compounds of Formula V may comprise a combination of two or more of the features described in this paragraph. As a non-limiting example, in certain preferred embodiments, subscripts f and j are both 1; subscripts e, g, i, and k are all 0; subscript m is 1, and $R^6$, $R^7$, and $R^8$ are independently selected from $C_{18}$ alkyl groups (e.g., $R^6$, $R^7$, and $R^8$ are all linoleyl moieties). Exemplary methods of making the dioxylanyl-containing lipids of Formula V are illustrated for compound 13 in Scheme 4 below.

In preferred embodiments, $R^1$ and $R^2$ are each independently methyl or ethyl groups; subscript a is 2, 3, or 4; subscripts f and j are both 1; $Z^2$ is oxygen (O); subscripts e, g, i and k are all 0; $T^1$ is H or OH; subscript m is 1; and $R^6$, $R^7$, and $R^8$ are independently selected from $C_{16}$-$C_{20}$ (e.g., $C_{18}$) alkyl groups (e.g., $R^6$, $R^7$, and $R^8$ are all linoleyl moieties or oleyl moieties; at least two of $R^6$, $R^7$, and $R^8$ are oleyl moieties and the other is a linoleyl moiety; or at least two of $R^6$, $R^7$, and $R^8$ are linoleyl moieties and the other is an oleyl moiety).

In particularly preferred embodiments, the cationic lipid of Formula V has the structure of compound 13 in Scheme 4.

In particularly preferred embodiments, the cationic lipid of Formula VI has one of the following structures:

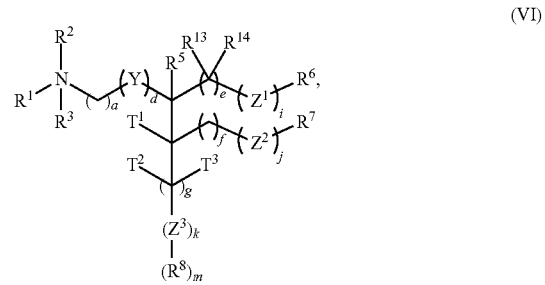

or salts and isomers thereof,
wherein $R^1$, $R^2$, $R^3$, $R^4$, $R^5$, $R^6$, $R^7$, $R^8$, $R^9$, $R^{10}$, $R^{11}$, $R^{12}$, Y, $Z^1$, $Z^2$, $Z^3$, $T^1$, $T^2$, $T^3$, and subscripts a, b, c, d, e, f, g, h, i, j, k, and m are the same as described above for Formula I.

In one embodiment, $R^1$ and $R^2$ are each independently hydrogen (H) or an optionally substituted $C_1$-$C_6$ alkyl, preferably $C_1$-$C_4$ alkyl (e.g., methyl, ethyl, propyl, butyl). In particular embodiments, $R^1$ and $R^2$ are both methyl groups (i.e., $C_1$ alkyls). In certain instances, $R^3$ is absent when the pH is above the $pK_a$ of the cationic lipid and $R^3$ is hydrogen (H) when the pH is below the $pK_a$ of the cationic lipid such that the amino head group is protonated. In another embodiment, subscript a is 2, 3, 4, 5, or 6. In another embodiment, subscript d is 0, 1, 2, or 3. In a preferred embodiment, subscript a is 2, 3, or 4. In another preferred embodiment, subscript d is 0. In still yet another embodiment, $R^5$ is hydrogen (H). In a further embodiment, subscripts e, f, and g are all 0. In another embodiment, subscript g is 1 and subscripts e and f are both 0. In another embodiment, subscripts i, j and k are all 0. In yet another embodiment, $T^1$ is hydrogen (H) or $OR^{10}$, wherein $R^{10}$ is H or optionally substituted $C_1$-$C_4$ alkyl. In one particular embodiment, $T^1$ is H or OH. In still yet another embodiment, subscript m is 1 and $R^6$, $R^7$, and $R^8$ are independently selected from an optionally substituted $C_{10}$-$C_{24}$ alkyl, $C_{10}$-$C_{24}$ alkenyl, and $C_{10}$-$C_{24}$ alkynyl. In some instances, $R^6$, $R^7$, and $R^8$ independently comprise an optionally substituted $C_{12}$-$C_{24}$, $C_{14}$-$C_{24}$, or $C_{16}$-$C_{20}$ alkyl group. In other instances, at least one, two, or all three of $R^6$, $R^7$, and $R^8$ independently comprises at least 1, 2, 3, 4, 5, or 6 sites of unsaturation or a substituted alkyl group such as a phytanyl moiety. The unsaturated side-chains may independently comprise a myristoleyl moiety, a palmitoleyl moiety, an oleyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, or an icosatrienyl moiety. In some instances, the octadecadienyl moiety is a linoleyl moiety. In particular embodiments, $R^6$, $R^7$, and $R^8$ are all linoleyl moieties. In other embodiments, $R^7$ and $R^8$ are the same and $R^6$ is different. In certain instances, $R^6$ is an oleyl moiety and $R^7$ and $R^8$ are linoleyl moieties. In certain other instances, $R^6$ is a linoleyl moiety and $R^7$ and $R^8$ are oleyl moieties. In some other instances, $R^6$ is an $C_{19}$ alkenyl optionally substituted with at least one substituent selected from methyl, ethyl, or hydroxyl. One of skill in the art will appreciate that the compounds of Formula VI may comprise a combination of two or more of the features described in this paragraph. As a non-limiting example, in certain preferred embodiments, subscript i is 1 and subscripts e, f, g, j, and k are all 0, $Z^1$ is oxygen (O), subscript m is 1, and $R^6$, $R^7$, and $R^8$ are independently selected optionally substituted $C_{18}$ alkyl groups (e.g., $R^6$, $R^7$, and $R^8$ are all linoleyl moieties). Exemplary methods of making the lipids of Formula VI are illustrated for compound 17 of Scheme 5.

In preferred embodiments, $R^1$ and $R^2$ are each independently methyl or ethyl groups; subscript a is 2, 3, or 4; $R^5$ is hydrogen (H); subscript g is 1; subscripts e, f, i, j, and k are all 0; $T^1$ is H or OH; subscript m is 1; and $R^6$, $R^7$, and $R^8$ are independently selected from $C_{16}$-$C_{20}$ (e.g., $C_{18}$) alkyl groups (e.g., $R^6$, $R^7$, and $R^8$ are all linoleyl moieties or oleyl moieties; at least two of $R^6$, $R^7$, and $R^8$ are oleyl moieties and the other is a linoleyl moiety; or at least two of $R^6$, $R^7$, and $R^8$ are linoleyl moieties and the other is an oleyl moiety). In some instances, $R^6$ is optionally substituted with groups selected from hydroxyl and $C_1$-$C_6$ alkyl, $C_1$-$C_6$ alkenyl, or $C_1$-$C_6$ alkynyl.

In another preferred embodiment, $R^1$ and $R^2$ are each independently methyl or ethyl groups; subscript a is 2, 3, or 4; $R^5$ is hydrogen (H); subscripts e and g are both 1; subscripts f, i, j, and k are all 0; $R^{13}$ is selected from methyl or ethyl; $R^{14}$ is selected from hydroxyl; $T^1$ is H or OH; subscript m is 1; and $R^6$, $R^7$, and $R^8$ are independently selected from $C_{16}$-$C_{20}$ (e.g., $C_{18}$) alkyl groups (e.g., $R^6$, $R^7$, and $R^8$ are all linoleyl moieties or oleyl moieties; at least two of $R^6$, $R^7$, and $R^8$ are oleyl moieties and the other is a linoleyl moiety; or at least two of $R^6$, $R^7$, and $R^8$ are linoleyl moieties and the other is an oleyl moiety). In some instances, $R^6$ is optionally substituted with groups selected from hydroxyl and $C_1$-$C_6$ alkyl, $C_1$-$C_6$ alkenyl, or $C_1$-$C_6$ alkynyl.

In particularly preferred embodiments, the cationic lipid of Formula VI has one of the structures in compound 17 of Scheme 5.

In one embodiment, $R^1$ and $R^2$ are each independently hydrogen (H) or an optionally substituted $C_1$-$C_6$ alkyl, preferably $C_1$-$C_4$ alkyl (e.g., methyl, ethyl, propyl, butyl). In particular embodiments, $R^1$ and $R^2$ are both methyl groups (i.e., $C_1$ alkyls). In certain instances, $R^3$ is absent when the pH is above the $pK_a$ of the cationic lipid and $R^3$ is hydrogen (H) when the pH is below the $pK_a$ of the cationic lipid such that the amino head group is protonated. In another embodiment, subscript a is 2, 3, 4, 5, or 6. In another embodiment, subscript d is 0, 1, 2, or 3. In a preferred embodiment, subscript a is 2, 3, or 4. In another preferred embodiment, subscript d is 1 and Y is —$CR^{11}R^{12}$— and $R^{11}$ and $R^{12}$ are independently selected from hydrogen (H), $C_1$-$C_6$ alkyl, $C_1$-$C_6$ alkenyl, $C_1$-$C_6$ alkynyl. In still another preferred embodiment, $R^{11}$ and $R^{12}$ are hydrogen (H) or methyl. In still yet another embodiment, $R^5$ is hydrogen (H). In a further embodiment, subscripts e, f, and g are all 0. In another embodiment, subscript i is 1 and subscripts j and k are both 0. $Z^1$ is oxygen (O). In yet another embodiment, $T^1$ is hydrogen (H) or $OR^{10}$, wherein $R^{10}$ is H or optionally substituted $C_1$-$C_4$ alkyl. In one particular embodiment, $T^1$ is H or OH. In still yet another embodiment, subscript m is 1 and $R^6$, $R^7$, and $R^8$ are independently selected from an optionally substituted $C_1$-$C_{24}$ alkyl, $C_1$-$C_{24}$ alkenyl, and $C_1$-$C_{24}$ alkynyl. In some instances, $R^6$, $R^7$, and $R^8$ independently comprise an optionally substituted $C_{12}$-$C_{24}$, $C_{10}$-$C_{24}$, or $C_{10}$-$C_{24}$ alkyl group. In other instances, at least one, two, or all three of $R^6$, $R^7$, and $R^8$ independently comprises at least 1, 2, 3, 4, 5, or 6 sites of unsaturation or a substituted alkyl group such as a phytanyl moiety. The unsaturated side-chains may independently comprise a myristoleyl moiety, a palmitoleyl moiety, an oleyl moiety, a dodecadienyl moiety, a tetradecadienyl moiety, a hexadecadienyl moiety, an octa-decadienyl moiety, an icosadienyl moiety, a dodecatrienyl moiety, a tetradectrienyl moiety, a hexadecatrienyl moiety, an octadecatrienyl moiety, or an icosatrienyl moiety. In some instances, the octadecadienyl moiety is a linoleyl moiety. In particular embodiments, $R^6$, $R^7$, and $R^8$ are all linoleyl moieties. In other embodiments, $R^7$ and $R^8$ are the same and $R^6$ is different. In certain instances, $R^6$ is an oleyl moiety and $R^7$ and $R^8$ are linoleyl moieties. In certain other instances, $R^6$ is a linoleyl moiety and $R^7$ and $R^8$ are oleyl moieties. One of skill in the art will appreciate that the compounds of Formula VI may comprise a combination of two or more of the features described in this paragraph. As a non-limiting example, in certain preferred embodiments, subscript i is 1 and subscripts e, f, g, j, and k are all 0, $Z^1$ is oxygen (O), subscript m is 1, and $R^6$, $R^7$, and $R^8$ are independently selected optionally substituted $C_{18}$ alkyl groups (e.g., $R^6$, $R^7$, and $R^8$ are all linoleyl moieties). Exemplary methods of making the lipids of Formula VI are illustrated for compound 9 of Scheme 3.

In preferred embodiments, $R^1$ and $R^2$ are each independently methyl or ethyl groups; subscript a is 2, 3, or 4; $R^5$ is hydrogen (H); subscript d is 1; Y is —$CR^{11}R^{12}$—; $R^{11}$ and $R^{12}$ are hydrogen (H), methyl, or ethyl; subscript i is 1 and subscripts e, f, g, j, and k are all 0; $Z^1$ is oxygen (O); $T^1$ is H or OH; subscript m is 1; and $R^6$, $R^7$, and $R^8$ are independently selected from $C_{16}$-$C_{20}$ (e.g., $C_{18}$) alkyl groups (e.g., $R^6$, $R^7$, and $R^8$ are all linoleyl moieties or oleyl moieties; at least two of $R^6$, $R^7$, and $R^8$ are oleyl moieties and the other is a linoleyl moiety; or at least two of $R^6$, $R^7$, and $R^8$ are linoleyl moieties and the other is an oleyl moiety). In some instances, $R^6$ is optionally substituted with groups selected from hydroxyl and $C_1$-$C_6$ alkyl, $C_1$-$C_6$ alkenyl, or $C_1$-$C_6$ alkynyl.

In particularly preferred embodiments, the cationic lipid of Formula VI has one of the structures in compound 9 in Scheme 3.

In one embodiment, $R^1$ and $R^2$ are each independently hydrogen (H) or an optionally substituted $C_1$-$C_6$ alkyl, preferably $C_1$-$C_4$ alkyl (e.g., methyl, ethyl, propyl, butyl). In particular embodiments, $R^1$ and $R^2$ are both methyl groups (i.e., $C_1$ alkyls). In certain instances, $R^3$ is absent when the pH is above the $pK_a$ of the cationic lipid and $R^3$ is hydrogen (H) when the pH is below the $pK_a$ of the cationic lipid such that the amino head group is protonated. In another embodiment, subscript a is 2, 3, 4, 5, or 6. In another embodiment, subscript d is 0, 1, 2, or 3. In a preferred embodiment, subscript a is 2, 3, or 4. In another preferred embodiment, subscript d is 0. In still yet another embodiment, $R^5$ is hydrogen (H). In a further embodiment, subscripts e, f, and g are all 0. In another embodiment, subscripts i, j and k are all 0. In yet another embodiment, $T^1$ is hydrogen (H) or $OR^{10}$, wherein $R^{10}$ is H or optionally substituted $C_1$-$C_4$ alkyl. In one particular embodiment, $T^1$ is H or OH. In still yet another embodiment, subscript m is 1 and $R^6$, $R^7$, and $R^8$ are independently selected from an optionally substituted $C_{10}$-$C_{24}$ alkyl, $C_{10}$-$C_{24}$ alkenyl, and $C_{10}$-$C_{24}$ alkynyl. In some instances, $R^6$, $R^7$, and $R^8$ independently comprise an optionally substituted $C_{12}$-$C_{24}$, $C_{14}$-$C_{24}$, or $C_{16}$-$C_{20}$ alkyl group. In other instances, at least one, two, or all three of $R^6$, $R^7$, and $R^8$ independently comprises at least 1, 2, 3, 4, 5, or 6 sites of unsaturation or a substituted alkyl group such as a phytanyl moiety. The unsaturated side-chains may independently comprise a myristoleyl moiety, a palmitoleyl moiety, an oleyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, or an icosatrienyl moiety. In some instances, the octadecadienyl moiety is a linoleyl moiety. In particular embodiments, $R^6$, $R^7$, and $R^8$ are all linoleyl moieties. In other embodiments, $R^7$ and $R^8$ are the same and $R^6$ is different. In certain instances, $R^6$ is an oleyl moiety and $R^7$ and $R^8$ are linoleyl moieties. In certain other instances, $R^6$ is a linoleyl moiety and $R^7$ and $R^8$ are oleyl moieties. One of skill in the art will appreciate that the compounds of Formula VI may comprise a combination of two or more of the features described in this paragraph. As a non-limiting example, in certain preferred embodiments, subscript i is 1 and subscripts e, f, g, j, and k are all 0, $Z^1$ is oxygen (O), subscript m is 1, and $R^6$, $R^7$, and $R^8$ are independently selected optionally substituted $C_{18}$ alkyl groups (e.g., $R^6$, $R^7$, and $R^8$ are all linoleyl moieties). Exemplary methods of making the lipids of Formula VI are illustrated for compound 18 in Scheme 6.

In preferred embodiments, $R^1$ and $R^2$ are each independently methyl or ethyl groups; subscript a is 2, 3, or 4; $R^5$ is a linoleyl moiety; subscripts j and k are both 1 and subscripts e, f, g, and i, are all 0; $Z^1$ and $Z^2$ are oxygen (O); $T^1$ is H or OH; subscript m is 0; and $R^6$ and $R^7$ are independently selected from $C_{16}$-$C_{20}$ (e.g., $C_{18}$) alkyl groups (e.g., $R^6$ and $R^7$ are linoleyl moieties or oleyl moieties;

In particularly preferred embodiments, the cationic lipid of Formula VI has one of the structures in compound 18 in Scheme 6.

B. Methods of Making Trialkyl Cationic Lipids

In the below schemes, the term "Lin" refers to linoleyl.

Non-limiting exemplified synthetic preparations of the trialkyl cationic lipids of the present invention are illustrated in Scheme 1 through Scheme 6 below:

Scheme 1 demonstrates a synthetic procedure to prepare tri-linoleyl cationic lipids with varying linking groups, including a dioxylanyl linker, a carbamate linker, an ether linker, and an ester linker. In part (i), the reagents used are MsCl, TEA, and $CH_2Cl_2$. In part (ii), the reagents used are NaCN and DMF. In part (iii), the reagents used are DIBAL and hexane. In part (iv), the reagents used are LinMgBr and THF. In part (v), the reagents used are LinMgBr and THF then $H_2O$. In part (vi), the reagents used are dimethylamino-diol, PPTS, and toluene. In part (vii), the reagents used are dimethylamino-carboxylic acid, EDC, DIPEA, and $CH_2Cl_2$. In part (viii), the reagents used are first, MsCl, TEA, and $CH_2Cl_2$, and then second, Dimethylamino-alcohol, NaH, benzene. In part (ix), the reagents used are first, Phosgene and $CH_2Cl_2$, and then, Dimethylamino-amine and $CH_2Cl_2$.

Scheme 1. Schematic of a synthetic preparation of cationic trialkyl lipids with varying linking groups.

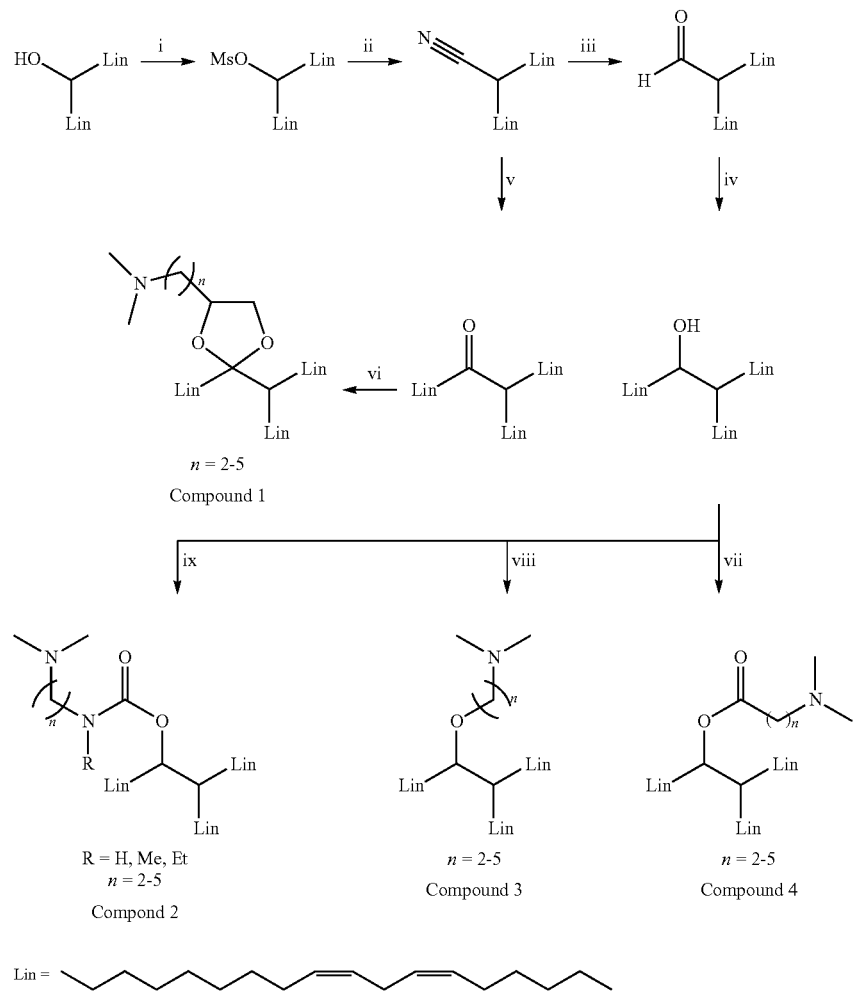

Scheme 2 demonstrates a synthetic procedure to prepare hydroxyl-substituted tri-linoleyl cationic lipids with varying linking groups, including a dioxylanyl linker, a carbamate linker, an ether linker, and an ester linker.

Scheme 2: Schematic of a synthetic preparation of trialkyl cationic lipids derived from ethyl glyoxalate.

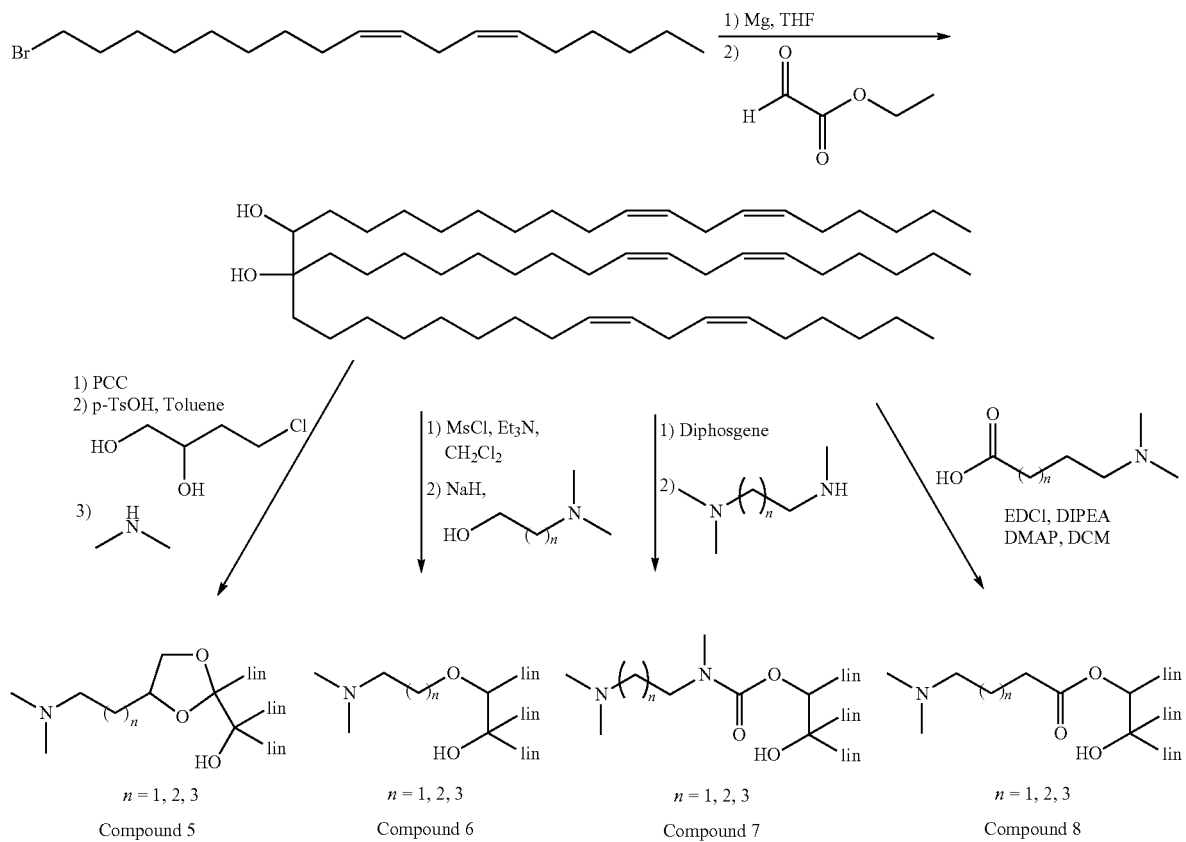

Scheme 3 demonstrates a synthetic procedure to prepare hydroxyl-substituted tri-linoleyl cationic lipids, wherein one linoleyl moiety is bonded to the rest of the molecule through an ether linkage, with varying linking groups, including an alkyl linker, a carbamate linker, an ether linker, and an ester linker.

Scheme 3: Schematic of a synthetic preparation of trialkyl lipids derived from α-hydroxybutyrolactone.

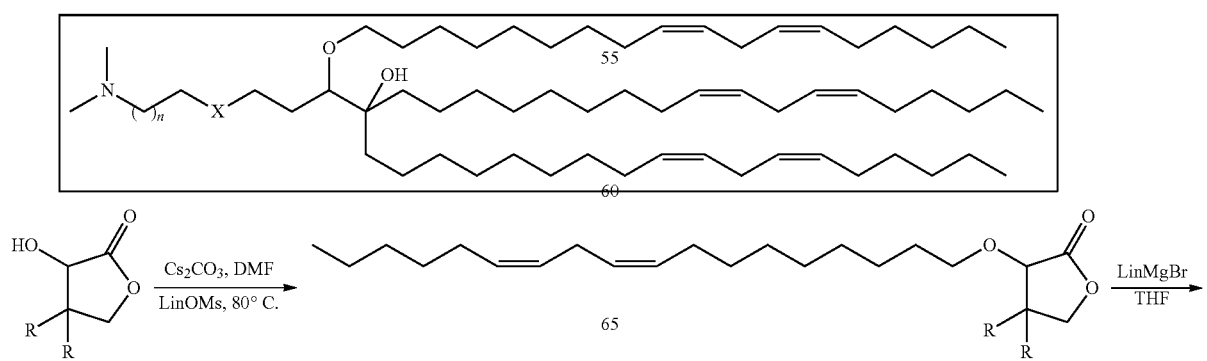

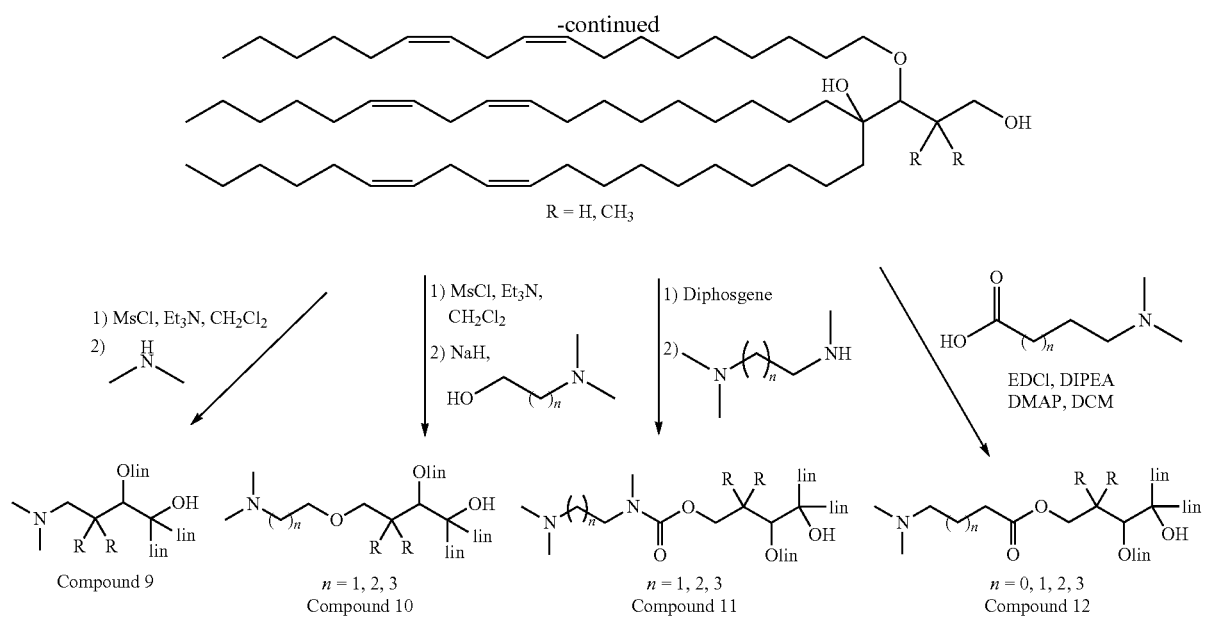

Scheme 4 demonstrates a synthetic procedure to prepare hydroxyl-substituted tri-linoleyl cationic lipids, wherein two linoleyl moieties are bonded to the rest of the molecule through ether linkages, with varying linking groups, including a dioxylanyl linker, a carbamate linker, an ether linker, and an ester linker.

Scheme 5 demonstrates a synthetic procedure to prepare hydroxyl-substituted tri-linoleyl cationic lipids, with an alkyl linker group.

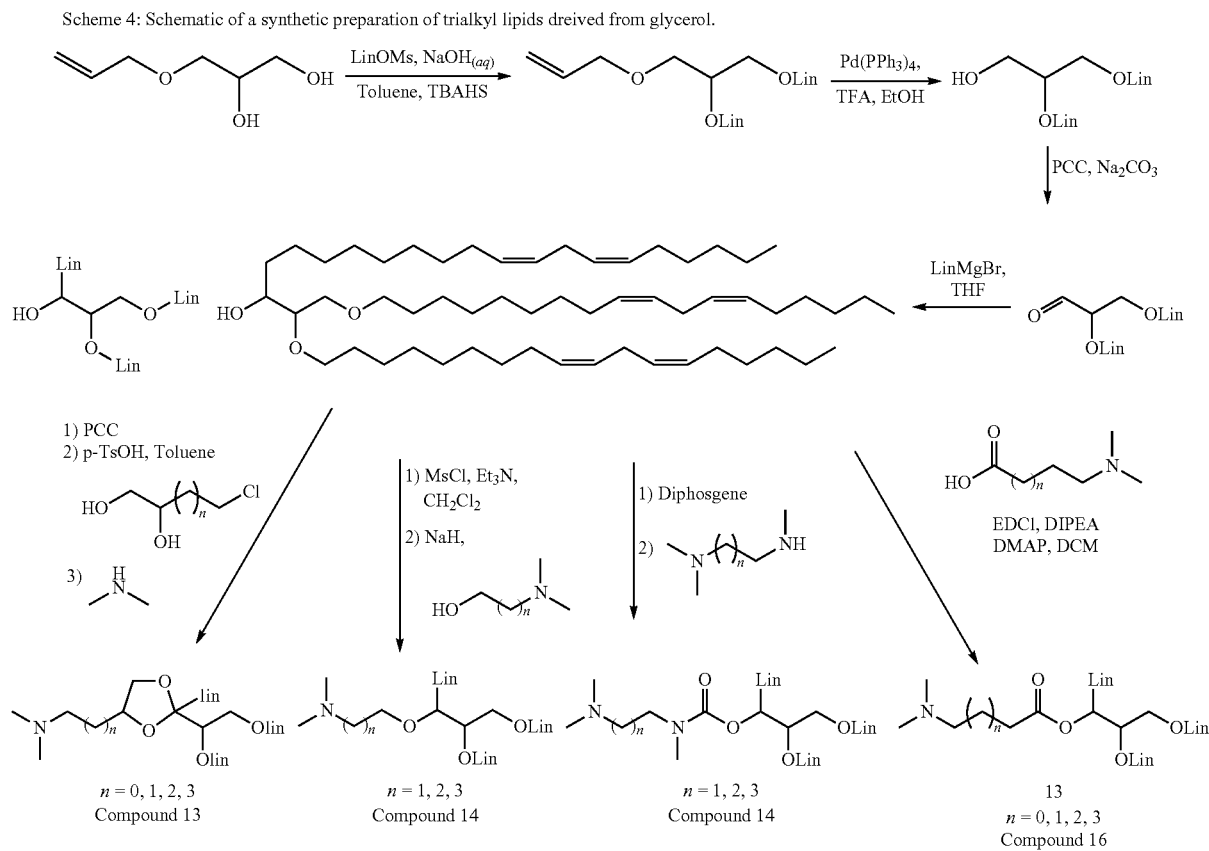

Scheme 5: Schematic of a synthetic preparation of trialkyl lipids with variable carbon linkers between the head group and the trialkyl moiety.

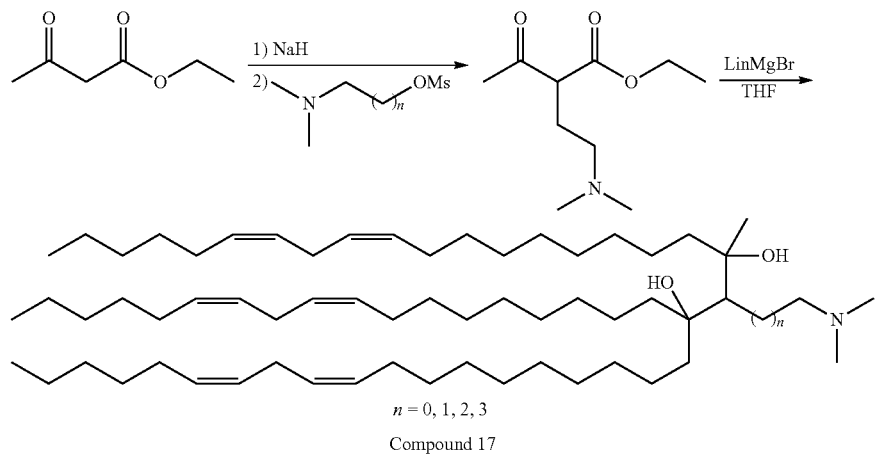

Compound 17

Scheme 6 demonstrates a synthetic procedure to prepare hydroxyl-substituted tri-linoleyl cationic lipids, wherein two linoleyl moieties are bonded to the rest of the molecule through ether linkages, with an alkyl linker moiety.

Scheme 6: Schematic of a synthetic preparation of trialkyl lipids derived from diethyl malonate.

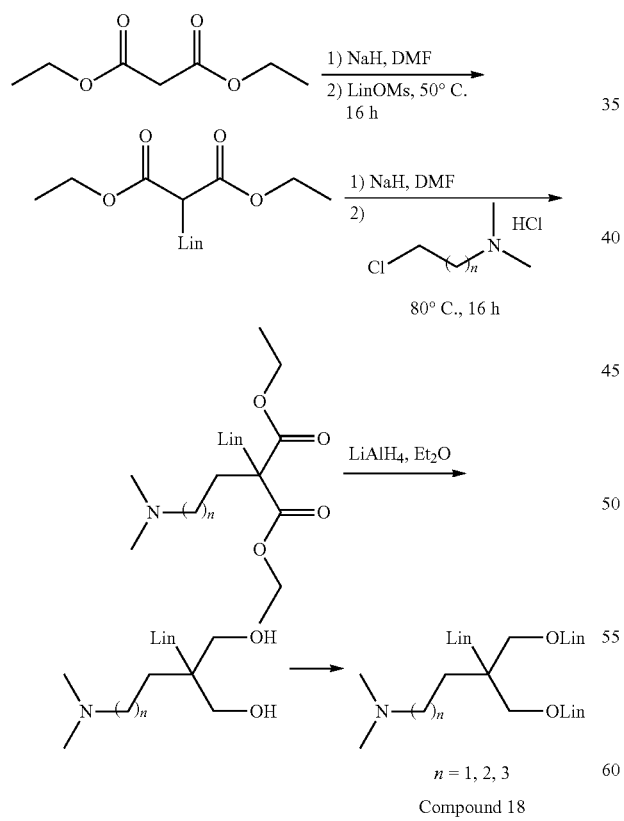

Compound 18

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, or physiological conditions.

The compounds of the invention can be synthesized by a variety of methods known to one of skill in the art (see *Comprehensive Organic Transformations* Richard C. Larock, 1989) or by an appropriate combination of generally well known synthetic methods. Techniques useful in synthesizing the compounds of the invention are both readily apparent and accessible to those of skill in the relevant art. The discussion above is offered to illustrate certain of the diverse methods available for use in assembling the compounds of the invention. However, the discussion is not intended to define the scope of reactions or reaction sequences that are useful in preparing the compounds of the present invention. One of skill in the art will appreciate that other methods of making the compounds are useful in the present invention. Although some compounds in Scheme 1 through Scheme 6 may indicate relative stereochemistry, the compounds may exist as a racemic mixture or as either enantiomer.

Linkers useful in the present invention includes those possessing one or more different reactive functional groups that allow for covalent attachment of moieties. Suitable linkers include, without limitation, those described herein as well as those available from Pierce Biotechnology, Inc. (Rockford, Ill.). Additional linkers can be found in *Bioconjugate Techniques*, Greg T. Hermanson, Academic Press, 2d ed., 2008 (incorporated by reference in its entirety herein).

IV. Active Agents

Active agents (e.g., therapeutic agents) include any molecule or compound capable of exerting a desired effect on a cell, tissue, organ, or subject. Such effects may be, e.g., biological, physiological, and/or cosmetic. Active agents may be any type of molecule or compound including, but not limited to, nucleic acids, peptides, polypeptides, small molecules, and mixtures thereof. Non-limiting examples of nucleic acids include interfering RNA molecules (e.g., siRNA, Dicer-substrate dsRNA, shRNA, aiRNA, and/or miRNA), antisense oligonucleotides, plasmids, ribozymes, immunostimulatory oligonucleotides, and mixtures thereof. Examples of peptides or polypeptides include, without limitation, antibodies (e.g., polyclonal antibodies, monoclonal antibodies, antibody fragments; humanized antibodies, recombinant antibodies, recombinant human antibodies, and/or Primatized™ antibodies), cytokines, growth factors, apoptotic factors, differentiation-inducing factors, cell-surface receptors and their ligands, hormones, and mixtures thereof. Examples of small molecules include, but are not limited to, small organic molecules or compounds such as any conventional agent or drug known to those of skill in the art.

In some embodiments, the active agent is a therapeutic agent, or a salt or derivative thereof. Therapeutic agent derivatives may be therapeutically active themselves or they may be prodrugs, which become active upon further modification. Thus, in one embodiment, a therapeutic agent derivative retains some or all of the therapeutic activity as compared to the unmodified agent, while in another embodiment, a therapeutic agent derivative is a prodrug that lacks therapeutic activity, but becomes active upon further modification.

A. Nucleic Acids

In certain embodiments, lipid particles of the present invention are associated with a nucleic acid, resulting in a nucleic acid-lipid particle (e.g., SNALP). In some embodiments, the nucleic acid is fully encapsulated in the lipid particle. As used herein, the term "nucleic acid" includes any oligonucleotide or polynucleotide, with fragments containing up to 60 nucleotides generally termed oligonucleotides, and longer fragments termed polynucleotides. In particular embodiments, oligonucleotides of the invention are from about 15 to about 60 nucleotides in length. Nucleic acid may be administered alone in the lipid particles of the invention, or in combination (e.g., co-administered) with lipid particles of the invention comprising peptides, polypeptides, or small molecules such as conventional drugs.

In the context of this invention, the terms "polynucleotide" and "oligonucleotide" refer to a polymer or oligomer of nucleotide or nucleoside monomers consisting of naturally-occurring bases, sugars and intersugar (backbone) linkages. The terms "polynucleotide" and "oligonucleotide" also include polymers or oligomers comprising non-naturally occurring monomers, or portions thereof, which function similarly. Such modified or substituted oligonucleotides are often preferred over native forms because of properties such as, for example, enhanced cellular uptake, reduced immunogenicity, and increased stability in the presence of nucleases.

Oligonucleotides are generally classified as deoxyribooligonucleotides or ribooligonucleotides. A deoxyribooligonucleotide consists of a 5-carbon sugar called deoxyribose joined covalently to phosphate at the 5' and 3' carbons of this sugar to form an alternating, unbranched polymer. A ribooligonucleotide consists of a similar repeating structure where the 5-carbon sugar is ribose.

The nucleic acid that is present in a nucleic acid-lipid particle according to this invention includes any form of nucleic acid that is known. The nucleic acids used herein can be single-stranded DNA or RNA, or double-stranded DNA or RNA, or DNA-RNA hybrids. Examples of double-stranded DNA are described herein and include, e.g., structural genes, genes including control and termination regions, and self-replicating systems such as viral or plasmid DNA. Examples of double-stranded RNA are described herein and include, e.g., siRNA and other RNAi agents such as Dicer-substrate dsRNA, shRNA, aiRNA, and pre-miRNA. Single-stranded nucleic acids include, e.g., antisense oligonucleotides, ribozymes, mature miRNA, and triplex-forming oligonucleotides.

Nucleic acids of the invention may be of various lengths, generally dependent upon the particular form of nucleic acid. For example, in particular embodiments, plasmids or genes may be from about 1,000 to about 100,000 nucleotide residues in length. In particular embodiments, oligonucleotides may range from about 10 to about 100 nucleotides in length. In various related embodiments, oligonucleotides, both single-stranded, double-stranded, and triple-stranded, may range in length from about 10 to about 60 nucleotides, from about 15 to about 60 nucleotides, from about 20 to about 50 nucleotides, from about 15 to about 30 nucleotides, or from about 20 to about 30 nucleotides in length.

In particular embodiments, an oligonucleotide (or a strand thereof) of the invention specifically hybridizes to or is complementary to a target polynucleotide sequence. The terms "specifically hybridizable" and "complementary" as used herein indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. In preferred embodiments, an oligonucleotide is specifically hybridizable when binding of the oligonucleotide to the target sequence interferes with the normal function of the target sequence to cause a loss of utility or expression therefrom, and there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted. Thus, the oligonucleotide may include 1, 2, 3, or more base substitutions as compared to the region of a gene or mRNA sequence that it is targeting or to which it specifically hybridizes.

1. siRNA

The siRNA component of the nucleic acid-lipid particles of the present invention is capable of silencing the expression of a target gene of interest. Each strand of the siRNA duplex is typically about 15 to about 60 nucleotides in length, preferably about 15 to about 30 nucleotides in length. In certain embodiments, the siRNA comprises at least one modified nucleotide. The modified siRNA is generally less immunostimulatory than a corresponding unmodified siRNA sequence and retains RNAi activity against the target gene of interest. In some embodiments, the modified siRNA contains at least one 2'OMe purine or pyrimidine nucleotide such as a 2'OMe-guanosine, 2'OMe-uridine, 2'OMe-adenosine, and/or 2'OMe-cytosine nucleotide. The modified nucleotides can be present in one strand (i.e., sense or antisense) or both strands of the siRNA. In some preferred embodiments, one or more of the uridine and/or guanosine nucleotides are modified (e.g., 2'OMe-modified) in one strand (i.e., sense or antisense) or both strands of the siRNA. In these embodiments, the modified siRNA can further comprise one or more modified (e.g., 2'OMe-modified) adenosine and/or modified (e.g., 2'OMe-modified) cytosine nucleotides. In other preferred embodiments, only uridine and/or guanosine nucleotides are modified (e.g., 2'OMe-modified) in one strand (i.e., sense or antisense) or both strands of the siRNA. The siRNA sequences may have overhangs (e.g., 3' or 5' overhangs as described in Elbashir et al., *Genes Dev.*, 15:188 (2001) or Nykänen et al., *Cell*, 107:309 (2001)), or may lack overhangs (i.e., have blunt ends).

In particular embodiments, the selective incorporation of modified nucleotides such as 2'OMe uridine and/or guanosine nucleotides into the double-stranded region of either or both strands of the siRNA reduces or completely abrogates the immune response to that siRNA molecule. In certain instances, the immunostimulatory properties of specific siRNA sequences and their ability to silence gene expression can be balanced or optimized by the introduction of minimal and selective 2'OMe modifications within the double-stranded region of the siRNA duplex. This can be achieved at therapeutically viable siRNA doses without cytokine induction, toxicity, and off-target effects associated with the use of unmodified siRNA.

The modified siRNA generally comprises from about 1% to about 100% (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 100%) modified nucleotides in the double-stranded region of the siRNA duplex. In certain embodiments, one, two, three, four, five, six, seven, eight, nine, ten, or more of the nucleotides in the double-stranded region of the siRNA comprise modified nucleotides. In certain other embodiments, some or all of the modified nucleotides in the double-stranded region of the siRNA are 1, 2, 3, 4, 5, 6, 7, 8, 9, 10, or more nucleotides apart from each other. In one preferred embodiment, none of the modified nucleotides in the double-stranded region of the siRNA are adjacent to each other (e.g., there is a gap of at least 1, 2, 3, 4, 5, 6, 7, 8, 9, or 10 unmodified nucleotides between each modified nucleotide).

In some embodiments, less than about 50% (e.g., less than about 49%, 48%, 47%, 46%, 45%, 44%, 43%, 42%, 41%, 40%, 39%, 38%, 37%, or 36%, preferably less than about 35%, 34%, 33%, 32%, 31%, or 30%) of the nucleotides in the double-stranded region of the siRNA comprise modified (e.g., 2'OMe) nucleotides. In one aspect of these embodiments, less than about 50% of the uridine and/or guanosine nucleotides in the double-stranded region of one or both strands of the siRNA are selectively (e.g., only) modified. In another aspect of these embodiments, less than about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein 2'OMe-guanosine nucleotides and 2'OMe-uridine nucleotides are the only 2'OMe nucleotides present in the double-stranded region. In yet another aspect of these embodiments, less than about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the siRNA does not comprise 2'OMe-cytosine nucleotides in the double-stranded region. In a further aspect of these embodiments, less than about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein the siRNA does not comprise 2'OMe-cytosine nucleotides in the double-stranded region. In another aspect of these embodiments, less than about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the 2'OMe nucleotides in the double-stranded region are not adjacent to each other.

In other embodiments, from about 1% to about 50% (e.g., from about 5%-50%, 10%-50%, 15%-50%, 20%-50%, 25%-50%, 30%-50%, 35%-50%, 40%-50%, 45%-50%, 5%-45%, 10%-45%, 15%-45%, 20%-45%, 25%-45%, 30%-45%, 35%-45%, 40%-45%, 5%-40%, 10%-40%, 15%-40%, 20%-40%, 25%-40%, 25%-39%, 25%-38%, 25%-37%, 25%-36%, 26%-39%, 26%-38%, 26%-37%, 26%-36%, 27%-39%, 27%-38%, 27%-37%, 27%-36%, 28%-39%, 28%-38%, 28%-37%, 28%-36%, 29%-39%, 29%-38%, 29%-37%, 29%-36%, 30%-40%, 30%-39%, 30%-38%, 30%-37%, 30%-36%, 31%-39%, 31%-38%, 31%-37%, 31%-36%, 32%-39%, 32%-38%, 32%-37%, 32%-36%, 33%-39%, 33%-38%, 33%-37%, 33%-36%, 34%-39%, 34%-38%, 34%-37%, 34%-36%, 35%-40%, 5%-35%, 10%-35%, 15%-35%, 20%-35%, 21%-35%, 22%-35%, 23%-35%, 24%-35%, 25%-35%, 26%-35%, 27%-35%, 28%-35%, 29%-35%, 30%-35%, 31%-35%, 32%-35%, 33%-35%, 34%-35%, 30%-34%, 31%-34%, 32%-34%, 33%-34%, 30%-33%, 31%-33%, 32%-33%, 30%-32%, 31%-32%, 25%-34%, 25%-33%, 25%-32%, 25%-31%, 26%-34%, 26%-33%, 26%-32%, 26%-31%, 27%-34%, 27%-33%, 27%-32%, 27%-31%, 28%-34%, 28%-33%, 28%-32%, 28%-31%, 29%-34%, 29%-33%, 29%-32%, 29%-31%, 5%-30%, 10%-30%, 15%-30%, 20%-34%, 20%-33%, 20%-32%, 20%-31%, 20%-30%, 21%-30%, 22%-30%, 23%-30%, 24%-30%, 25%-30%, 25%-29%, 25%-28%, 25%-27%, 25%-26%, 26%-30%, 26%-29%, 26%-28%, 26%-27%, 27%-30%, 27%-29%, 27%-28%, 28%-30%, 28%-29%, 29%-30%, 5%-25%, 10%-25%, 15%-25%, 20%-29%, 20%-28%, 20%-27%, 20%-26%, 20%-25%, 5%-20%, 10%-20%, 15%-20%, 5%-15%, 10%-15%, or 5%-10%) of the nucleotides in the double-stranded region of the siRNA comprise modified nucleotides. In one aspect of these embodiments, from about 1% to about 50% of the uridine and/or guanosine nucleotides in the double-stranded region of one or both strands of the siRNA are selectively (e.g., only) modified. In another aspect of these embodiments, from about 1% to about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein 2'OMe-guanosine nucleotides and 2'OMe-uridine nucleotides are the only 2'OMe nucleotides present in the double-stranded region. In yet another aspect of these embodiments, from about 1% to about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the siRNA does not comprise 2'OMe-cytosine nucleotides in the double-stranded region. In a further aspect of these embodiments, from about 1% to about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein the siRNA does not comprise 2'OMe-cytosine nucleotides in the double-stranded region. In another aspect of these embodiments, from about 1% to about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the 2'OMe nucleotides in the double-stranded region are not adjacent to each other.

Additional ranges, percentages, and patterns of modifications that may be introduced into siRNA are described in U.S. Patent Publication No. 20070135372, the disclosure of which is herein incorporated by reference in its entirety for all purposes.

a) Selection of siRNA Sequences

Suitable siRNA sequences can be identified using any means known in the art. Typically, the methods described in Elbashir et al., *Nature*, 411:494-498 (2001) and Elbashir et al., *EMBO J.*, 20:6877-6888 (2001) are combined with rational design rules set forth in Reynolds et al., *Nature Biotech.*, 22(3):326-330 (2004).

As a non-limiting example, the nucleotide sequence 3' of the AUG start codon of a transcript from the target gene of interest may be scanned for dinucleotide sequences (e.g., AA, NA, CC, GG, or UU, wherein N=C, G, or U) (see, e.g., Elbashir et al., *EMBO J.*, 20:6877-6888 (2001)). The nucleotides immediately 3' to the dinucleotide sequences are identified as potential siRNA sequences (i.e., a target sequence or a sense strand sequence). Typically, the 19, 21, 23, 25, 27, 29, 31, 33, 35, or more nucleotides immediately 3' to the dinucleotide sequences are identified as potential siRNA sequences. In some embodiments, the dinucleotide sequence is an AA or NA sequence and the 19 nucleotides immediately 3' to the AA or NA dinucleotide are identified as potential siRNA sequences. siRNA sequences are usually spaced at different positions along the length of the target gene. To further enhance silencing efficiency of the siRNA sequences, potential siRNA sequences may be analyzed to identify sites that do not contain regions of homology to other coding sequences, e.g., in the target cell or organism. For example, a suitable siRNA sequence of about 21 base pairs typically will not have more than 16-17 contiguous base pairs of homology to coding sequences in the target cell or organism. If the siRNA sequences are to be expressed from an RNA Pol III promoter, siRNA sequences lacking more than 4 contiguous A's or T's are selected.

Once a potential siRNA sequence has been identified, a complementary sequence (i.e., an antisense strand sequence) can be designed. A potential siRNA sequence can also be analyzed using a variety of criteria known in the art. For example, to enhance their silencing efficiency, the siRNA sequences may be analyzed by a rational design algorithm to identify sequences that have one or more of the following features: (1) G/C content of about 25% to about 60% G/C; (2) at least 3 A/Us at positions 15-19 of the sense strand; (3) no internal repeats; (4) an A at position 19 of the sense strand; (5) an A at position 3 of the sense strand; (6) a U at position 10 of the sense strand; (7) no G/C at position 19 of the sense strand; and (8) no G at position 13 of the sense strand. siRNA design tools that incorporate algorithms that assign suitable values of each of these features and are useful for selection of siRNA can be found at, e.g., http://ihome.ust.hk/~bokcmho/siRNA/siRNA.html. One of skill in the art will appreciate that sequences with one or more of the foregoing characteristics may be selected for further analysis and testing as potential siRNA sequences.

Additionally, potential siRNA sequences with one or more of the following criteria can often be eliminated as siRNA: (1) sequences comprising a stretch of 4 or more of the same base in a row; (2) sequences comprising homopolymers of Gs (i.e., to reduce possible non-specific effects due to structural characteristics of these polymers; (3) sequences comprising triple base motifs (e.g., GGG, CCC, AAA, or TTT); (4) sequences comprising stretches of 7 or more G/Cs in a row; and (5) sequences comprising direct repeats of 4 or more bases within the candidates resulting in internal fold-back structures. However, one of skill in the art will appreciate that sequences with one or more of the foregoing characteristics may still be selected for further analysis and testing as potential siRNA sequences.

In some embodiments, potential siRNA sequences may be further analyzed based on siRNA duplex asymmetry as described in, e.g., Khvorova et al., *Cell*, 115:209-216 (2003); and Schwarz et al., *Cell*, 115:199-208 (2003). In other embodiments, potential siRNA sequences may be further analyzed based on secondary structure at the target site as described in, e.g., Luo et al., *Biophys. Res. Commun.*, 318:303-310 (2004). For example, secondary structure at the target site can be modeled using the Mfold algorithm (available at http://mfold.burnet.edu.au/rna_form) to select siRNA sequences which favor accessibility at the target site where less secondary structure in the form of base-pairing and stem-loops is present.

Once a potential siRNA sequence has been identified, the sequence can be analyzed for the presence of any immunostimulatory properties, e.g., using an in vitro cytokine assay or an in vivo animal model. Motifs in the sense and/or antisense strand of the siRNA sequence such as GU-rich motifs (e.g., 5'-GU-3',5'-UGU-3',5'-GUGU-3',5'-UGUGU-3', etc.) can also provide an indication of whether the sequence may be immunostimulatory. Once an siRNA molecule is found to be immunostimulatory, it can then be modified to decrease its immunostimulatory properties as described herein. As a non-limiting example, an siRNA sequence can be contacted with a mammalian responder cell under conditions such that the cell produces a detectable immune response to determine whether the siRNA is an immunostimulatory or a non-immunostimulatory siRNA. The mammalian responder cell may be from a naïve mammal (i.e., a mammal that has not previously been in contact with the gene product of the siRNA sequence). The mammalian responder cell may be, e.g., a peripheral blood mononuclear cell (PBMC), a macrophage, and the like. The detectable immune response may comprise production of a cytokine or growth factor such as, e.g., TNF-α, IFN-α, IFN-β, IFN-γ, IL-6, IL-12, or a combination thereof. An siRNA molecule identified as being immunostimulatory can then be modified to decrease its immunostimulatory properties by replacing at least one of the nucleotides on the sense and/or antisense strand with modified nucleotides. For example; less than about 30% (e.g., less than about 30%, 25%, 20%, 15%, 10%, or 5%) of the nucleotides in the double-stranded region of the siRNA duplex can be replaced with modified nucleotides such as 2'OMe nucleotides. The modified siRNA can then be contacted with a mammalian responder cell as described above to confirm that its immunostimulatory properties have been reduced or abrogated.

Suitable in vitro assays for detecting an immune response include, but are not limited to, the double monoclonal antibody sandwich immunoassay technique of David et al. (U.S. Pat. No. 4,376,110); monoclonal-polyclonal antibody sandwich assays (Wide et al., in Kirkham and Hunter, eds., *Radioimmunoassay Methods*, E. and S. Livingstone, Edinburgh (1970)); the "Western blot" method of Gordon et al. (U.S. Pat. No. 4,452,901); immunoprecipitation of labeled ligand (Brown et al., *J. Biol. Chem.,* 255:4980-4983 (1980)); enzyme-linked immunosorbent assays (ELISA) as described, for example, by Raines et al., *J. Biol. Chem.,* 257:5154-5160 (1982); immunocytochemical techniques, including the use of fluorochromes (Brooks et al., *Clin. Exp. Immunol.,* 39:477 (1980)); and neutralization of activity (Bowen-Pope et al., *Proc. Natl. Acad. Sci. USA,* 81:2396-2400 (1984)). In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876. The disclosures of these references are herein incorporated by reference in their entirety for all purposes.

A non-limiting example of an in vivo model for detecting an immune response includes an in vivo mouse cytokine induction assay as described in, e.g., Judge et al., *Mol. Ther.,* 13:494-505 (2006). In certain embodiments, the assay that can be performed as follows: (1) siRNA can be administered by standard intravenous injection in the lateral tail vein; (2) blood can be collected by cardiac puncture about 6 hours after administration and processed as plasma for cytokine analysis; and (3) cytokines can be quantified using sandwich ELISA kits according to the manufacturer's instructions (e.g., mouse and human IFN-α (PBL Biomedical; Piscataway, N.J.); human IL-6 and TNF-α (eBioscience; San Diego, Calif.); and mouse IL-6, TNF-α, and IFN-γ (BD Biosciences; San Diego, Calif.)).

Monoclonal antibodies that specifically bind cytokines and growth factors are commercially available from multiple sources and can be generated using methods known in the art (see, e.g., Kohler et al., *Nature,* 256: 495-497 (1975) and Harlow and Lane, ANTIBODIES, A LABORATORY MANUAL, Cold Spring Harbor Publication, New York (1999)). Generation of monoclonal antibodies has been previously described and can be accomplished by any means known in the art (Buhring et al., in Hybridoma, Vol. 10, No. 1, pp. 77-78 (1991)). In some methods, the monoclonal antibody is labeled (e.g., with any composition detectable by spectroscopic, photochemical, biochemical, electrical, optical, or chemical means) to facilitate detection.

b) Generating siRNA Molecules siRNA can be provided in several forms including, e.g., as one or more isolated small-interfering RNA (siRNA) duplexes, as longer double-stranded RNA (dsRNA), or as siRNA or dsRNA transcribed from a transcriptional cassette in a DNA plasmid. In some embodiments, siRNA may be produced enzymatically or by partial/total organic synthesis, and modified ribonucleotides can be introduced by in vitro enzymatic or organic synthesis. In certain instances, each strand is prepared chemically. Methods of synthesizing RNA molecules are known in the art, e.g., the chemical synthesis methods as described in Verma and Eckstein (1998) or as described herein.

An RNA population can be used to provide long precursor RNAs, or long precursor RNAs that have substantial or complete identity to a selected target sequence can be used to make the siRNA. The RNAs can be isolated from cells or tissue, synthesized, and/or cloned according to methods well known to those of skill in the art. The RNA can be a mixed population (obtained from cells or tissue, transcribed from cDNA, subtracted, selected, etc.), or can represent a single target sequence. RNA can be naturally occurring (e.g., isolated from tissue or cell samples), synthesized in vitro (e.g., using T7 or SP6 polymerase and PCR products or a cloned cDNA), or chemically synthesized.

To form a long dsRNA, for synthetic RNAs, the complement is also transcribed in vitro and hybridized to form a dsRNA. If a naturally occurring RNA population is used, the RNA complements are also provided (e.g., to form dsRNA for digestion by *E. coli* RNAse III or Dicer), e.g., by transcribing cDNAs corresponding to the RNA population, or by using RNA polymerases. The precursor RNAs are then hybridized to form double stranded RNAs for digestion. The dsRNAs can be directly administered to a subject or can be digested in vitro prior to administration.

Methods for isolating RNA, synthesizing RNA, hybridizing nucleic acids, making and screening cDNA libraries, and performing PCR are well known in the art (see, e.g., Gubler and Hoffman, *Gene,* 25:263-269 (1983); Sambrook et al., supra; Ausubel et al., supra), as are PCR methods (see, U.S. Pat. Nos. 4,683,195 and 4,683,202; *PCR Protocols. A Guide to Methods and Applications* (Innis et al., eds, 1990)). Expression libraries are also well known to those of skill in the art. Additional basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994). The disclosures of these references are herein incorporated by reference in their entirety for all purposes.

Preferably, siRNA are chemically synthesized. The oligonucleotides that comprise the siRNA molecules of the invention can be synthesized using any of a variety of techniques known in the art, such as those described in Usman et al., *J. Am. Chem. Soc.,* 109:7845 (1987); Scaringe et al., *Nucl. Acids Res.,* 18:5433 (1990); Wincott et al., *Nucl. Acids Res.,* 23:2677-2684 (1995); and Wincott et al., *Methods Mol. Bio.,* 74:59 (1997). The synthesis of oligonucleotides makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 μmol scale protocol. Alternatively, syntheses at the 0.2 μmol scale can be performed on a 96-well plate synthesizer from Protogene (Palo Alto, Calif.). However, a larger or smaller scale of synthesis is also within the scope of this invention. Suitable reagents for oligonucleotide synthesis, methods for RNA deprotection, and methods for RNA purification are known to those of skill in the art.

siRNA molecules can also be synthesized via a tandem synthesis technique, wherein both strands are synthesized as a single continuous oligonucleotide fragment or strand separated by a cleavable linker that is subsequently cleaved to provide separate fragments or strands that hybridize to form the siRNA duplex. The linker can be a polynucleotide linker or a non-nucleotide linker. The tandem synthesis of siRNA can be readily adapted to both multiwell/multiplate synthesis platforms as well as large scale synthesis platforms employing batch reactors, synthesis columns, and the like. Alternatively, siRNA molecules can be assembled from two distinct oligonucleotides, wherein one oligonucleotide comprises the sense strand and the other comprises the antisense strand of the siRNA. For example, each strand can be synthesized separately and joined together by hybridization or ligation following synthesis and/or deprotection. In certain other instances, siRNA molecules can be synthesized as a single continuous oligonucleotide fragment, where the self-complementary sense and antisense regions hybridize to form an siRNA duplex having hairpin secondary structure.

c) Modifying siRNA Sequences

In certain aspects, siRNA molecules comprise a duplex having two strands and at least one modified nucleotide in the double-stranded region, wherein each strand is about 15 to about 60 nucleotides in length. Advantageously, the modified siRNA is less immunostimulatory than a corresponding unmodified siRNA sequence, but retains the capability of silencing the expression of a target sequence. In preferred embodiments, the degree of chemical modifications introduced into the siRNA molecule strikes a balance between reduction or abrogation of the immunostimulatory properties of the siRNA and retention of RNAi activity. As a non-limiting example, an siRNA molecule that targets a gene of interest can be minimally modified (e.g., less than about 30%, 25%, 20%, 15%, 10%, or 5% modified) at selective uridine and/or guanosine nucleotides within the siRNA duplex to eliminate the immune response generated by the siRNA while retaining its capability to silence target gene expression.

Examples of modified nucleotides suitable for use in the invention include, but are not limited to, ribonucleotides having a 2'-O-methyl (2'OMe), 2'-deoxy-2'-fluoro (2'F), 2'-deoxy, 5-C-methyl, 2'-O-(2-methoxyethyl) (MOE), 4'-thio, 2'-amino, or 2'-C-allyl group. Modified nucleotides having a Northern conformation such as those described in, e.g., Saenger, *Principles of Nucleic Acid Structure*, Springer-Verlag Ed. (1984), are also suitable for use in siRNA molecules. Such modified nucleotides include, without limitation, locked nucleic acid (LNA) nucleotides (e.g., 2'-O, 4'-C-methylene-(D-ribofuranosyl) nucleotides), 2'-O-(2-methoxyethyl) (MOE) nucleotides, 2'-methyl-thio-ethyl nucleotides, 2'-deoxy-2'-fluoro (2'F) nucleotides, 2'-deoxy-2'-chloro (2'Cl) nucleotides, and 2'-azido nucleotides. In certain instances, the siRNA molecules described herein include one or more G-clamp nucleotides. A G-clamp nucleotide refers to a modified cytosine analog wherein the modifications confer the ability to hydrogen bond both Watson-Crick and Hoogsteen faces of a complementary guanine nucleotide within a duplex (see, e.g., Lin et al., *J. Am. Chem. Soc.*, 120:8531-8532 (1998)). In addition, nucleotides having a nucleotide base analog such as, for example, C-phenyl, C-naphthyl, other aromatic derivatives, inosine, azole carboxamides, and nitroazole derivatives such as 3-nitropyrrole, 4-nitroindole, and 5-nitroindole (see, e.g., Loakes, *Nucl. Acids Res.*, 29:2437-2447 (2001)) can be incorporated into siRNA molecules.

In certain embodiments, siRNA molecules may further comprise one or more chemical modifications such as terminal cap moieties, phosphate backbone modifications, and the like. Examples of terminal cap moieties include, without limitation, inverted deoxy abasic residues, glyceryl modifications, 4',5'-methylene nucleotides, 1-(β-D-erythrofuranosyl) nucleotides, 4'-thio nucleotides, carbocyclic nucleotides, 1,5-anhydrohexitol nucleotides, L-nucleotides, α-nucleotides, modified base nucleotides, threo-pentofuranosyl nucleotides, acyclic 3',4'-seco nucleotides, acyclic 3,4-dihydroxybutyl nucleotides, acyclic 3,5-dihydroxypentyl nucleotides, 3'-3'-inverted nucleotide moieties, 3'-3'-inverted abasic moieties, 3'-2'-inverted nucleotide moieties, 3'-2'-inverted abasic moieties, 5'-5'-inverted nucleotide moieties, 5'-5'-inverted abasic moieties, 3'-5'-inverted deoxy abasic moieties, 5'-amino-alkyl phosphate, 1,3-diamino-2-propyl phosphate, 3-aminopropyl phosphate, 6-aminohexyl phosphate, 1,2-aminododecyl phosphate, hydroxypropyl phosphate, 1,4-butanediol phosphate, 3'-phosphoramidate, 5'-phosphoramidate, hexylphosphate, aminohexyl phosphate, 3'-phosphate, 5'-amino, 3'-phosphorothioate, 5'-phosphorothioate, phosphorodithioate, and bridging or non-bridging methylphosphonate or 5'-mercapto moieties (see, e.g., U.S. Pat. No. 5,998,203; Beaucage et al., *Tetrahedron* 49:1925 (1993)). Non-limiting examples of phosphate backbone modifications (i.e., resulting in modified internucleotide linkages) include phosphorothioate, phosphorodithioate, methylphosphonate, phosphotriester, morpholino, amidate, carbamate, carboxymethyl, acetamidate, polyamide, sulfonate, sulfonamide, sulfamate, formacetal, thioformacetal, and alkylsilyl substitutions (see, e.g., Hunziker et al., *Nucleic Acid Analogues: Synthesis and Properties*, in *Modern Synthetic Methods*, VCH, 331-417 (1995); Mesmaeker et al., *Novel Backbone Replacements for Oligonucleotides*, in *Carbohydrate Modifications in Antisense Research*, ACS, 24-39 (1994)). Such chemical modifications can occur at the 5'-end and/or 3'-end of the sense strand, antisense strand, or both strands of the siRNA. The disclosures of these references are herein incorporated by reference in their entirety for all purposes.

In some embodiments, the sense and/or antisense strand of the siRNA molecule can further comprise a 3'-terminal overhang having about 1 to about 4 (e.g., 1, 2, 3, or 4) 2'-deoxy ribonucleotides, modified (e.g., 2'OMe) and/or unmodified uridine ribonucleotides, and/or any other combination of modified (e.g., 2'OMe) and unmodified nucleotides.

Additional examples of modified nucleotides and types of chemical modifications that can be introduced into siRNA molecules are described, in UK Patent No. GB 2,397,818 B and U.S. Patent Publication Nos. 20040192626, 20050282188, and 20070135372, the disclosures of which are herein incorporated by reference in their entirety for all purposes.

The siRNA molecules described herein can optionally comprise one or more non-nucleotides in one or both strands of the siRNA. As used herein, the term "non-nucleotide" refers to any group or compound that can be incorporated into a nucleic acid chain in the place of one or more nucleotide units, including sugar and/or phosphate substitutions, and allows the remaining bases to exhibit their activity. The group or compound is abasic in that it does not contain a commonly recognized nucleotide base such as adenosine, guanine, cytosine, uracil, or thymine and therefore lacks a base at the 1'-position.

In other embodiments, chemical modification of the siRNA comprises attaching a conjugate to the siRNA molecule. The conjugate can be attached at the 5' and/or 3'-end of the sense and/or antisense strand of the siRNA via a covalent attachment such as, e.g., a biodegradable linker. The conjugate can also be attached to the siRNA, e.g., through a carbamate group or other linking group (see, e.g., U.S. Patent Publication Nos. 20050074771, 20050043219, and 20050158727). In certain instances, the conjugate is a molecule that facilitates the delivery of the siRNA into a cell. Examples of conjugate molecules suitable for attachment to siRNA include, without limitation, steroids such as cholesterol, glycols such as polyethylene glycol (PEG), human serum albumin (HSA), fatty acids, carotenoids, terpenes, bile acids, folates (e.g., folic acid, folate analogs and derivatives thereof), sugars (e.g., galactose, galactosamine, N-acetyl galactosamine, glucose, mannose, fructose, fucose, etc.), phospholipids, peptides, ligands for cellular receptors capable of mediating cellular uptake, and combinations thereof (see, e.g., U.S. Patent Publication Nos. 20030130186, 20040110296, and 20040249178; U.S. Pat. No. 6,753,423). Other examples include the lipophilic moiety, vitamin, polymer, peptide, protein, nucleic acid, small molecule, oligosaccharide, carbohydrate cluster, intercalator, minor groove binder, cleaving agent, and cross-linking agent conjugate molecules described in U.S. Patent Publication Nos. 20050119470 and 20050107325. Yet other examples include the 2'-O-alkyl amine, 2'-β-alkoxyalkyl amine, polyamine, C5-cationic modified pyrimidine, cationic peptide, guanidinium group, amidininium group, cationic amino acid conjugate molecules described in U.S. Patent Publication No. 20050153337. Additional examples include the hydrophobic group, membrane active compound, cell penetrating compound, cell targeting signal, interaction modifier, and steric stabilizer conjugate molecules described in U.S. Patent Publication No. 20040167090. Further examples include the conjugate molecules described in U.S. Patent Publication No. 20050239739. The type of conjugate used and the extent of conjugation to the siRNA molecule can be evaluated for improved pharmacokinetic profiles, bioavailability, and/or stability of the siRNA while retaining RNAi activity. As such, one skilled in the art can screen siRNA molecules having various conjugates attached thereto to identify ones having improved properties and full RNAi activity using any of a variety of well-known in vitro cell culture or in vivo animal models. The disclosures of the above-described patent documents are herein incorporated by reference in their entirety for all purposes.

d) Target Genes

The siRNA component of the nucleic acid-lipid particles described herein can be used to downregulate or silence the translation (i.e., expression) of a gene of interest. Genes of interest include, but are not limited to, genes associated with viral infection and survival, genes associated with metabolic diseases and disorders (e.g., liver diseases and disorders), genes associated with tumorigenesis or cell transformation (e.g., cancer), angiogenic genes, immunomodulator genes such as those associated with inflammatory and autoimmune responses, receptor ligand genes, and genes associated with neurodegenerative disorders.

In particular embodiments, the present invention provides a cocktail of two, three, four, five, six, seven, eight, nine, ten, or more siRNA molecules that silences the expression of multiple genes of interest. In some embodiments, the cocktail of siRNA molecules is fully encapsulated in a lipid particle such as a nucleic acid-lipid particle (e.g., SNALP). The siRNA molecules may be co-encapsulated in the same lipid particle, or each siRNA species present in the cocktail may be formulated in separate particles.

Genes associated with viral infection and survival include those expressed by a host (e.g., a host factor such as tissue factor (TF)) or a virus in order to bind, enter, and replicate in a cell. Of particular interest are viral sequences associated with chronic viral diseases. Viral sequences of particular interest include sequences of Filoviruses such as Ebola virus and Marburg virus (see, e.g., Geisbert et al., *J. Infect. Dis.*, 193:1650-1657 (2006)); Arenaviruses such as Lassa virus, Junin virus, Machupo virus, Guanarito virus, and Sabia virus (Buchmeier et al., Arenaviridae: the viruses and their replication, In: FIELDS VIROLOGY, Knipe et al. (eds.), 4th ed., Lippincott-Raven, Philadelphia, (2001)); Influenza viruses such as Influenza A, B, and C viruses, (see, e.g., Steinhauer et al., *Annu Rev Genet.*, 36:305-332 (2002); and Neumann et al., *J Gen Virol.*, 83:2635-2662 (2002)); Hepatitis viruses (see, e.g., Hamasaki et al., *FEBS Lett.*, 543:51 (2003); Yokota et al., *EMBO Rep.*, 4:602 (2003); Schlomai et al., *Hepatology*, 37:764 (2003); Wilson et al., *Proc. Natl. Acad. Sci. USA*, 100:2783 (2003); Kapadia et al., *Proc. Natl. Acad. Sci. USA*, 100:2014 (2003); and FIELDS VIROLOGY, Knipe et al. (eds.), 4th ed., Lippincott-Raven, Philadelphia (2001)); Human Immunodeficiency Virus (HIV) (Banerjea et al., *Mol. Ther.*, 8:62 (2003); Song et al., *J. Virol.*, 77:7174 (2003); Stephenson, *JAMA*, 289:1494 (2003); Qin et al., *Proc. Natl. Acad. Sci. USA*, 100:183 (2003)); Herpes viruses (Jia et al., *J. Virol.*, 77:3301 (2003)); and Human Papilloma Viruses (HIV) (Hall et al., *J. Virol.*, 77:6066 (2003); Jiang et al., *Oncogene*, 21:6041 (2002)).

Exemplary Filovirus nucleic acid sequences that can be silenced include, but are not limited to, nucleic acid sequences encoding structural proteins (e.g., VP30, VP35, nucleoprotein (NP), polymerase protein (L-pol)) and membrane-associated proteins (e.g., VP40, glycoprotein (GP), VP24). Complete genome sequences for Ebola virus are set forth in, e.g., Genbank Accession Nos. NC_002549; AY769362; NC_006432; NC_004161; AY729654; AY354458; AY142960; AB050936; AF522874; AF499101; AF272001; and AF086833. Ebola virus VP24 sequences are set forth in, e.g., Genbank Accession Nos. U77385 and AY058897. Ebola virus L-pol sequences are set forth in, e.g., Genbank Accession No. X67110. Ebola virus VP40 sequences are set forth in, e.g., Genbank Accession No. AY058896. Ebola virus NP sequences are set forth in, e.g., Genbank Accession No. AY058895. Ebola virus GP sequences are set forth in, e.g., Genbank Accession No. AY058898; Sanchez et al., *Virus Res.*, 29:215-240 (1993); Will et al., *J. Virol.*, 67:1203-1210 (1993); Volchkov et al., *FEBS Lett.*, 305:181-184 (1992); and U.S. Pat. No. 6,713,069. Additional Ebola virus sequences are set forth in, e.g., Genbank Accession Nos. L11365 and X61274. Complete genome sequences for Marburg virus are set forth in, e.g., Genbank Accession Nos. NC_001608; AY430365; AY430366; and AY358025. Marburg virus GP sequences are set forth in, e.g., Genbank Accession Nos. AF005734; AF005733; and AF005732. Marburg virus VP35 sequences are set forth in, e.g., Genbank Accession Nos. AF005731 and AF005730. Additional Marburg virus sequences are set forth in, e.g., Genbank Accession Nos. X64406; Z29337; AF005735; and Z12132. Non-limiting examples of siRNA molecules targeting Ebola virus and Marburg virus nucleic acid sequences include those described in U.S. Patent Publication No. 20070135370 and U.S. application Ser. No. 12/840,225, filed Jul. 20, 2010, the disclosures of which are herein incorporated by reference in their entirety for all purposes.

Exemplary Arenavirus nucleic acid sequences that can be silenced include, but are not limited to, nucleic acid sequences encoding nucleoprotein (NP), glycoprotein (GP), L-polymerase (L), and Z protein (Z). Complete genome sequences for Lassa virus are set forth in, e.g., Genbank Accession Nos. NC_004296 (LASV segment S) and NC_004297 (LASV segment L). Non-limiting examples of siRNA molecules targeting Lassa virus nucleic acid sequences include those described in U.S. Provisional Application No. 61/319,855, filed Mar. 31, 2010, the disclosure of which is herein incorporated by reference in its entirety for all purposes.

Exemplary host nucleic acid sequences that can be silenced include, but are not limited to, nucleic acid sequences encoding host factors such as tissue factor (TF) that are known to play a role in the pathogenesis of hemorrhagic fever viruses. The mRNA sequence of TF is set forth in Genbank Accession No. NM_001993. Those of skill in the art will appreciate that TF is also known as F3, coagulation factor III, thromboplastin, and CD142. Non-limiting examples of siRNA molecules targeting TF nucleic acid sequences include those described in U.S. Provisional Application No. 61/319,855, filed Mar. 31, 2010, the disclosure of which is herein incorporated by reference in its entirety for all purposes.

Exemplary Influenza virus nucleic acid sequences that can be silenced include, but are not limited to, nucleic acid sequences encoding nucleoprotein (NP), matrix proteins (M1 and M2), nonstructural proteins (NS1 and NS2), RNA polymerase (PA, PB1, PB2), neuraminidase (NA), and haemagglutinin (HA). Influenza A NP sequences are set forth in, e.g., Genbank Accession Nos. NC_004522; AY818138; AB166863; AB188817; AB189046; AB189054; AB189062; AY646169; AY646177; AY651486; AY651493; AY651494; AY651495; AY651496; AY651497; AY651498; AY651499; AY651500; AY651501; AY651502; AY651503; AY651504; AY651505; AY651506; AY651507; AY651509; AY651528; AY770996; AY790308; AY818138; and AY818140. Influenza A PA sequences are set forth in, e.g., Genbank Accession Nos. AY818132; AY790280; AY646171; AY818132; AY818133; AY646179; AY818134; AY551934; AY651613; AY651610; AY651620; AY651617; AY651600; AY651611; AY651606; AY651618; AY651608; AY651607; AY651605; AY651609; AY651615; AY651616; AY651640; AY651614; AY651612; AY651621; AY651619; AY770995; and AY724786. Non-limiting examples of siRNA molecules targeting Influenza virus nucleic acid sequences include those described in U.S. Patent Publication No. 20070218122, the disclosure of which is herein incorporated by reference in its entirety for all purposes.

Exemplary hepatitis virus nucleic acid sequences that can be silenced include, but are not limited to, nucleic acid sequences involved in transcription and translation (e.g., En1, En2, X, P) and nucleic acid sequences encoding structural proteins (e.g., core proteins including C and C-related proteins, capsid and envelope proteins including S, M, and/or L proteins, or fragments thereof) (see, e.g., FIELDS VIROLOGY, supra). Exemplary Hepatitis C virus (HCV) nucleic acid sequences that can be silenced include, but are not limited to, the 5'-untranslated region (5'-UTR), the 3'-untranslated region (3'-UTR), the polyprotein translation initiation codon region, the internal ribosome entry site (IRES) sequence, and/or nucleic acid sequences encoding the core protein, the E1 protein, the E2 protein, the p7 protein, the NS2 protein, the NS3 protease/helicase, the NS4A protein, the NS4B protein, the NS5A protein, and/or the NS5B RNA-dependent RNA polymerase. HCV genome sequences are set forth in, e.g., Genbank Accession Nos. NC_004102 (HCV genotype 1a), AJ238799 (HCV genotype 1b), NC_009823 (HCV genotype 2), NC_009824 (HCV genotype 3), NC_009825 (HCV genotype 4), NC_009826 (HCV genotype 5), and NC_009827 (HCV genotype 6). Hepatitis A virus nucleic acid sequences are set forth in, e.g., Genbank Accession No. NC_001489; Hepatitis B virus nucleic acid sequences are set forth in, e.g., Genbank Accession No. NC_003977; Hepatitis D virus nucleic acid sequence are set forth in, e.g., Genbank Accession No. NC_001653; Hepatitis E virus nucleic acid sequences are set forth in, e.g., Genbank Accession No. NC_001434; and Hepatitis G virus nucleic acid sequences are set forth in, e.g., Genbank Accession No. NC_001710. Silencing of sequences that encode genes associated with viral infection and survival can conveniently be used in combination with the administration of conventional agents used to treat the viral condition. Non-limiting examples of siRNA molecules targeting hepatitis virus nucleic acid sequences include those described in U.S. Patent Publication Nos. 20060281175, 20050058982, and 20070149470; U.S. Pat. No. 7,348,314; and PCT Application No. PCT/CA2010/000444, entitled "Compositions and Methods for Silencing Hepatitis C Virus Expression," filed Mar. 19, 2010, the disclosures of which are herein incorporated by reference in their entirety for all purposes.

Genes associated with metabolic diseases and disorders (e.g., disorders in which the liver is the target and liver diseases and disorders) include, but are not limited to, genes expressed in dyslipidemia, such as, e.g., apolipoprotein B (APOB) (Genbank Accession No. NM_000384), apolipoprotein CIII (APOC3) (Genbank Accession Nos. NM_000040 and NG_008949 REGION: 5001.8164), apolipoprotein E (APOE) (Genbank Accession Nos. NM_000041 and NG_007084 REGION: 5001 . . . 8612), proprotein convertase subtilisin/kexin type 9 (PCSK9) (Genbank Accession No. NM_174936), diacylglycerol O-acyltransferase type 1 (DGAT1) (Genbank Accession No. NM_012079), diacylglycerol O-acyltransferase type 2 (DGAT2) (Genbank Accession No. NM_032564), liver X receptors such as LXRα and LXRβ (Genbank Accession No. NM_007121), farnesoid X receptors (FXR) (Genbank Accession No. NM_005123), sterol-regulatory element binding protein (SREBP), site-1 protease (S1P), 3-hydroxy-3-methylglutaryl coenzyme-A reductase (HMG coenzyme-A reductase); and genes expressed in diabetes, such as, e.g., glucose 6-phosphatase (see, e.g., Forman et al., *Cell*, 81:687 (1995); Seol et al., *Mol. Endocrinol.*, 9:72 (1995), Zavacki et al., *Proc. Natl. Acad. Sci. USA*, 94:7909 (1997); Sakai et al., *Cell*, 85:1037-1046 (1996); Duncan et al., *J. Biol. Chem.*, 272:12778-12785 (1997); Willy et al., *Genes Dev.*, 9:1033-1045 (1995); Lehmann et al., *J. Biol. Chem.*, 272:3137-3140 (1997); Janowski et al., *Nature*, 383:728-731 (1996); and Peet et al., *Cell*, 93:693-704 (1998)).

One of skill in the art will appreciate that genes associated with metabolic diseases and disorders (e.g., diseases and disorders in which the liver is a target and liver diseases and disorders) include genes that are expressed in the liver itself as well as and genes expressed in other organs and tissues. Silencing of sequences that encode genes associated with metabolic diseases and disorders can conveniently be used in combination with the administration of conventional agents used to treat the disease or disorder. Non-limiting examples of siRNA molecules targeting the APOB gene include those described in U.S. Patent Publication Nos. 20060134189, 20060105976, and 20070135372, and PCT Publication No. WO 04/091515, the disclosures of which are herein incorporated by reference in their entirety for all purposes. Non-limiting examples of siRNA molecules targeting the APOC3 gene include those described in PCT Application No. PCT/CA2010/000120, filed Jan. 26, 2010, the disclosure of which is herein incorporated by reference in its entirety for all purposes. Non-limiting examples of siRNA molecules targeting the PCSK9 gene include those described in U.S. Patent Publication Nos. 20070173473, 20080113930, and 20080306015, the disclosures of which are herein incorporated by reference in their entirety for all purposes. Exemplary siRNA molecules targeting the DGAT1 gene may be designed using the antisense compounds described in U.S. Patent Publication No. 20040185559, the disclosure of which is herein incorporated by reference in its entirety for all purposes. Exemplary siRNA molecules targeting the DGAT2 gene may be designed using the antisense compounds described in U.S. Patent Publication No. 20050043524, the disclosure of which is herein incorporated by reference in its entirety for all purposes.

Genes associated with tumorigenesis or cell transformation (e.g., cancer or other neoplasia) include, for example, genes involved in p53 ubiquitination, c-Jun ubiquitination, histone deacetylation, cell cycle regulation, transcriptional regulation, and combinations thereof. Non-limiting examples of gene sequences associated with tumorigenesis or cell transformation include serine/threonine kinases such as polo-like kinase 1 (PLK-1) (Genbank Accession No. NM_005030; Barr et al., *Nat. Rev. Mol. Cell Biol.*, 5:429-440 (2004)) and cyclin-dependent kinase 4 (CDK4) (Genbank Accession No. NM_000075); ubiquitin ligases such as COP1 (RFWD2; Genbank Accession Nos. NM_022457 and NM_001001740) and ring-box 1 (RBX1) (ROC1; Genbank Accession No. NM_014248); tyrosine kinases such as WEE1 (Genbank Accession Nos. NM_003390 and NM_001143976); mitotic kinesins such as Eg5 (KSP, KIF11; Genbank Accession No. NM_004523); transcription factors such as forkhead box M1 (FOXM1) (Genbank Accession Nos. NM_202002, NM_021953, and NM_202003) and RAM2 (R1 or CDCA7L; Genbank Accession Nos. NM_018719, NM_001127370, and NM_001127371); inhibitors of apoptosis such as XIAP (Genbank Accession No. NM_001167); COP9 signalosome subunits such as CSN1, CSN2, CSN3, CSN4, CSN5 (JAB1; Genbank Accession No. NM_006837); CSN6, CSN7A, CSN7B, and CSN8; and histone deacetylases such as HDAC1, HDAC2 (Genbank Accession No. NM_001527), HDAC3, HDAC4, HDAC5, HDAC6, HDAC7, HDAC8, HDAC9, etc.

Non-limiting examples of siRNA molecules targeting the PLK-1 gene include those described in U.S. Patent Publication Nos. 20050107316 and 20070265438; and PCT Publication No. WO 09/082,817, the disclosures of which are herein incorporated by reference in their entirety for all purposes. Non-limiting examples of siRNA molecules targeting the Eg5 and XIAP genes include those described in U.S. Patent Publication No. 20090149403, the disclosure of which is herein incorporated by reference in its entirety for all purposes. Non-limiting examples of siRNA molecules targeting the CSN5 gene include those described in PCT Publication No. WO 09/129,319, the disclosure of which is herein incorporated by reference in its entirety for all purposes. Non-limiting examples of siRNA molecules targeting the COP1, CSN5, RBX1, HDAC2, CDK4, WEE1, FOXM1, and RAM2 genes include those described in U.S. Provisional Application No. 61/245,143, filed Sep. 23, 2009, the disclosure of which is herein incorporated by reference in its entirety for all purposes.

Additional examples of gene sequences associated with tumorigenesis or cell transformation include translocation sequences such as MLL fusion genes, BCR-ABL (Wilda et al., *Oncogene*, 21:5716 (2002); Scherr et al., *Blood*, 101:1566 (2003)), TEL-AML1, EWS-FLI1, TLS-FUS, PAX3-FKHR, BCL-2, AML1-ETO, and AML1-MTG8 (Heidenreich et al., *Blood*, 101:3157 (2003)); overexpressed sequences such as multidrug resistance genes (Nieth et al., *FEBS Lett.*, 545:144 (2003); Wu et al, *Cancer Res.* 63:1515 (2003)), cyclins (Li et al., *Cancer Res.*, 63:3593 (2003); Zou et al., *Genes Dev.*, 16:2923 (2002)), beta-catenin (Verma et al., *Clin Cancer Res.*, 9:1291 (2003)), telomerase genes (Kosciolek et al., *Mol Cancer Ther.*, 2:209 (2003)), c-MYC, N-MYC, BCL-2, growth factor receptors (e.g., EGFR/ErbB1 (Genbank Accession Nos. NM_005228, NM_201282, NM_201283, and NM_201284; see also, Nagy et al. *Exp. Cell Res.*, 285:39-49 (2003)), ErbB2/HER-2 (Genbank Accession Nos. NM_004448 and NM_001005862), ErbB3 (Genbank Accession Nos. NM_001982 and NM_001005915), and ErbB4 (Genbank Accession Nos. NM_005235 and NM_001042599)), and mutated sequences such as RAS (Tuschl and Borkhardt, *Mol. Interventions*, 2:158 (2002)). Non-limiting examples of siRNA molecules targeting the EGFR gene include those described in U.S. Patent Publication No. 20090149403, the disclosure of which is herein incorporated by reference in its entirety for all purposes. siRNA molecules that target VEGFR genes are set forth in, e.g., GB 2396864; U.S. Patent Publication No. 20040142895; and CA 2456444, the disclosures of which are herein incorporated by reference in their entirety for all purposes.

Silencing of sequences that encode DNA repair enzymes find use in combination with the administration of chemotherapeutic agents (Collis et al., *Cancer Res.*, 63:1550 (2003)). Genes encoding proteins associated with tumor migration are also target sequences of interest, for example, integrins, selectins, and metalloproteinases. The foregoing examples are not exclusive. Those of skill in the art will understand that any whole or partial gene sequence that facilitates or promotes tumorigenesis or cell transformation, tumor growth, or tumor migration can be included as a template sequence.

Angiogenic genes are able to promote the formation of new vessels. Angiogenic genes of particular interest include, but are not limited to, vascular endothelial growth factor (VEGF) (Reich et al., *Mol. Vis.*, 9:210 (2003)), placental growth factor (PGF), VEGFR-1 (Flt-1), VEGFR-2 (KDR/Flk-1), and the like. siRNA molecules that target VEGFR genes are set forth in, e.g., GB 2396864; U.S. Patent Publication No. 20040142895; and CA 2456444, the disclosures of which are herein incorporated by reference in their entirety for all purposes.

Immunomodulator genes are genes that modulate one or more immune responses. Examples of immunomodulator genes include, without limitation, growth factors (e.g., TGF-α, TGF-β, EGF, FGF, IGF, NGF, PDGF, CGF, GM-CSF, SCF, etc.), interleukins (e.g., IL-2, IL-4, IL-12 (Hill et al., *J. Immunol.*, 171:691 (2003)), IL-15, IL-18, IL-20, etc.), interferons (e.g., IFN-α, IFN-β, IFN-γ, etc.), and TNF. Fas and Fas ligand genes are also immunomodulator target sequences of interest (Song et al., *Nat. Med.*, 9:347 (2003)). Genes encoding secondary signaling molecules in hematopoietic and lymphoid cells are also included in the present invention, for example, Tec family kinases such as Bruton's tyrosine kinase (Btk) (Heinonen et al., *FEBS Lett.*, 527:274 (2002)).

Cell receptor ligand genes include ligands that are able to bind to cell surface receptors (e.g., cytokine receptors, growth factor receptors, receptors with tyrosine kinase activity, G-protein coupled receptors, insulin receptor, EPO receptor, etc.) to modulate (e.g., inhibit) the physiological pathway that the receptor is involved in (e.g., cell proliferation, tumorigenesis, cell transformation, mitogenesis, etc.). Non-limiting examples of cell receptor ligand genes include cytokines (e.g., TNF-α, interferons such as IFN-α, IFN-β, and IFN-γ, interleukins such as IL-1α, IL-1β, IL-2, IL-4, IL-5, IL-6, IL-7, IL-8, IL-9, IL-10, IL-12, IL-13, IL-15, IL-17, IL-23, IL-27, chemokines, etc.), growth factors (e.g., EGF, HB-EGF, VEGF, PEDF, SDGF, bFGF, HGF, TGF-α, TGF-β, BMP1-BMP15, PDGF, IGF, NGF, β-NGF, BDNF, NT3, NT4, GDF-9, CGF, G-CSF, GM-CSF, GDF-8, EPO, TPO, etc.), insulin, glucagon, G-protein coupled receptor ligands, etc.

Templates coding for an expansion of trinucleotide repeats (e.g., CAG repeats) find use in silencing pathogenic sequences in neurodegenerative disorders caused by the expansion of trinucleotide repeats, such as spinobulbular muscular atrophy and Huntington's Disease (Caplen et al., *Hum. Mol. Genet.*, 11:175 (2002)).

In addition to its utility in silencing the expression of any of the above-described genes for therapeutic purposes, the siRNA described herein are also useful in research and development applications as well as diagnostic, prophylactic, prognostic, clinical, and other healthcare applications. As a non-limiting example, the siRNA can be used in target validation studies directed at testing whether a gene of interest has the potential to be a therapeutic target. The siRNA can also be used in target identification studies aimed at discovering genes as potential therapeutic targets.

e) Exemplary siRNA Embodiments

In some embodiments, each strand of the siRNA molecule comprises from about 15 to about 60 nucleotides in length (e.g., about 15-60, 15-50, 15-40, 15-30, 15-25, or 19-25 nucleotides in length, or 15, 16, 17, 18, 19, 20, 21, 22, 23, 24, or 25 nucleotides in length). In one particular embodiment, the siRNA is chemically synthesized. The siRNA molecules of the invention are capable of silencing the expression of a target sequence in vitro and/or in vivo.

In other embodiments, the siRNA comprises at least one modified nucleotide. In certain embodiments, the siRNA comprises one, two, three, four, five, six, seven, eight, nine, ten, or more modified nucleotides in the double-stranded region. In particular embodiments, less than about 50% (e.g., less than about 50%, 45%, 40%, 35%, 30%, 25%, 20%, 15%, 10%, or 5%) of the nucleotides in the double-stranded region of the siRNA comprise modified nucleotides. In preferred embodiments, from about 1% to about 50% (e.g., from about 5% 50%, 10%-50%, 15%-50%, 20%-50%, 25%-50%, 30%-50%, 35%-50%, 40%-50%, 45%-50%, 5%-45%, 10%-45%, 15%-45%, 20%-45%, 25%-45%, 30%-45%, 35%-45%, 40%-45%, 5%-40%, 10%-40%, 15%-40%, 20%-40%, 25%-40%, 30%-40%, 35%-40%, 5%-35%, 10%-35%, 15%-35%, 20%-35%, 25%-35%, 30%-35%, 5%-30%, 10%-30%, 15%-30%, 20%-30%, 25%-30%, 5%-25%, 10%-25%, 15%-25%, 20%-25%, 5%-20%, 10%-20%, 15%-20%, 5%-15%, 10%15%, or 5%-10%) of the nucleotides in the double-stranded region of the siRNA comprise modified nucleotides.

In further embodiments, the siRNA comprises modified nucleotides including, but not limited to, 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, locked nucleic acid (LNA) nucleotides, and mixtures thereof. In preferred embodiments, the siRNA comprises 2'OMe nucleotides (e.g., 2'OMe purine and/or pyrimidine nucleotides) such as, e.g., 2'OMe-guanosine nucleotides, 2'OMe-uridine nucleotides, 2'OMe-adenosine nucleotides, 2'OMe-cytosine nucleotides, or mixtures thereof. In one particular embodiment, the siRNA comprises at least one 2'OMe-guanosine nucleotide, 2'OMe-uridine nucleotide, or mixtures thereof. In certain instances, the siRNA does not comprise 2'OMe-cytosine nucleotides. In other embodiments, the siRNA comprises a hairpin loop structure.

In certain embodiments, the siRNA comprises modified nucleotides in one strand (i.e., sense or antisense) or both strands of the double-stranded region of the siRNA molecule. Preferably, uridine and/or guanosine nucleotides are modified at selective positions in the double-stranded region of the siRNA duplex. With regard to uridine nucleotide modifications, at least one, two, three, four, five, six, or more of the uridine nucleotides in the sense and/or antisense strand can be a modified uridine nucleotide such as a 2'OMe-uridine nucleotide. In some embodiments, every uridine nucleotide in the sense and/or antisense strand is a 2'OMe-uridine nucleotide. With regard to guanosine nucleotide modifications, at least one, two, three, four, five, six, or more of the guanosine nucleotides in the sense and/or antisense strand can be a modified guanosine nucleotide such as a 2'OMe-guanosine nucleotide. In some embodiments, every guanosine nucleotide in the sense and/or antisense strand is a 2'OMe-guanosine nucleotide.

In certain embodiments, at least one, two, three, four, five, six, seven, or more 5'-GU-3' motifs in an siRNA sequence may be modified, e.g., by introducing mismatches to eliminate the 5'-GU-3' motifs and/or by introducing modified nucleotides such as 2'OMe nucleotides. The 5'-GU-3' motif can be in the sense strand, the antisense strand, or both strands of the siRNA sequence. The 5'-GU-3' motifs may be adjacent to each other or, alternatively, they may be separated by 1, 2, 3, 4, 5, 6, 7, 8, 9, 10, 11, 12, or more nucleotides.

In some embodiments, a modified siRNA molecule is less immunostimulatory than a corresponding unmodified siRNA sequence. In such embodiments, the modified siRNA molecule with reduced immunostimulatory properties advantageously retains RNAi activity against the target sequence. In another embodiment, the immunostimulatory properties of the modified siRNA molecule and its ability to silence target gene expression can be balanced or optimized by the introduction of minimal and selective 2'OMe modifications within the siRNA sequence such as, e.g., within the double-stranded region of the siRNA duplex. In certain instances, the modified siRNA is at least about 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% less immunostimulatory than the corresponding unmodified siRNA. It will be readily apparent to those of skill in the art that the immunostimulatory properties of the modified siRNA molecule and the corresponding unmodified siRNA molecule can be determined by, for example, measuring INF-α and/or IL-6 levels from about two to about twelve hours after systemic administration in a mammal or transfection of a mammalian responder cell using an appropriate lipid-based delivery system (such as the SNALP delivery system disclosed herein).

In other embodiments, a modified siRNA molecule has an $IC_{50}$ (i.e., half-maximal inhibitory concentration) less than or equal to ten-fold that of the corresponding unmodified siRNA (i.e., the modified siRNA has an $IC_{50}$ that is less than or equal to ten-times the $IC_{50}$ of the corresponding unmodified siRNA). In other embodiments, the modified siRNA has an $IC_{50}$ less than or equal to three-fold that of the corresponding unmodified siRNA sequence. In yet other embodiments, the modified siRNA has an $IC_{50}$ less than or equal to two-fold that of the corresponding unmodified siRNA. It will be readily apparent to those of skill in the art that a dose-response curve can be generated and the $IC_{50}$ values for the modified siRNA and the corresponding unmodified siRNA can be readily determined using methods known to those of skill in the art.

In another embodiment, an unmodified or modified siRNA molecule is capable of silencing at least about 5%, 10%, 15%, 20%, 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the expression of the target sequence relative to a negative control (e.g., buffer only, an siRNA sequence that targets a different gene, a scrambled siRNA sequence, etc.).

In yet another embodiment, a modified siRNA molecule is capable of silencing at least about 5%, 10%, 15%, 20%, 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the expression of the target sequence relative to the corresponding unmodified siRNA sequence.

In some embodiments, the siRNA molecule does not comprise phosphate backbone modifications, e.g., in the sense and/or antisense strand of the double-stranded region. In other embodiments, the siRNA comprises one, two, three, four, or more phosphate backbone modifications, e.g., in the sense and/or antisense strand of the double-stranded region. In preferred embodiments, the siRNA does not comprise phosphate backbone modifications.

In further embodiments, the siRNA does not comprise 2'-deoxy nucleotides, e.g., in the sense and/or antisense strand of the double-stranded region. In yet further embodiments, the siRNA comprises one, two, three, four, or more 2'-deoxy nucleotides, e.g., in the sense and/or antisense strand of the double-stranded region. In preferred embodiments, the siRNA does not comprise 2'-deoxy nucleotides.

In certain instances, the nucleotide at the 3'-end of the double-stranded region in the sense and/or antisense strand is not a modified nucleotide. In certain other instances, the nucleotides near the 3'-end (e.g., within one, two, three, or four nucleotides of the 3'-end) of the double-stranded region in the sense and/or antisense strand are not modified nucleotides.

The siRNA molecules described herein may have 3' overhangs of one, two, three, four, or more nucleotides on one or both sides of the double-stranded region, or may lack overhangs (i.e., have blunt ends) on one or both sides of the double-stranded region. In certain embodiments, the 3' overhang on the sense and/or antisense strand independently comprises one, two, three, four, or more modified nucleotides such as 2'OMe nucleotides and/or any other modified nucleotide described herein or known in the art.

In particular embodiments, siRNAs are administered using a carrier system such as a nucleic acid-lipid particle. In a preferred embodiment, the nucleic acid-lipid particle comprises: (a) one or more siRNA molecules; (b) a cationic lipid of Formula I or a salt thereof; and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA and/or POZ-DAA).

2. Dicer-Substrate dsRNA

As used herein, the term "Dicer-substrate dsRNA" or "precursor RNAi molecule" is intended to include any precursor molecule that is processed in vivo by Dicer to produce an active siRNA which is incorporated into the RISC complex for RNA interference of a target gene.

In one embodiment, the Dicer-substrate dsRNA has a length sufficient such that it is processed by Dicer to produce an siRNA. According to this embodiment, the Dicer-substrate dsRNA comprises (i) a first oligonucleotide sequence (also termed the sense strand) that is between about 25 and about 60 nucleotides in length (e.g., about 25-60, 25-55, 25-50, 25-45, 25-40, 25-35, or 25-30 nucleotides in length), preferably between about 25 and about 30 nucleotides in length (e.g., 25, 26, 27, 28, 29, or 30 nucleotides in length), and (ii) a second oligonucleotide sequence (also termed the antisense strand) that anneals to the first sequence under biological conditions, such as the conditions found in the cytoplasm of a cell. The second oligonucleotide sequence may be between about 25 and about 60 nucleotides in length (e.g., about 25-60, 25-55, 25-50, 25-45, 25-40, 25-35, or 25-30 nucleotides in length), and is preferably between about 25 and about 30 nucleotides in length (e.g., 25, 26, 27, 28, 29, or 30 nucleotides in length). In addition, a region of one of the sequences, particularly of the antisense strand, of the Dicer-substrate dsRNA has a sequence length of at least about 19 nucleotides, for example, from about 19 to about 60 nucleotides (e.g., about 19-60, 19-55, 19-50, 19-45, 19-40, 19-35, 19-30, or 19-25 nucleotides), preferably from about 19 to about 23 nucleotides (e.g., 19, 20, 21, 22, or 23 nucleotides) that are sufficiently complementary to a nucleotide sequence of the RNA produced from the target gene to trigger an RNAi response.

In a second embodiment, the Dicer-substrate dsRNA has several properties which enhance its processing by Dicer. According to this embodiment, the dsRNA has a length sufficient such that it is processed by Dicer to produce an siRNA and has at least one of the following properties: (i) the dsRNA is asymmetric, e.g., has a 3'-overhang on the antisense strand; and/or (ii) the dsRNA has a modified 3'-end on the sense strand to direct orientation of Dicer binding and processing of the dsRNA to an active siRNA. According to this latter embodiment, the sense strand comprises from about 22 to about 28 nucleotides and the antisense strand comprises from about 24 to about 30 nucleotides.

In one embodiment, the Dicer-substrate dsRNA has an overhang on the 3'-end of the antisense strand. In another embodiment, the sense strand is modified for Dicer binding and processing by suitable modifiers located at the 3'-end of the sense strand. Suitable modifiers include nucleotides such as deoxyribonucleotides, acyclonucleotides, and the like, and sterically hindered molecules such as fluorescent molecules and the like. When nucleotide modifiers are used, they replace ribonucleotides in the dsRNA such that the length of the dsRNA does not change. In another embodiment, the Dicer-substrate dsRNA has an overhang on the 3'-end of the antisense strand and the sense strand is modified for Dicer processing. In another embodiment, the 5'-end of the sense strand has a phosphate. In another embodiment, the 5'-end of the antisense strand has a phosphate. In another embodiment, the antisense strand or the sense strand or both strands have one or more 2'-β-methyl (2'OMe) modified nucleotides. In another embodiment, the antisense strand contains 2'OMe modified nucleotides. In another embodiment, the antisense stand contains a 3'-overhang that is comprised of 2'OMe modified nucleotides. The antisense strand could also include additional 2'OMe modified nucleotides. The sense and antisense strands anneal under biological conditions, such as the conditions found in the cytoplasm of a cell. In addition, a region of one of the sequences, particularly of the antisense strand, of the Dicer-substrate dsRNA has a sequence length of at least about 19 nucleotides, wherein these nucleotides are in the 21-nucleotide region adjacent to the 3'-end of the antisense strand and are sufficiently complementary to a nucleotide sequence of the RNA produced from the target gene. Further, in accordance with this embodiment, the Dicer-substrate dsRNA may also have one or more of the following additional properties: (a) the antisense strand has a right shift from the typical 21-mer (i.e., the antisense strand includes nucleotides on the right side of the molecule when compared to the typical 21-mer); (b) the strands may not be completely complementary, i.e., the strands may contain simple mismatch pairings; and (c) base modifications such as locked nucleic acid(s) may be included in the 5'-end of the sense strand.

In a third embodiment, the sense strand comprises from about 25 to about 28 nucleotides (e.g., 25, 26, 27, or 28 nucleotides), wherein the 2 nucleotides on the 3'-end of the sense strand are deoxyribonucleotides. The sense strand contains a phosphate at the 5'-end. The antisense strand comprises from about 26 to about 30 nucleotides (e.g., 26, 27, 28, 29, or 30 nucleotides) and contains a 3'-overhang of 1-4 nucleotides. The nucleotides comprising the 3'-overhang are modified with 2'OMe modified ribonucleotides. The antisense strand contains alternating 2'OMe modified nucleotides beginning at the first monomer of the antisense strand adjacent to the 3'-overhang, and extending 15-19 nucleotides from the first monomer adjacent to the 3'-overhang. For example, for a 27-nucleotide antisense strand and counting the first base at the 5'-end of the antisense strand as position number 1, 2'OMe modifications would be placed at bases 9, 11, 13, 15, 17, 19, 21, 23, 25, 26, and 27. In one embodiment, the Dicer-substrate dsRNA has the following structure:

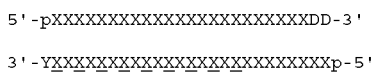

wherein "X"=RNA, "p"=a phosphate group, "X"=2'OMe RNA, "Y" is an overhang domain comprised of $\overline{1}$, 2, 3, or 4 RNA monomers that are optionally 2'OMe RNA monomers, and "D"=DNA. The top strand is the sense strand, and the bottom strand is the antisense strand.

In a fourth embodiment, the Dicer-substrate dsRNA has several properties which enhance its processing by Dicer. According to this embodiment, the dsRNA has a length sufficient such that it is processed by Dicer to produce an siRNA and at least one of the following properties: (i) the dsRNA is asymmetric, e.g., has a 3'-overhang on the sense strand; and (ii) the dsRNA has a modified 3'-end on the antisense strand to direct orientation of Dicer binding and processing of the dsRNA to an active siRNA. According to this embodiment, the sense strand comprises from about 24 to about 30 nucleotides (e.g., 24, 25, 26, 27, 28, 29, or 30 nucleotides) and the antisense strand comprises from about 22 to about 28 nucleotides (e.g., 22, 23, 24, 25, 26, 27, or 28 nucleotides). In one embodiment, the Dicer-substrate dsRNA has an overhang on the 3'-end of the sense strand. In another embodiment, the antisense strand is modified for Dicer binding and processing by suitable modifiers located at the 3'-end of the antisense strand. Suitable modifiers include nucleotides such as deoxyribonucleotides, acyclonucleotides, and the like, and sterically hindered molecules such as fluorescent molecules and the like. When nucleotide modifiers are used, they replace ribonucleotides in the dsRNA such that the length of the dsRNA does not change. In another embodiment, the dsRNA has an overhang on the 3'-end of the sense strand and the antisense strand is modified for Dicer processing. In one embodiment, the antisense strand has a 5'-phosphate. The sense and antisense strands anneal under biological conditions, such as the conditions found in the cytoplasm of a cell. In addition, a region of one of the sequences, particularly of the antisense strand, of the dsRNA has a sequence length of at least 19 nucleotides, wherein these nucleotides are adjacent to the 3'-end of antisense strand and are sufficiently complementary to a nucleotide sequence of the RNA produced from the target gene. Further, in accordance with this embodiment, the Dicer-substrate dsRNA may also have one or more of the following additional properties: (a) the antisense strand has a left shift from the typical 21-mer (i.e., the antisense strand includes nucleotides on the left side of the molecule when compared to the typical 21-mer); and (b) the strands may not be completely complementary, i.e., the strands may contain simple mismatch pairings.

In a preferred embodiment, the Dicer-substrate dsRNA has an asymmetric structure, with the sense strand having a 25-base pair length, and the antisense strand having a 27-base pair length with a 2 base 3'-overhang. In certain instances, this dsRNA having an asymmetric structure further contains 2 deoxynucleotides at the 3'-end of the sense strand in place of two of the ribonucleotides. In certain other instances, this dsRNA having an asymmetric structure further contains 2'OMe modifications at positions 9, 11, 13, 15, 17, 19, 21, 23, and 25 of the antisense strand (wherein the first base at the 5'-end of the antisense strand is position 1). In certain additional instances, this dsRNA having an asymmetric structure further contains a 3'-overhang on the antisense strand comprising 1, 2, 3, or 4 2'OMe nucleotides (e.g., a 3'-overhang of 2'OMe nucleotides at positions 26 and 27 on the antisense strand).

In another embodiment, Dicer-substrate dsRNAs may be designed by first selecting an antisense strand siRNA sequence having a length of at least 19 nucleotides. In some instances, the antisense siRNA is modified to include about 5 to about 11 ribonucleotides on the 5'-end to provide a length of about 24 to about 30 nucleotides. When the antisense strand has a length of 21 nucleotides, 3-9, preferably 4-7, or more preferably 6 nucleotides may be added on the 5'-end. Although the added ribonucleotides may be complementary to the target gene sequence, full complementarity between the target sequence and the antisense siRNA is not required. That is, the resultant antisense siRNA is sufficiently complementary with the target sequence. A sense strand is then produced that has about 22 to about 28 nucleotides. The sense strand is substantially complementary with the antisense strand to anneal to the antisense strand under biological conditions. In one embodiment, the sense strand is synthesized to contain a modified 3'-end to direct Dicer processing of the antisense strand. In another embodiment, the antisense strand of the dsRNA has a 3'-overhang. In a further embodiment, the sense strand is synthesized to contain a modified 3'-end for Dicer binding and processing and the antisense strand of the dsRNA has a 3'-overhang.

In a related embodiment, the antisense siRNA may be modified to include about 1 to about 9 ribonucleotides on the 5'-end to provide a length of about 22 to about 28 nucleotides. When the antisense strand has a length of 21 nucleotides, 1-7, preferably 2-5, or more preferably 4 ribonucleotides may be added on the 3'-end. The added ribonucleotides may have any sequence. Although the added ribonucleotides may be complementary to the target gene sequence, full complementarity between the target sequence and the antisense siRNA is not required. That is, the resultant antisense siRNA is sufficiently complementary with the target sequence. A sense strand is then produced that has about 24 to about 30 nucleotides. The sense strand is substantially complementary with the antisense strand to anneal to the antisense strand under biological conditions. In one embodiment, the antisense strand is synthesized to contain a modified 3'-end to direct Dicer processing. In another embodiment, the sense strand of the dsRNA has a 3'-overhang. In a further embodiment, the antisense strand is synthesized to contain a modified 3'-end for Dicer binding and processing and the sense strand of the dsRNA has a 3'-overhang.

Suitable Dicer-substrate dsRNA sequences can be identified, synthesized, and modified using any means known in the art for designing, synthesizing, and modifying siRNA sequences. In particular embodiments, Dicer-substrate dsRNAs are administered using a carrier system such as a nucleic acid-lipid particle. In a preferred embodiment, the nucleic acid-lipid particle comprises: (a) one or more Dicer-substrate dsRNA molecules; (b) a cationic lipid of Formula I or a salt thereof; and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA and/or POZ-DAA).

Additional embodiments related to the Dicer-substrate dsRNAs of the invention, as well as methods of designing and synthesizing such dsRNAs, are described in U.S. Patent Publication Nos. 20050244858, 20050277610, and 20070265220, and U.S. application Ser. No. 12/794,701, filed Jun. 4, 2010, the disclosures of which are herein incorporated by reference in their entirety for all purposes.

3. shRNA

A "small hairpin RNA" or "short hairpin RNA" or "shRNA" includes a short RNA sequence that makes a tight hairpin turn that can be used to silence gene expression via RNA interference. The shRNAs of the invention may be chemically synthesized or transcribed from a transcriptional cassette in a DNA plasmid. The shRNA hairpin structure is cleaved by the cellular machinery into siRNA, which is then bound to the RNA-induced silencing complex (RISC).

The shRNAs of the invention are typically about 15-60, 15-50, or 15-40 (duplex) nucleotides in length, more typically about 15-30, 15-25, or 19-25 (duplex) nucleotides in length, and are preferably about 20-24, 21-22, or 21-23 (duplex) nucleotides in length (e.g., each complementary sequence of the double-stranded shRNA is 15-60, 15-50, 15-40, 15-30, 15-25, or 19-25 nucleotides in length, preferably about 20-24, 21-22, or 21-23 nucleotides in length, and the double-stranded shRNA is about 15-60, 15-50, 15-40, 15-30, 15-25, or 19-25 base pairs in length, preferably about 18-22, 19-20, or 19-21 base pairs in length). shRNA duplexes may comprise 3' overhangs of about 1 to about 4 nucleotides or about 2 to about 3 nucleotides on the antisense strand and/or 5'-phosphate termini on the sense strand. In some embodiments, the shRNA comprises a sense strand and/or antisense strand sequence of from about 15 to about 60 nucleotides in length (e.g., about 15-60, 15-55, 15-50, 15-45, 15-40, 15-35, 15-30, or 15-25 nucleotides in length), preferably from about 19 to about 40 nucleotides in length (e.g., about 19-40, 19-35, 19-30, or 19-25 nucleotides in length), more preferably from about 19 to about 23 nucleotides in length (e.g., 19, 20, 21, 22, or 23 nucleotides in length).

Non-limiting examples of shRNA include a double-stranded polynucleotide molecule assembled from a single-stranded molecule, where the sense and antisense regions are linked by a nucleic acid-based or non-nucleic acid-based linker; and a double-stranded polynucleotide molecule with a hairpin secondary structure having self-complementary sense and antisense regions. In preferred embodiments, the sense and antisense strands of the shRNA are linked by a loop structure comprising from about 1 to about 25 nucleotides, from about 2 to about 20 nucleotides, from about 4 to about 15 nucleotides, from about 5 to about 12 nucleotides, or 1, 2, 3, 4, 5, 6, 7, 8, 9, 10, 11, 12, 13, 14, 15, 16, 17, 18, 19, 20, 21, 22, 23, 24, 25, or more nucleotides.

Suitable shRNA sequences can be identified, synthesized, and modified using any means known in the art for designing, synthesizing, and modifying siRNA sequences. In particular embodiments, shRNAs are administered using a carrier system such as a nucleic acid-lipid particle. In a preferred embodiment, the nucleic acid-lipid particle comprises: (a) one or more shRNA molecules; (b) a cationic lipid of Formula I or a salt thereof; and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA and/or POZ-DAA).

Additional embodiments related to the shRNAs of the invention, as well as methods of designing and synthesizing such shRNAs, are described in U.S. application Ser. No. 12/794,701, filed Jun. 4, 2010, the disclosure of which is herein incorporated by reference in its entirety for all purposes.

4. aiRNA

Like siRNA, asymmetrical interfering RNA (aiRNA) can recruit the RNA-induced silencing complex (RISC) and lead to effective silencing of a variety of genes in mammalian cells by mediating sequence-specific cleavage of the target sequence between nucleotide 10 and 11 relative to the 5' end of the antisense strand (Sun et al., *Nat. Biotech.*, 26:1379-1382 (2008)). Typically, an aiRNA molecule comprises a short RNA duplex having a sense strand and an antisense strand, wherein the duplex contains overhangs at the 3' and 5' ends of the antisense strand. The aiRNA is generally asymmetric because the sense strand is shorter on both ends when compared to the complementary antisense strand. In some aspects, aiRNA molecules may be designed, synthesized, and annealed under conditions similar to those used for siRNA molecules. As a non-limiting example, aiRNA sequences may be selected and generated using the methods described above for selecting siRNA sequences.

In another embodiment, aiRNA duplexes of various lengths (e.g., about 10-25, 12-20, 12-19, 12-18, 13-17, or 14-17 base pairs, more typically 12, 13, 14, 15, 16, 17, 18, 19, or base pairs) may be designed with overhangs at the 3' and 5' ends of the antisense strand to target an mRNA of interest. In certain instances, the sense strand of the aiRNA molecule is about 10-25, 12-20, 12-19, 12-18, 13-17, or 14-17 nucleotides in length, more typically 12, 13, 14, 15, 16, 17, 18, 19, or 20 nucleotides in length. In certain other instances, the antisense strand of the aiRNA molecule is about 15-60, 15-50, or 15-40 nucleotides in length, more typically about 15-30, 15-25, or 19-25 nucleotides in length, and is preferably about 20-24, 21-22, or 21-23 nucleotides in length.

In some embodiments, the 5' antisense overhang contains one, two, three, four, or more nontargeting nucleotides (e.g., "AA", "UU", "dTdT", etc.). In other embodiments, the 3' antisense overhang contains one, two, three, four, or more nontargeting nucleotides (e.g., "AA", "UU", "dTdT", etc.). In certain aspects, the aiRNA molecules described herein may comprise one or more modified nucleotides, e.g., in the double-stranded (duplex) region and/or in the antisense overhangs. As a non-limiting example, aiRNA sequences may comprise one or more of the modified nucleotides described above for siRNA sequences. In a preferred embodiment, the aiRNA molecule comprises 2'OMe nucleotides such as, for example, 2'OMe-guanosine nucleotides, 2'OMe-uridine nucleotides, or mixtures thereof.

In certain embodiments, aiRNA molecules may comprise an antisense strand which corresponds to the antisense strand of an siRNA molecule, e.g., one of the siRNA molecules described herein. In particular embodiments, aiRNAs are administered using a carrier system such as a nucleic acid-lipid particle. In a preferred embodiment, the nucleic acid-lipid particle comprises: (a) one or more aiRNA molecules; (b) a cationic lipid of Formula I or a salt thereof; and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA and/or POZ-DAA).

Suitable aiRNA sequences can be identified, synthesized, and modified using any means known in the art for designing, synthesizing, and modifying siRNA sequences. Additional embodiments related to the aiRNA molecules of the invention are described in U.S. Patent Publication No. 20090291131 and PCT Publication No. WO 09/127,060, the disclosures of which are herein incorporated by reference in their entirety for all purposes.

5. miRNA

Generally, microRNAs (miRNA) are single-stranded RNA molecules of about 21-23 nucleotides in length which regulate gene expression. miRNAs are encoded by genes from whose DNA they are transcribed, but miRNAs are not translated into protein (non-coding RNA); instead, each primary transcript (a pri-miRNA) is processed into a short stem-loop structure called a pre-miRNA and finally into a functional mature miRNA. Mature miRNA molecules are either partially or completely complementary to one or more messenger RNA (mRNA) molecules, and their main function is to downregulate gene expression. The identification of miRNA molecules is described, e.g., in Lagos-Quintana et al., *Science*, 294:853-858; Lau et al., *Science*, 294:858-862; and Lee et al., *Science*, 294:862-864.

The genes encoding miRNA are much longer than the processed mature miRNA molecule. miRNA are first transcribed as primary transcripts or pri-miRNA with a cap and poly-A tail and processed to short, ~70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha (Denli et al., *Nature*, 432:231-235 (2004)). These pre-miRNA are then processed to mature miRNA in the cytoplasm by interaction with the endonuclease Dicer, which also initiates the formation of the RNA-induced silencing complex (RISC) (Bernstein et al., *Nature*, 409:363-366 (2001). Either the sense strand or antisense strand of DNA can function as templates to give rise to miRNA.

When Dicer cleaves the pre-miRNA stem-loop, two complementary short RNA molecules are formed, but only one is integrated into the RISC complex. This strand is known as the guide strand and is selected by the argonaute protein, the catalytically active RNase in the RISC complex, on the basis of the stability of the 5' end (Preall et al., *Curr. Biol.*, 16:530-535 (2006)). The remaining strand, known as the anti-guide or passenger strand, is degraded as a RISC complex substrate (Gregory et al., *Cell*, 123:631-640 (2005)). After integration into the active RISC complex, miRNAs base pair with their complementary mRNA molecules and induce target mRNA degradation and/or translational silencing.

Mammalian miRNA molecules are usually complementary to a site in the 3' UTR of the target mRNA sequence. In certain instances, the annealing of the miRNA to the target mRNA inhibits protein translation by blocking the protein translation machinery. In certain other instances, the annealing of the miRNA to the target mRNA facilitates the cleavage and degradation of the target mRNA through a process similar to RNA interference (RNAi). miRNA may also target methylation of genomic sites which correspond to targeted mRNA. Generally, miRNA function in association with a complement of proteins collectively termed the miRNP.

In certain aspects, the miRNA molecules described herein are about 15-100, 15-90, 15-80, 15-75, 15-70, 15-60, 15-50, or 15-40 nucleotides in length, more typically about 15-30, 15-25, or 19-25 nucleotides in length, and are preferably about 20-24, 21-22, or 21-23 nucleotides in length. In certain other aspects, miRNA molecules may comprise one or more modified nucleotides. As a non-limiting example, miRNA sequences may comprise one or more of the modified nucleotides described above for siRNA sequences. In a preferred embodiment, the miRNA molecule comprises 2'OMe nucleotides such as, for example, 2'OMe-guanosine nucleotides, 2'OMe-uridine nucleotides, or mixtures thereof.

In particular embodiments, miRNAs are administered using a carrier system such as a nucleic acid-lipid particle. In a preferred embodiment, the nucleic acid-lipid particle comprises: (a) one or more miRNA molecules; (b) a cationic lipid of Formula I or a salt thereof; and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA and/or POZ-DAA).

In other embodiments, one or more agents that block the activity of an miRNA targeting an mRNA of interest are administered using a lipid particle of the invention (e.g., a nucleic acid-lipid particle such as SNALP). Examples of blocking agents include, but are not limited to, steric blocking oligonucleotides, locked nucleic acid oligonucleotides, and Morpholino oligonucleotides. Such blocking agents may bind directly to the miRNA or to the miRNA binding site on the target mRNA.

Additional embodiments related to the miRNA molecules of the invention are described in U.S. Patent Publication No. 20090291131 and PCT Publication No. WO 09/127,060, the disclosures of which are herein incorporated by reference in their entirety for all purposes.

6. Antisense Oligonucleotides

In one embodiment, the nucleic acid is an antisense oligonucleotide directed to a target gene or sequence of interest. The terms "antisense oligonucleotide" or "antisense" include oligonucleotides that are complementary to a targeted polynucleotide sequence. Antisense oligonucleotides are single strands of DNA or RNA that are complementary to a chosen sequence. Antisense RNA oligonucleotides prevent the translation of complementary RNA strands by binding to the RNA. Antisense DNA oligonucleotides can be used to target a specific, complementary (coding or non-coding) RNA. If binding occurs, this DNA/RNA hybrid can be degraded by the enzyme RNase H. In a particular embodiment, antisense oligonucleotides comprise from about 10 to about 60 nucleotides, more preferably from about 15 to about 30 nucleotides. The term also encompasses antisense oligonucleotides that may not be exactly complementary to the desired target gene. Thus, the invention can be utilized in instances where non-target specific-activities are found with antisense, or where an antisense sequence containing one or more mismatches with the target sequence is the most preferred for a particular use.

Antisense oligonucleotides have been demonstrated to be effective and targeted inhibitors of protein synthesis, and, consequently, can be used to specifically inhibit protein synthesis by a targeted gene. The efficacy of antisense oligonucleotides for inhibiting protein synthesis is well established. For example, the synthesis of polygalactauronase and the muscarine type 2 acetylcholine receptor are inhibited by antisense oligonucleotides directed to their respective mRNA sequences (see, U.S. Pat. Nos. 5,739,119 and 5,759,829). Furthermore, examples of antisense inhibition have been demonstrated with the nuclear protein cyclin, the multiple drug resistance gene (MDR1), ICAM-1, E-selectin, STK-1, striatal GABAA receptor, and human EGF (see, Jaskulski et al., *Science*, 240:1544-6 (1988); Vasanthakumar et al., *Cancer Commun.*, 1:225-32 (1989); Peris et al., *Brain Res Mol Brain Res.*, 15; 57:310-20 (1998); and U.S. Pat. Nos. 5,801, 154; 5,789,573; 5,718,709 and 5,610,288). Moreover, antisense constructs have also been described that inhibit and can be used to treat a variety of abnormal cellular proliferations, e.g., cancer (see, U.S. Pat. Nos. 5,747,470; 5,591,317; and 5,783,683). The disclosures of these references are herein incorporated by reference in their entirety for all purposes.

Methods of producing antisense oligonucleotides are known in the art and can be readily adapted to produce an antisense oligonucleotide that targets any polynucleotide sequence. Selection of antisense oligonucleotide sequences specific for a given target sequence is based upon analysis of the chosen target sequence and determination of secondary structure, $T_m$, binding energy, and relative stability. Antisense oligonucleotides may be selected based upon their relative inability to form dimers, hairpins, or other secondary structures that would reduce or prohibit specific binding to the target mRNA in a host cell. Highly preferred target regions of the mRNA include those regions at or near the AUG translation initiation codon and those sequences that are substantially complementary to 5' regions of the mRNA. These secondary structure analyses and target site selection considerations can be performed, for example, using v.4 of the OLIGO primer analysis software (Molecular Biology Insights) and/or the BLASTN 2.0.5 algorithm software (Altschul et al., *Nucleic Acids Res.*, 25:3389-402 (1997)).

7. Ribozymes

According to another embodiment of the invention, nucleic acid-lipid particles are associated with ribozymes. Ribozymes are RNA-protein complexes having specific catalytic domains that possess endonuclease activity (see, Kim et al., *Proc. Natl. Acad. Sci. USA.*, 84:8788-92 (1987); and Forster et al., *Cell*, 49:211-20 (1987)). For example, a large number of ribozymes accelerate phosphoester transfer reactions with a high degree of specificity, often cleaving only one of several phosphoesters in an oligonucleotide substrate (see, Cech et al., *Cell*, 27:487-96 (1981); Michel et al., *J. Mol. Biol.*, 216:585-610 (1990); Reinhold-Hurek et al., *Nature*, 357:173-6 (1992)). This specificity has been attributed to the requirement that the substrate bind via specific base-pairing interactions to the internal guide sequence ("IGS") of the ribozyme prior to chemical reaction.

At least six basic varieties of naturally-occurring enzymatic RNA molecules are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nucleic acid molecule may be formed in a hammerhead, hairpin, hepatitis δ virus, group I intron or RNaseP RNA (in association with an RNA guide sequence), or *Neurospora* VS RNA motif, for example. Specific examples of hammerhead motifs are described in, e.g., Rossi et al., *Nucleic Acids Res.*, 20:4559-65 (1992). Examples of hairpin motifs are described in, e.g., EP 0360257, Hampel et al., *Biochemistry*, 28:4929-33 (1989); Hampel et al., *Nucleic Acids Res.*, 18:299-304 (1990); and U.S. Pat. No. 5,631,359. An example of the hepatitis δ virus motif is described in, e.g., Perrotta et al., *Biochemistry*, 31:11843-52 (1992). An example of the RNaseP motif is described in, e.g., Guerrier-Takada et al., *Cell*, 35:849-57 (1983). Examples of the *Neurospora* VS RNA ribozyme motif is described in, e.g., Saville et al., *Cell*, 61:685-96 (1990); Saville et al., *Proc. Natl. Acad. Sci. USA*, 88:8826-30 (1991); Collins et al., *Biochemistry*, 32:2795-9 (1993). An example of the Group I intron is described in, e.g., U.S. Pat. No. 4,987,071. Important characteristics of enzymatic nucleic acid molecules used according to the invention are that they have a specific substrate binding site which is complementary to one or more of the target gene DNA or RNA regions, and that they have nucleotide sequences within or surrounding that substrate binding site which impart an RNA cleaving activity to the molecule. Thus, the ribozyme constructs need not be limited to specific motifs mentioned herein. The disclosures of these references are herein incorporated by reference in their entirety for all purposes.

Methods of producing a ribozyme targeted to any polynucleotide sequence are known in the art. Ribozymes may be designed as described in, e.g., PCT Publication Nos. WO 93/23569 and WO 94/02595, and synthesized to be tested in vitro and/or in vivo as described therein. The disclosures of these PCT publications are herein incorporated by reference in their entirety for all purposes.

Ribozyme activity can be optimized by altering the length of the ribozyme binding arms or chemically synthesizing ribozymes with modifications that prevent their degradation by serum ribonucleases (see, e.g., PCT Publication Nos. WO 92/07065, WO 93/15187, WO 91/03162, and WO 94/13688; EP 92110298.4; and U.S. Pat. No. 5,334,711, which describe various chemical modifications that can be made to the sugar moieties of enzymatic RNA molecules, the disclosures of which are each herein incorporated by reference in their entirety for all purposes), modifications which enhance their efficacy in cells, and removal of stem II bases to shorten RNA synthesis times and reduce chemical requirements.

8. Immunostimulatory Oligonucleotides

Nucleic acids associated with the lipid particles of the present invention may be immunostimulatory, including immunostimulatory oligonucleotides (ISS; single- or double-stranded) capable of inducing an immune response when administered to a subject, which may be a mammal such as a human. ISS include, e.g., certain palindromes leading to hairpin secondary structures (see, Yamamoto et al., *J. Immunol.*, 148:4072-6 (1992)), or CpG motifs, as well as other known ISS features (such as multi-G domains; see; PCT Publication No. WO 96/11266, the disclosure of which is herein incorporated by reference in its entirety for all purposes).

Immunostimulatory nucleic acids are considered to be non-sequence specific when it is not required that they specifically bind to and reduce the expression of a target sequence in order to provoke an immune response. Thus, certain immunostimulatory nucleic acids may comprise a sequence corresponding to a region of a naturally-occurring gene or mRNA, but they may still be considered non-sequence specific immunostimulatory nucleic acids.

In one embodiment, the immunostimulatory nucleic acid or oligonucleotide comprises at least one CpG dinucleotide. The oligonucleotide or CpG dinucleotide may be unmethylated or methylated. In another embodiment, the immunostimulatory nucleic acid comprises at least one CpG dinucleotide having a methylated cytosine. In one embodiment, the nucleic acid comprises a single CpG dinucleotide, wherein the cytosine in the CpG dinucleotide is methylated. In an alternative embodiment, the nucleic acid comprises at least two CpG dinucleotides, wherein at least one cytosine in the CpG dinucleotides is methylated. In a further embodiment, each cytosine in the CpG dinucleotides present in the sequence is methylated. In another embodiment, the nucleic acid comprises a plurality of CpG dinucleotides, wherein at least one of the CpG dinucleotides comprises a methylated cytosine. Examples of immunostimulatory oligonucleotides suitable for use in the compositions and methods of the present invention are described in PCT Publication Nos. WO 02/069369, WO 01/15726, and WO 09/086,558; U.S. Pat. No. 6,406,705; and Raney et al., *J. Pharm. Exper. Ther.*, 298:1185-92 (2001), the disclosures of which are herein incorporated by reference in their entirety for all purposes. In certain embodiments, the oligonucleotides used in the compositions and methods of the invention have a phosphodiester ("PO") backbone or a phosphorothioate ("PS") backbone, and/or at least one methylated cytosine residue in a CpG motif.

B. Other Active Agents

In certain embodiments, the active agent associated with the lipid particles of the invention may comprise one or more therapeutic proteins, polypeptides, or small organic molecules or compounds. Non-limiting examples of such therapeutically effective agents or drugs include oncology drugs (e.g., chemotherapy drugs, hormonal therapeutic agents, immunotherapeutic agents, radiotherapeutic agents, etc.), lipid-lowering agents, anti-viral drugs, anti-inflammatory compounds, antidepressants, stimulants, analgesics, antibiotics, birth control medication, antipyretics, vasodilators, anti-angiogenics, cytovascular agents, signal transduction inhibitors, cardiovascular drugs such as anti-arrhythmic agents, hormones, vasoconstrictors, and steroids. These active agents may be administered alone in the lipid particles of the invention, or in combination (e.g., co-administered) with lipid particles of the invention comprising nucleic acid such as interfering RNA.

Non-limiting examples of chemotherapy drugs include platinum-based drugs (e.g., oxaliplatin, cisplatin, carboplatin, spiroplatin, iproplatin, satraplatin, etc.), alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil (5-FU), azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel (taxol), docetaxel, etc.), topoisomerase inhibitors (e.g., irinotecan (CPT-11; Camptosar), topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), tyrosine kinase inhibitors (e.g., gefitinib (Iressa®), sunitinib (Sutent®; SU11248), erlotinib (Tarceva®; OSI-1774), lapatinib (GW572016; GW2016), canertinib (CI 1033), semaxinib (SU5416), vatalanib (PTK787/ZK222584), sorafenib (BAY 43-9006), imatinib (Gleevec®; STI571), dasatinib (BMS-354825), leflunomide (SU101), vandetanib (Zactima™; ZD6474), etc.), pharmaceutically acceptable salts thereof, stereoisomers thereof, derivatives thereof, analogs thereof, and combinations thereof.

Examples of conventional hormonal therapeutic agents include, without limitation, steroids (e.g., dexamethasone), finasteride, aromatase inhibitors, tamoxifen, and goserelin as well as other gonadotropin-releasing hormone agonists (GnRH).

Examples of conventional immunotherapeutic agents include, but are not limited to, immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y, or $^{131}$I, etc.).

Examples of conventional radiotherapeutic agents include, but are not limited to, radionucleotides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

Additional oncology drugs that may be used according to the invention include, but are not limited to, alkeran, allopurinol, altretamine, amifostine, anastrozole, araC, arsenic trioxide, bexarotene, biCNU, carmustine, CCNU, celecoxib, cladribine, cyclosporin A, cytosine arabinoside, cytoxan, dexrazoxane, DTIC, estramustine, exemestane, FK506, gemtuzumab-ozogamicin, hydrea, hydroxyurea, idarubicin, interferon, letrozole, leustatin, leuprolide, litretinoin, megastrol, L-PAM, mesna, methoxsalen, mithramycin, nitrogen mustard, pamidronate, Pegademase, pentostatin, porfimer sodium, prednisone, rituxan, streptozocin, STI-571, taxotere, temozolamide, VM-26, toremifene, tretinoin, ATRA, valrubicin, and velban. Other examples of oncology drugs that may be used according to the invention are ellipticin and ellipticin analogs or derivatives, epothilones, intracellular kinase inhibitors, and camptothecins.

Non-limiting examples of lipid-lowering agents for treating a lipid disease or disorder associated with elevated triglycerides, cholesterol, and/or glucose include statins, fibrates, ezetimibe, thiazolidinediones, niacin, beta-blockers, nitroglycerin, calcium antagonists, fish oil, and mixtures thereof.

Examples of anti-viral drugs include, but are not limited to, abacavir, aciclovir, acyclovir, adefovir, amantadine, amprenavir, arbidol, atazanavir, atripla, cidofovir, combivir, darunavir, delavirdine, didanosine, docosanol, edoxudine, efavirenz, emtricitabine, enfuvirtide, entecavir, entry inhibitors, famciclovir, fixed dose combinations, fomivirsen, fosamprenavir, foscarnet, fosfonet, fusion inhibitors, ganciclovir, ibacitabine, immunovir, idoxuridine, imiquimod, indinavir, inosine, integrase inhibitors, interferon type III (e.g., IFN-λ molecules such as IFN-λ1, IFN-λ2, and IFN-λ3), interferon type II (e.g., IFN-γ), interferon type I (e.g., IFN-α such as PEGylated IFN-α, IFN-β, IFN-κ, IFN-δ, IFN-ε, IFN-τ, IFN-ω, and IFN-ζ, interferon, lamivudine, lopinavir, loviride, MK-0518, maraviroc, moroxydine, nelfinavir, nevirapine, nexavir, nucleoside analogues, oseltamivir, penciclovir, peramivir, pleconaril, podophyllotoxin, protease inhibitors, reverse transcriptase inhibitors, ribavirin, rimantadine, ritonavir, saquinavir, stavudine, synergistic enhancers, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, zidovudine, pharmaceutically acceptable salts thereof, stereoisomers thereof, derivatives thereof, analogs thereof, and mixtures thereof.

V. Lipid Particles

In certain aspects, the present invention provides lipid particles comprising one or more of the cationic (amino) lipids or salts thereof described herein. In some embodiments, the lipid particles of the invention further comprise one or more non-cationic lipids. In other embodiments, the lipid particles further comprise one or more conjugated lipids capable of reducing or inhibiting particle aggregation. In additional embodiments, the lipid particles further comprise one or more active agents or therapeutic agents such as therapeutic nucleic acids (e.g., interfering RNA such as siRNA).

Lipid particles include, but are not limited to, lipid vesicles such as liposomes. As used herein, a lipid vesicle includes a structure having lipid-containing membranes enclosing an aqueous interior. In particular embodiments, lipid vesicles comprising one or more of the cationic lipids described herein are used to encapsulate nucleic acids within the lipid vesicles. In other embodiments, lipid vesicles comprising one or more of the cationic lipids described herein are complexed with nucleic acids to form lipoplexes.

The lipid particles of the invention typically comprise an active agent or therapeutic agent, a cationic lipid, a non-cationic lipid, and a conjugated lipid that inhibits aggregation of particles. In some embodiments, the active agent or therapeutic agent is fully encapsulated within the lipid portion of the lipid particle such that the active agent or therapeutic agent in the lipid particle is resistant in aqueous solution to enzymatic degradation, e.g., by a nuclease or protease. In other embodiments, the lipid particles described herein are substantially non-toxic to mammals such as humans. The lipid particles of the invention typically have a mean diameter of from about 30 nm to about 150 nm, from about 40 nm to about 150 nm, from about 50 nm to about 150 nm, from about 60 nm to about 130 nm, from about 70 nm to about 110 nm, or from about 70 to about 90 nm. The lipid particles of the invention also typically have a lipid:therapeutic agent (e.g., lipid:nucleic acid) ratio (mass/mass ratio) of from about 1:1 to about 100:1, from about 1:1 to about 50:1, from about 2:1 to about 25:1, from about 3:1 to about 20:1, from about 5:1 to about 15:1, or from about 5:1 to about 10:1.

In preferred embodiments, the lipid particles of the invention are serum-stable nucleic acid-lipid particles (SNALP) which comprise an interfering RNA (e.g., siRNA, Dicer-substrate dsRNA, shRNA, aiRNA, and/or miRNA), a cationic lipid (e.g., one or more cationic lipids of Formula I or salts thereof as set forth herein), a non-cationic lipid (e.g., mixtures of one or more phospholipids and cholesterol), and a conjugated lipid that inhibits aggregation of the particles (e.g., one or more PEG-lipid and/or POZ-lipid conjugates). The SNALP may comprise at least 1, 2, 3, 4, 5, 6, 7, 8, 9, 10, or more unmodified and/or modified interfering RNA molecules. Nucleic acid-lipid particles and their method of preparation are described in, e.g., U.S. Pat. Nos. 5,753,613; 5,785,992; 5,705,385; 5,976,567; 5,981,501; 6,110,745; and 6,320,017; and PCT Publication No. WO 96/40964, the disclosures of which are each herein incorporated by reference in their entirety for all purposes.

In the nucleic acid-lipid particles of the invention, the nucleic acid may be fully encapsulated within the lipid portion of the particle, thereby protecting the nucleic acid from nuclease degradation. In preferred embodiments, a SNALP comprising a nucleic acid such as an interfering RNA is fully encapsulated within the lipid portion of the particle, thereby protecting the nucleic acid from nuclease degradation. In certain instances, the nucleic acid in the SNALP is not substantially degraded after exposure of the particle to a nuclease at 37° C. for at least about 20, 30, 45, or 60 minutes. In certain other instances, the nucleic acid in the SNALP is not substantially degraded after incubation of the particle in serum at 37° C. for at least about 30, 45, or 60 minutes or at least about 2, 3, 4, 5, 6, 7, 8, 9, 10, 12, 14, 16, 18, 20, 22, 24, 26, 28, 30, 32, 34, or 36 hours. In other embodiments, the nucleic acid is complexed with the lipid portion of the particle. One of the benefits of the formulations of the present invention is that the nucleic acid-lipid particle compositions are substantially non-toxic to mammals such as humans.

The term "fully encapsulated" indicates that the nucleic acid in the nucleic acid-lipid particle is not significantly degraded after exposure to serum or a nuclease assay that would significantly degrade free DNA or RNA. In a fully encapsulated system, preferably less than about 25% of the nucleic acid in the particle is degraded in a treatment that would normally degrade 100% of free nucleic acid, more preferably less than about 10%, and most preferably less than about 5% of the nucleic acid in the particle is degraded. "Fully encapsulated" also indicates that the nucleic acid-lipid particles are serum-stable, that is, that they do not rapidly decompose into their component parts upon in vivo administration.

In the context of nucleic acids, full encapsulation may be determined by performing a membrane-impermeable fluorescent dye exclusion assay, which uses a dye that has enhanced fluorescence when associated with nucleic acid. Specific dyes such as OliGreen® and RiboGreen® (Invitrogen Corp.; Carlsbad, Calif.) are available for the quantitative determination of plasmid DNA, single-stranded deoxyribonucleotides, and/or single- or double-stranded ribonucleotides. Encapsulation is determined by adding the dye to a liposomal formulation, measuring the resulting fluorescence, and comparing it to the fluorescence observed upon addition of a small amount of nonionic detergent. Detergent-mediated disruption of the liposomal bilayer releases the encapsulated nucleic acid, allowing it to interact with the membrane-impermeable dye. Nucleic acid encapsulation may be calculated as $E=(I_o-I)/I_o$, where I and $I_o$ refer to the fluorescence intensities before and after the addition of detergent (see, Wheeler et al., Gene Ther., 6:271-281 (1999)).

In other embodiments, the present invention provides a nucleic acid-lipid particle (e.g., SNALP) composition comprising a plurality of nucleic acid-lipid particles.

In some instances, the SNALP composition comprises nucleic acid that is fully encapsulated within the lipid portion of the particles, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the particles have the nucleic acid encapsulated therein.

In other instances, the SNALP composition comprises nucleic acid that is fully encapsulated within the lipid portion of the particles, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the input nucleic acid is encapsulated in the particles.

Depending on the intended use of the lipid particles of the invention, the proportions of the components can be varied and the delivery efficiency of a particular formulation can be measured using, e.g., an endosomal release parameter (ERP) assay.

In particular embodiments, the present invention provides a lipid particle (e.g., SNALP) composition comprising a plurality of lipid particles described herein and an antioxidant. In certain instances, the antioxidant in the lipid particle composition reduces, prevents, and/or inhibits the degradation of a cationic lipid present in the lipid particle. In instances wherein the active agent is a therapeutic nucleic acid such as an interfering RNA (e.g., siRNA), the antioxidant in the lipid particle composition reduces, prevents, and/or inhibits the degradation of the nucleic acid payload, e.g., by reducing, preventing, and/or inhibiting the formation of adducts between the nucleic acid and the cationic lipid. Non-limiting examples of antioxidants include hydrophilic antioxidants such as chelating agents (e.g., metal chelators such as ethylenediaminetetraacetic acid (EDTA), citrate, and the like), lipophilic antioxidants (e.g., vitamin E isomers, polyphenols, and the like), salts thereof; and mixtures thereof. If needed, the antioxidant is typically present in an amount sufficient to prevent, inhibit, and/or reduce the degradation of the cationic lipid and/or active agent present in the particle, e.g., at least about 20 mM EDTA or a salt thereof, or at least about 100 mM citrate or a salt thereof. An antioxidant such as EDTA and/or citrate may be included at any step or at multiple steps in the lipid particle formation process described in Section VI (e.g., prior to, during, and/or after lipid particle formation).

Additional embodiments related to methods of preventing the degradation of cationic lipids and/or active agents (e.g., therapeutic nucleic acids) present in lipid particles, compositions comprising lipid particles stabilized by these methods, methods of making these lipid particles, and methods of delivering and/or administering these lipid particles are described in U.S. Provisional Application No. 61/265,671, entitled "SNALP Formulations Containing Antioxidants," filed Dec. 1, 2009, the disclosure of which is herein incorporated by reference in its entirety for all purposes.

A. Cationic Lipids

Any of the novel cationic lipids of Formula I or salts thereof as set forth herein may be used in the lipid particles of the present invention (e.g., SNALP), either alone or in combination with one or more other cationic lipid species or non-cationic lipid species.

Other cationic lipids or salts thereof which may also be included in the lipid particles of the present invention include, but are not limited to, 1,2-dilinoleyloxy-N,N-dimethylaminopropane (DLinDMA), 1,2-dilinolenyloxy-N,N-dimethylaminopropane (DLenDMA), 1,2-di-γ-linolenyloxy-N,N-dimethylaminopropane (γ-DLenDMA), 1,2-dilinoleyloxy-(N,N-dimethyl)-butyl-4-amine (C2-DLinDMA), 1,2-dilinoleoyloxy-(N,N-dimethyl)-butyl-4-amine (C2-DLinDAP), 2,2-dilinoleyl-4-(2-dimethylaminoethyl)-[1,3]-dioxolane (DLin-K-C2-DMA; also known as "XTC2" or "C2K"), 2,2-dilinoleyl-4-(3-dimethylaminopropyl)-[1,3]-dioxolane (DLin-K-C3-DMA; "C3K"), 2,2-dilinoleyl-4-(4-dimethylaminobutyl)-[1,3]-dioxolane (DLin-K-C4-DMA; "C4K"), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dilinoleyl-4-dimethylaminomethyl[1,3]-dioxolane (DLin-K-DMA), 2,2-dioleoyl-4-dimethylaminomethyl-[1,3]-dioxolane (DO-K-DMA), 2,2-distearoyl-4-dimethylaminomethyl-[1,3]-dioxolane (DS-K-DMA), 2,2-dilinoleyl-4-N-morpholino-[1,3]-dioxolane (DLin-K-MA), 2,2-Dilinoleyl-4-trimethylamino-[1,3]-dioxolane chloride (DLin-K-TMA.Cl), 2,2-dilinoleyl-4,5-bis(dimethylaminomethyl)-[1,3]-dioxolane (DLin-K$^2$-DMA), 2,2-dilinoleyl-4-methylpiperzine-[1,3]-dioxolane (D-Lin-K-N-methylpiperzine), (6Z,9Z,28Z,31Z)-heptatriaconta-6,9,28,31-tetraen-19-yl 4-(dimethylamino) butanoate (DLin-M-C3-DMA; "MC3"), dilinoleylmethyl-3-dimethylaminopropionate (DLin-M-C2-DMA; also known as DLin-M-K-DMA or DLin-M-DMA), 1,2-dioeylcarbamoyloxy-3-dimethylaminopropane (DO-C-DAP), 1,2-dimyristoleoyl-3-dimethylaminopropane (DMDAP), 1,2-dioleoyl-3-trimethylaminopropane chloride (DOTAP.Cl), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethyl-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-dilinoleylcarbamyl-3-dimethylaminopropane (DLincarbDAP), N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl) cholesterol (DC-Chol), N-(1,2-dimyristyloxyprop-3-yl)-N,N-dimethyl-N-hydroxyethyl ammonium bromide (DMRIE), 2,3-dioleyloxy-N-[2(spermine-carboxamido)ethyl]-N,N-dimethyl-1-propanaminiumtrifluoroacetate (DOSPA), dioctadecylamidoglycyl spermine (DOGS), and mixtures thereof.

Additional cationic lipids or salts thereof which may be present in the lipid particles described herein include novel cyclic cationic lipids such as CP-LenMC3, CP-γ-LenMC3, CP-MC3, CP-DLen-C2K-DMA, CP-γDLen-C2K-DMA, CP-C2K-DMA, CP-DODMA, CP-DPetroDMA, CP-DLinDMA, CP-DLenDMA, CP-γDLenDMA, analogs thereof, and combinations thereof, as described in U.S. Provisional Application No. 61/334,096, entitled "Novel Cyclic Cationic Lipids and Methods of Use Thereof,", filed May 12, 2010. Additional cationic lipids or salts thereof which may be present in the lipid particles described herein include novel cationic lipids such as 4-B10, 4-B12, 4-B13, 4-B14, 4-B15, 4-B16, γ-4-B10, N,N-dimethyl-2-((11Z,14Z)-3-((9Z,12Z)-octadeca-9,12-dienyloxy)icosa-11,14-dienyloxy)ethanamine (4-B10 Ether), (11Z,14Z)-3-(dimethylamino)propyl 3-((9Z,12Z)-octadeca-9,12-dienoyloxy)icosa-11,14-dienoate, CP-4-B10, analogs thereof, and combinations thereof, as described in U.S. Provisional Application No. 61/334,087, entitled "Novel Cationic Lipids and Methods of Use Thereof,", filed May 12, 2010. Additional cationic lipids or salts thereof which may be present in the lipid particles described herein include the novel cationic lipids described in U.S. Provisional Application No. 61/295,134, entitled "Improved Cationic Lipids and Methods for the Delivery of Nucleic Acids," filed Jan. 14, 2010. Additional cationic lipids or salts thereof which may be present in the lipid particles described herein include the cationic lipids described in U.S. Patent Publication No. 20090023673. The disclosures of each of these patent documents are herein incorporated by reference in their entirety for all purposes.

In some embodiments, the additional cationic lipid forms a salt (preferably a crystalline salt) with one or more anions. In one particular embodiment, the additional cationic lipid is the oxalate (e.g., hemioxalate) salt thereof, which is preferably a crystalline salt.

The synthesis of cationic lipids such as DLinDMA and DLenDMA, as well as additional cationic lipids, is described in U.S. Patent Publication No. 20060083780, the disclosure of which is herein incorporated by reference in its entirety for all purposes.

The synthesis of cationic lipids such as γ-DLenDMA, C2-DLinDMA and C2-DLinDAP, as well as additional cationic lipids, is described in U.S. Provisional Application No. 61/295,134, entitled "Improved Cationic Lipids and Methods for the Delivery of Nucleic Acids," filed Jan. 14, 2010, the disclosure of which is herein incorporated by reference in its entirety for all purposes.

The synthesis of cationic lipids such as DLin-K-DMA, as well as additional cationic lipids, is described in PCT Publication No. WO 09/086,558, the disclosure of which is herein incorporated by reference in its entirety for all purposes.

The synthesis of cationic lipids such as DLin-K-C2-DMA, DLin-K-C3-DMA, DLin-K-C4-DMA, DLin-K6-DMA, DLin-K-MPZ, DO-K-DMA, DS-K-DMA, DLin-K-MA, DLin-K-TMA.Cl, DLin-K$^2$-DMA, D-Lin-K-N-methylpiperzine, DLin-M-C2-DMA, DO-C-DAP, DMDAP, and DOT-AP.Cl, as well as additional cationic lipids, is described in PCT Publication No. WO 2010/042877, entitled "Improved Amino Lipids and Methods for the Delivery of Nucleic Acids," filed Oct. 9, 2009, the disclosure of which is incorporated herein by reference in its entirety for all purposes.

The synthesis of DLin-M-C3-DMA ("MC3"), as well as additional cationic lipids (e.g., certain analogs of MC3), is described herein and in U.S. Provisional Application No. 61/185,800, entitled "Novel Lipids and Compositions for the Delivery of Therapeutics," filed Jun. 10, 2009, and U.S. Provisional Application No. 61/287,995, entitled "Methods and Compositions for Delivery of Nucleic Acids," filed Dec. 18, 2009, the disclosures of which are herein incorporated by reference in their entirety for all purposes.

The synthesis of cationic lipids such as DLin-C-DAP, DLinDAC, DLinMA, DLinDAP, DLin-S-DMA, DLin-2-DMAP, DLinTMA.Cl, DLinTAP.Cl, DLinMPZ, DLinAP, DOAP, and DLin-EG-DMA, as well as additional cationic lipids, is described in PCT Publication No. WO 09/086,558, the disclosure of which is herein incorporated by reference in its entirety for all purposes.

The synthesis of cationic lipids such as CLinDMA, as well as additional cationic lipids, is described in U.S. Patent Publication No. 20060240554, the disclosure of which is herein incorporated by reference in its entirety for all purposes.

The synthesis of a number of other cationic lipids and related analogs has been described in U.S. Pat. Nos. 5,208, 036; 5,264,618; 5,279,833; 5,283,185; 5,753,613; and 5,785, 992; and PCT Publication No. WO 96/10390, the disclosures of which are each herein incorporated by reference in their entirety for all purposes. Additionally, a number of commercial preparations of cationic lipids can be used, such as, e.g., LIPOFECTIN® (including DOTMA and DOPE, available from GIBCO/BRL); LIPOFECTAMINE® (including DOSPA and DOPE, available from GIBCO/BRL); and TRANSFECTAM® (including DOGS, available from Promega Corp.).

In some embodiments, the cationic lipid comprises from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, from about 50 mol % to about 60 mol %, from about 55 mol % to about 65 mol %, or from about 55 mol % to about 70 mol % (or any fraction thereof or range therein) of the total lipid present in the particle. In particular embodiments, the cationic lipid comprises about 50 mol %, 51 mol %, 52 mol %, 53 mol %, 54 mol %, 55 mol %, 56 mol %, 57 mol %, 58 mol %, 59 mol %, 60 mol %, 61 mol %, 62 mol %, 63 mol %, 64 mol %, or 65 mol % (or any fraction thereof) of the total lipid present in the particle.

In other embodiments, the cationic lipid comprises from about 2 mol % to about 60 mol %, from about 5 mol % to about 50 mol %, from about 10 mol % to about 50 mol %, from about 20 mol % to about 50 mol %, from about 20 mol % to about 40 mol %, from about 30 mol % to about 40 mol %, or about 40 mol % (or any fraction thereof or range therein) of the total lipid present in the particle.

Additional percentages and ranges of cationic lipids suitable for use in the lipid particles of the present invention are described in PCT Publication No. WO 09/127,060, U.S. application Ser. No. 12/794,701, filed Jun. 4, 2010, U.S. Provisional Application No. 61/295,134, filed Jan. 14, 2010, and U.S. application Ser. No. 12/828,189, filed Jun. 30, 2010, the disclosures of which are herein incorporated by reference in their entirety for all purposes.

It should be understood that the percentage of cationic lipid present in the lipid particles of the invention is a target amount, and that the actual amount of cationic lipid present in the formulation may vary, for example, by ±5 mol %. For example, in the 1:57 lipid particle (e.g., SNALP) formulation, the target amount of cationic lipid is 57.1 mol %, but the actual amount of cationic lipid may be ±5 mol %, ±4 mol %, ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle).

B. Non-Cationic Lipids

The non-cationic lipids used in the lipid particles of the invention (e.g., SNALP) can be any of a variety of neutral uncharged, zwitterionic, or anionic lipids capable of producing a stable complex.

Non-limiting examples of non-cationic lipids include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lyso-phosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, palmitoyl, stearoyl, or oleoyl.

Additional examples of non-cationic lipids include sterols such as cholesterol and derivatives thereof. Non-limiting examples of cholesterol derivatives include polar analogues such as 5α-cholestanol, 5β-coprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5β-cholestanone, and cholesteryl decanoate; and mixtures thereof. In preferred embodiments, the cholesterol derivative is a polar analogue such as cholesteryl-(4'-hydroxy)-butyl ether. The synthesis of cholesteryl-(2'-hydroxy)-ethyl ether is described in PCT Publication No. WO 09/127,060, the disclosure of which is herein incorporated by reference in its entirety for all purposes.

In some embodiments, the non-cationic lipid present in the lipid particles (e.g., SNALP) comprises or consists of a mixture of one or more phospholipids and cholesterol or a derivative thereof. In other embodiments, the non-cationic lipid present in the lipid particles (e.g., SNALP) comprises or consists of one or more phospholipids, e.g., a cholesterol-free lipid particle formulation. In yet other embodiments, the non-cationic lipid present in the lipid particles (e.g., SNALP) comprises or consists of cholesterol or a derivative thereof, e.g., a phospholipid-free lipid particle formulation.

Other examples of non-cationic lipids suitable for use in the present invention include nonphosphorous containing lipids such as, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, sphingomyelin, and the like.

In some embodiments, the non-cationic lipid comprises from about 10 mol % to about 60 mol %, from about 20 mol % to about 55 mol %, from about 20 mol % to about 45 mol %, from about 20 mol % to about 40 mol %, from about 25 mol % to about 50 mol %, from about 25 mol % to about 45 mol %, from about 30 mol % to about 50 mol %, from about 30 mol % to about 45 mol %, from about 30 mol % to about 40 mol %, from about 35 mol % to about 45 mol %, from about 37 mol % to about 42 mol %, or about 35 mol %, 36 mol %, 37 mol %, 38 mol %, 39 mol %, 40 mol %, 41 mol %, 42 mol %, 43 mol %, 44 mol %, or 45 mol % (or any fraction thereof or range therein) of the total lipid present in the particle.

In embodiments where the lipid particles contain a mixture of phospholipid and cholesterol or a cholesterol derivative, the mixture may comprise up to about 40 mol %, 45 mol %, 50 mol %, 55 mol %, or 60 mol % of the total lipid present in the particle.

In some embodiments, the phospholipid component in the mixture may comprise from about 2 mol % to about 20 mol %, from about 2 mol % to about 15 mol %, from about 2 mol % to about 12 mol %, from about 4 mol % to about 15 mol %, or from about 4 mol % to about 10 mol % (or any fraction thereof or range therein) of the total lipid present in the particle. In certain preferred embodiments, the phospholipid component in the mixture comprises from about 5 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. As a non-limiting example, a 1:57 lipid particle formulation comprising a mixture of phospholipid and cholesterol may comprise a phospholipid such as DPPC or DSPC at about 7 mol % (or any fraction thereof), e.g., in a mixture with cholesterol or a cholesterol derivative at about 34 mol % (or any fraction thereof) of the total lipid present in the particle. As another non-limiting example, a 7:54 lipid particle formulation comprising a mixture of phospholipid and cholesterol may comprise a phospholipid such as DPPC or DSPC at about 7 mol % (or any fraction thereof), e.g., in a mixture with cholesterol or a cholesterol derivative at about 32 mol % (or any fraction thereof) of the total lipid present in the particle.

In other embodiments, the cholesterol component in the mixture may comprise from about 25 mol % to about 45 mol %, from about 25 mol % to about 40 mol %, from about 30 mol % to about 45 mol %, from about 30 mol % to about 40 mol %, from about 27 mol % to about 37 mol %, from about 25 mol % to about 30 mol %, or from about 35 mol % to about 40 mol % (or any fraction thereof or range therein) of the total lipid present in the particle. In certain preferred embodiments, the cholesterol component in the mixture comprises from about 25 mol % to about 35 mol %, from about 27 mol % to about 35 mol %, from about 29 mol % to about 35 mol %, from about 30 mol % to about 35 mol %, from about 30 mol % to about 34 mol %, from about 31 mol % to about 33 mol %, or about 30 mol %, 31 mol %, 32 mol %, 33 mol %, 34 mol %, or 35 mol % (or any fraction thereof or range therein) of the total lipid present in the particle. Typically, a 1:57 lipid particle formulation comprising a mixture of phospholipid and cholesterol may comprise cholesterol or a cholesterol derivative at about 34 mol (or any fraction thereof), e.g., in a mixture with a phospholipid such as DPPC or DSPC at about 7 mol % (or any fraction thereof) of the total lipid present in the particle. Typically, a 7:54 lipid particle formulation comprising a mixture of phospholipid and cholesterol may comprise cholesterol or a cholesterol derivative at about 32 mol (or any fraction thereof), e.g., in a mixture with a phospholipid such as DPPC or DSPC at about 7 mol % (or any fraction thereof) of the total lipid present in the particle.

In embodiments where the lipid particles are phospholipid-free, the cholesterol or derivative thereof may comprise up to about 25 mol %, 30 mol %, 35 mol %, 40 mol %, 45 mol %, 50 mol %, 55 mol %, or 60 mol % of the total lipid present in the particle.

In some embodiments, the cholesterol or derivative thereof in the phospholipid-free lipid particle formulation may comprise from about 25 mol % to about 45 mol %, from about mol % to about 40 mol %, from about 30 mol % to about 45 mol %, from about 30 mol % to about 40 mol %, from about 31 mol % to about 39 mol %, from about 32 mol % to about 38 mol %, from about 33 mol % to about 37 mol %, from about 35 mol % to about 45 mol %, from about 30 mol % to about 35 mol %, from about 35 mol % to about 40 mol %, or about mol %, 31 mol %, 32 mol %, 33 mol %, 34 mol %, 35 mol %, 36 mol %, 37 mol %, 38 mol %, 39 mol %, or 40 mol % (or any fraction thereof or range therein) of the total lipid present in the particle. As a non-limiting example, a 1:62 lipid particle formulation may comprise cholesterol at about 37 mol (or any fraction thereof) of the total lipid present in the particle. As another non-limiting example, a 7:58 lipid particle formulation may comprise cholesterol at about 35 mol (or any fraction thereof) of the total lipid present in the particle.

In other embodiments, the non-cationic lipid comprises from about 5 mol % to about 90 mol %, from about 10 mol % to about 85 mol %, from about 20 mol % to about 80 mol %, about 10 mol % (e.g., phospholipid only), or about 60 mol %

(e.g., phospholipid and cholesterol or derivative thereof) (or any fraction thereof or range therein) of the total lipid present in the particle.

Additional percentages and ranges of non-cationic lipids suitable for use in the lipid particles of the present invention are described in PCT Publication No. WO 09/127,060, U.S. application Ser. No. 12/794,701, filed Jun. 4, 2010, U.S. Provisional Application No. 61/295,134, filed Jan. 14, 2010, and U.S. application Ser. No. 12/828,189, filed Jun. 30, 2010, the disclosures of which are herein incorporated by reference in their entirety for all purposes.

It should be understood that the percentage of non-cationic lipid present in the lipid particles of the invention is a target amount, and that the actual amount of non-cationic lipid present in the formulation may vary, for example, by ±5 mol %. For example, in the 1:57 lipid particle (e.g., SNALP) formulation, the target amount of phospholipid is 7.1 mol % and the target amount of cholesterol is 34.3 mol %, but the actual amount of phospholipid may be ±2 mol %, ±1.5 mol %, ±1 mol %, ±0.75 mol %, ±0.5 mol %, ±0.25 mol %, or ±0.1 mol % of that target amount, and the actual amount of cholesterol may be ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle). Similarly, in the 7:54 lipid particle (e.g., SNALP) formulation, the target amount of phospholipid is 6.75 mol % and the target amount of cholesterol is 32.43 mol %, but the actual amount of phospholipid may be ±2 mol %, 1.5 mol %, ±1 mol %, ±0.75 mol %, ±0.5 mol %, ±0.25 mol %, or ±0.1 mol % of that target amount, and the actual amount of cholesterol may be ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle).

C. Lipid Conjugates

In addition to cationic and non-cationic lipids, the lipid particles of the invention (e.g., SNALP) may further comprise a lipid conjugate. The conjugated lipid is useful in that it prevents the aggregation of particles. Suitable conjugated lipids include, but are not limited to, PEG-lipid conjugates, POZ-lipid conjugates, ATTA-lipid conjugates, cationic-polymer-lipid conjugates (CPLs), and mixtures thereof. In certain embodiments, the particles comprise either a PEG-lipid conjugate or an ATTA-lipid conjugate together with a CPL.

In a preferred embodiment, the lipid conjugate is a PEG-lipid. Examples of PEG-lipids include, but are not limited to, PEG coupled to dialkyloxypropyls (PEG-DAA) as described in, e.g., PCT Publication No. WO 05/026372, PEG coupled to diacylglycerol (PEG-DAG) as described in, e.g., U.S. Patent Publication Nos. 20030077829 and 2005008689, PEG coupled to phospholipids such as phosphatidylethanolamine (PEG-PE), PEG conjugated to ceramides as described in, e.g., U.S. Pat. No. 5,885,613, PEG conjugated to cholesterol or a derivative thereof, and mixtures thereof. The disclosures of these patent documents are herein incorporated by reference in their entirety for all purposes.

Additional PEG-lipids suitable for use in the invention include, without limitation, mPEG2000-1,2-di-O-alkyl-sn3-carbomoylglyceride (PEG-C-DOMG). The synthesis of PEG-C-DOMG is described in PCT Publication No. WO 09/086,558, the disclosure of which is herein incorporated by reference in its entirety for all purposes. Yet additional suitable PEG-lipid conjugates include, without limitation, 1-[8'-(1,2-dimyristoyl-3-propanoxy)-carboxamido-3',6'-dioxaoctanyl]carbamoyl-w-methyl-poly(ethylene glycol) (2 KPEG-DMG). The synthesis of 2 KPEG-DMG is described in U.S. Pat. No. 7,404,969, the disclosure of which is herein incorporated by reference in its entirety for all purposes.

PEG is a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, but are not limited to, the following: monomethoxypolyethylene glycol (MePEG-OH), monomethoxypolyethylene glycol-succinate (MePEG-S), monomethoxypolyethylene glycol-succinimidyl succinate (MePEG-S—NHS), monomethoxypolyethylene glycol-amine (MePEG-NH$_2$), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g., HO-PEG-S, HO-PEG-S—NHS, HO-PEG-NH$_2$, etc.). Other PEGs such as those described in U.S. Pat. Nos. 6,774,180 and 7,053,150 (e.g., mPEG (20 KDa) amine) are also useful for preparing the PEG-lipid conjugates of the present invention. The disclosures of these patents are herein incorporated by reference in their entirety for all purposes. In addition, monomethoxypolyethyleneglycol-acetic acid (MePEG-CH$_2$COOH) is particularly useful for preparing PEG-lipid conjugates including, e.g., PEG-DAA conjugates.

The PEG moiety of the PEG-lipid conjugates described herein may comprise an average molecular weight ranging from about 550 daltons to about 10,000 daltons. In certain instances, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In preferred embodiments, the PEG moiety has an average molecular weight of about 2,000 daltons or about 750 daltons.

In certain instances, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In a preferred embodiment, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CCH$_2$CH$_2$C(O)—), succinamidyl (—NHC(O)CH$_2$CH$_2$C(O)NH—), ether, disulphide, as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the lipid conjugate. Such phosphatidylethanolamines are commercially available, or can be isolated or synthesized using conventional techniques known to those of skilled in the art. Phosphatidyl-ethanolamines containing saturated or unsaturated fatty acids with carbon chain lengths in the range of $C_{10}$ to $C_{20}$ are preferred. Phosphatidylethanolamines with mono- or diunsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoylphosphatidylethanolamine (DOPE), and distearoyl-phosphatidylethanolamine (DSPE).

The term "ATTA" or "polyamide" includes, without limitation, compounds described in U.S. Pat. Nos. 6,320,017 and 6,586,559, the disclosures of which are herein incorporated by reference in their entirety for all purposes. These compounds include a compound having the formula:

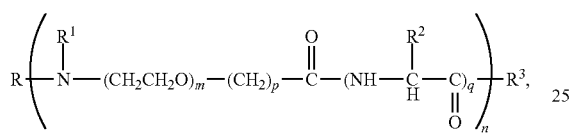

(VII)

wherein R is a member selected from the group consisting of hydrogen, alkyl and acyl; $R^1$ is a member selected from the group consisting of hydrogen and alkyl; or optionally, R and $R^1$ and the nitrogen to which they are bound form an azido moiety; $R^2$ is a member of the group selected from hydrogen, optionally substituted alkyl, optionally substituted aryl and a side chain of an amino acid; $R^3$ is a member selected from the group consisting of hydrogen, halogen, hydroxy, alkoxy, mercapto, hydrazino, amino and $NR^4R^5$, wherein $R^4$ and $R^5$ are independently hydrogen or alkyl; n is 4 to 80; m is 2 to 6; p is 1 to 4; and q is 0 or 1. It will be apparent to those of skill in the art that other polyamides can be used in the compounds of the present invention.

The term "diacylglycerol" or "DAG" includes a compound having 2 fatty acyl chains, $R^1$ and $R^2$, both of which have independently between 2 and 30 carbons bonded to the 1- and 2-position of glycerol by ester linkages. The acyl groups can be saturated or have varying degrees of unsaturation. Suitable acyl groups include, but are not limited to, lauroyl ($C_{12}$), myristoyl ($C_{14}$), palmitoyl ($C_{16}$), stearoyl ($C_{18}$), and icosoyl ($C_{20}$). In preferred embodiments, $R^1$ and $R^2$ are the same, i.e., $R^1$ and $R^2$ are both myristoyl (i.e., dimyristoyl), $R^1$ and $R^2$ are both stearoyl (i.e., distearoyl), etc. Diacylglycerols have the following general formula:

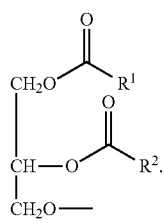

(VIII)

The term "dialkyloxypropyl" or "DAA" includes a compound having 2 alkyl chains, $R^1$ and $R^2$, both of which have independently between 2 and 30 carbons. The alkyl groups can be saturated or have varying degrees of unsaturation. Dialkyloxypropyls have the following general formula:

(IX)

In a preferred embodiment, the PEG-lipid is a PEG-DAA conjugate having the following formula:

(X)

wherein $R^1$ and $R^2$ are independently selected and are long-chain alkyl groups having from about 10 to about 22 carbon atoms; PEG is a polyethyleneglycol; and L is a non-ester containing linker moiety or an ester containing linker moiety as described above. The long-chain alkyl groups can be saturated or unsaturated. Suitable alkyl groups include, but are not limited to, decyl ($C_{10}$), lauryl ($C_{12}$), myristyl ($C_{14}$), palmityl ($C_{16}$), stearyl ($C_{18}$), and icosyl ($C_{20}$). In preferred embodiments, $R^1$ and $R^2$ are the same, i.e., $R^1$ and $R^2$ are both myristyl (i.e., dimyristyl), $R^1$ and $R^2$ are both stearyl (i.e., distearyl), etc.

In Formula X above, the PEG has an average molecular weight ranging from about 550 daltons to about 10,000 daltons. In certain instances, the PEG has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In preferred embodiments, the PEG has an average molecular weight of about 2,000 daltons or about 750 daltons. The PEG can be optionally substituted with alkyl, alkoxy, acyl, or aryl groups. In certain embodiments, the terminal hydroxyl group is substituted with a methoxy or methyl group.

In a preferred embodiment, "L" is a non-ester containing linker moiety. Suitable non-ester containing linkers include, but are not limited to, an amido linker moiety, an amino linker moiety, a carbonyl linker moiety, a carbamate linker moiety, a urea linker moiety, an ether linker moiety, a disulphide linker moiety, a succinamidyl linker moiety, and combinations thereof. In a preferred embodiment, the non-ester containing linker moiety is a carbamate linker moiety (i.e., a PEG-C-DAA conjugate). In another preferred embodiment, the non-ester containing linker moiety is an amido linker moiety (i.e., a PEG-A-DAA conjugate). In yet another preferred embodiment, the non-ester containing linker moiety is a succinamidyl linker moiety (i.e., a PEG-S-DAA conjugate).

In particular embodiments, the PEG-lipid conjugate is selected from:

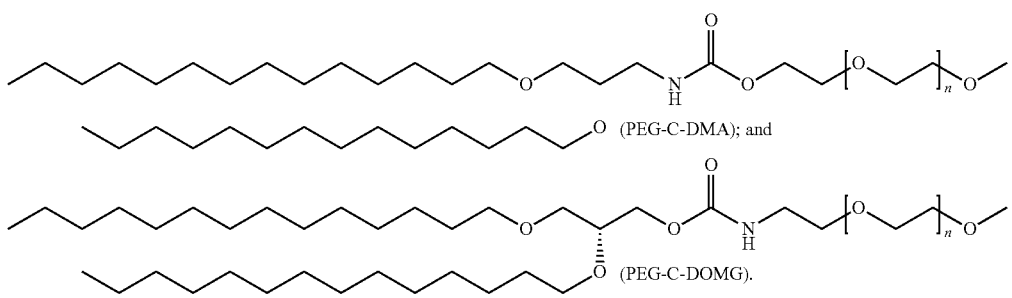

The PEG-DAA conjugates are synthesized using standard techniques and reagents known to those of skill in the art. It will be recognized that the PEG-DAA conjugates will contain various amide, amine, ether, thio, carbamate, and urea linkages. Those of skill in the art will recognize that methods and reagents for forming these bonds are well known and readily available. See, e.g., March, ADVANCED ORGANIC CHEMISTRY (Wiley 1992); Larock, COMPREHENSIVE ORGANIC TRANSFORMATIONS (VCH 1989); and Furniss, VOGEL'S TEXTBOOK OF PRACTICAL ORGANIC CHEMISTRY, 5th ed. (Longman 1989). It will also be appreciated that any functional groups present may require protection and deprotection at different points in the synthesis of the PEG-DAA conjugates. Those of skill in the art will recognize that such techniques are well known. See, e.g., Green and Wuts, PROTECTIVE GROUPS IN ORGANIC SYNTHESIS (Wiley 1991).

Preferably, the PEG-DAA conjugate is a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, or a PEG-distearyloxypropyl ($C_{18}$) conjugate. In these embodiments, the PEG preferably has an average molecular weight of about 750 or about 2,000 daltons. In one particularly preferred embodiment, the PEG-lipid conjugate comprises PEG2000-C-DMA, wherein the "2000" denotes the average molecular weight of the PEG, the "C" denotes a carbamate linker moiety, and the "DMA" denotes dimyristyloxypropyl. In another particularly preferred embodiment, the PEG-lipid conjugate comprises PEG750-C-DMA, wherein the "750" denotes the average molecular weight of the PEG, the "C" denotes a carbamate linker moiety, and the "DMA" denotes dimyristyloxypropyl. In particular embodiments, the terminal hydroxyl group of the PEG is substituted with a methyl group. Those of skill in the art will readily appreciate that other dialkyloxypropyls can be used in the PEG-DAA conjugates of the present invention.

In addition to the foregoing, it will be readily apparent to those of skill in the art that other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses such as hydroxymethylcellulose or hydroxyethylcellulose.

In addition to the foregoing components, the lipid particles (e.g., SNALP) of the present invention can further comprise cationic poly(ethylene glycol) (PEG) lipids or CPLs (see, e.g., Chen et al., *Bioconj. Chem.*, 11:433-437 (2000); U.S. Pat. No. 6,852,334; PCT Publication No. WO 00/62813, the disclosures of which are herein incorporated by reference in their entirety for all purposes).

Suitable CPLs include compounds of Formula XI:

A-W—Y          (XI), wherein A, W, and Y are as described below.

With reference to Formula XI, "A" is a lipid moiety such as an amphipathic lipid, a neutral lipid, or a hydrophobic lipid that acts as a lipid anchor. Suitable lipid examples include, but are not limited to, diacylglycerolyls, dialkylglycerolyls, N—N-dialkylaminos, 1,2-diacyloxy-3-aminopropanes, and 1,2-dialkyl-3-aminopropanes.

"W" is a polymer or an oligomer such as a hydrophilic polymer or oligomer. Preferably, the hydrophilic polymer is a biocompatible polymer that is nonimmunogenic or possesses low inherent immunogenicity. Alternatively, the hydrophilic polymer can be weakly antigenic if used with appropriate adjuvants. Suitable nonimmunogenic polymers include, but are not limited to, PEG, polyamides, polylactic acid, polyglycolic acid, polylactic acid/polyglycolic acid copolymers, and combinations thereof. In a preferred embodiment, the polymer has a molecular weight of from about 250 to about 7,000 daltons.

"Y" is a polycationic moiety. The term polycationic moiety refers to a compound, derivative, or functional group having a positive charge, preferably at least 2 positive charges at a selected pH, preferably physiological pH. Suitable polycationic moieties include basic amino acids and their derivatives such as arginine, asparagine, glutamine, lysine, and histidine; spermine; spermidine; cationic dendrimers; polyamines; polyamine sugars; and amino polysaccharides. The polycationic moieties can be linear, such as linear tetralysine, branched or dendrimeric in structure. Polycationic moieties have between about 2 to about 15 positive charges, preferably between about 2 to about 12 positive charges, and more preferably between about 2 to about 8 positive charges at selected pH values. The selection of which polycationic moiety to employ may be determined by the type of particle application which is desired.

The charges on the polycationic moieties can be either distributed around the entire particle moiety, or alternatively, they can be a discrete concentration of charge density in one particular area of the particle moiety e.g., a charge spike. If the charge density is distributed on the particle, the charge density can be equally distributed or unequally distributed. All variations of charge distribution of the polycationic moiety are encompassed by the present invention.

The lipid "A" and the nonimmunogenic polymer "W" can be attached by various methods and preferably by covalent attachment. Methods known to those of skill in the art can be used for the covalent attachment of "A" and "W." Suitable linkages include, but are not limited to, amide, amine, carboxyl, carbonate, carbamate, ester, and hydrazone linkages. It will be apparent to those skilled in the art that "A" and "W" must have complementary functional groups to effectuate the linkage. The reaction of these two groups, one on the lipid and the other on the polymer, will provide the desired linkage. For example, when the lipid is a diacylglycerol and the terminal hydroxyl is activated, for instance with NHS and DCC, to form an active ester, and is then reacted with a polymer which contains an amino group, such as with a polyamide (see, e.g., U.S. Pat. Nos. 6,320,017 and 6,586,559, the disclosures of which are herein incorporated by reference in their entirety for all purposes), an amide bond will form between the two groups.

In certain instances, the polycationic moiety can have a ligand attached, such as a targeting ligand or a chelating moiety for complexing calcium. Preferably, after the ligand is attached, the cationic moiety maintains a positive charge. In certain instances, the ligand that is attached has a positive charge. Suitable ligands include, but are not limited to, a compound or device with a reactive functional group and include lipids, amphipathic lipids, carrier compounds, bioaffinity compounds, biomaterials, biopolymers, biomedical devices, analytically detectable compounds, therapeutically active compounds, enzymes, peptides, proteins, antibodies, immune stimulators, radiolabels, fluorogens, biotin, drugs, haptens, DNA, RNA, polysaccharides, liposomes, virosomes, micelles, immunoglobulins, functional groups, other targeting moieties, or toxins.

In some embodiments, the lipid conjugate (e.g., PEG-lipid) comprises from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 0.9 mol % to about 1.6 mol %, from about 0.9 mol % to about 1.8 mol %, from about 1 mol % to about 1.8 mol %, from about 1 mol % to about 1.7 mol %, from about 1.2 mol % to about 1.8 mol %, from about 1.2 mol % to about 1.7 mol %, from about 1.3 mol % to about 1.6 mol %, or from about 1.4 mol % to about 1.5 mol % (or any fraction thereof or range therein) of the total lipid present in the particle.

In other embodiments, the lipid conjugate (e.g., PEG-lipid) comprises from about 0 mol % to about 20 mol %, from about 0.5 mol % to about 20 mol %, from about 2 mol % to about 20 mol %, from about 1.5 mol % to about 18 mol %, from about 2 mol % to about 15 mol %, from about 4 mol % to about 15 mol %, from about 2 mol % to about 12 mol %, from about 5 mol % to about 12 mol %, or about 2 mol % (or any fraction thereof or range therein) of the total lipid present in the particle.

In further embodiments, the lipid conjugate (e.g., PEG-lipid) comprises from about 4 mol % to about 10 mol %, from about 5 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle.

Additional examples, percentages, and/or ranges of lipid conjugates suitable for use in the lipid particles of the present invention are described in, e.g., PCT Publication No. WO 09/127,060, U.S. application Ser. No. 12/794,701, filed Jun. 4, 2010, U.S. Provisional Application No. 61/295,134, filed Jan. 14, 2010, U.S. application Ser. No. 12/828,189, filed Jun. 30, 2010, U.S. Provisional Application No. 61/294,828, filed Jan. 13, 2010, U.S. Provisional Application No. 61/295,140, filed Jan. 14, 2010, and PCT Publication No. WO 2010/006282, the disclosures of which are herein incorporated by reference in their entirety for all purposes.

It should be understood that the percentage of lipid conjugate (e.g., PEG-lipid) present in the lipid particles of the invention is a target amount, and that the actual amount of lipid conjugate present in the formulation may vary, for example, by ±2 mol %. For example, in the 1:57 lipid particle (e.g., SNALP) formulation, the target amount of lipid conjugate is 1.4 mol %, but the actual amount of lipid conjugate may be ±0.5 mol %, ±0.4 mol %, ±0.3 mol %, ±0.2 mol %, ±0.1 mol %, or ±0.05 mol % of that target amount, with the balance of the formulation being made up of other lipid components (adding up to 100 mol % of total lipids present in the particle). Similarly, in the 7:54 lipid particle (e.g., SNALP) formulation, the target amount of lipid conjugate is 6.76 mol %, but the actual amount of lipid conjugate may be ±2 mol %, ±1.5 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle).

One of ordinary skill in the art will appreciate that the concentration of the lipid conjugate can be varied depending on the lipid conjugate employed and the rate at which the lipid particle is to become fusogenic.

By controlling the composition and concentration of the lipid conjugate, one can control the rate at which the lipid conjugate exchanges out of the lipid particle and, in turn, the rate at which the lipid particle becomes fusogenic. For instance, when a PEG-DAA conjugate is used as the lipid conjugate, the rate at which the lipid particle becomes fusogenic can be varied, for example, by varying the concentration of the lipid conjugate, by varying the molecular weight of the PEG, or by varying the chain length and degree of saturation of the alkyl groups on the PEG-DAA conjugate. In addition, other variables including, for example, pH, temperature, ionic strength, etc. can be used to vary and/or control the rate at which the lipid particle becomes fusogenic. Other methods which can be used to control the rate at which the lipid particle becomes fusogenic will become apparent to those of skill in the art upon reading this disclosure. Also, by controlling the composition and concentration of the lipid conjugate, one can control the lipid particle (e.g., SNALP) size.

VI. Preparation of Lipid Particles

The lipid particles of the present invention, e.g., SNALP, in which an active agent or therapeutic agent such as an interfering RNA (e.g., siRNA) is entrapped within the lipid portion of the particle and is protected from degradation, can be formed by any method known in the art including, but not limited to, a continuous mixing method, a direct dilution process, and an in-line dilution process.

In particular embodiments, the cationic lipids may comprise lipids of Formula I or salts thereof, alone or in combination with other cationic lipids. In other embodiments, the non-cationic lipids are egg sphingomyelin (ESM), distearoylphosphatidylcholine (DSPC), dioleoylphosphatidylcholine (DOPC), 1-palmitoyl-2-oleoyl-phosphatidylcholine (POPC), dipalmitoyl-phosphatidylcholine (DPPC), monomethyl-phosphatidylethanolamine, dimethyl-phosphatidylethanolamine, 14:0 PE (1,2-dimyristoyl-phosphatidylethanolamine (DMPE)), 16:0 PE (1,2-dipalmitoyl-phosphatidylethanolamine (DPPE)), 18:0 PE (1,2-distearoyl-phosphatidylethanolamine (DSPE)), 18:1 PE (1,2-dioleoyl-phosphatidylethanolamine (DOPE)), 18:1 trans PE (1,2-dielaidoyl-phosphatidylethanolamine (DEPE)), 18:0-18:1

PE (1-stearoyl-2-oleoyl-phosphatidylethanolamine (SOPE)), 16:0-18:1 PE (1-palmitoyl-2-oleoyl-phosphatidylethanolamine (POPE)), polyethylene glycol-based polymers (e.g., PEG 2000, PEG 5000, PEG-modified diacylglycerols, or PEG-modified dialkyloxypropyls), cholesterol, derivatives thereof, or combinations thereof.

In certain embodiments, the present invention provides nucleic acid-lipid particles (e.g., SNALP) produced via a continuous mixing method, e.g., a process that includes providing an aqueous solution comprising a nucleic acid (e.g., interfering RNA) in a first reservoir, providing an organic lipid solution in a second reservoir (wherein the lipids present in the organic lipid solution are solubilized in an organic solvent, e.g., a lower alkanol such as ethanol), and mixing the aqueous solution with the organic lipid solution such that the organic lipid solution mixes with the aqueous solution so as to substantially instantaneously produce a lipid vesicle (e.g., liposome) encapsulating the nucleic acid within the lipid vesicle. This process and the apparatus for carrying out this process are described in detail in U.S. Patent Publication No. 20040142025, the disclosure of which is herein incorporated by reference in its entirety for all purposes.

The action of continuously introducing lipid and buffer solutions into a mixing environment, such as in a mixing chamber, causes a continuous dilution of the lipid solution with the buffer solution, thereby producing a lipid vesicle substantially instantaneously upon mixing. As used herein, the phrase "continuously diluting a lipid solution with a buffer solution" (and variations) generally means that the lipid solution is diluted sufficiently rapidly in a hydration process with sufficient force to effectuate vesicle generation. By mixing the aqueous solution comprising a nucleic acid with the organic lipid solution, the organic lipid solution undergoes a continuous stepwise dilution in the presence of the buffer solution (i.e., aqueous solution) to produce a nucleic acid-lipid particle.

The nucleic acid-lipid particles formed using the continuous mixing method typically have a size of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, less than about 120 nm, 110 nm, 100 nm, 90 nm, or 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm (or any fraction thereof or range therein). The particles thus formed do not aggregate and are optionally sized to achieve a uniform particle size.

In another embodiment, the present invention provides nucleic acid-lipid particles (e.g., SNALP) produced via a direct dilution process that includes forming a lipid vesicle (e.g., liposome) solution and immediately and directly introducing the lipid vesicle solution into a collection vessel containing a controlled amount of dilution buffer. In preferred aspects, the collection vessel includes one or more elements configured to stir the contents of the collection vessel to facilitate dilution. In one aspect, the amount of dilution buffer present in the collection vessel is substantially equal to the volume of lipid vesicle solution introduced thereto. As a non-limiting example, a lipid vesicle solution in 45% ethanol when introduced into the collection vessel containing an equal volume of dilution buffer will advantageously yield smaller particles.

In yet another embodiment, the present invention provides nucleic acid-lipid particles (e.g., SNALP) produced via an in-line dilution process in which a third reservoir containing dilution buffer is fluidly coupled to a second mixing region. In this embodiment, the lipid vesicle (e.g., liposome) solution formed in a first mixing region is immediately and directly mixed with dilution buffer in the second mixing region. In preferred aspects, the second mixing region includes a T-connector arranged so that the lipid vesicle solution and the dilution buffer flows meet as opposing 180° flows; however, connectors providing shallower angles can be used, e.g., from about 27° to about 180° (e.g., about 90°). A pump mechanism delivers a controllable flow of buffer to the second mixing region. In one aspect, the flow rate of dilution buffer provided to the second mixing region is controlled to be substantially equal to the flow rate of lipid vesicle solution introduced thereto from the first mixing region. This embodiment advantageously allows for more control of the flow of dilution buffer mixing with the lipid vesicle solution in the second mixing region, and therefore also the concentration of lipid vesicle solution in buffer throughout the second mixing process. Such control of the dilution buffer flow rate advantageously allows for small particle size formation at reduced concentrations.

These processes and the apparatuses for carrying out these direct dilution and in-line dilution processes are described in detail in U.S. Patent Publication No. 20070042031, the disclosure of which is herein incorporated by reference in its entirety for all purposes.

The nucleic acid-lipid particles formed using the direct dilution and in-line dilution processes typically have a size of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, less than about 120 nm, 110 nm, 100 nm, 90 nm, or 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm (or any fraction thereof or range therein). The particles thus formed do not aggregate and are optionally sized to achieve a uniform particle size.

If needed, the lipid particles of the invention (e.g., SNALP) can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles, is described in U.S. Pat. No. 4,737,323, the disclosure of which is herein incorporated by reference in its entirety for all purposes. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and about 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In some embodiments, the nucleic acids present in the particles are precondensed as described in, e.g., U.S. patent application Ser. No. 09/744,103, the disclosure of which is herein incorporated by reference in its entirety for all purposes.

In other embodiments, the methods may further comprise adding non-lipid polycations which are useful to effect the lipofection of cells using the present compositions. Examples of suitable non-lipid polycations include, hexadimethrine bromide (sold under the brand name POLYBRENE®, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine, and polyethyleneimine. Addition of these salts is preferably after the particles have been formed.

In some embodiments, the nucleic acid to lipid ratios (mass/mass ratios) in a formed nucleic acid-lipid particle (e.g., SNALP) will range from about 0.01 to about 0.2, from about 0.05 to about 0.2, from about 0.02 to about 0.1, from about 0.03 to about 0.1, or from about 0.01 to about 0.08. The ratio of the starting materials (input) also falls within this range. In other embodiments, the particle preparation uses about 400 μg nucleic acid per 10 mg total lipid or a nucleic acid to lipid mass ratio of about 0.01 to about 0.08 and, more preferably, about 0.04, which corresponds to 1.25 mg of total lipid per 50 μg of nucleic acid. In other preferred embodiments, the particle has a nucleic acid:lipid mass ratio of about 0.08.

In other embodiments, the lipid to nucleic acid ratios (mass/mass ratios) in a formed nucleic acid-lipid particle (e.g., SNALP) will range from about 1 (1:1) to about 100 (100:1), from about 5 (5:1) to about 100 (100:1), from about 1 (1:1) to about 50 (50:1), from about 2 (2:1) to about 50 (50:1), from about 3 (3:1) to about 50 (50:1), from about 4 (4:1) to about 50 (50:1), from about 5 (5:1) to about 50 (50:1), from about 1 (1:1) to about 25 (25:1), from about 2 (2:1) to about 25 (25:1), from about 3 (3:1) to about 25 (25:1), from about 4 (4:1) to about 25 (25:1), from about 5 (5:1) to about 25 (25:1), from about 5 (5:1) to about 20 (20:1), from about 5 (5:1) to about 15 (15:1), from about 5 (5:1) to about 10 (10:1), or about 5 (5:1), 6 (6:1), 7 (7:1), 8 (8:1), 9 (9:1), 10 (10:1), 11 (11:1), 12 (12:1), 13 (13:1), 14 (14:1), 15 (15:1), 16 (16:1), 17 (17:1), 18 (18:1), 19 (19:1), 20 (20:1), 21 (21:1), 22 (22:1), 23 (23:1), 24 (24:1), or 25 (25:1), or any fraction thereof or range therein. The ratio of the starting materials (input) also falls within this range.

As previously discussed, the conjugated lipid may further include a CPL. A variety of general methods for making SNALP-CPLs (CPL-containing SNALP) are discussed herein. Two general techniques include the "post-insertion" technique, that is, insertion of a CPL into, for example, a pre-formed SNALP, and the "standard" technique, wherein the CPL is included in the lipid mixture during, for example, the SNALP formation steps. The post-insertion technique results in SNALP having CPLs mainly in the external face of the SNALP bilayer membrane, whereas standard techniques provide SNALP having CPLs on both internal and external faces. The method is especially useful for vesicles made from phospholipids (which can contain cholesterol) and also for vesicles containing PEG-lipids (such as PEG-DAAs and PEG-DAGs). Methods of making SNALP-CPLs are taught, for example, in U.S. Pat. Nos. 5,705,385; 6,586,410; 5,981,501; 6,534,484; and 6,852,334; U.S. Patent Publication No. 20020072121; and PCT Publication No. WO 00/62813, the disclosures of which are herein incorporated by reference in their entirety for all purposes.

VII. Kits

The present invention also provides lipid particles (e.g., SNALP) in kit form. In some embodiments, the kit comprises a container which is compartmentalized for holding the various elements of the lipid particles (e.g., the active agents or therapeutic agents such as nucleic acids and the individual lipid components of the particles). Preferably, the kit comprises a container (e.g., a vial or ampoule) which holds the lipid particles of the invention (e.g., SNALP), wherein the particles are produced by one of the processes set forth herein. In certain embodiments, the kit may further comprise an endosomal membrane destabilizer (e.g., calcium ions). The kit typically contains the particle compositions of the invention, either as a suspension in a pharmaceutically acceptable carrier or in dehydrated form, with instructions for their rehydration (if lyophilized) and administration.

The lipid particles of the present invention can be tailored to preferentially target particular tissues, organs, or tumors of interest. In some instances, the 1:57 lipid particle (e.g., SNALP) formulation can be used to preferentially target the liver (e.g., normal liver tissue). In other instances, the 7:54 lipid particle (e.g., SNALP) formulation can be used to preferentially target solid tumors such as liver tumors and tumors outside of the liver. In preferred embodiments, the kits of the invention comprise these liver-directed and/or tumor-directed lipid particles, wherein the particles are present in a container as a suspension or in dehydrated form.

In certain other instances, it may be desirable to have a targeting moiety attached to the surface of the lipid particle to further enhance the targeting of the particle. Methods of attaching targeting moieties (e.g., antibodies, proteins, etc.) to lipids (such as those used in the present particles) are known to those of skill in the art.

VIII. Administration of Lipid Particles

Once formed, the lipid particles of the invention (e.g., SNALP) are useful for the introduction of active agents or therapeutic agents (e.g., nucleic acids such as interfering RNA) into cells. Accordingly, the present invention also provides methods for introducing an active agent or therapeutic agent such as a nucleic acid (e.g., interfering RNA) into a cell. In some instances, the cell is a liver cell such as, e.g., a hepatocyte present in liver tissue. In other instances, the cell is a tumor cell such as, e.g., a tumor cell present in a solid tumor. The methods are carried out in vitro or in vivo by first forming the particles as described above and then contacting the particles with the cells for a period of time sufficient for delivery of the active agent or therapeutic agent to the cells to occur.

The lipid particles of the invention (e.g., SNALP) can be adsorbed to almost any cell type with which they are mixed or contacted. Once adsorbed, the particles can either be endocytosed by a portion of the cells, exchange lipids with cell membranes, or fuse with the cells. Transfer or incorporation of the active agent or therapeutic agent (e.g., nucleic acid) portion of the particle can take place via any one of these pathways. In particular, when fusion takes place, the particle membrane is integrated into the cell membrane and the contents of the particle combine with the intracellular fluid.

The lipid particles of the invention (e.g., SNALP) can be administered either alone or in a mixture with a pharmaceutically acceptable carrier (e.g., physiological saline or phosphate buffer) selected in accordance with the route of administration and standard pharmaceutical practice. Generally, normal buffered saline (e.g., 135-150 mM NaCl) will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. Additional suitable carriers are described in, e.g., REMINGTON'S PHARMACEUTICAL SCIENCES, Mack Publishing Company, Philadelphia, Pa., 17th ed. (1985). As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The phrase "pharmaceutically acceptable" refers to molecular entities and compositions that do not produce an allergic or similar untoward reaction when administered to a human.

The pharmaceutically acceptable carrier is generally added following lipid particle formation. Thus, after the lipid particle (e.g., SNALP) is formed, the particle can be diluted into pharmaceutically acceptable carriers such as normal buffered saline.

The concentration of particles in the pharmaceutical formulations can vary widely, i.e., from less than about 0.05%, usually at or at least about 2 to 5%, to as much as about 10 to 90% by weight, and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration.

The pharmaceutical compositions of the present invention may be sterilized by conventional, well-known sterilization techniques. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alphatocopherol, and water-soluble iron-specific chelators, such as ferrioxamine, are suitable.

In some embodiments, the lipid particles of the invention (e.g., SNALP) are particularly useful in methods for the therapeutic delivery of one or more nucleic acids comprising an interfering RNA sequence (e.g., siRNA). In particular, it is an object of this invention to provide in vitro and in vivo methods for treatment of a disease or disorder in a mammal (e.g., a rodent such as a mouse or a primate such as a human, chimpanzee, or monkey) by downregulating or silencing the transcription and/or translation of one or more target nucleic acid sequences or genes of interest. As a non-limiting example, the methods of the invention are useful for in vivo delivery of interfering RNA (e.g., siRNA) to the liver and/or tumor of a mammalian subject. In certain embodiments, the disease or disorder is associated with expression and/or overexpression of a gene and expression or overexpression of the gene is reduced by the interfering RNA (e.g., siRNA). In certain other embodiments, a therapeutically effective amount of the lipid particle may be administered to the mammal. In some instances, an interfering RNA (e.g., siRNA) is formulated into a SNALP, and the particles are administered to patients requiring such treatment. In other instances, cells are removed from a patient, the interfering RNA is delivered in vitro (e.g., using a SNALP described herein), and the cells are reinjected into the patient.

A. In Vivo Administration

Systemic delivery for in vivo therapy, e.g., delivery of a therapeutic nucleic acid to a distal target cell via body systems such as the circulation, has been achieved using nucleic acid-lipid particles such as those described in PCT Publication Nos. WO 05/007196, WO 05/121348, WO 05/120152, and WO 04/002453, the disclosures of which are herein incorporated by reference in their entirety for all purposes. The present invention also provides fully encapsulated lipid particles that protect the nucleic acid from nuclease degradation in serum, are non-immunogenic, are small in size, and are suitable for repeat dosing.

For in vivo administration, administration can be in any manner known in the art, e.g., by injection, oral administration, inhalation (e.g., intransal or intratracheal), transdermal application, or rectal administration. Administration can be accomplished via single or divided doses. The pharmaceutical compositions can be administered parenterally, i.e., intraarticularly, intravenously, intraperitoneally, subcutaneously, or intramuscularly. In some embodiments, the pharmaceutical compositions are administered intravenously or intraperitoneally by a bolus injection (see, e.g., U.S. Pat. No. 5,286,634). Intracellular nucleic acid delivery has also been discussed in Straubringer et al., *Methods Enzymol.*, 101:512 (1983); Mannino et al., *Biotechniques*, 6:682 (1988); Nicolau et al., *Crit. Rev. Ther. Drug Carrier Syst.*, 6:239 (1989); and Behr, *Acc. Chem. Res.*, 26:274 (1993). Still other methods of administering lipid-based therapeutics are described in, for example, U.S. Pat. Nos. 3,993,754; 4,145,410; 4,235,871; 4,224,179; 4,522,803; and 4,588,578. The lipid particles can be administered by direct injection at the site of disease or by injection at a site distal from the site of disease (see, e.g., Culver, HUMAN GENE THERAPY, MaryAnn Liebert, Inc., Publishers, New York. pp. 70-71 (1994)). The disclosures of the above-described references are herein incorporated by reference in their entirety for all purposes.

In embodiments where the lipid particles of the present invention (e.g., SNALP) are administered intravenously, at least about 5%, 10%, 15%, 20%, or 25% of the total injected dose of the particles is present in plasma about 8, 12, 24, 36, or 48 hours after injection. In other embodiments, more than about 20%, 30%, 40% and as much as about 60%, 70% or 80% of the total injected dose of the lipid particles is present in plasma about 8, 12, 24, 36, or 48 hours after injection. In certain instances, more than about 10% of a plurality of the particles is present in the plasma of a mammal about 1 hour after administration. In certain other instances, the presence of the lipid particles is detectable at least about 1 hour after administration of the particle. In certain embodiments, the presence of a therapeutic agent such as a nucleic acid is detectable in cells of the lung, liver, tumor, or at a site of inflammation at about 8, 12, 24, 36, 48, 60, 72 or 96 hours after administration. In other embodiments, downregulation of expression of a target sequence by an interfering RNA (e.g., siRNA) is detectable at about 8, 12, 24, 36, 48, 60, 72 or 96 hours after administration. In yet other embodiments, downregulation of expression of a target sequence by an interfering RNA (e.g., siRNA) occurs preferentially in liver cells (e.g., hepatocytes), tumor cells, or in cells at a site of inflammation. In further embodiments, the presence or effect of an interfering RNA (e.g., siRNA) in cells at a site proximal or distal to the site of administration or in cells of the lung, liver, or a tumor is detectable at about 12, 24, 48, 72, or 96 hours, or at about 6, 8, 10, 12, 14, 16, 18, 19, 20, 22, 24, 26, or 28 days after administration. In additional embodiments, the lipid particles (e.g., SNALP) of the invention are administered parenterally or intraperitoneally.

The compositions of the present invention, either alone or in combination with other suitable components, can be made into aerosol formulations (i.e., they can be "nebulized") to be administered via inhalation (e.g., intranasally or intratracheally) (see, Brigham et al., *Am. J. Sci.,* 298:278 (1989)). Aerosol formulations can be placed into pressurized acceptable propellants, such as dichlorodifluoromethane, propane, nitrogen, and the like.

In certain embodiments, the pharmaceutical compositions may be delivered by intranasal sprays, inhalation, and/or other aerosol delivery vehicles. Methods for delivering nucleic acid compositions directly to the lungs via nasal aerosol sprays have been described, e.g., in U.S. Pat. Nos. 5,756,353 and 5,804,212. Likewise, the delivery of drugs using intranasal microparticle resins and lysophosphatidyl-glycerol compounds (U.S. Pat. No. 5,725,871) are also well-known in the pharmaceutical arts. Similarly, transmucosal drug delivery in the form of a polytetrafluoroethylene support matrix is described in U.S. Pat. No. 5,780,045. The disclosures of the above-described patents are herein incorporated by reference in their entirety for all purposes.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions are preferably administered, for example, by intravenous infusion, orally, topically, intraperitoneally, intravesically, or intrathecally.

Generally, when administered intravenously, the lipid particle formulations are formulated with a suitable pharmaceutical carrier. Many pharmaceutically acceptable carriers may be employed in the compositions and methods of the present invention. Suitable formulations for use in the present invention are found, for example, in REMINGTON'S PHARMACEUTICAL SCIENCES, Mack Publishing Company, Philadelphia, Pa., 17th ed. (1985). A variety of aqueous carriers may be used, for example, water, buffered water, 0.4% saline, 0.3% glycine, and the like, and may include glycoproteins for enhanced stability, such as albumin, lipoprotein, globulin, etc. Generally, normal buffered saline (135-150 mM NaCl) will be employed as the pharmaceutically acceptable carrier, but other suitable carriers will suffice. These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. These compositions can be sterilized using the techniques referred to above or, alternatively, they can be produced under sterile conditions. The resulting aqueous solutions may be packaged for use or filtered under aseptic conditions and lyophilized, the lyophilized preparation being combined with a sterile aqueous solution prior to administration.

In certain applications, the lipid particles disclosed herein may be delivered via oral administration to the individual. The particles may be incorporated with excipients and used in the form of ingestible tablets, buccal tablets, troches, capsules, pills, lozenges, elixirs, mouthwash, suspensions, oral sprays, syrups, wafers, and the like (see, e.g., U.S. Pat. Nos. 5,641,515, 5,580,579, and 5,792,451, the disclosures of which are herein incorporated by reference in their entirety for all purposes). These oral dosage forms may also contain the following: binders, gelatin; excipients, lubricants, and/or flavoring agents. When the unit dosage form is a capsule, it may contain, in addition to the materials described above, a liquid carrier. Various other materials may be present as coatings or to otherwise modify the physical form of the dosage unit. Of course, any material used in preparing any unit dosage form should be pharmaceutically pure and substantially non-toxic in the amounts employed.

Typically, these oral formulations may contain at least about 0.1% of the lipid particles or more, although the percentage of the particles may, of course, be varied and may conveniently be between about 1% or 2% and about 60% or 70% or more of the weight or volume of the total formulation. Naturally, the amount of particles in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Formulations suitable for oral administration can consist of: (a) liquid solutions, such as an effective amount of a packaged therapeutic agent such as nucleic acid (e.g., interfering RNA) suspended in diluents such as water, saline, or PEG 400; (b) capsules, sachets, or tablets, each containing a predetermined amount of a therapeutic agent such as nucleic acid (e.g., interfering RNA), as liquids, solids, granules, or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise a therapeutic agent such as nucleic acid (e.g., interfering RNA) in a flavor, e.g., sucrose, as well as pastilles comprising the therapeutic agent in an inert base, such as gelatin and glycerin or sucrose and acacia emulsions, gels, and the like containing, in addition to the therapeutic agent, carriers known in the art.

In another example of their use, lipid particles can be incorporated into a broad range of topical dosage forms. For instance, a suspension containing nucleic acid-lipid particles such as SNALP can be formulated and administered as gels, oils, emulsions, topical creams, pastes, ointments, lotions, foams, mousses, and the like.

When preparing pharmaceutical preparations of the lipid particles of the invention, it is preferable to use quantities of the particles which have been purified to reduce or eliminate empty particles or particles with therapeutic agents such as nucleic acid associated with the external surface.

The methods of the present invention may be practiced in a variety of hosts. Preferred hosts include mammalian species, such as primates (e.g., humans and chimpanzees as well as other nonhuman primates), canines, felines, equines, bovines, ovines, caprines, rodents (e.g., rats and mice), lagomorphs, and swine.

The amount of particles administered will depend upon the ratio of therapeutic agent (e.g., nucleic acid) to lipid, the particular therapeutic agent (e.g., nucleic acid) used, the disease or disorder being treated, the age, weight, and condition of the patient, and the judgment of the clinician, but will generally be between about 0.01 and about 50 mg per kilogram of body weight, preferably between about 0.1 and about 5 mg/kg of body weight, or about $10^8$-$10^{10}$ particles per administration (e.g., injection).

B. In Vitro Administration

For in vitro applications, the delivery of therapeutic agents such as nucleic acids (e.g., interfering RNA) can be to any cell grown in culture, whether of plant or animal origin, vertebrate or invertebrate, and of any tissue or type. In preferred embodiments, the cells are animal cells, more preferably mammalian cells, and most preferably human cells (e.g., tumor cells or hepatocytes).

Contact between the cells and the lipid particles, when carried out in vitro, takes place in a biologically compatible medium. The concentration of particles varies widely depending on the particular application, but is generally between about 1 µmol and about 10 mmol. Treatment of the cells with the lipid particles is generally carried out at physiological temperatures (about 37° C.) for periods of time of from about 1 to 48 hours, preferably of from about 2 to 4 hours.

In one group of preferred embodiments, a lipid particle suspension is added to 60-80% confluent plated cells having a cell density of from about $10^3$ to about $10^5$ cells/ml, more preferably about $2 \times 10^4$ cells/ml. The concentration of the suspension added to the cells is preferably of from about 0.01 to 0.2 µg/ml, more preferably about 0.1 µg/ml.

To the extent that tissue culture of cells may be required, it is well-known in the art. For example, Freshney, Culture of Animal Cells, a Manual of Basic Technique, 3rd Ed., Wiley-Liss, New York (1994), Kuchler et al., Biochemical Methods in Cell Culture and Virology, Dowden, Hutchinson and Ross, Inc. (1977), and the references cited therein provide a general guide to the culture of cells. Cultured cell systems often will be in the form of monolayers of cells, although cell suspensions are also used.

Using an Endosomal Release Parameter (ERP) assay, the delivery efficiency of the SNALP or other lipid particle of the invention can be optimized. An ERP assay is described in detail in U.S. Patent Publication No. 20030077829, the disclosure of which is herein incorporated by reference in its entirety for all purposes. More particularly, the purpose of an ERP assay is to distinguish the effect of various cationic lipids and helper lipid components of SNALP or other lipid particle based on their relative effect on binding/uptake or fusion with/destabilization of the endosomal membrane. This assay allows one to determine quantitatively how each component of the SNALP or other lipid particle affects delivery efficiency, thereby optimizing the SNALP or other lipid particle. Usually, an ERP assay measures expression of a reporter protein (e.g., luciferase, β-galactosidase, green fluorescent protein (GFP), etc.), and in some instances, a SNALP formulation optimized for an expression plasmid will also be appropriate for encapsulating an interfering RNA. In other instances, an ERP assay can be adapted to measure down-regulation of transcription or translation of a target sequence in the presence or absence of an interfering RNA (e.g., siRNA). By comparing the ERPs for each of the various SNALP or other lipid particles, one can readily determine the optimized system, e.g., the SNALP or other lipid particle that has the greatest uptake in the cell.

C. Cells for Delivery of Lipid Particles

The compositions and methods of the present invention are used to treat a wide variety of cell types, in vivo and in vitro. Suitable cells include, but are not limited to, hepatocytes, reticuloendothelial cells (e.g., monocytes, macrophages, etc.), fibroblast cells, endothelial cells, platelet cells, other cell types infected and/or susceptible of being infected with viruses, hematopoietic precursor (stem) cells, keratinocytes, skeletal and smooth muscle cells, osteoblasts, neurons, quiescent lymphocytes, terminally differentiated cells, slow or noncycling primary cells, parenchymal cells, lymphoid cells, epithelial cells, bone cells, and the like.

In particular embodiments, an active agent or therapeutic agent such as a nucleic acid (e.g., an interfering RNA) is delivered to cancer cells (e.g., cells of a solid tumor) including, but not limited to, liver cancer cells, lung cancer cells, colon cancer cells, rectal cancer cells, anal cancer cells, bile duct cancer cells, small intestine cancer cells, stomach (gastric) cancer cells, esophageal cancer cells, gallbladder cancer cells, pancreatic cancer cells, appendix cancer cells, breast cancer cells, ovarian cancer cells, cervical cancer cells, prostate cancer cells, renal cancer cells, cancer cells of the central nervous system, glioblastoma tumor cells, skin cancer cells, lymphoma cells, choriocarcinoma tumor cells, head and neck cancer cells, osteogenic sarcoma tumor cells, and blood cancer cells.

In vivo delivery of lipid particles such as SNALP encapsulating a nucleic acid (e.g., an interfering RNA) is suited for targeting cells of any cell type. The methods and compositions can be employed with cells of a wide variety of vertebrates, including mammals, such as, e.g, canines, felines, equines, bovines, ovines, caprines, rodents (e.g., mice, rats, and guinea pigs), lagomorphs, swine, and primates (e.g. monkeys, chimpanzees, and humans).

D. Detection of Lipid Particles

In some embodiments, the lipid particles of the present invention (e.g., SNALP) are detectable in the subject at about 1, 2, 3, 4, 5, 6, 7, 8 or more hours. In other embodiments, the lipid particles of the present invention (e.g., SNALP) are detectable in the subject at about 8, 12, 24, 48, 60, 72, or 96 hours, or about 6, 8, 10, 12, 14, 16, 18, 19, 22, 24, 25, or 28 days after administration of the particles. The presence of the particles can be detected in the cells, tissues, or other biological samples from the subject. The particles may be detected, e.g., by direct detection of the particles, detection of a therapeutic nucleic acid such as an interfering RNA (e.g., siRNA) sequence, detection of the target sequence of interest (i.e., by detecting expression or reduced expression of the sequence of interest), or a combination thereof.

1. Detection of Particles

Lipid particles of the invention such as SNALP can be detected using any method known in the art. For example, a label can be coupled directly or indirectly to a component of the lipid particle using methods well-known in the art. A wide variety of labels can be used, with the choice of label depending on sensitivity required, ease of conjugation with the lipid particle component, stability requirements, and available instrumentation and disposal provisions. Suitable labels include, but are not limited to, spectral labels such as fluorescent dyes (e.g., fluorescein and derivatives, such as fluorescein isothiocyanate (FITC) and Oregon Green™; rhodamine and derivatives such Texas red, tetrarhodimine isothiocynate (TRITC), etc., digoxigenin, biotin, phycoerythrin, AMCA, CyDyes™, and the like; radiolabels such as $^3$H, $^{125}$I, $^{35}$S, $^{14}$C, $^{32}$P, $^{33}$P, etc.; enzymes such as horse radish peroxidase, alkaline phosphatase, etc.; spectral colorimetric labels such as colloidal gold or colored glass or plastic beads such as polystyrene, polypropylene, latex, etc. The label can be detected using any means known in the art.

2. Detection of Nucleic Acids

Nucleic acids (e.g., interfering RNA) are detected and quantified herein by any of a number of means well-known to those of skill in the art. The detection of nucleic acids may proceed by well-known methods such as Southern analysis, Northern analysis, gel electrophoresis, PCR, radiolabeling, scintillation counting, and affinity chromatography. Additional analytic biochemical methods such as spectrophotometry, radiography, electrophoresis, capillary electrophoresis, high performance liquid chromatography (HPLC), thin layer chromatography (TLC), and hyperdiffusion chromatography may also be employed.

The selection of a nucleic acid hybridization format is not critical. A variety of nucleic acid hybridization formats are known to those skilled in the art. For example, common formats include sandwich assays and competition or displacement assays. Hybridization techniques are generally described in, e.g., "Nucleic Acid Hybridization, A Practical Approach," Eds. Hames and Higgins, IRL Press (1985).

The sensitivity of the hybridization assays may be enhanced through the use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR), the ligase chain reaction (LCR), Qβ-replicase amplification, and other RNA polymerase mediated techniques (e.g., NASBA™) are found in Sambrook et al., *In Molecular Cloning: A Laboratory Manual*, Cold Spring Harbor Laboratory Press (2000); and Ausubel et al., SHORT PROTOCOLS IN MOLECULAR BIOLOGY, eds., Current Protocols, Greene Publishing Associates, Inc. and John Wiley & Sons, Inc. (2002); as well as U.S. Pat. No. 4,683,202; PCR Protocols, A Guide to Methods and Applications (Innis et al. eds.) Academic Press Inc. San Diego, Calif. (1990); Arnheim & Levinson (Oct. 1, 1990), *C&EN* 36; *The Journal Of NIH Research*, 3:81 (1991); Kwoh et al., *Proc. Natl. Acad. Sci. USA*, 86:1173 (1989); Guatelli et al., *Proc. Natl. Acad. Sci. USA*, 87:1874 (1990); Lomeli et al., *J. Clin. Chem.*, 35:1826 (1989); Landegren et al., *Science*, 241:1077 (1988); Van Brunt, *Biotechnology*, 8:291 (1990); Wu and Wallace, *Gene*, 4:560 (1989); Barringer et al., *Gene*, 89:117 (1990); and Sooknanan and Malek, *Biotechnology*, 13:563 (1995). Improved methods of cloning in vitro amplified nucleic acids are described in U.S. Pat. No. 5,426,039. Other methods described in the art are the nucleic acid sequence based amplification (NASBA™, Cangene, Mississauga, Ontario) and Qβ-replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation. The disclosures of the above-described references are herein incorporated by reference in their entirety for all purposes.

Nucleic acids for use as probes, e.g., in in vitro amplification methods, for use as gene probes, or as inhibitor components are typically synthesized chemically according to the solid phase phosphoramidite triester method described by Beaucage et al., *Tetrahedron Letts.*, 22:1859 1862 (1981), e.g., using an automated synthesizer, as described in Needham VanDevanter et al., *Nucleic Acids Res.*, 12:6159 (1984). Purification of polynucleotides, where necessary, is typically performed by either native acrylamide gel electrophoresis or by anion exchange HPLC as described in Pearson et al., *J. Chrom.*, 255:137 149 (1983). The sequence of the synthetic polynucleotides can be verified using the chemical degradation method of Maxam and Gilbert (1980) in Grossman and Moldave (eds.) Academic Press, New York, *Methods in Enzymology*, 65:499.

An alternative means for determining the level of transcription is in situ hybridization. In situ hybridization assays are well-known and are generally described in Angerer et al., *Methods Enzymol.*, 152:649 (1987). In an in situ hybridization assay, cells are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

IX. Examples

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

Synthesis of 13-B1

Synthesis of compound 13-B1,(13Z,16Z)-4-hydroxy-4-((9Z,12Z)-octadeca-9,12-dienyl)-3-((9Z,12Z)-octadeca-9,12-dienyloxy)docosa-13,16-dienyl 4-(dimethylamino)butanoate, having structure (B) below, was synthesized as described in Scheme 7 below

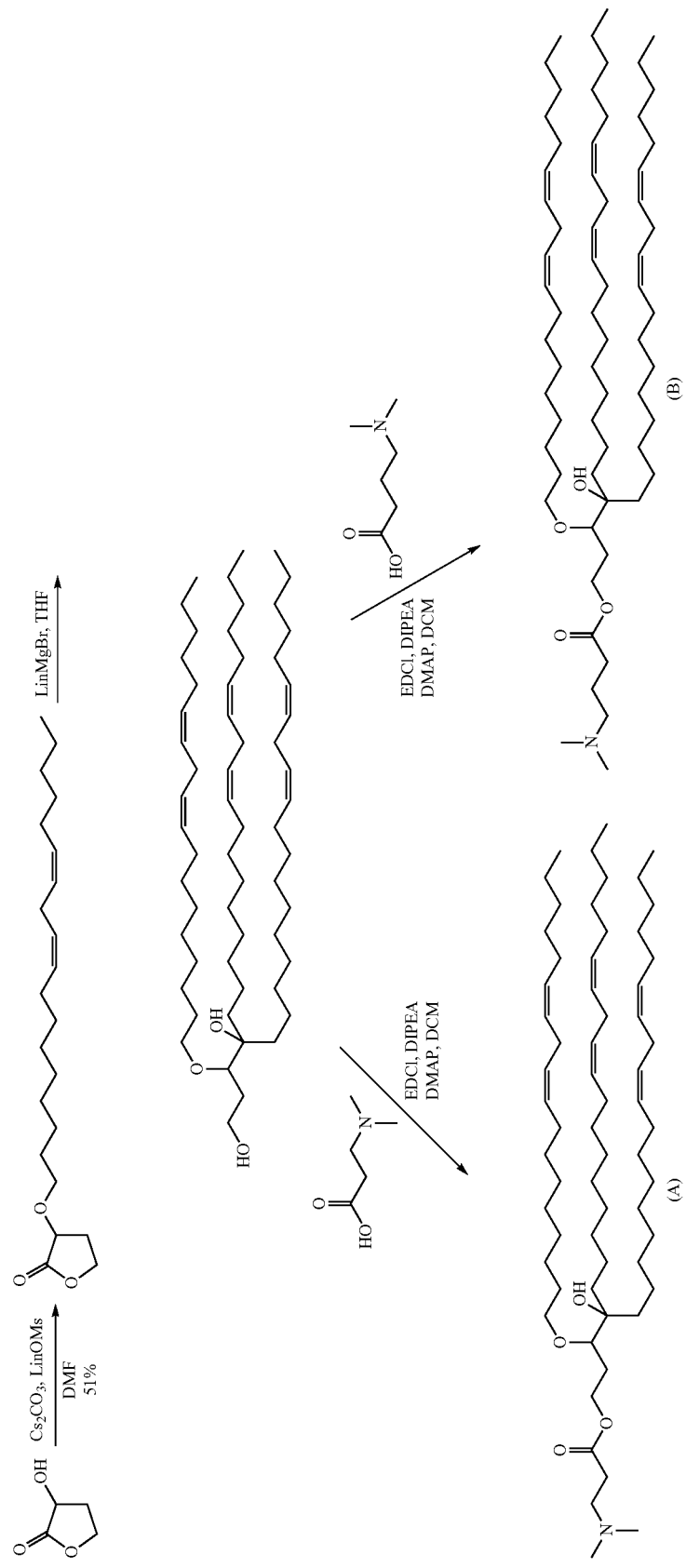
Scheme 7. Synthetic preparation of compounds 13-B1 and 13-B3.

Step 1: Synthesis of 3-((9Z,12Z)-octadeca-9,12-dienyloxy)dihydrofuran-2(3H)-one, having the structure below

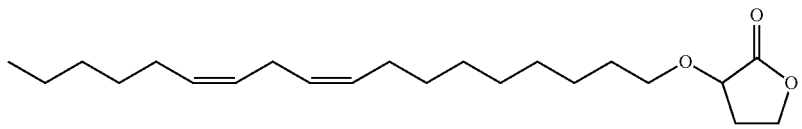 [SMILES: CCCCC/C=C\C/C=C\CCCCCCCCOC1CCOC1=O]

To a solution of α-hydroxybutyrolactone (2.0 g, 19.6 mmol) and linoleyl methane sulfonate (5.4 g, 15.7 mmol) in anhydrous DMF (60 mL), was added cesium carbonate (8.0 g, 24.5 mmol). The solution was stirred overnight under nitrogen at 80° C. Upon completion, the reaction was poured into water (100 mL) and extracted with ethyl acetate (3×100 mL). The combined ethyl acetate extracts were washed with brine (3×50 mL), dried on magnesium sulfate, filtered and concentrated in vacuo to dryness. The residue was purified by column chromatography on silica gel 60 (eluted with 10% ethyl acetate in hexanes) to afford 3-((9Z,12Z)-octadeca-9,12-dienyloxy)dihydrofuran-2(3H)-one as a pale yellow oil (3.5 g, 51%).

Step 2: Synthesis of (14Z,17Z)-4-((9Z,12Z)-octadeca-9,12-dienyl)-3-((9Z,12Z)-octadeca-9,12-dienyloxy)tricosa-14,17-diene-1,4-diol, having the following structure

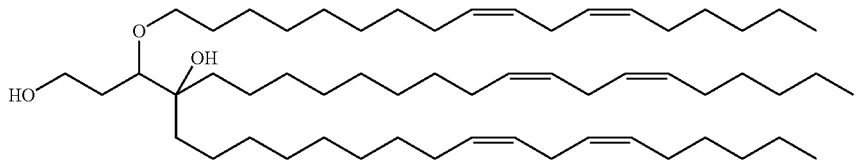 [SMILES: CCCCC/C=C\C/C=C\CCCCCCCCOC(CCO)C(O)(CCCCCCCC/C=C\C/C=C\CCCCC)CCCCCCCC/C=C\C/C=C\CCCCC]

A 100 mL round bottom flask charged with magnesium turnings (250 mg) and a stir bar was dried with a heat gun for 5 minutes then cooled under nitrogen. The flask was charged with dry THF (10 mL) and a small grain of iodine. A solution of linoleyl bromide (3 g, 9.1 mmol) in diethyl ether was added slowly and the mixture was stirred at room temperature. The Grignard did not initiate so the solution was concentrated to ~5 mL then stirred for 2 minutes until the solution turned opaque and the iodine color disappeared. After 20 minutes, a colorless solid precipitated so the reaction was diluted with THF (15 mL) and stirred overnight. The next day 3-((9Z,12Z)-octadeca-9,12-dienyloxy)dihydrofuran-2(3H)-one (1.3 g, 3.6 mmol) was added and the solution was stirred for 3 hours. The reaction was diluted with ether (100 mL) and washed with 5% HCl (50 mL). The ether layer was dried on magnesium sulfate, filtered and concentrated in vacuo to dryness. The residue was purified by column chromatography on silica gel 60 (eluted with 10% ether in hexanes) to afford (14Z,17Z)-4-((9Z,12Z)-octadeca-9,12-dienyl)-3-((9Z,12Z)-octadeca-9,12-dienyloxy)tricosa-14,17-diene-1,4-diol as a colorless oil (1.75 g, 56%).

Step 3: Synthesis of compound 13-B1, (13Z,16Z)-4-hydroxy-4-((9Z,12Z)-octadeca-9,12-dienyl)-3-((9Z,12Z)-octadeca-9,12-dienyloxy)docosa-13,16-dienyl 4-(dimethylamino)butanoate, having the following structure

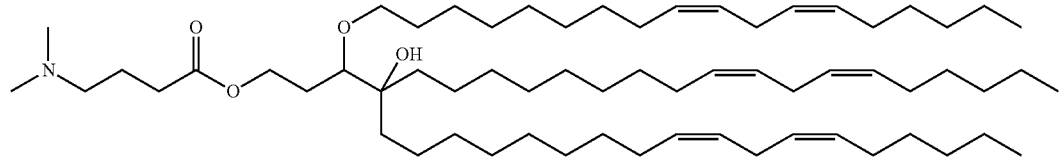 [SMILES: CCCCC/C=C\C/C=C\CCCCCCCCOC(CCOC(=O)CCCN(C)C)C(O)(CCCCCCCC/C=C\C/C=C\CCCCC)CCCCCCCC/C=C\C/C=C\CCCCC]

To a solution of (14Z,17Z)-4-((9Z,12Z)-octadeca-9,12-dienyl)-3-((9Z,12Z)-octadeca-9,12-dienyloxy)tricosa-14,17-diene-1,4-diol (450 mg, 0.52 mmol), 4-(dimethylamino)butanoic acid hydrochloride (105 mg, 0.62 mmol), EDCI hydrochloride (120 mg, 0.62 mmol), DIPEA (225 μL, 1.3 mmol) in anhydrous dichloromethane (10 mL) was added DMAP (5 mg). The solution was stirred at room temperature under nitrogen for 64 hours. Upon completion, the solution was concentrated in vacuo to dryness and purified by column chromatography on silica gel 60 (eluted with 1:1 hexanes/ Ethyl acetate) to afford (13Z,16Z)-4-hydroxy-4-((9Z,12Z)-octadeca-9,12-dienyl)-3-((9Z,12Z)-octadeca-9,12-dienyloxy)docosa-13,16-dienyl 4-(dimethylamino)butanoate as a colorless oil (375 mg, 75%). $^1$H NMR (400 MHz, CDCl$_3$) δ 5.43-5.29 (m, 12H), 4.31-4.11 (m, 2H), 3.60-5.29 (m, 2H), 3.27-3.22 (m, 1H), 2.78 (t, 6H, J=6.4 Hz), 2.39-2.28 (m, 3H), 2.24 (s, 6H), 2.09-2.02 (m, 12H), 1.91-1.72 (m, 4H), 1.61-1.23 (m, 60H), 0.90 (t, 9H, J=7.0 Hz).

Example 2

Synthesis of 13-B3

See steps 1 and 2 of Example 1.

Step 3: Synthesis of compound 13-B3,(13Z,16Z)-4-hydroxy-4-((9Z,12Z)-octadeca-9,12-dienyl)-3-((9Z,12Z)-octadeca-9,12-dienyloxy)docosa-13,16-dienyl 3-(dimethylamino)propanoate, having the following structure, was synthesized as described above in Scheme 7 for structure (A)

To a solution of (14Z,17Z)-4-((9Z,12Z)-octadeca-9,12-dienyl)-3-((9Z,12Z)-octadeca-9,12-dienyloxy)tricosa-14,17-diene-1,4-diol (1.5 g, 1.73 mmol), 4-(dimethylamino)propanoic acid hydrochloride (500 mg, 3.3 mmol), EDCI hydrochloride (750 mg, 3.9 mmol), DIPEA (225 μL, 1.3 mmol) in anhydrous dichloromethane (15 mL) was added DMAP (5 mg). The solution was stirred at room temperature under nitrogen for 20 hours. Upon completion, the solution was concentrated in vacuo to dryness and purified by column chromatography on silica gel 60 (eluted with 1:1 hexanes/ Ethyl acetate) to afford (13Z,16Z)-4-hydroxy-4-((9Z,12Z)-octadeca-9,12-dienyl)-3-((9Z,12Z)-octadeca-9,12-dienyloxy)docosa-13,16-dienyl 3-(dimethylamino)propanoate as a colorless oil (275 mg). $^1$H NMR (400 MHz, CDCl$_3$) δ 5.43-5.29 (m, 12H), 4.34-4.14 (m, 2H), 3.60-3.43 (m, 2H), 3.25 (dd, 1H, J=8.8, 2.8 Hz), 2.81-2.68 (m, 8H), 2.62-2.53 (m, 2H), 2.33 (s, 6H), 2.10-2.00 (m, 12H), 1.04-1.72 (m, 2H), 1.62-1.15 (m, 60H), 0.90 (t, 9H, J=7.0 Hz).

Example 3

Synthesis of 13-B2

Compound 13-B2, having structure (C) below, was synthesized as described in Scheme 8 below.

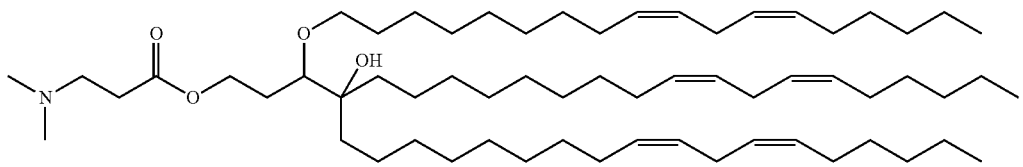 [SMILES: CCCCC/C=C\C/C=C\CCCCCCCCOC(CCOC(=O)CCN(C)C)C(O)(CCCCCCCC/C=C\C/C=C\CCCCC)CCCCCCCC/C=C\C/C=C\CCCCC]

Scheme 8: Synthetic preparation of compounds 13B2 and 13B4.

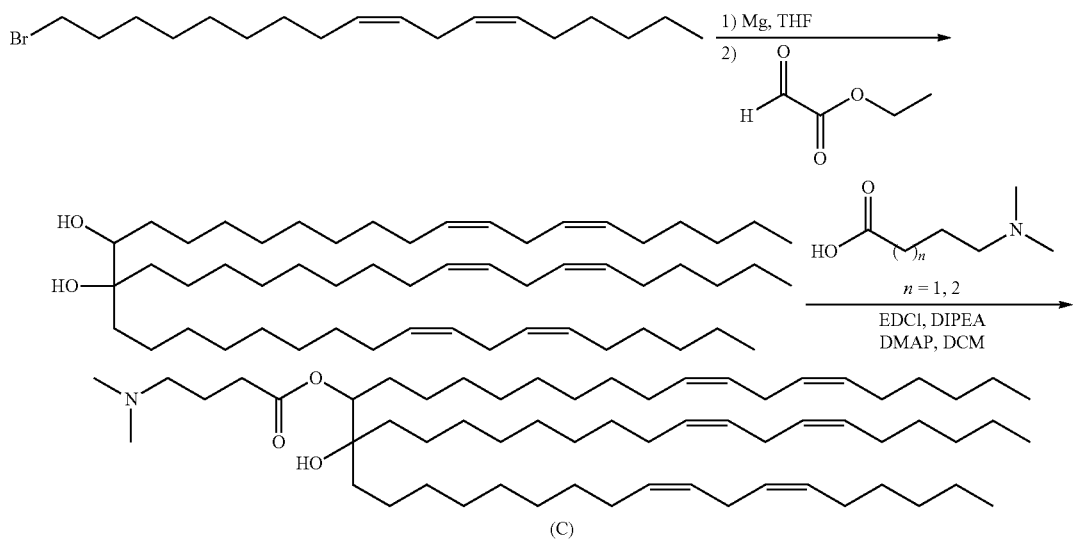

(C)

-continued

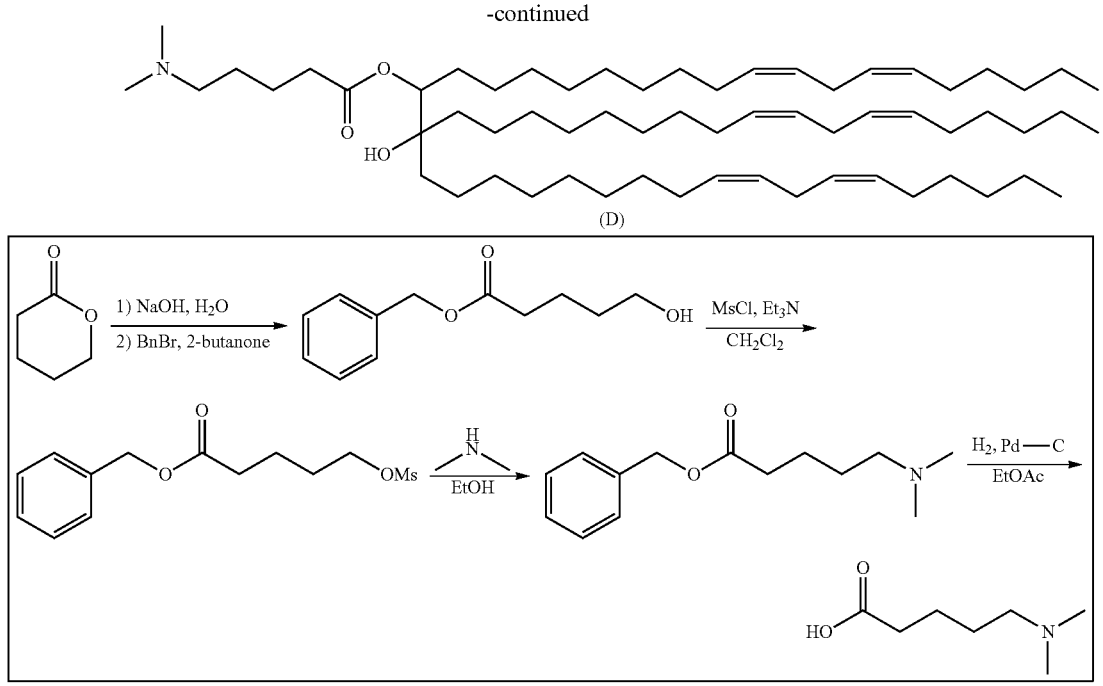

(D)

Step 1: Synthesis of (6Z,9Z,29Z,32Z)-19-((9Z,12Z)-octadeca-9,12-dienyl)octatriaconta-6,9,29,32-tetraene-19,20-diol, having the following structure

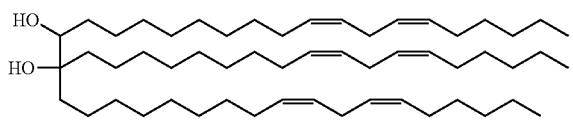 [SMILES: CCCCC/C=C\C/C=C\CCCCCCCCC(O)C(O)(CCCCCCCC/C=C\C/C=C\CCCCC)CCCCCCCC/C=C\C/C=C\CCCCC]

Step 2: Compound 13-B2, synthesis of (6Z,9Z,29Z,32Z)-20-hydroxy-20-((9Z,12Z)-octadeca-9,12-dienyl)octatriaconta-6,9,29,32-tetraen-19-yl-4-(dimethylamino)butanoate

A 100 mL round bottom flask was charged with magnesium turnings (360 mg, 14.6 mmol) and a stir bar. The flask was dried with a heat gun for 5 minutes then cooled under nitrogen. The flask was charged with THF (5 mL) and a small grain of iodine. A solution of linoleyl bromide (4 g, 12.1 mmol) in THF (5 mL) was added slowly and after 5 minutes the reaction initiated vigorously. The solution was stirred at room temperature for 2 hours, and then ethyl glyoxalate (0.5 mL, 2.42 mmol, 50% solution in toluene) was added. The exothermic reaction was finished immediately and quenched with saturated ammonium chloride solution (5 mL). The solution diluted with water and extracted with diethyl ether (3×50 mL). The combined diethyl ether extracts were dried on magnesium sulfate, filtered and concentrated in vacuo to dryness. The oil was purified by column chromatography on silica gel 60 (eluted with 100% Hexanes to 15% Et$_2$O in hexanes) to afford (6Z,9Z,29Z,32Z)-19-((9Z,12Z)-octadeca-9,12-dienyl)octatriaconta-6,9,29,32-tetraene-19,20-diol as a colorless oil (945 mg, 48%).

To a solution of (6Z,9Z,29Z,32Z)-19-((9Z,12Z)-octadeca-9,12-dienyl)octatriaconta-6,9,29,32-tetraene-19,20-diol (500 mg, 0.65 mmol), 4-(dimethylamino)butanoic acid hydrochloride (131 mg, 0.78 mmol), EDCI hydrochloride (150 mg, 0.78 mmol), DIPEA (285 µL, 1.63 mmol) in anhydrous dichloromethane (10 mL) was added DMAP (5 mg). The solution was stirred at room temperature under nitrogen for 16 hours. The reaction was not complete so additional 4-(dimethylamino)butanoic acid hydrochloride (131 mg, 0.78 mmol), EDCI hydrochloride (150 mg, 0.78 mmol), DIPEA (285 µL, 1.63 mmol) and DMAP (5 mg) were added. The solution was refluxed for 6 hours and cooled to room temperature. The reaction mixture (10 mL loaded directly onto column) was purified by column chromatography on silica gel 60 (eluted with 100% hexanes→2:1→1:1 hexanes/ ethyl acetate) to afford (6Z,9Z,29Z,32Z)-20-hydroxy-20-((9Z,12Z)-octadeca-9,12-dienyl)octatriaconta-6,9,29,32-tetraen-19-yl-4-(dimethylamino)butanoate as a colorless oil (440 mg, 77%). $^1$H NMR (400 MHz, CDCl$_3$) δ 5.42-5.31 (m, 12H), 4.98 (dd, 1H, J=10.5, 2.3 Hz), 2.78 (t, 6H, J=6.9 Hz), 2.45-2.33 (m, 4H), 2.26 (s, 6H), 2.09-2.02 (m, 12H), 1.93-1.77 (m, 2H), 1.62-1.42 (m, 4H), 1.41-1.20 (m, 52H), 0.90 (t, 9H, J=6.7 Hz).

Example 4

Synthesis of 13-B4

See step 1 of Example 3.

Step 2: Synthesis of 5-Hydroxy benzylpentanoate, having the following structure

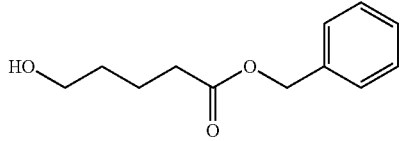 [SMILES: O=C(CCCCO)OCc1ccccc1]

A solution of δ-valerolactone (10.0 g, 100 mmol) in a 1M aqueous sodium hydroxide solution (100 mL) was heated for 16 hours at 65° C. The residue was concentrated in vacuo and the remaining white powder dried under high vacuum at 60° C. The white powder was pulverized and suspended in acetone (40 mL). With stirring, benzyl bromide (17.0 g, 101 mmol) and tetrabutylammonium bromide (0.82 g) were added. The mixture was heated with stirring for 72 hours at 45° C. It was then cooled to room temperature, concentrated in vacuo to dryness and dissolved in ethyl acetate (250 mL). The ethyl acetate solution was washed with saturated sodium bicarbonate (2×50 mL) and brine (2×50 mL). The organic portion was dried on magnesium sulfate, filtered, and concentrated in vacuo to dryness. The resulting yellow oil was purified by column chromatography on silica gel 60 (eluted with a gradient of 100% hexanes→30%→50% ethyl acetate in hexanes) to afford 5-hydroxy benzylpentanoate as a yellow oil (3.11 g, 15%).

Step 3: Synthesis of 5-Methanesulfonyl benzylpentanoate, having the following structure

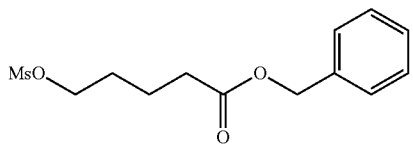 [SMILES: CS(=O)(=O)OCCCCC(=O)OCc1ccccc1]

To a solution of 5-hydroxy benzylpentanoate (1.46 g, 7.0 mmol) and triethylamine (1.95 mL, 14.0 mmol) in anhydrous dichloromethane (30 mL) at −10° C. was added a solution of methanesulfonyl chloride (0.68 mL, 8.8 mmol) in dry dichloromethane (10 mL) drop wise over 1 hour. The solution was stirred overnight at room temperature. TLC (3:1 ethyl acetate/hexanes) indicated that the reaction was complete so the solution was diluted with dichloromethane and washed saturated sodium bicarbonate (3×50 mL). The combined aqueous layers were back extracted twice with dichloromethane. The combined organic layers were dried on magnesium sulfate, filtered, and concentrated in vacuo to dryness. The resulting yellow oil was purified by column chromatography on silica gel 60 (eluted with a gradient of 10%→20%→30% ethyl acetate in hexanes) to afford 5-Methanesulfonyl benzylpentanoate as a pale yellow oil (1.76 g, 88%).

Step 4: Synthesis of 5-(dimethylamino) benzylpentanoate, having the following structure

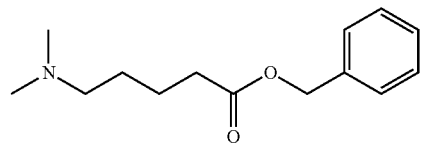 [SMILES: CN(C)CCCCC(=O)OCc1ccccc1]

A solution of 5-(Methanesulfonyl)benzylpentanoate (1.76 g, 6.2 mmol) in 5.6M dimethylamine in ethanol (100 mL) was stirred at room temperature for 72 hours. Upon completion, the solution was concentrated in vacuo to dryness and the resulting brown oil purified by column chromatography on silica gel 60 (eluted with 2% MeOH and 0.3% NH$_4$OH(aq) in dichloromethane) to afford 5-(dimethylamino) benzylpentanoate as a brown oil (577 mg, 40%).

Step 5: Synthesis of 5-(Dimethylamino)pentanoic Acid, having the following structure

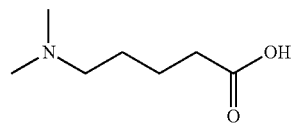

To a solution of 5-(dimethylamino) benzylpentanoate (577 mg, 2.45 mmol) in ethyl acetate (20 mL) was added 10% palladium on carbon (80 mg). The solution was stirred vigorously under hydrogen and monitored by TLC (10% MeOH, 1% NH4OH in dichloromethane). After 4 hours the reaction was approximately 50% complete, so additional palladium on carbon (160 mg) was added and hydrogen gas bubbled through the solution. The solution was then left stirring under hydrogen overnight. Upon completion, the solution was filtered through celite and concentrated in vacuo to afford 5-(Dimethylamino)pentanoic Acid as a yellow solid (357 mg, quantitative).

Step 6: Synthesis of compound 13-B4, (6Z,9Z,29Z, 32Z)-20-hydroxy-20-((9Z,12Z)-octadeca-9,12-dienyl)octatriaconta-6,9,29,32-tetraen-19-yl 5-(dimethylamino)pentanoate, having the following structure

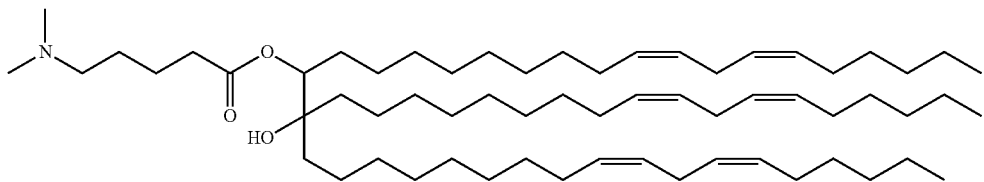 [SMILES: CCCCC/C=C\C/C=C\CCCCCCCCC(OC(=O)CCCCN(C)C)C(O)(CCCCCCCC/C=C\C/C=C\CCCCC)CCCCCCCC/C=C\C/C=C\CCCCC]

To a solution of (6Z,9Z,29Z,32Z)-19-((9Z,12Z)-octadeca-9,12-dienyl)octatriaconta-6,9,29,32-tetraene-19,20-diol (0.75 g, 0.98 mmol), 5-(dimethylamino)pentanoic acid (285 mg, 2.0 mmol), EDC hydrochloride (378 mg, 2.0 mmol), and 4-(N,N-dimethylamino)pyridine (5 mg) in anhydrous dichloromethane (10 mL) was added DIPEA (0.68 mL, 3.9 mmol). The reaction was stirred for 16 hours at room temperature under nitrogen. TLC (1:1 hexanes/ethyl acetate) indicated that the reaction had stalled, so additional 5-(dimethylamino) pentanoic acid (70 mg, 0.5 mmol) and fresh EDC hydrochloride (300 mg, 1.6 mmol) were added. The reaction was stirred for an additional 24 hours under nitrogen at room temperature. The solution was diluted with dichloromethane (100 mL) and washed with saturated sodium bicarbonate (50 mL), water (50 mL), and brine (50 mL). The combined aqueous layers were back extracted once with dichloromethane (50 mL). The combined dichloromethane extracts were dried on magnesium sulfate, filtered, and concentrated in vacuo to dryness. The resulting orange oil was purified by column chromatography on silica gel 60 (eluted with a gradient of 25%→50% ethyl acetate in hexanes) to afford (6Z,9Z,29Z, 32Z)-20-hydroxy-20-((9Z,12Z)-octadeca-9,12-dienyl)octa-triaconta-6,9,29,32-tetraen-19-yl 5-(dimethylamino)pentanoate as a pale yellow oil (560 mg, 64%). 1H NMR (400 MHz, CDCl$_3$) δ 5.43-5.29 (m, 12H), 4.95 (dd, 1H, J=10.1, 2.7 Hz), 2.78 (t, 6H, J=6.5 Hz), 2.38 (t, 2H, J=7.5 Hz), 2.28 (t, 2H, J=7.5 Hz), 2.22 (s, 6H), 2.09-2.02 (m, 12H), 1.72-1.42 (m, 13H), 1.41-1.19 (m, 56H), 0.90 (t, 9H, J=6.7 Hz).

Example 5

Synthesis of 13-B5

Scheme 9: Synthetic preparation of compounds 13-B5.

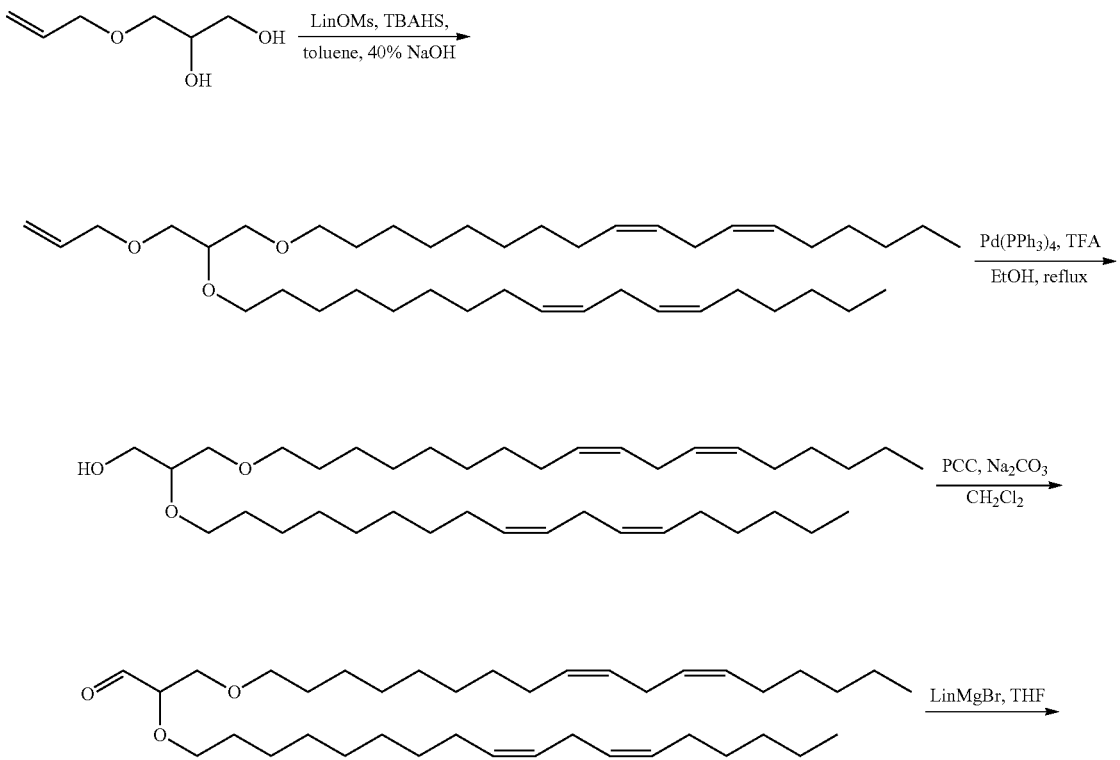

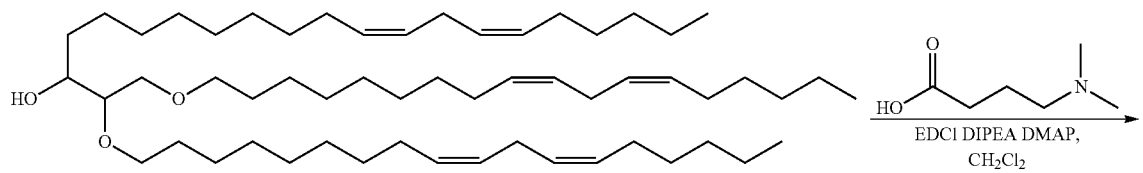

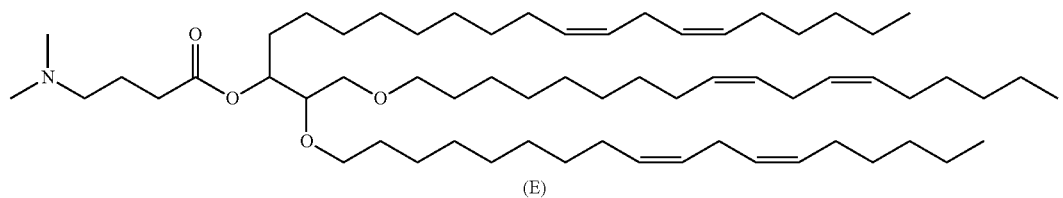

(E)

Step 1: Synthesis of (6Z,9Z)-18-(3-(allyloxy)-2-((9Z,12Z)-octadeca-9,12-dienyloxy)propoxy)octadeca-6,9-diene, having the following structure

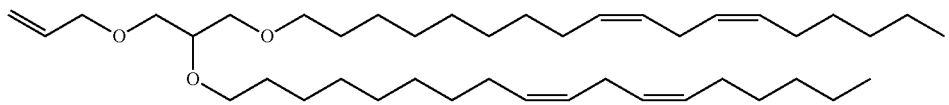 [SMILES: C=CCOCC(COCCCCCCCC/C=C\C/C=C\CCCCC)OCCCCCCCC/C=C\C/C=C\CCCCC]

A 500 mL round bottom flask was charged with 3-(allyloxy)propane-1,2-diol (2.6 g, 19.8 mmol), linoleyl mesylate (15.0 g, 43.5 mmol), tetrabutylammonium hydrogen sulfate (3.4 g, 9.9 mmol), toluene (600 mL) and 40% NaOH (30 mL). The reagents were vigorously stirred (emulsified) for 80 hours at room temperature. Upon completion, the solution was diluted with water (100 mL) and toluene (100 mL). The toluene was separated and the remaining aqueous solution was extracted with toluene (150 mL). The combine toluene extracts were dried on magnesium sulfate, filtered and concentrated in vacuo to dryness. The residue was purified by column chromatography on silica gel 60 (eluted with 5% diethyl ether in hexanes) to afford (6Z,9Z)-18-(3-(allyloxy)-2-((9Z,12Z)-octadeca-9,12-dienyloxy)propoxy)octadeca-6,9-diene as a colorless oil (9.1 g, 73%).

Step 2: Synthesis of 2,3-bis((9Z,12Z)-octadeca-9,12-dienyloxy)propan-1-ol, having the following structure

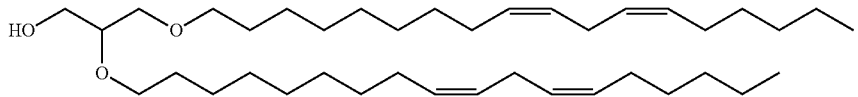 [SMILES: CCCCC/C=C\C/C=C\CCCCCCCCOCC(CO)OCCCCCCCC/C=C\C/C=C\CCCCC]

To a solution of (6Z,9Z)-18-(3-(allyloxy)-2-((9Z,12Z)-octadeca-9,12-dienyloxy)propoxy)octadeca-6,9-diene (9.1 g, 14.3 mmol) in ethanol (100 ml) was added trifluoroacetic acid (15.0 mL) and tetrakis(triphenylphosphine)palladium(0) (1.65 g, 1.43 mmol). The solution was refluxed for 16 hours, cooled to room temperature and concentrated in vacuo to dryness. The residue was purified by column chromatography on silica gel 60 (eluted with a gradient of 100% hexanes to 1:1 hexanes/DCM to 100% DCM) to afford 2,3-bis((9Z,12Z)-octadeca-9,12-dienyloxy)propan-1-ol as a colorless oil (6.1 g, 54%).

Step 3: Synthesis of 2,3-bis((9Z,12Z)-octadeca-9,12-dienyloxy)propanal, having the following structure

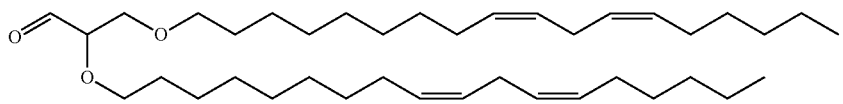

To a solution of 2,3-bis((9Z,12Z)-octadeca-9,12-dienyloxy)propan-1-ol (4.0 g, 7.0 mmol) and PCC (4.5 g, 21.0 mmol) in dichloromethane (75 mL) was added sodium carbonate (375 mg, 3.5 mmol). The solution was stirred for 6 hours at room temperature then filtered through silica with diethyl ether rinses (250 mL). The filtrate was concentrated in vacuo to dryness and purified by column chromatography on silica gel 60 (eluted with a gradient of 100% hexanes to 5% ether in hexanes) to afford 2,3-bis((9Z,12Z)-octadeca-9,12-dienyloxy)propanal as a colorless oil (1.6 g, 39%)

Step 4: Synthesis of (12Z,15Z)-1,2-bis((9Z,12Z)-octadeca-9,12-dienyloxy)henicosa-12,15-dien-3-ol, having the following structure

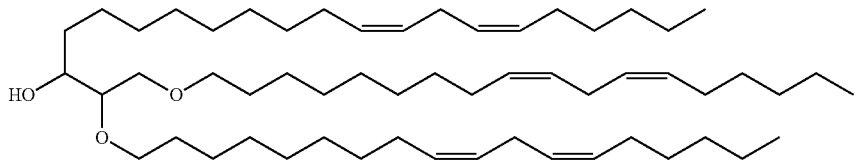 [SMILES: CCCCC/C=C\C/C=C\CCCCCCCCOCC(OCCCCCCCC/C=C\C/C=C\CCCCC)C(O)CCCCCCCC/C=C\C/C=C\CCCCC]

To a solution of 2,3-bis((9Z,12Z)-octadeca-9,12-dienyloxy)propanal (1.5 g, 2.62 mmol) in anhydrous diethyl ether (10 mL) was added LinMgBr Grignard (2.56 mL, 5.23 mmol). Upon completion, the solution was quenched with 5% HCl (50 mL) and washed with diethyl ether (3×50 mL). The combined ethyl ether extracts were dried on magnesium sulfate, filtered and concentrated in vacuo to dryness. The residue was purified by column chromatography on silica gel 60 (eluted with a gradient of 100% hexanes to 2% ethyl acetate in hexanes) to afford (12Z,15Z)-1,2-bis((9Z,12Z)-octadeca-9,12-dienyloxy)henicosa-12,15-dien-3-ol as a colorless oil (460 mg, 21%).

Step 5: Synthesis of compound 13-B5, (12Z,15Z)-1,2-bis((9Z,12Z)-octadeca-9,12-dienyloxy)henicosa-12,15-dien-3-yl-4-(dimethylamino)butanoate, having the following structure

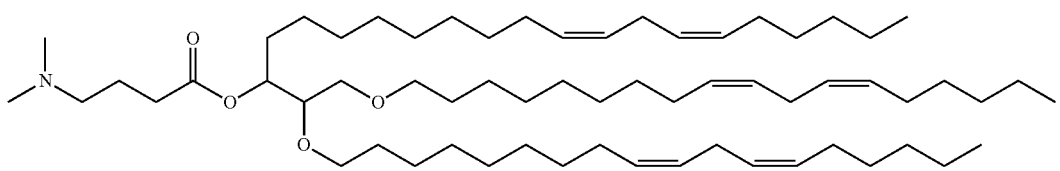 [SMILES: CCCCC/C=C\C/C=C\CCCCCCCCOCC(OCCCCCCCC/C=C\C/C=C\CCCCC)C(CCCCCCCC/C=C\C/C=C\CCCCC)OC(=O)CCCN(C)C]

To a solution of (12Z,15Z)-1,2-bis((9Z,12Z)-octadeca-9,12-dienyloxy)henicosa-12,15-dien-3-ol (450 mg, 0.54 mmol), 4-(dimethylamino)butanoic acid hydrochloride (135 mg, 0.8 mmol), EDCI hydrochloride (153 mg, 0.8 mmol), DIPEA (260 µL, 1.6 mmol) in anhydrous dichloromethane (10 mL) was added DMAP (5 mg). The solution was refluxed for 3 hours, cooled to room temperature and concentrated in vacuo to dryness. The reaction mixture was purified by column chromatography on silica gel 60 (eluted with a gradient of 100% hexanes to 1:1 hexanes/ethyl acetate) to afford (12Z,15Z)-1,2-bis((9Z,12Z)-octadeca-9,12-dienyloxy)henicosa-12,15-dien-3-yl 4-(dimethylamino)butanoate as a colorless oil (236 mg). 5.43-5.29 (m, 2H), 5.05-4.98 (m, 1H), 3.68-3.64 (m, 1H), 3.52-3.46 (m, 1H), 3.40 (t, 2H, J=6.7 Hz), 2.78 (t, 6H, J=6.4 Hz), 2.46-2.35 (m, 4H), 2.32 (s, 6H), 2.09-2.02 (m, 12H), 1.91-1.81 (m, 2H), 1.70-1.48 (m, 6H), 1.41-1.23 (m, 50H), 0.90 (t, 9H, J=6.7 Hz).

Example 6

Synthesis of 13-B6

Step 1: Synthesis of Di-Linoleyl acetonitrile, having the following structure

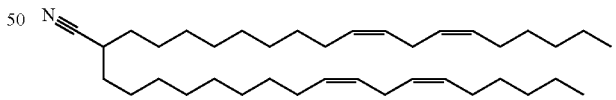

A solution of di-lin-OMs (2.0 g, 3.3 mmol) in anhydrous DMF (15 mL) was treated with NaCN (809 mg, 16.5 mmol) and heated (55° C., 16 h). The DMF was then removed under reduced pressure. The residue was dissolved in EtOAc and washed with H₂O and brine, then dried (Na₂SO₄), filtered and concentrated. The crude material was subjected to chromatography (heptane→2% EtOAc-heptane) to yield Di-Linoleyl acetonitrile (1.2 g, 69%) as a pale yellow oil. Rf 0.84 (10% EtOAc-hexanes), FW 537.95, $C_{38}H_{67}N$.

Step 2: Synthesis of the Di-Linoleyl acetylaldehyde, having the following structure

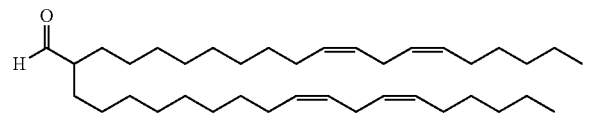 [SMILES: CCCCC/C=C\C/C=C\CCCCCCCCC(C=O)CCCCCCCC/C=C\C/C=C\CCCCC]

A solution of the nitrile, Di-Linoleyl acetonitrile, (1.01 g, 1.88 mmol) in anhydrous $CH_2Cl_2$ (25 mL) was cooled (−78° C.) and treated, dropwise, with DIBAL (3.75 mL, 3.75 mmol; 1.0M in hexanes). The solution was warmed (−25° C.--−30° C.) and stirred (3 h), then carefully poured into cold HCl (5%, aq.) and extracted with EtOAc. The organic extract was washed with brine, dried (Na₂SO₄), filtered and concentrated. The crude material was subjected to chromatography (2% EtOAc-hexanes) to yield Di-Linoleyl acetylaldehyde (552 mg, 54%) as a colorless oil. Rf 0.62 (10% EtOAc-hexanes), FW 540.95, $C_{38}H_{68}O$.

Step 3: Synthesis of the Tri-linoleyl alcohol, referred to as Compound AM-246 below, having the following structure

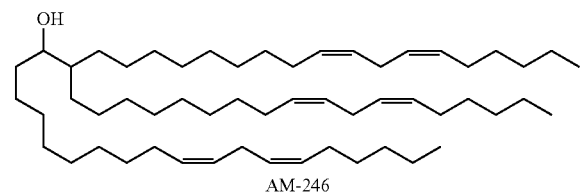

AM-246

A solution of the above di-linoleyl acetylaldehyde from step 2 (520 mg, 0.96 mmol) in anhydrous THF (5 mL) was cooled (0° C.) and treated, dropwise, with LinMgBr (0.93 mL, 1.90 mmol; 2.04M in THF), and stirred (16 h). The solution was poured into H₂O and extracted with hexanes. The organic extract was washed with HCL (5M, aq.) and H₂O, dried (Na₂SO₄), filtered and concentrated. The crude material was subjected to chromatography (1% EtOAc-hexanes) to yield AM-246 (600 mg, 79%) as a colorless oil. Rf 0.66 (10% EtOAc-hexanes), FW 791.41, $C_{56}H_{102}O$.

Step 4: Synthesis of compound 13-B6, having the following structure

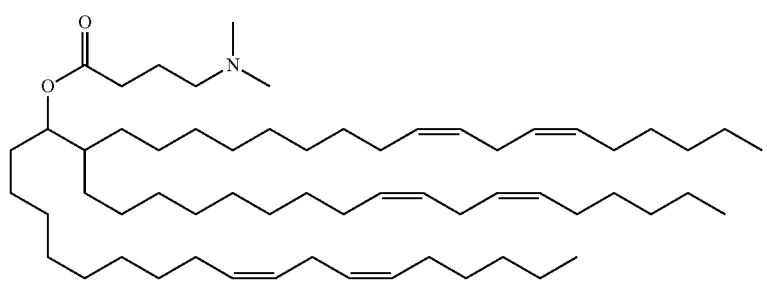

13-B6

A solution of the Tri-linoleyl alcohol of step 3 above, AM-246, (600 mg, 0.76 mmol) and N,N-dimethylaminobutyric acid hydrochloride (165 mg, 0.99 mmol) in anhydrous $CH_2Cl_2$ (5 mL) was treated with EDC (189 mg, 0.99 mmol), Hünig's base (400 μL, 2.3 mmol) and DMAP (7 mg). After stirring (16 h) the solution was diluted with $CH_2Cl_2$, washed with NaHCO₃ (sat. aq.) and brine then dried (Na₂SO₄), filtered and concentrated. The crude material was subjected to chromatography ($CH_2Cl_2$→2% $CH_3OH$—$CH_2Cl_2$) to yield AM-250 (499 mg, 73%) as a pale yellow oil. Rf 0.51 (8% $CH_3OH$—$CHCl_3$), $^1H$ NMR (400 MHz, $CDCl_3$, δH) 5.43-5.30 (m, 12H, C═CH×12), 4.96-4.91 (m 1H, $CHO_2CR$), 2.82-2.75 (app. t, 6H, C═$CHCH_2HC$═C×3) 2.35-2.28 (m, 4H, $CH_2CO_2R$, $CH_2N(CH_3)_2$), 2.23 (s, 6H, $N(CH_3)_2$), 2.10-2.04 (m, 13H, $CH_2HC$═C×6, $O_2CHCH$ $(CH_2)2$), 1.84-1.75 (m, 2H, $CH_2$), 1.55-1.42 (m, 2H, $CH_2$), 1.41-1.14 (m, 58H, $CH_2$×29), 0.90 (t, 9H, $CH_3$×3); FW 904.57, $C_{62}H_{113}NO_2$.

Example 7

Synthesis of 13-B7

Synthesis of Compound 13-B7, (6Z,9Z,28Z,31Z)-heptatriaconta-6,9,28,31 tetraen-19-yl 3-(dimethylamino)propyl((9Z,12Z)-octadeca-9,12-dienyl)carbamate, having the following structure

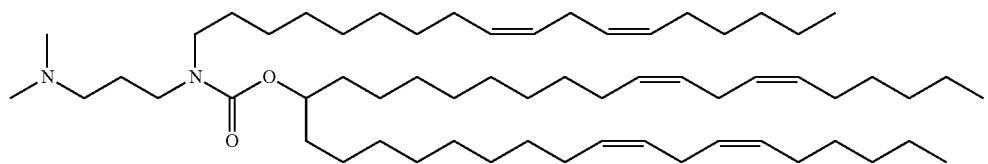

Chemical Formula: $C_{61}H_{112}N_2O_2$
Molecular Weight: 905.6

Step 1: Synthesis of (9Z,12Z)-octadeca-9,12-dienal, having the following structure

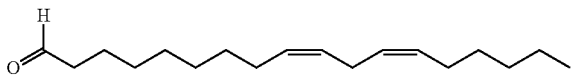

A solution of linoleyl alcohol (15 g, 56 mmol) in anhydrous $CH_2Cl_2$ (400 mL) was treated with pyridinium chlorochromate (36.4 g, 169 mmol) and $Na_2CO_3$ (2.98 g, 28.2 mmol) and then stirred (4 h). The reaction mixture was diluted with EtOAc and filtered through a pad of silica and then concentrated. The crude material was subjected to chromatography (1%→3%→6% EtOAc-heptane) to yield (9Z,12Z)-octadeca-9,12-dienal (10.5 g, 71%) as a colorless oil. Rf 0.58 (10% EtOAc-hexanes), FW 264.45, $C_{18}H_{32}O$.

A solution of (9Z,12Z)-octadeca-9,12-dienal (1.06 g, 4.0 mmol) and N,N-dimethylpropane-1,3-diamine (408 mg, 4.0 mmol) in anhydrous tetrahydrofuran (15 mL) was stirred under nitrogen for 15 minutes then sodium triacetoxyborohydride (1.7 g, 8.0 mmol). The solution was stirred for 2 hours at room temperature. Upon completion, the solution was diluted with ethyl acetate (20 mL) and washed with sodium bicarbonate (2×15 mL) and brine (15 mL). The ethyl acetate layer was dried on magnesium sulfate, filtered and concentrated in vacuo to dryness. The oil was purified by column chromatography on silica gel (eluted with 100% $CH_2Cl_2$ to 1/5/94 $NH_4OH/MeOH/CH_2Cl_2$) to afford N,N-dimethyl-N'-((9Z,12Z)-octadeca-9,12-dienyl)propane-1,3-diamine as a colorless oil (420 mg, 30%).

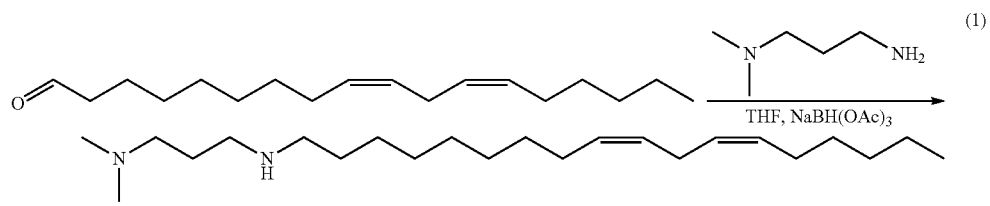

Step 2: Synthesis of N,N-dimethyl-N'-((9Z,12Z)-octadeca-9,12-dienyl)propane-1,3-diamine, having the following structure

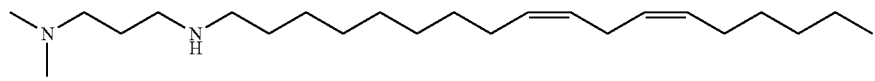 [SMILES: CCCCC/C=C\C/C=C\CCCCCCCCNCCCN(C)C]

Step 3: Synthesis of (6Z,9Z,28Z,31Z)-heptatriaconta-6,9,28,31-tetraen-19-yl 3-(dimethylamino) propyl((9Z,12Z)-octadeca-9,12-dienyl)carbamate, having the following structure

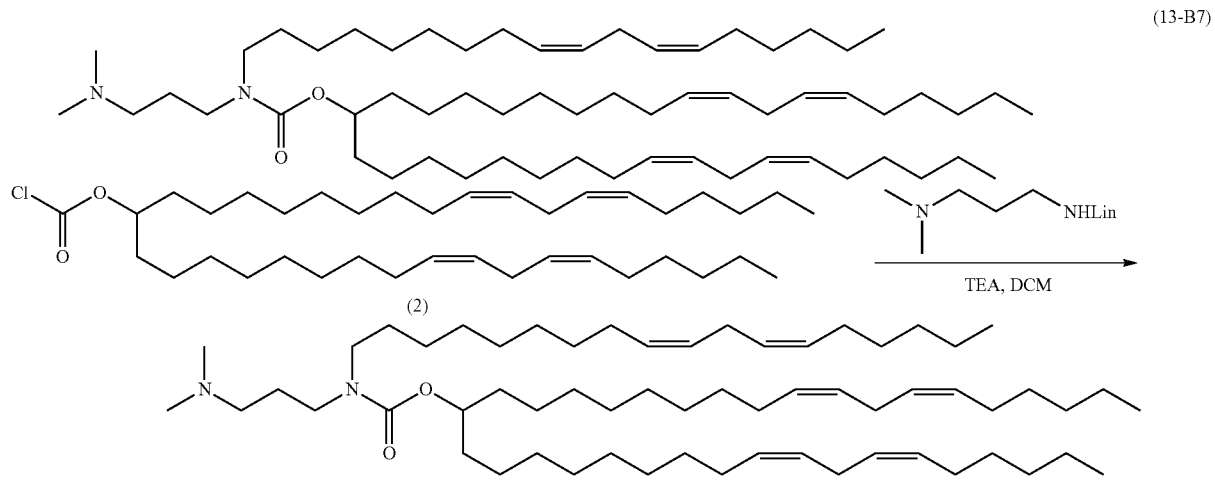

To a solution of (6Z,9Z,28Z,31Z)-heptatriaconta-6,9,28,31-tetraen-19-yl carbonochloridate (590 mg, 1.0 mmol), N,N-dimethyl-N'-((9Z,12Z)-octadeca-9,12-dienyl)propane-1,3-diamine (350 mg, 1 mmol) and triethylamine (500 μL, 3.6 mmol) in dichloromethane (8 mL) was stirred overnight at room temperature. Upon completion, the solution was concentrated in vacuo to dryness and purified by column chromatography on silica gel to afford (6Z,9Z,28Z,31Z)-heptatriaconta-6,9,28,31-tetraen-19-yl 3-(dimethylamino)propyl ((9Z,12Z)-octadeca-9,12-dienyl)carbamate as a colorless oil (500 mg, 55%). $^1$H NMR (CDCl$_3$, 400 MHz) δ 5.42-5.28 (m, 12H), 4.79-4.70 (m, 1H), 3.32-3.12 (m, 4H), 2.78 (t, 6H, J=6.3 Hz), 2.38-2.20 (m, 8H), 2.09-2.02 (m, 12H), 1.82-1.63 (m, 2H), 1.57-1.43 (m, 6H), 1.41-1.23 (m, 52H), 0.89 (t, 9H, J=7.0 Hz).

Example 8

Synthesis of 13-B8

Compound 13B-8, having structure (G) below, was synthesized as described in Scheme 10 below:

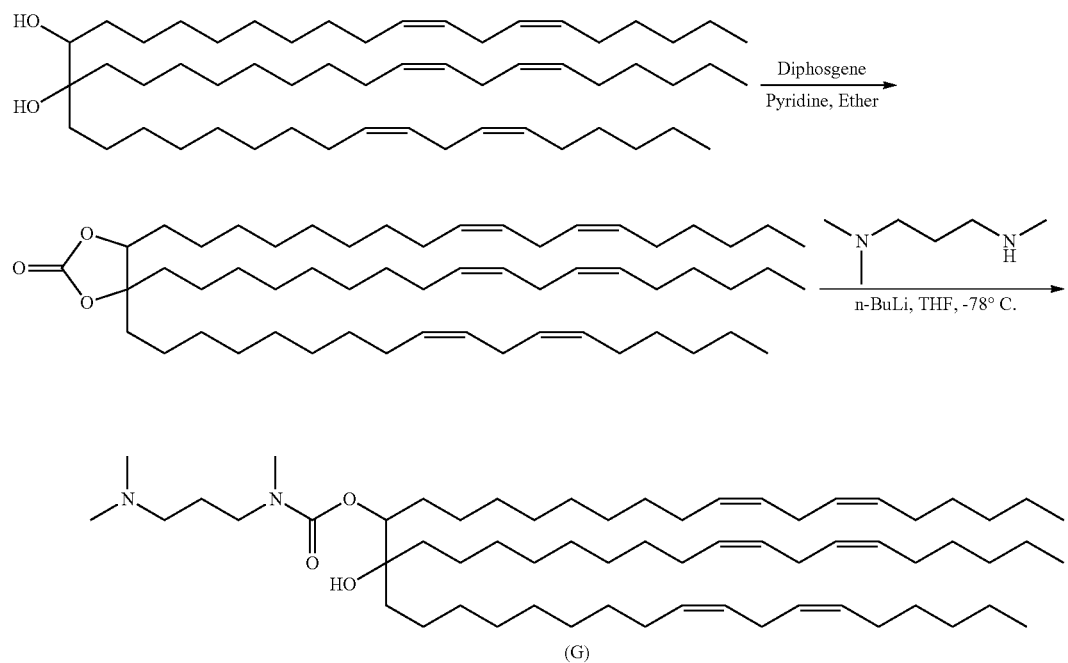

Step 1: Preparation of 4,5-di((8Z,11Z)-heptadeca-8,11-dienyl)-4-((9Z,12Z)-octadeca-9,12-dienyl)-1,3-dioxolan-2-one

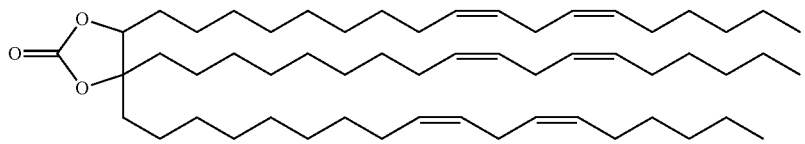 [SMILES: CCCCC/C=C\C/C=C\CCCCCCCCC1OC(=O)OC1(CCCCCCCC/C=C\C/C=C\CCCCC)CCCCCCCC/C=C\C/C=C\CCCCC]

To a solution of (6Z,9Z,28Z,31Z)-19-((8Z,11Z)-heptadeca-8,11-dienyl)heptatriaconta-6,9,28,31-tetraene-18,19-diol (540 mg, 0.67 mmol) in anhydrous ether (5 mL) was added pyridine (81 μL, 1.0 mmol). To this solution was added diphosgene (132 μL, 1.1 mmol) slowly over 5 minutes. The solution was stirred for 2 hours at room temperature then concentrated in vacuo to dryness and purified by column chromatography on silica gel 60 (eluted with 5% ether in hexanes) to afford 4,5-di((8Z,11Z)-heptadeca-8,11-dienyl)-4-((9Z,12Z)-octadeca-9,12-dienyl)-1,3-dioxolan-2-one as a colorless oil (310 mg, 57%).

Step 2: Synthesis of Compound 13-B8, (6Z,9Z,28Z,31Z)-19-((9Z,12Z)-heptadeca-9,12-dienyl)-19-hydroxyhexatriaconta-6,9,28,31-tetraen-18-yl 3-(dimethylamino)propyl(methyl)carbamate, having the following structure

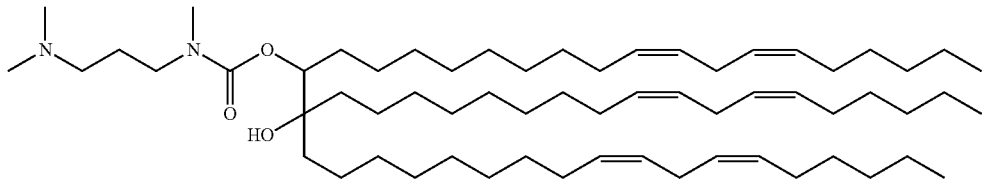 [SMILES: CCCCC/C=C\C/C=C\CCCCCCCCC(OC(=O)N(C)CCCN(C)C)C(O)(CCCCCCCC/C=C\C/C=C\CCCCC)CCCCCCCC/C=C\C/C=C\CCCCC]

To a solution of N,N,N-Trimethyl propane-1,3-diamine (87 mg, 0.75 mmol) in anhydrous THF (5 mL) cooled to −78° C. was added slowly 2.5M n-BuLi in hexanes (0.3 mL, 0.75 mmol). The solution was stirred for 30 minutes at −78° C. then a solution of the cyclic carbamate (200 mg, 0.25 mmol) in THF (5 mL). The solution was slowly warmed to room temperature and stirred for 1 hour. The solution was diluted with ethyl acetate (75 mL) and washed with water (1×50 mL) and brine (1×50 mL). The ethyl acetate solution was dried on magnesium sulfate, filtered and concentrated in vacuo to dryness. The residue was purified by column chromatography on silica gel 60 (eluted with 100% ethyl acetate) to afford (6Z,9Z,28Z,31Z)-19-((9Z,12Z)-heptadeca-9,12-dienyl)-19-hydroxyhexatriaconta-6,9,28,31-tetraen-18-yl 3-(dimethylamino)propyl(methyl)carbamate (196 mg, 86%). $^1$H NMR (400 MHz, CDCl$_3$) δ 5.43-5.29 (m, 12H), 4.81-4.78 (m, 1H), 3.43-3.25 (m, 2H), 2.93 (s, 3H), 2.77 (t, 6H, J=6.4 Hz), 2.39-2.20 (m, 12H), 1.76-1.45 (m, 9H), 1.42-1.21 (m, 54H), 0.90 (t, 9H, J=6.8 Hz).

Example 9

Lipid Encapsulation of siRNA

All siRNA molecules used in these studies were chemically synthesized and annealed using standard procedures.

In some embodiments, siRNA molecules were encapsulated into serum-stable nucleic acid-lipid particles (SNALP) composed of the following lipids: (1) the lipid conjugate PEG2000-C-DMA (3-N-[(-methoxypoly(ethylene glycol)2000)carbamoyl]-1,2-dimyristyloxypropylamine); (2) one or more cationic lipids or salts thereof (e.g., cationic lipids of Formula I of the invention and/or other cationic lipids described herein); (3) the phospholipid DPPC (1,2-dipalmitoyl-sn-glycero-3-phosphocholine) (Avanti Polar Lipids; Alabaster, Ala.); and (4) synthetic cholesterol (Sigma-Aldrich Corp.; St. Louis, Mo.) in the molar ratio 1.4:57.1:7.1:34.3, respectively. In other words, siRNA molecules were encapsulated into SNALP of the following "1:57" formulation: 1.4% PEG2000-C-DMA; 57.1% cationic lipid; 7.1% DPPC; and 34.3% cholesterol. It should be understood that the 1:57 formulation is a target formulation, and that the amount of lipid (both cationic and non-cationic) present and the amount of lipid conjugate present in the formulation may vary. Typically, in the 1:57 formulation, the amount of cationic lipid will be 57.1 mol %±5 mol %, and the amount of lipid conjugate will be 1.4 mol %±0.5 mol %, with the balance of the 1:57 formulation being made up of non-cationic lipid (e.g., phospholipid, cholesterol, or a mixture of the two).

In other embodiments, siRNA may be encapsulated into SNALP composed of the following lipids: (1) the lipid conjugate PEG750-C-DMA (3-N-[(-Methoxypoly(ethylene glycol)750)carbamoyl]-1,2-dimyristyloxypropylamine); (2) one or more cationic lipids or salts thereof (e.g., cationic lipids of Formula I of the invention and/or other cationic lipids described herein); (3) the phospholipid DPPC; and (4) synthetic cholesterol in the molar ratio 6.76:54.06:6.75:32.43, respectively. In other words, siRNA may be encapsulated into SNALP of the following "7:54" formulation: 6.76 mol % PEG750-C-DMA; 54.06 mol % cationic lipid; 6.75 mol % DPPC; and 32.43 mol % cholesterol. Typically, in the 7:54 formulation, the amount of cationic lipid will be 54.06 mol %±5 mol %, and the amount of lipid conjugate will be 6.76 mol %±1 mol %, with the balance of the 7:54 formulation being made up of non-cationic lipid (e.g., phospholipid, cholesterol, or a mixture of the two).

For vehicle controls, empty particles with identical lipid composition may be formed in the absence of siRNA.

Example 10 pKa Measurements of SNALP Formulations Containing Novel Trialkyl Cationic Lipids This example demonstrates the determination of $pK_a$ values of various SNALP formulations containing the novel trialkyl cationic lipids described herein. In particular, SNALP formulations containing encapsulated siRNA may be prepared as described in Example 9 and section IV above with one or more cationic lipids of Formula I of the invention.

In certain embodiments, the apparent $pK_a$ of the cationic lipids present in these SNALP formulations may be determined using a 2-(p-toluidinyl)-naphthalene-6-sodium sulfonate (TNS) assay. TNS is a negatively-charged indicator of membrane potential that is electrostatically attracted to positively charged membranes (see, Bailey and Cullis, *Biochem.*, 33 12573-80 (1994)). Subsequent adsorption to the lipid membrane results in the immediate environment of the TNS becoming more lipophilic, removing the water molecules that otherwise quench TNS fluorescence. As a result, TNS measures the surface potential of the particle, wherein the more positive the surface potential, the greater the level of fluorescence. The surface $pK_a$ values of a SNALP formulation may be determined by varying the local pH in the presence of TNS. By plotting fluorescence versus pH, the $pK_a$ of a cationic lipid can be estimated in the particle as the pH where fluorescence equals 50% of total fluorescence. In other words, the $pK_a$ of a cationic lipid is the pH at which 50% of the cationic lipid present in the particle is charged.

Example 11

Characterization of SNALP Formulations Containing Novel Trialkyl Cationic Lipids This example demonstrates the efficacy of 1:57 SNALP formulations containing various novel trialkyl cationic lipids of Formula I described herein with an siRNA targeting ApoB in a mouse liver model. In particular, the objective of this study was to assess the ApoB dose response gene silencing activity in the mouse liver of 1:57 SNALP containing various novel trialkyl cationic lipids of Formula I. The ApoB siRNA sequence used in this study is provided in Table 1.

I. Experimental Design

The experimental design for this study is set forth in Table 2.

TABLE 2

| Group | Test Article | IV Bolus siRNA Dose | Dosing days | End Point | Collections |
|---|---|---|---|---|---|
| 1 | PBS | — | Day 0 | Day 2 48 hours | Plasma for cholesterol Half of Left Lateral Lobe into RNA later |
| 2 | 1:57 C2K | 0.05 mg/kg | | | |
| 3 | 1:57 MC3 | | | | |
| 4 | 1:57 MC3MC | | | | |
| 5 | 1:57 13-B1 | | | | |
| 6 | 1:57 13-B2 (formulated at low pH) | | | | |
| 7 | 1:57 13-B3 (formulated at low pH) | | | | |
| 8 | 1:57 13-B4 | | | | |
| 9 | 1:57 1-B17 | | | | |
| 10 | 1:57 MC3 Thioester | | | | |

In Table 2, Group Size: n = 3, female BALB/c mice

II. Test Articles

Ready-to-inject vials of test article, diluted to the appropriate concentrations, were prepared no sooner than 3 days before use. Test articles were provided as 0.22 μm filter sterilized liquids in crimp top glass vials. All vials were labeled with the study #, group #, lot #, and siRNA concentration. For control formulations lacking siRNA, the total lipid concentration was provided instead. Test article vials were stored at 2-8° C. and removed from storage 30-60 minutes before use in order to equilibrate to room temperature.

Brief description of formulations & controls used:
- The PBS used for dilution of SNALP (test article preparation) is Hyclone lot #ATL33632
- "Base" lipid composition 1.4|57.1|7.1|34.3 is described in molar percentages of $PEG_{2000}$-C-DMA, cationic lipid, DPPC, and cholesterol (in that order). Input lipid:drug ratio is 6.
- siRNA: Test articles contain GMP-grade siApoB-8 manufactured by Avecia Lot 100,000 (11.632 mg/mL solution).
- Drug concentration is expressed as total siRNA content.
- Batch size is 0.34 mg, ethanol is removed via Slide-A-Lyzer bag dialysis.

TABLE 1

| siRNA | ApoB siRNA Sequence | % 2'OMe-Modified | % Modified in DS Region |
|---|---|---|---|
| ApoB-10164 | 5'-AGUGUCAUCACACUGAAUACC-3' (SEQ ID NO: 1) | 7/42 = 16.7% | 7/38 = 18.4% |
| | 3'-GUUCACAGUAGUGUGACUUAU-5' (SEQ ID NO: 2) | | |

Column 1: The number after "ApoB" refers to the nucleotide position of the 5' base of the sense strand relative to the human ApoB mRNA sequence NM_000384. Column 2: 2'OMe nucleotides are indicated in bold and underlined. The 3'-overhangs on one or both strands of the siRNA molecule may alternatively comprise 1-4 deoxythymidine (dT) nucleotides, 1-4 modified and/or unmodified uridine (U) ribonucleotides, or 1-2 additional ribonucleotides having complementarity to the target sequence or the complementary strand thereof. Column 3: The number and percentage of 2'OMe-modified nucleotides in the siRNA molecule are provided. Column 4: The number and percentage of modified nucleotides in the double-stranded (DS) region of the siRNA molecule are provided.

1:57 SNALP formulations containing encapsulated ApoB siRNA were prepared as described in Sections V and VI above with the following cationic lipids: (1) DLin-C2K-DMA ("C2K"); (2) MC3; (3) MC3MC; (4) 13-B1; (5) 13-B2; (6) 13-B3; (7) 13-B4; (8) MC4 Ether ("1-B17"); and (9) MC3 Thioester. The synthesis of MC3, MC3MC, MC4 Ether, and MC3 Thioester is described in U.S. Provisional Application No. 61/384,050, entitled "Novel Cationic Lipids and Methods of Use Thereof,", filed Sep. 17, 2010. The synthesis of 13-B1,13-B2,13-B3, and 13-B4 is described herein. Table 3 provides exemplary features of these SNALP formulations, including particle size (Z-average), polydispersity, and percent encapsulation.

TABLE 3

| Description | Total siRNA (mg/mL) | Encap. (%) | Z-average (nm) | Polydispersity |
|---|---|---|---|---|
| PBS | N/A | N/A | N/A | N/A |
| 1:57 C2K | 0.135 | 85 | 82.60 | 0.059 |
| 1:57 MC3 | 0.128 | 79 | 80.05 | 0.048 |
| 1:57 MC3MC | 0.137 | 87 | 90.19 | 0.019 |
| 1:57 13-B1 | 0.122 | 86 | 88.88 | 0.094 |
| 1:57 13-B2 (formulated at low pH) | 0.141 | 86 | 84.73 | 0.060 |
| 1:57 13-B3 (formulated at low pH) | 0.131 | 84 | 81.54 | 0.030 |
| 1:57 13-B4 | 0.131 | 87 | 95.07 | 0.033 |
| 1:57 MC4 Ether | 0.132 | 85 | 84.85 | 0.034 |
| 1:57 MC3 Thioester | 0.126 | 75 | 80.57 | 0.069 |

III. Procedures

Identification:

Groups were assigned numbers 1-10 as listed in Section I. Animal IDs were assigned two ways: a) for visual identification during the in-life phase, animals within a cage were differentiated by 'color' code (R=red, G=green, W=no color); and b) for specimen identification during the analytical phase, animals were assigned a number based on group order.

Cage-Sorting:

At least 1 day (preferably at least 2-3 days, and as much as 7 days) before the study begins, animals were sorted in order to normalize body weight distribution such that a) the mean for each cage was similar by targeting all cage means to be within 2.0 g and b) the range within a cage was similar between cages. Also, a routine health check was performed and any abnormal animals (including unusually heavy or light animals) were noted and replaced with spares as available.

Treatment:

Just prior to the first treatment, animals were weighed and dose amounts were calculated based on the weight of individual animals (equivalent to 10 mL/kg, rounded to the nearest 10 μL). The test article was administered by IV injection through the tail vein once on Day 0 (1 dose total per animal).

Monitoring:

Body weight was measured at cage-sort, as well as on every day from Day 0 through Day 2. Weights for all groups were taken at the same time of day (for convenience), at a consistent time of day to minimize effects of circadian fluctuation in this parameter. Cageside observations were taken in concert with body weight measurements, at 1 hour after treatment, at end-of-day on the day of dosing, and additionally as warranted (recorded for all on-study animals whenever abnormal behavior in a subset of animals was detected).

Nonterminal Collections:

None.

Terminal Collection:

Animals were sacrificed on Day 2, 48 h after test article administration. Animals were anaesthetized with a lethal dose of ketamine/xylazine; then exsanguination was performed via cardiac puncture (no cervical dislocation). Blood was collected by cardiac puncture. For each animal, blood (target 0.5 mL) was collected into a lavender EDTA microtainer for plasma: Invert 10×, then immediately centrifuge for 5 min at 16,000×g and 16° C., transfer plasma into a clean 1.5 mL microfuge tube (target 250 μL, record volume and appearance), store at 4° C. prior to further analyses. A brief necropsy was performed and observations recorded. Approximately 200-300 mg of the bottom (unattached) half of the left liver lobe was cut off and submerged in ≧5 volumes of RNAlater (≦0.3 g into a 2.0 mL tube containing 1.5 mL RNAlater), stored at least 16 hours (and no more than one month) at +4° C. prior to analysis. Following analysis, samples were transferred into long term storage at −80° C. for archival purposes.

Euthanization:

Formulations were expected to be well tolerated. Mice which exhibited signs of distress associated with the treatment were terminated at the discretion of the core facility staff.

Data Analysis:

Body weight was reported for individual animals in addition to group mean and standard deviation of the group mean. Data were expressed in terms of the measured unit (grams) and the group mean difference from PBS vehicle control treatment was calculated for this expression (include SD). For body weights, individual animal data were also expressed as % of pre-treatment value and the group means were expressed as % change from pre-treatment value (include SD). Cageside observations were reported as raw tabulated data entries (generally line entries were organized by clock time with granularity to the level of individual animals) as well as a tabulated summary containing treatment groups on the left column and study timeline running left-to-right on the top row as header. Necropsy gross observations were reported as raw tabulated data entries (with granularity to the level of individual animals) as well as a tabulated summary containing treatment groups on the left column and selected key tissues and/or findings on the top row as header. Drug activity was measured using a QuantiGene assay for ApoB mRNA level in the liver (normalized to GAPDH mRNA level). An ELISA for ApoB-100 protein in plasma and/or colorimetric enzymatic assay for plasma total cholesterol may also be conducted. For any given activity assay, individual animal data were reported in addition to group mean and standard deviation of the group mean. Data were expressed in terms of the measured unit as well as difference from PBS vehicle control treatment. KD50 ("50% knockdown") values were interpolated from QuantiGene measurements for those test articles for which a dose response was performed.

IV. Results

The FIGURE shows a comparison of the liver ApoB mRNA knockdown activity of each of these SNALP formulations (Error bars=SD). In particular, the FIGURE shows that a SNALP formulation containing either 13-B1 or 13-B2 displayed similar ApoB silencing activity compared to SNALP containing the C2K benchmark cationic lipid. Notably, the FIGURE also shows that a SNALP formulation containing 13-B4, in which subscript a of Formula I is 4 (i.e., there is a 4-carbon spacer between the amino head group and the ester linker), displayed unexpectedly improved ApoB silencing activity compared to SNALP containing the C2K benchmark cationic lipid.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents, PCT publications, and Genbank Accession Nos., are incorporated herein by reference for all purposes.

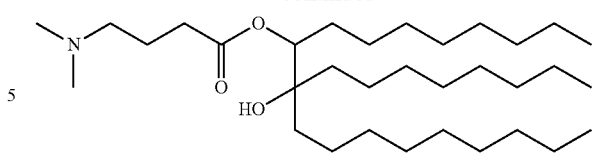

What is claimed is:

1. A cationic lipid having one of the following structures:

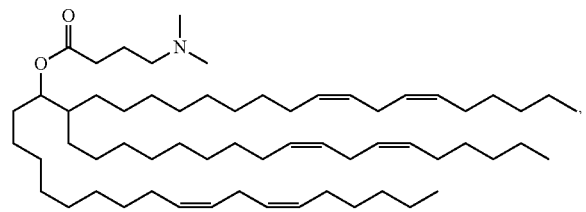

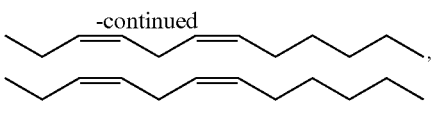

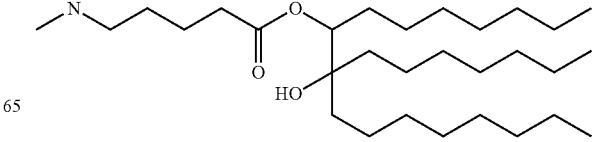

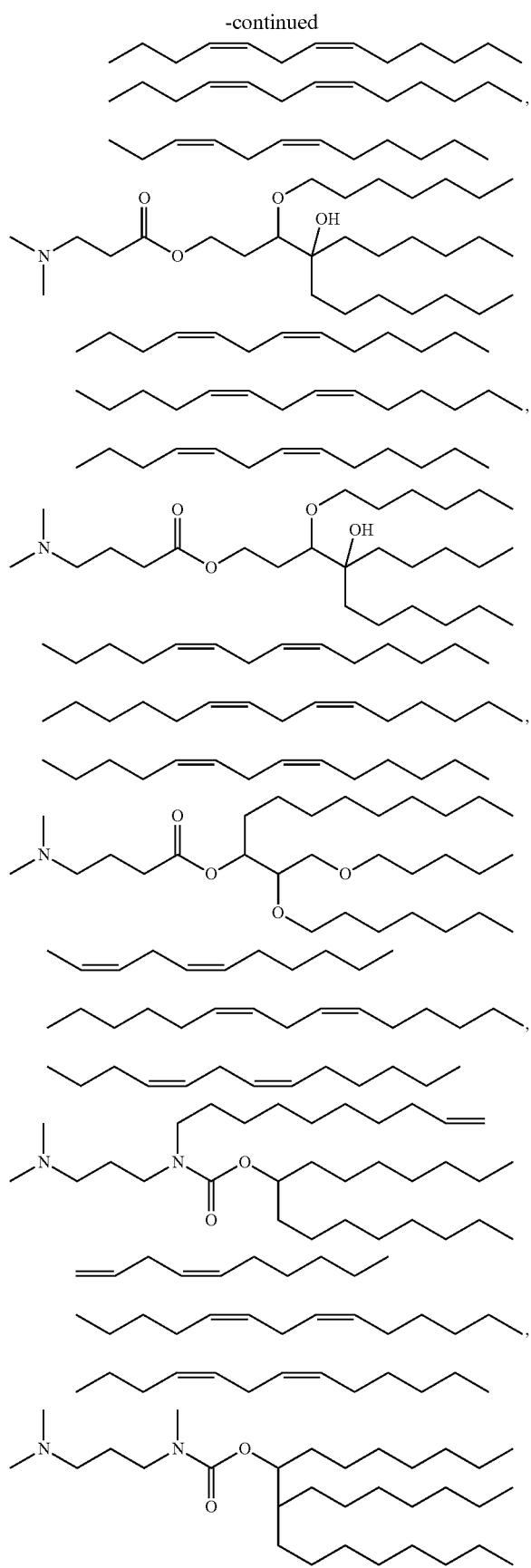

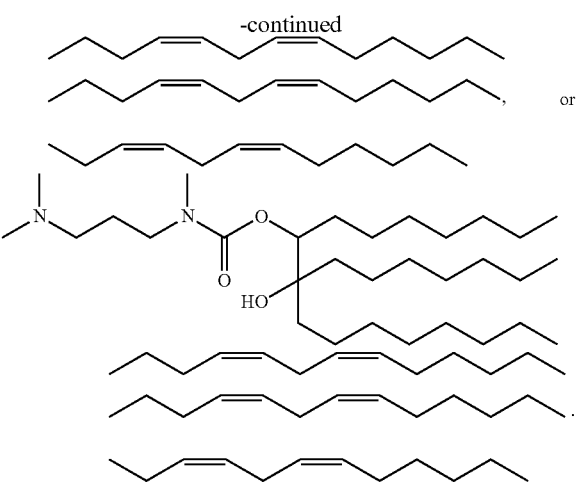

2. A lipid particle comprising a cationic lipid of claim 1.

3. The lipid particle of claim 2, wherein the particle further comprises a non-cationic lipid.

4. The lipid particle of claim 3, wherein the non-cationic lipid is selected from the group consisting of a phospholipid, cholesterol, or a mixture of a phospholipid and cholesterol.

5. The lipid particle of claim 4, wherein the phospholipid comprises dipalmitoylphosphatidylcholine (DPPC), distearoylphosphatidylcholine (DSPC), or a mixture thereof.

6. The lipid particle of claim 4, wherein the cholesterol is a cholesterol derivative.

7. The lipid particle of claim 3, wherein the particle further comprises a conjugated lipid that inhibits aggregation of particles.

8. The lipid particle of claim 7, wherein the conjugated lipid that inhibits aggregation of particles comprises a polyethyleneglycol (PEG)-lipid conjugate.

9. The lipid particle of claim 8, wherein the PEG-lipid conjugate comprises a PEG-diacylglycerol (PEG-DAG) conjugate, a PEG-dialkyloxypropyl (PEG-DAA) conjugate, or a mixture thereof.

10. The lipid particle of claim 7, wherein the particle further comprises a therapeutic agent.

11. The lipid particle of claim 10, wherein the therapeutic agent is a nucleic acid.

12. The lipid particle of claim 11, wherein the nucleic acid is an interfering RNA.

13. The lipid particle of claim 12, wherein the interfering RNA is selected from the group consisting of a small interfering RNA (siRNA), an asymmetrical interfering RNA (aiRNA), a microRNA (miRNA), a Dicer-substrate dsRNA, a small hairpin RNA (shRNA), and mixtures thereof.

14. The lipid particle of claim 12, wherein the interfering RNA is an siRNA.

15. A pharmaceutical composition comprising a lipid particle of claim 10 and a pharmaceutically acceptable carrier.

16. A method for introducing a therapeutic agent into a cell, the method comprising:
    contacting the cell with a lipid particle of claim 10.

17. A method for the in vivo delivery of a therapeutic agent, the method comprising:
    administering to a mammal a lipid particle of claim 10.

18. A method for treating a disease or disorder in a mammal in need thereof, the method comprising:
    administering to the mammal a therapeutically effective amount of a lipid particle of claim 10.

* * * * *

SEQUENCE LISTING

```
<160> NUMBER OF SEQ ID NOS: 2

<210> SEQ ID NO 1
<211> LENGTH: 21
<212> TYPE: RNA
<213> ORGANISM: Artificial Sequence
<220> FEATURE:
<223> OTHER INFORMATION: synthetic apolipoprotein B (ApoB, APOB) siRNA
      ApoB-10164
<220> FEATURE:
<221> NAME/KEY: modified_base
<222> LOCATION: (4)...(4)
<223> OTHER INFORMATION: n = gm
<220> FEATURE:
<221> NAME/KEY: modified_base
<222> LOCATION: (8)...(14)
<223> OTHER INFORMATION: n = um

<400> SEQUENCE: 1
agunucanca cacngaauac c                                              21

<210> SEQ ID NO 2
<211> LENGTH: 21
<212> TYPE: RNA
<213> ORGANISM: Artificial Sequence
<220> FEATURE:
<223> OTHER INFORMATION: synthetic apolipoprotein B (ApoB, APOB) siRNA
      ApoB-10164
<220> FEATURE:
<221> NAME/KEY: modified_base
<222> LOCATION: (4)...(4)
<223> OTHER INFORMATION: n = um
<220> FEATURE:
<221> NAME/KEY: modified_base
<222> LOCATION: (7)...(9)
<223> OTHER INFORMATION: n = gm
<220> FEATURE:
<221> NAME/KEY: modified_base
<222> LOCATION: (19)...(19)
<223> OTHER INFORMATION: n = um

<400> SEQUENCE: 2
uauncanunu gaugacacnu g                                              21
```